United States Patent
Cren et al.

(10) Patent No.: US 9,527,867 B2
(45) Date of Patent: Dec. 27, 2016

(54) ANTIBACTERIAL BIAROMATIC DERIVATIVES

(71) Applicant: Actelion Pharmaceuticals Ltd., Allschwil (CH)

(72) Inventors: Sylvaine Cren, Allschwil (CH); Astrid Friedli, Allschwil (CH); Christian Hubschwerlen, Durmenach (FR); Georg Rueedi, Allschwil (CH); Cornelia Zumbrunn, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/784,602

(22) PCT Filed: Apr. 15, 2014

(86) PCT No.: PCT/IB2014/060724
§ 371 (c)(1),
(2) Date: Oct. 15, 2015

(87) PCT Pub. No.: WO2014/170821
PCT Pub. Date: Oct. 23, 2014

(65) Prior Publication Data
US 2016/0075722 A1 Mar. 17, 2016

(30) Foreign Application Priority Data
Apr. 16, 2013 (WO) .................. PCT/IB2013/053021

(51) Int. Cl.
C07D 513/04 (2006.01)
C07D 417/04 (2006.01)
C07D 498/04 (2006.01)
C07D 417/14 (2006.01)
C07D 413/14 (2006.01)
C07D 413/04 (2006.01)

(52) U.S. Cl.
CPC .......... C07D 513/04 (2013.01); C07D 413/04 (2013.01); C07D 413/14 (2013.01); C07D 417/04 (2013.01); C07D 417/14 (2013.01); C07D 498/04 (2013.01)

(58) Field of Classification Search
CPC ... C07D 513/04; C07D 417/04; C07D 498/04; C07D 417/14; C07D 413/14; C07D 413/04
See application file for complete search history.

(56) References Cited

U.S. PATENT DOCUMENTS 8,349,826 B2  1/2013  Hubschwerlen et al.
8,349,828 B2  1/2013  Hubschwerlen et al.
8,618,092 B2  12/2013  Hubschwerlen et al.
9,079,922 B2  7/2015  Hubschwerlen et al.
2014/0142093 A1  5/2014  Hubschwerlen et al.

FOREIGN PATENT DOCUMENTS

| EP | 0 297 042 A1 | 6/1988 |
|---|---|---|
| WO | WO 99/37641 A1 | 7/1999 |
| WO | WO 01/30782 A2 | 5/2001 |
| WO | WO 03/043997 A1 | 5/2003 |
| WO | WO 2004/002992 A1 | 1/2004 |
| WO | WO 2006/102674 A2 | 9/2006 |
| WO | WO 2007/058602 A2 | 5/2007 |
| WO | WO 2008/120655 A1 | 10/2008 |
| WO | WO 2008/126024 A2 | 10/2008 |
| WO | WO 2009/080761 A1 | 7/2009 |
| WO | WO 2009/104147 A2 | 8/2009 |
| WO | WO 2009/104159 A1 | 8/2009 |
| WO | WO 2010/015985 A1 | 2/2010 |
| WO | WO 2010/041194 A1 | 4/2010 |
| WO | WO 2010/041219 A1 | 4/2010 |
| WO | WO 2013/068948 A1 | 5/2013 |

OTHER PUBLICATIONS

"Methods for Dilution Antimicrobial Susceptibility Tests for Bacteria that Grow Aerobically", Approved standard, 7th ed., Clinical and Laboratory Standards Institute (CLSI) Document M7-A7, Wayne, PA, USA (2006).
Fu, "The Development of Versatile Methods for Palladium-Catalyzed Coupling Reactions of Aryl Electrophiles through the Use of P(t-Bu)3 and PCy3 as Ligands", Acc. Chem. Res. (2008), 41, 1555-1564.
Istrate et al., "Synthesis of Functionalized Oxazolones by a Sequence of Cu(II)- and Au(I)-Catalyzed Transformations", Org. Lett. (2008), 10, 925-928.
Jensen et al., "Biomimetic Aryl Hydroxylation Derived from Alkyl Hydroperoxide at a Nonheme Iron Center. Evidence for an FE(iv)=O Oxidant", J. Am. Chem. Soc. (2003), 125, 2113-2128.

(Continued)

Primary Examiner — Kahsay Habte
(74) Attorney, Agent, or Firm — Arent Fox LLP

(57) ABSTRACT

The invention relates to antibacterial compounds of formula I and salts thereof and methods of treating bacterial infection using the compounds.

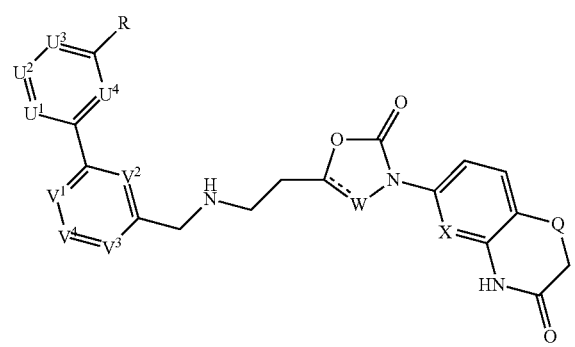

18 Claims, No Drawings

(56) References Cited

OTHER PUBLICATIONS

Johan Wouters and Luc Quéré, Pharmaceutical Salts and Co-crystals, (2012).
Kantchev et al., "Pd-N-Heterocyclic Carbene (NHC) Catalysts for Cross-Coupling Reactions", Aldrichimica Acta (2006), 39, 97-111.
Mauger and Mignani, "Synthetic Applications of Buchwald's Phosphines in Palladium-Catalyzed Aromatic-Bond-Forming Reactions", Aldrichimica Acta (2006), 39, 17-24.
Miyaura and Suzuki, "Palladium-Catalyzed Cross-Coupling Reactions of Organoboron Compounds", Chem. Rev. (1995), 95, 2457-2483.
P. Heinrich Stahl, Camille G. Wermuth, Handbook of Pharmaceutical Salts. Properties, Selection and Use, (2008).
Ramesh et al., "A simple and facile route for the synthesis of 2H-1,4-benzoxazin-3-(4H)-ones via reductive cyclization of 2-(2-nitrophenoxy) acetonitrile adducts in the presence of Fe/acetic acid", Tetrahedron (2011), 67, 1187-1192.
Remington, The Science and Practice of Pharmacy, 21st Edition (2005), Part 5, "Pharmaceutical Manufacturing".
Sato et al., "One-pot reductive amination of aldehydes and ketones with alpha-picoline-borane in methanol, in water, and in neat conditions", Tetrahedron (2004), 60, 7899-7906.
T.W. Greene, P.G.M. Wuts, Protecting Groups in Organic Synthesis, 3rd Ed (1999), 133-139.
T.W. Greene, P.G.M. Wuts, Protecting Groups in Organic Synthesis, 3rd Ed (1999), 142-143.
T.W. Greene, P.G.M. Wuts, Protecting Groups in Organic Synthesis, 3rd Ed (1999), 23-147.
T.W. Greene, P.G.M. Wuts, Protecting Groups in Organic Synthesis, 3rd Ed (1999), 494-653.
T.W. Greene, P.G.M. Wuts, Protective Groups in Organic Synthesis, (1999).
Thaler et al., "Synthesis and Biological Evaluation of N-Hydroxyphenylacrylamides and N-Hydroxypyridin-2-ylacrylamides as Novel Histone Deacetylase Inhibitors", J. Med. Chem. (2010), 53(2), 822-839.
Villeneuve et al., "Ruthenium-Catalyzed [2+2] Cycloadditions between Bicyclic Alkenes and Alkynyl Halides", Org. Letters (2004), 6(24), 4543-4546.

ANTIBACTERIAL BIAROMATIC DERIVATIVES

CROSS-REFERENCE TO RELATED APPLICATIONS

This application is a 35 U.S.C. 371 National Phase of PCT application Ser. No. PCT/IB2014/060724 filed Apr. 15, 2014, which claims priority to International Patent Application Serial No. PCT/IB2013/053021 filed Apr. 16, 2013, the disclosure of these prior applications are hereby incorporated in their entirety by reference.

The present invention concerns antibacterial biaromatic derivatives, pharmaceutical compositions containing them and uses of these compounds in the manufacture of medicaments for the treatment of bacterial infections. These compounds are useful antimicrobial agents effective against a variety of human and veterinary pathogens including among others Gram-positive and Gram-negative aerobic and anaerobic bacteria and mycobacteria.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriacea and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- *Enterobacteriacea* are cephalosporin and quinolone resistant;
- *P. aeruginosa* is β-lactam and quinolone resistant.

Furthermore, the incidence of multi-drug-resistant Gram-negative strains such as *Enterobacteriacae* and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome these multidrug-resistant bacilli.

In addition, microorganisms that are causing persistent infections are increasingly being recognized as causative agents or cofactors of severe chronic diseases like peptic ulcers or heart diseases.

WO 2008/126024 describes antibacterial compounds of formula (A1)

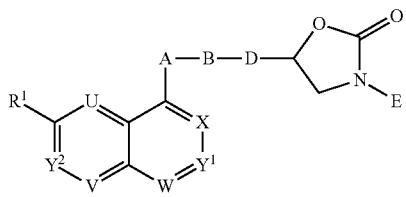

(A1)

wherein
$R^1$ is hydrogen, halogen, hydroxy, alkoxy or cyano;
$Y^1$ and $Y^2$ each represent CH and one or two of U, V, W and X represent(s) N and the remaining each represent CH or, in the case of X, may also represent $CR^a$, and, in the case of W, may also represent $CR^b$, or
each of U, V, W, X, $Y^1$ and $Y^2$ represents CH or each of U, V, W, X and $Y^1$ represents CH and $Y^2$ represents N, or also one or, provided $R^1$ is hydrogen, two of U, V, W, X, $Y^1$ and $Y^2$ represent(s) $CR^c$ and the remaining each represent CH;
$R^a$ represents halogen;
$R^b$ represents alkoxy, alkoxycarbonyl or alkoxyalkoxy;
$R^c$, each time it occurs, independently represents hydroxy or alkoxy;
A-B-D can (notably) be such that:
 A is $CH_2N(R^7)$ and either B is $CH_2CH_2$, $COCH_2$ or $CH_2CH(OH)$ and D is $CH_2$ or B is $CH_2CH_2$ or $CH_2CH(OH)$ and D is $CH(OH)$ or $CH(NH_2)$, or
 A is CONH or $CH_2O$, B is $CH_2CH_2$ and D is $CH_2$;
$R^7$ is hydrogen or $(CH_2)_r$—$COOR^{7'}$, or also $R^7$ is alkyl which may be substituted once or twice by groups independently selected from hydroxy, halogen, amino and dimethylamino, r being an integer from 1 to 4 and $R^{7'}$ being hydrogen or alkyl;
E can (notably) be one of the following groups:

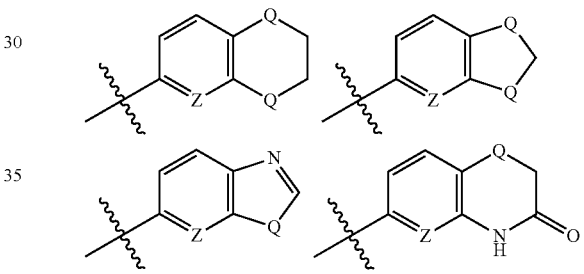

wherein Z is CH or N and Q is O or S.

WO 2010/041219 describes antibacterial compounds of formula (A2)

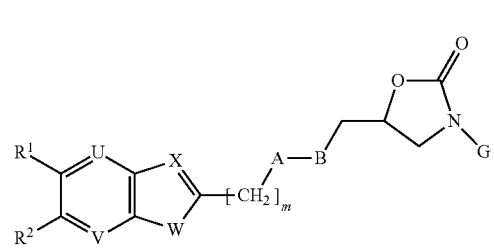

(A2)

wherein
$R^1$ represents hydrogen, $(C_1-C_4)$alkoxy or halogen;
$R^2$ represents hydrogen or $(C_1-C_4)$alkoxy;
U represents N or CH;
V represents N or $CR^b$, wherein $R^b$ is hydrogen or halogen;
W represents *—CH=$CR^a$—, *—N=CH— or S, wherein the asterisks indicate the bond which is linked to the carbon atom connecting V and W and wherein $R^a$ represents hydrogen or halogen;
X represents N or $CR^c$, wherein $R^c$ is hydrogen, $(C_1-C_4)$ alkyl or halogen;

with the proviso that the group of formula (D)

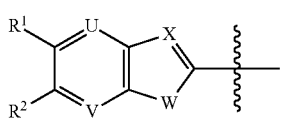

(D)

contains between none and three heteroatoms, wherein the heteroatoms are independently selected from nitrogen and, in case of W, sulfur;

m, A and B are (notably) such that m represents 1, A represents —NHCH$_2$—#, —CH$_2$NH—#, —NHCH$_2$CH$_2$—#, —CH$_2$NHCH$_2$—, —CH$_2$CH$_2$NH—#, —NHCH$_2$CH$_2$NH—, —CH$_2$NHCH$_2$CH$_2$—# or piperazin-1,4-diyl, wherein the hash indicates the bond which is linked to B, and B represents a bond; and G represents (notably) a group of the formula (G1)

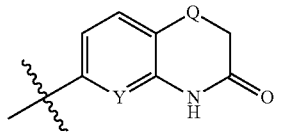

(G1)

wherein Y represents CH or N, and Q represents O or S.

Besides, WO 99/37641 describes antibacterial compounds of formula (A3)

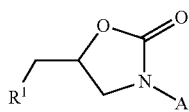

(A3)

wherein

A can notably represent a group of formula

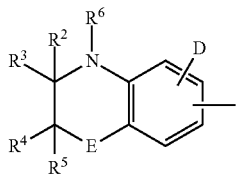

wherein

D, R$^4$, R$^5$ and R$^6$ can each notably represent H;

E can notably represent O or S; and

R$^2$ and R$^3$ can notably represent together a group of formula =O; and

R$^1$ can notably represent a group of formula —NR$^{18}$R$^{19}$ wherein R$^{18}$ and R$^{19}$ can notably be such that R$^{18}$ represents H and R$^{19}$ represents a group —C(=O)—R$^{20}$ wherein R$^{20}$ can notably represent an aryl group with 6 to 10 carbon atoms or a heteroaromatic ring with up to 3 heteroatoms independently selected from S, N and O, which aryl or heteroaromatic ring may itself optionally be substituted with up to two identical or different substituents selected from halogen, cyano, nitro, hydroxy or phenyl.

The instant invention provides new antibacterial biaromatic derivatives based on a biphenyl or heteroaromatic biphenyl-like motif, namely the compounds of formula I described herein.

Various embodiments of the invention are presented hereafter:

1) The invention relates to compounds of formula I

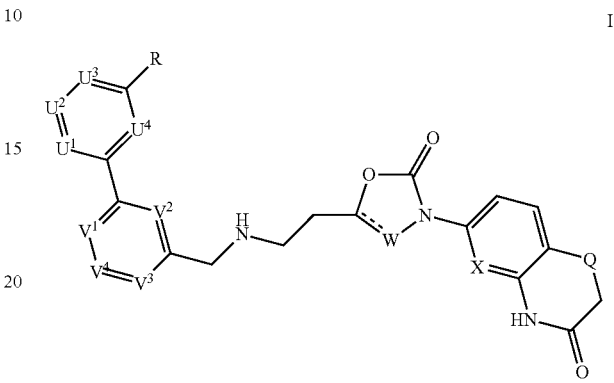

I wherein

R represents H, cyano, (C$_1$-C$_3$)alkoxy, cyanomethoxy, (C$_3$-C$_6$)cycloalkylmethoxy, hydroxy(C$_2$-C$_4$)alkoxy, (C$_1$-C$_3$)alkoxy-(C$_2$-C$_3$)alkoxy, (C$_1$-C$_4$)alkoxycarbonyl, 2-ethoxy-2-oxoethoxy, 2-(methylamino)-2-oxoethoxy, (1-cyanocyclobutyl)methoxy, 3-hydroxy-pyrrolidin-1-yl or (3,4-dihydroxycyclopentyl)methoxy;

U$^1$ represents N or CR$^1$, U$^2$ represents N or CR$^2$, U$^3$ represents N or CR$^3$ and U$^4$ represents N or CR$^4$, it being understood that at most three of U$^1$, U$^2$, U$^3$ and U$^4$ can represent N at the same time;

V$^1$ represents N or CR$^5$, V$^2$ represents N or CR$^6$, V$^3$ represents N or CR$^7$ and V$^4$ represents N or CH, it being understood that at most two of V$^1$, V$^2$, V$^3$ and V$^4$ can represent N at the same time;

R$^1$ represents H, cyano, hydroxy or (C$_1$-C$_3$)alkoxy;

R$^2$ represents H, hydroxy or (C$_1$-C$_3$)alkoxy;

R$^3$ represents H, cyano, hydroxy, (C$_1$-C$_3$)alkoxy or carboxamido;

R$^4$ represents H, cyano, hydroxy or (C$_1$-C$_3$)alkoxy;

R$^5$ represents H, hydroxy or halogen;

R$^6$ represents H, hydroxy or halogen;

R$^7$ represents H;

the dotted line "-----" represents a bond or is absent;

W represents CH or N when the dotted line "-----" is a bond, or W represents CH$_2$ when the dotted line "-----" is absent;

X represents CH or N; and

Q represents O or S;

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "(C$_1$-C$_x$)alkyl" (x being an integer) refers to a straight or branched chain alkyl group containing 1 to x carbon atoms. For example, a (C$_1$-C$_3$)alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "alkoxy", used alone or in combination, refers to a straight or branched chain alkoxy group containing from one to four carbon atoms. The term "$(C_x$-$C_y)$alkoxy" (x and y each being an integer) refers to an alkoxy group as defined before containing x to y carbon atoms. For example, a $(C_1$-$C_3)$alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "hydroxyalkoxy" refers to an alkoxy group as defined previously which contains from two to four carbon atoms and wherein one of the carbon atoms bears a hydroxy group. The term "hydroxy$(C_x$-$C_y)$alkoxy" (x and y each being an integer) refers to a hydroxyalkoxy group as defined before containing x to y carbon atoms. For example, a hydroxy$(C_2$-$C_4)$alkoxy group contains from two to four carbon atoms. Representative examples of hydroxy$(C_2$-$C_4)$alkoxy groups include 2-hydroxyethoxy, 2-hydroxypropoxy, 3-hydroxypropoxy and 4-hydroxybutoxy. Preferred are 3-hydroxypropoxy and 4-hydroxybutoxy.

The term "alkoxyalkoxy" refers to an alkoxy group of two to four carbon atoms as defined previously wherein one of the carbon atoms bears another alkoxy group from one to four carbon atoms. The term "$(C_w$-$C_x)$alkoxy $(C_y$-$C_z)$alkoxy" (w, x, y and z each being an integer) refers to an alkoxyalkoxy group wherein the alkoxy group attached to the rest of the molecule contains y to z carbon atoms and the alkoxy group attached to a carbon atom of the first alkoxy group contains w to x carbon atoms. Representative examples of $(C_1$-$C_3)$alkoxy-$(C_2$-$C_3)$alkoxy groups include 2-methoxyethoxy and 3-methoxypropoxy. Preferred is 2-methoxyethoxy.

The term "alkoxycarbonyl" refers to a carbonyl group wherein the hydrogen has been replaced an alkoxy group as defined previously which contains from two to four carbon atoms and wherein one of the carbon atoms bears a hydroxy group. The term "$(C_x$-$C_y)$alkoxycarbonyl" (x and y each being an integer) refers to an alkoxycarbonyl group as defined before wherein the alkoxy group contains x to y carbon atoms. For example, a $(C_1$-$C_4)$alkoxycarbonyl group contains from one to four carbon atoms in addition to the carbon atom bearing the oxo group. Representative examples of $(C_1$-$C_4)$alkoxycarbonyl groups include methoxycarbonyl, ethoxycarbonyl and n-butoxycarbonyl. Preferred is methoxycarbonyl.

The term "cycloalkyl", used alone or in combination, refers to a saturated cyclic hydrocarbon moiety containing 3 to 6 carbon atoms. The term "$(C_x$-$C_y)$cycloalkyl" (x and y each being an integer) refers to a cycloalkyl group as defined before containing x to y carbon atoms. For example, a $(C_3$-$C_6)$cycloalkyl group contains from three to six carbon atoms. Representative examples of $(C_3$-$C_6)$cycloalkyl groups include, but are not limited to, cyclopropyl and cyclopentyl.

The term "cycloalkylmethoxy", used alone or in combination, refers to a methoxy group wherein one of the hydrogen atoms has been replaced by a cycloalkyl group as defined previously. The term "$(C_x$-$C_y)$cycloalkylmethoxy" (x and y each being an integer) refers to a cycloalkylmethoxy group as defined previously wherein the cycloalkyl group contains x to y carbon atoms. For example, a "$(C_3$-$C_6)$cycloalkylmethoxy" group is a cycloalkylmethoxy group wherein the cycloalkyl group contains from three to six carbon atoms. Representative examples of $(C_3$-$C_6)$cycloalkylmethoxy groups include, but are not limited to, cyclopropylmethoxy, cyclobutylmethoxy and cyclopentylmethoxy. Preferred is cyclobutylmethoxy.

The term "halogen" refers to fluorine, chlorine, bromine or iodine, and preferably to fluorine or chlorine, and most preferably to fluorine.

The term "quinolone-resistant", when used in this text, refers to a bacterial strain against which ciprofloxacin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA (2006)).

The term "methicillin-resistant", when used in this text, refers to a bacterial strain against which methicillin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006).

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example '*Handbook of Pharmaceutical Salts. Properties, Selection and Use.*', P. Heinrich Stahl, Camille G. Wermuth (Eds.), Wiley-VCH (2008) and '*Pharmaceutical Salts and Co-crystals*', Johan Wouters and Luc Quere (Eds.), RSC Publishing (2012).

In this text, a bond interrupted by a wavy line shows a point of attachment of the radical drawn to the rest of the molecule. For example, the radical drawn below

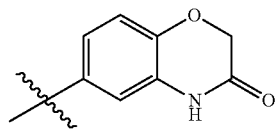 [SMILES: *c1ccc2c(c1)NC(=O)CO2]

is the 3-oxo-3,4-dihydro-2H-benzo[b][1,4]oxazin-6-yl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) A second embodiment of the invention relates to the compounds of formula I according to embodiment 1) wherein the dotted line "-----" is absent which are also compounds of formula $I_{E1}$

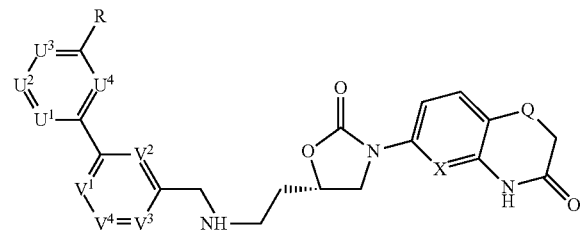

$I_{E1}$ wherein the absolute configuration of the asymmetric carbon of the oxazolidinone ring is as depicted in formula $I_{E1}$ [i.e. the absolute configuration of the asymmetric carbon of the oxazolidinone ring is (S)].

3) A third embodiment of the invention relates to the compounds of formula I according to embodiment 1) wherein the dotted line "-----" is absent which are also compounds of formula $I_{E2}$

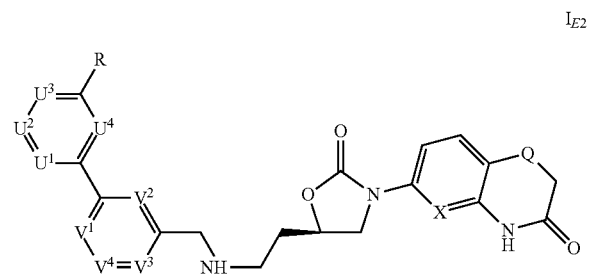

$I_{E2}$ wherein the absolute configuration of the asymmetric carbon of the oxazolidinone ring is as depicted in formula $I_{E2}$ [i.e. the absolute configuration of the asymmetric carbon of the oxazolidinone ring is (R)].

4) In particular, the invention relates to compounds of formula I according to embodiment 1) that are also compounds of formula $I_{CE}$

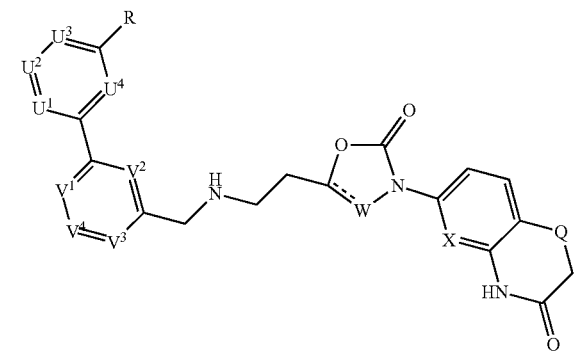

$I_{CE}$ wherein

R represents H, cyano, $(C_1-C_3)$alkoxy, cyanomethoxy, $(C_3-C_6)$cycloalkylmethoxy, hydroxy$(C_2-C_4)$alkoxy, $(C_1-C_3)$alkoxy-$(C_2-C_3)$alkoxy, $(C_1-C_4)$alkoxycarbonyl, 2-ethoxy-2-oxoethoxy, 2-(methylamino)-2-oxoethoxy, (1-cyanocyclobutyl)methoxy, 3-hydroxy-pyrrolidin-1-yl or (3,4-dihydroxycyclopentyl)methoxy;

$U^1$ represents $CR^1$, $U^2$ represents $CR^2$, $U^3$ represents $CR^3$, $U^4$ represents $CR^4$, $V^1$ represents $CR^5$, $V^2$ represents $CR^6$, $V^3$ represents $CR^7$ and $V^4$ represents CH, or $U^1$ represents N, $U^2$ represents $CR^2$, $U^3$ represents $CR^3$, $V^1$ represents $CR^5$, $V^2$ represents $CR^6$ and each of $U^4$, $V^3$ and $V^4$ represents CH, or $U^2$ represents N, $U^1$ represents $CR^1$, $U^3$ represents $CR^3$, and each of $U^4$, $V^1$, $V^2$, $V^3$ and $V^4$ represents CH, or $U^3$ represents N and each of $U^1$, $U^2$, $U^4$, $V^1$, $V^2$, $V^3$ and $V^4$ represents CH, or $U^4$ represents N, $U^1$ represents $CR^1$, $V^1$ represents $CR^5$, $V^2$ represents $CR^6$ and each of $U^2$, $U^3$, $V^3$ and $V^4$ represents CH, or each of $U^1$ and $U^2$ represents N, $U^3$ represents $CR^3$, $V^1$ represents $CR^5$, and each of $U^4$, $V^2$, $V^3$ and $V^4$ represents CH, or each of $U^1$ and $U^3$ represents N and each of $U^2$, $U^4$, $V^1$, $V^2$, $V^3$ and $V^4$ represents CH, or each of $U^1$ and $U^4$ represents N, $U^2$ represents $CR^2$ and each of $U^3$, $V^1$, $V^2$, $V^3$ and $V^4$ represents CH, or each of $U^2$ and $U^3$ represents N and each of $U^1$, $U^4$, $V^1$, $V^2$, $V^3$ and $V^4$ represents CH, or each of $U^2$ and $U^4$ represents N and each of $U^1$, $U^3$, $V^1$, $V^2$, $V^3$ and $V^4$ represents CH, or each of $U^3$ and $U^4$ represents N, $U^2$ represents $CR^2$ and each of $U^1$, $V^1$, $V^2$, $V^3$ and $V^4$ represents CH, or each of $U^1$, $U^3$ and $U^4$ represents N, $U^2$ represents $CR^2$ and each of $V^1$, $V^2$, $V^3$ and $V^4$ represents CH, or $V^1$ represents N, $U^1$ represents $CR^1$ and each of $U^2$, $U^3$, $U^4$, $V^2$, $V^3$ and $V^4$ represents CH, or $V^2$ represents N and each of $U^1$, $U^2$, $U^3$, $U^4$, $V^1$, $V^3$ and $V^4$ represents CH, or $V^3$ represents N and each of $U^1$, $U^2$, $U^3$, $U^4$, $V^1$, $V^2$ and $V^4$ represents CH, or $V^4$ represents N and each of $U^1$, $U^2$, $U^3$, $U^4$, $V^1$, $V^2$ and $V^3$ represents CH, or each of $U^4$ and $V^1$ represents N and each of $U^1$, $U^2$, $U^3$, $V^2$, $V^3$ and $V^4$ represents CH, or each of $V^1$ and $V^2$ represents N and each of $U^1$, $U^2$, $U^3$, $U^4$, $V^3$ and $V^4$ represents CH, or each of $V^1$ and $V^4$ represents N and each of $U^1$, $U^2$, $U^3$, $U^4$, $V^2$ and $V^3$ represents CH, or each of $V^2$ and $V^4$ represents N and each of $U^1$, $U^2$, $U^3$, $U^4$, $V^1$ and $V^3$ represents CH, or each of $V^3$ and $V^4$ represents N and each of $U^1$, $U^2$, $U^3$, $U^4$, $V^1$ and $V^2$ represents CH, or each of $U^1$, $U^2$ and $V^3$ represents N and each of $U^3$, $U^4$, $V^1$, $V^2$ and $V^4$ represents CH, or each of $U^1$, $U^2$ and $V^4$ represents N and each of $U^3$, $U^4$, $V^1$, $V^2$ and $V^3$ represents CH;

$R^1$ represents H, cyano, hydroxy or $(C_1-C_3)$alkoxy;

$R^2$ represents H, hydroxy or $(C_1-C_3)$alkoxy;

$R^3$ represents H, cyano, hydroxy, $(C_1-C_3)$alkoxy or carboxamido;

$R^4$ represents H or $(C_1-C_3)$alkoxy;

$R^5$ represents H, hydroxy or halogen;

$R^6$ represents H, hydroxy or halogen;

$R^7$ represents H;

the dotted line "-----" represents a bond or is absent;

W represents CH or N when the dotted line "-----" is a bond, or W represents $CH_2$ when the dotted line "-----" is absent;

X represents CH or N; and

Q represents O or S;

and to salts (in particular pharmaceutically acceptable salts) of compounds of formula $I_{CE}$.

5) The invention notably relates to compounds of formula I according to embodiment 1) that are also compounds of formula $I_P$

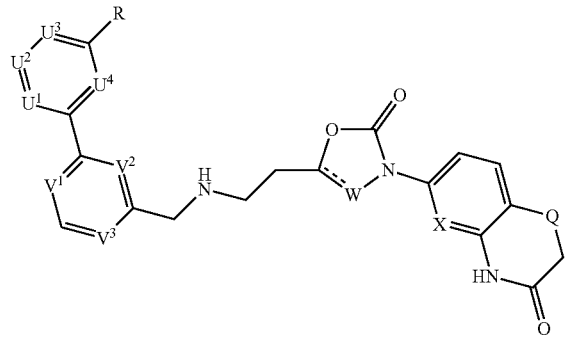

$I_P$ wherein
R represents H, $(C_1-C_3)$alkoxy or cyano;
$U^1$ represents N or $CR^1$, $U^2$ represents N or $CR^2$, $U^3$ represents N or $CR^3$ and $U^4$ represents N or $CR^4$, it being understood that at most three of $U^1$, $U^2$, $U^3$ and $U^4$ can represent N at the same time;
$V^1$ represents N or $CR^5$, $V^2$ represents N or $CR^6$ and $V^3$ represents N or $CR^7$, it being understood that at most one of $V^1$, $V^2$ and $V^3$ can represent N at the same time;
$R^1$ represents H, hydroxy or cyano;
$R^2$ represents H, hydroxy or $(C_1-C_3)$alkoxy;
$R^3$ represents H, hydroxy, $(C_1-C_3)$alkoxy or carboxamido;
$R^4$ represents H;
$R^5$ represents H or halogen (notably H or fluorine);
$R^6$ represents H or halogen (notably H or fluorine);
$R^7$ represents H;
the dotted line "-----" represents a bond or is absent;
W represents CH or N when the dotted line "-----" is a bond, or W represents $CH_2$ when the dotted line "-----" is absent;
X represents CH or N; and
Q represents O or S;
and to salts (in particular pharmaceutically acceptable salts) of compounds of formula $I_P$.

6) A further embodiment of the invention relates to compounds of formula $I_P$ according to embodiment 5) wherein the dotted line "-----" is absent, which are also compounds of formula $I_{PE1}$ $I_{PE1}$

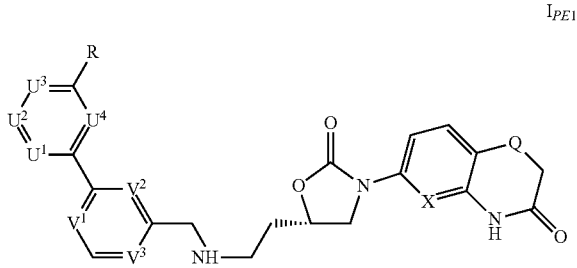

wherein the absolute configuration of the asymmetric carbon of the oxazolidinone ring is as depicted in formula $I_{PE1}$ [i.e. the absolute configuration of the asymmetric carbon of the oxazolidinone ring is (S)].

7) Yet a further embodiment of the invention relates to compounds of formula $I_P$ according to embodiment 5) wherein the dotted line "-----" is absent, which are also compounds of formula $I_{PE2}$ $I_{PE2}$

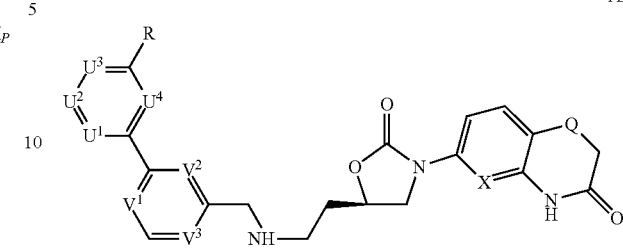

wherein the absolute configuration of the asymmetric carbon of the oxazolidinone ring is as depicted in formula $I_{PE2}$ [i.e. the absolute configuration of the asymmetric carbon of the oxazolidinone ring is (R)].

8) According to one aspect of this invention, the compounds of formula I as defined in one of embodiments 1), 4) or 5) will be such that the dotted line "-----" is absent.

9) According to the other aspect of this invention, the compounds of formula I as defined in one of embodiments 1), 4) or 5) will be such that the dotted line "-----" represents a bond.

10) According to one sub-embodiment of embodiment 9), the compounds of formula I as defined in embodiment 9) will be such that W represents CH.

11) According to the other sub-embodiment of embodiment 9), the compounds of formula I as defined in embodiment 9) will be such that W represents N.

12) According to one main variant of this invention, the compounds of formula I as defined in embodiments 1) to 11) will be such that X represents CH.

13) Preferably, the compounds of formula I as defined in embodiment 12) will be such that Q represents S.

14) According to the other main variant of this invention, the compounds of formula I as defined in embodiments 1) to 11) will be such that X is N.

15) Preferably, the compounds of formula I as defined in embodiment 14) will be such that Q is O.

16) A particular embodiment of this invention relates to the compounds of formula I as defined in embodiments 1) to 11) wherein X represents CH and Q represents S or X represents N and Q represents O.

17) According to one main embodiment of this invention, the compounds of formula I as defined in embodiments 1) to 16) will be such that none of $V^1$, $V^2$, $V^3$ and $V^4$, if present, represents N.

18) One sub-embodiment of embodiment 17) relates to compounds of formula I as defined in embodiment 17) wherein none of $U^1$, $U^2$, $U^3$ and $U^4$ represents N.

19) Another sub-embodiment of embodiment 17) relates to the compounds of formula I as defined in embodiment 17) wherein one of $U^1$, $U^2$, $U^3$ and $U^4$ represents N.

20) A further sub-embodiment of embodiment 17) relates to the compounds of formula I as defined in embodiment 17) wherein two of $U^1$, $U^2$, $U^3$ and $U^4$ represent N.

21) Yet a further sub-embodiment of embodiment 17) relates to the compounds of formula I as defined in embodiment 17) wherein three of $U^1$, $U^2$, $U^3$ and $U^4$ represent N.

22) According to another main embodiment of this invention, the compounds of formula I as defined in embodiments 1) to 16) will be such that one of $V^1$, $V^2$ and $V^3$ represents N and $V^4$, if present, represents CH.

23) One sub-embodiment of embodiment 22) relates to the compounds of formula I as defined in embodiment 22) wherein none of $U^1$, $U^2$, $U^3$ and $U^4$ represents N.

24) Another sub-embodiment of embodiment 22) relates to the compounds of formula I as defined in embodiment 22) wherein one of $U^1$, $U^2$, $U^3$ and $U^4$ represents N.
25) According to yet another main embodiment of this invention, the compounds of formula I as defined in embodiments 1) to 16) will be such that one of $V^1$, $V^2$, $V^3$ and $V^4$ represents N.
26) One sub-embodiment of embodiment 25) relates to the compounds of formula I as defined in embodiment 25) wherein none of $U^1$, $U^2$, $U^3$ and $U^4$ represents N.
27) Another sub-embodiment of embodiment 25) relates to the compounds of formula I as defined in embodiment 25) wherein one of $U^1$, $U^2$, $U^3$ and $U^4$ represents N.
28) Yet another sub-embodiment of embodiment 25) relates to the compounds of formula I as defined in embodiment 25) wherein two of $U^1$, $U^2$, $U^3$ and $U^4$ represent N.
29) In particular, the compounds of formula I of embodiment 28) will be such that $U^1$ and $U^2$ each represent N and one of $V^3$ and $V^4$ also represents N.
30) According to yet another main embodiment of this invention, the compounds of formula I as defined in embodiments 1) to 16) will be such that two of $V^1$, $V^2$, $V^3$ and $V^4$ represent N.
31) Preferably, the compounds of formula I as defined in embodiment 30) will be such that each of $U^1$, $U^2$, $U^3$ and $U^4$ represents CH.
32) According to one further embodiment of this invention, the compounds of formula I as defined in one of embodiments 1) to 31) will be such that R represents H.
33) According to yet a further embodiment of this invention, the compounds of formula I as defined in one of embodiments 1) to 31) will be such that R is different from H.
34) According to a variant of embodiment 33), the compounds of formula I as defined in embodiment 33) will be such that R represents $(C_1-C_3)$alkoxy or cyano.
35) According to one sub-embodiment of embodiment 34), the compounds of formula I as defined in embodiment 34) will be such that R represents $(C_1-C_3)$alkoxy (and in particular methoxy).
36) According the other sub-embodiment of embodiment 34), the compounds of formula I as defined in embodiment 34) will be such that R represents cyano.
37) According to another variant of embodiment 33), the compounds of formula I as defined in embodiment 33) will be such that R represents cyanomethoxy, hydroxy $(C_2-C_4)$alkoxy, $(C_1-C_3)$alkoxy-$(C_2-C_3)$alkoxy, 2-ethoxy-2-oxoethoxy or 2-(methylamino)-2-oxoethoxy.
38) According to yet another variant of embodiment 33), the compounds of formula I as defined in embodiment 33) will be such that R represents $(C_1-C_4)$alkoxycarbonyl.
39) According to yet another variant of embodiment 33), the compounds of formula I as defined in embodiment 33) will be such that R represents $(C_3-C_6)$cycloalkylmethoxy, (1-cyanocyclobutyl)methoxy or (3,4-dihydroxycyclopentyl)methoxy 40) According to yet another variant of embodiment 33), the compounds of formula I as defined in embodiment 33) will be such that R represents 3-hydroxy-pyrrolidin-1-yl.
41) Preferably, the compounds of formula I as defined in embodiments 1) to 16) will be such that the respective meanings of R, $U^1$, $U^2$, $U^3$, $U^4$, $V^1$, $V^2$ and $V^3$ are as follows:
R represents H, $U^3$ represents $CR^3$ wherein $R^3$ is methoxy and $U^1$, $U^2$, $U^4$, $V^1$, $V^2$ and $V^3$ each represent CH; or
R represents H, $U^2$ represents N, $U^3$ represents $CR^3$ wherein $R^3$ is methoxy and $U^1$, $U^4$, $V^1$, $V^2$ and $V^3$ each represent CH; or R represents methoxy and $U^1$, $U^2$, $U^3$, $U^4$, $V^1$, $V^2$ and $V^3$ each represent CH, or $U^1$ represents $CR^1$ wherein $R^1$ is cyano and $U^2$, $U^3$, $U^4$, $V^1$, $V^2$ and $V^3$ each represent CH, or $U^2$ represents $CR^2$ wherein $R^2$ is hydroxy and $U^1$, $U^3$, $U^4$, $V^1$, $V^2$ and $V^3$ each represent CH, or $U^3$ represents $CR^3$ wherein $R^3$ is hydroxy or carboxamido and $U^1$, $U^3$, $U^4$, $V^1$, $V^2$ and $V^3$ each represent CH, or $U^1$, $U^2$, $U^3$, $U^4$, $V^2$ and $V^3$ each represent CH and $V^1$ represents $CR^5$ wherein $R^5$ is fluorine, or also $U^1$, $U^2$, $U^3$, $U^4$, $V^1$ and $V^3$ each represent CH and $V^2$ represents $CR^6$ wherein $R^6$ is fluorine; or
R represents methoxy and $U^1$ represents N and $U^2$, $U^3$, $U^4$, $V^1$, $V^2$ and $V^3$ each represent CH, or $U^2$ represents N and $U^1$, $U^3$, $U^4$, $V^1$, $V^2$ and $V^3$ each represent CH, or $U^4$ represents N, $V^2$ represents CH or N and $U^1$, $U^2$, $U^3$, $V^1$ and $V^3$ each represent CH, or $V^1$ represents N and $U^1$, $U^2$, $U^3$, $U^4$, $V^2$ and $V^3$ each represent CH, or $V^2$ represents N and $U^1$, $U^2$, $U^3$, $U^4$, $V^1$ and $V^3$ each represent CH, or $V^3$ represents N and $U^1$, $U^2$, $U^3$, $U^4$, $V^1$ and $V^2$ each represent CH, or $U^1$ and $U^2$ each represent N and $U^3$, $U^4$, $V^1$, $V^2$ and $V^3$ each represent CH, or $U^1$ and $U^3$ each represent N and $U^2$, $U^4$, $V^1$, $V^2$ and $V^3$ each represent CH, or $U^1$ and $U^4$ each represent N, $U^2$ represents CH or $CR^2$ wherein $R^2$ is methoxy and $U^3$, $V^1$, $V^2$ and $V^3$ each represent CH, or $U^2$ and $U^4$ each represent N and $U^1$, $U^3$, $V^1$, $V^2$ and $V^3$ each represent CH, or $U^3$ and $U^4$ each represent N, $U^2$ represents $CR^2$ wherein $R^2$ is methoxy and $U^1$, $V^1$, $V^2$ and $V^3$ each represent CH, or also $U^1$, $U^3$ and $U^4$ each represent N, $U^2$ represents $CR^2$ wherein $R^2$ is methoxy and $V^1$, $V^2$ and $V^3$ each represent CH; or
R represents cyano and $U^1$, $U^2$, $U^3$, $U^4$, $V^1$, $V^2$ and $V^3$ each represent CH, or $U^1$ represents $CR^1$ wherein $R^1$ is hydroxy and $U^2$, $U^3$, $U^4$, $V^1$, $V^2$ and $V^3$ each represent CH, or also $U^2$ represents $CR^2$ wherein $R^2$ is methoxy and $U^1$, $U^3$, $U^4$, $V^1$, $V^2$ and $V^3$ each represent CH; or also
R represents cyano and $U^1$ represents N, $U^2$ represents $CR^2$ wherein $R^2$ is methoxy and $U^3$, $U^4$, $V^1$, $V^2$ and $V^3$ each represent CH, or $U^2$ represents N, $U^1$ represents CH or $CR^1$ wherein $R^1$ is hydroxy and $U^3$, $U^4$, $V^1$, $V^2$ and $V^3$ each represent CH, or $U^4$ represents N and $U^1$, $U^2$, $U^3$, $V^1$, $V^2$ and $V^3$ each represent CH, or also $V^1$ represents N, $U^1$ represents $CR^1$ wherein $R^1$ is H or hydroxy and $U^2$, $U^3$, $U^4$, $V^2$ and $V^3$ each represent CH.
42) More preferably, the compounds of formula I as defined in embodiment 41) will be such that:
R represents methoxy and $U^1$ represents N and $U^2$, $U^3$, $U^4$, $V^1$, $V^2$ and $V^3$ each represent CH, or $U^2$ represents N and $U^1$, $U^3$, $U^4$, $V^1$, $V^2$ and $V^3$ each represent CH, or $U^4$ represents N, $V^2$ represents CH or N and $U^1$, $U^2$, $U^3$, $V^1$ and $V^3$ each represent CH, or $U^1$ and $U^2$ each represent N and $U^3$, $U^4$, $V^1$, $V^2$ and $V^3$ each represent CH, or $U^1$ and $U^3$ each represent N and $U^2$, $U^4$, $V^1$, $V^2$ and $V^3$ each represent CH, or $U^1$ and $U^4$ each represent N, $U^2$ represents CH or $CR^2$ wherein $R^2$ is methoxy and $U^3$, $V^1$, $V^2$ and $V^3$ each represent CH, or $U^2$ and $U^4$ each represent N and $U^1$, $U^3$, $V^1$, $V^2$ and $V^3$ each represent CH, or $U^3$ and $U^4$ each represent N, $U^2$ represents $CR^2$ wherein $R^2$ is methoxy and $U^1$, $V^1$, $V^2$ and $V^3$ each represent CH, or also $U^1$, $U^3$ and $U^4$ each represent N, $U^2$ represents $CR^2$ wherein $R^2$ is methoxy and $V^1$, $V^2$ and $V^3$ each represent CH; or
R represents cyano and $U^1$ represents N, $U^2$ represents $CR^2$ wherein $R^2$ is methoxy and $U^3$, $U^4$, $V^1$, $V^2$ and $V^3$ each represent CH, or $U^2$ represents N, $U^1$ represents CH or $CR^1$ wherein $R^1$ is hydroxy and $U^3$, $U^4$, $V^1$, $V^2$ and $V^3$ each represent CH, or also $U^4$ represents N and $U^1$, $U^2$, $U^3$, $V^1$, $V^2$ and $V^3$ each represent CH.

43) A preferred embodiment of this invention relates to the compounds of formula I according to embodiment 5), wherein:
the dotted line "-----" is absent and W represents $CH_2$ or the dotted line "-----" is a bond and W represents CH;
R represents methoxy or cyano;
$U^2$, $U^3$ or $U^4$ each represent CH and $U^1$ represents $CR^1$ wherein $R^1$ represents H or hydroxy, or $U^1$ represents N, $U^2$ represents $CR^2$, $U^3$ represents $CR^3$ and $U^4$ represents $CR^4$, or $U^1$ represents $CR^1$, $U^2$ represents N, $U^3$ represents $CR^3$ and $U^4$ represents $CR^4$, or $U^1$ represents $CR^1$, $U^2$ represents $CR^2$, $U^3$ represents N and $U^4$ represents $CR^4$, or $U^1$ represents $CR^1$, $U^2$ represents $CR^2$, $U^3$ represents $CR^3$ and $U^4$ represents N, or also $U^1$ and $U^2$ represent N and $U^3$ and $U^4$ represent CH; and $V^1$ represents CH or N and $V^2$ and $V^3$ each represent CH.

44) According to one sub-embodiment of embodiment 43), the compounds of formula I as defined in embodiment 43) will be such that R represents methoxy.

45) According to the other sub-embodiment of embodiment 43), the compounds of formula I as defined in embodiment 43) will be such that R represents cyano.

46) According to one more preferred sub-embodiment, the compounds according to embodiment 43) will be such that R represents cyano, $U^1$ represents $CR^1$ wherein $R^1$ represents H or hydroxy and $V^1$ represents CH or N (and in particular such that R represents cyano, $U^1$ represents $CR^1$ wherein $R^1$ represents hydroxy, $V^1$ represents N).

47) According to another more preferred sub-embodiment, the compounds according to embodiment 43) will be such that:
R represents methoxy;
$U^1$ represents N, $U^2$ represents $CR^2$ wherein $R^2$ represents H or methoxy and $U^3$ and $U^4$ each represent CH, or $U^2$ represents N and $U^1$, $U^3$ and $U^4$ each represent CH, or $U^3$ represents N, $U^2$ represents $CR^2$ wherein $R^2$ represents H or methoxy, and $U^1$ and $U^4$ each represent CH, or $U^4$ represents N, $U^2$ represents $CR^2$ wherein $R^2$ represents H or methoxy, and $U^1$ and $U^3$ each represent CH, 48) According to yet another more preferred sub-embodiment, the compounds according to embodiment 43) will be such that R represents methoxy, $U^1$ and $U^2$ each represent N and $U^3$ and $U^4$ each represent CH.

49) A particular embodiment of this invention relates to the compounds of formula I according to one of embodiments 1) to 31) wherein R represents H, methoxy or cyano.

50) Preferably, the compounds of formula I as defined in embodiment 1) or 4) will be such that:
R represents H, cyano or $(C_1-C_3)$alkoxy;
$U^1$ represents $CR^1$, $U^2$ represents $CR^2$, $U^3$ represents $CR^3$, $U^4$ represents $CR^4$, $V^1$ represents $CR^5$, $V^2$ represents $CR^6$, $V^3$ represents $CR^7$ and $V^4$ represents CH, or $U^1$ represents N, $U^2$ represents $CR^2$, $U^3$ represents $CR^3$, $V^1$ represents $CR^5$, $V^2$ represents $CR^6$ and each of $U^4$, $V^3$ and $V^4$ represents CH, or $U^2$ represents N, $U^1$ represents $CR^1$, $U^3$ represents $CR^3$, and each of $U^4$, $V^1$, $V^2$, $V^3$ and $V^4$ represents CH, or $U^4$ represents N, $U^1$ represents $CR^1$, $V^1$ represents $CR^5$, $V^2$ represents $CR^6$ and each of $U^2$, $U^3$, $V^3$ and $V^4$ represents CH, or each of $U^1$ and $U^2$ represents N, $U^3$ represents $CR^3$, $V^1$ represents $CR^5$ and each of $U^4$, $V^2$, $V^3$ and $V^4$ represents CH, or each of $U^1$ and $U^3$ represents N and each of $U^2$, $U^4$, $V^1$, $V^2$, $V^3$ and $V^4$ represents CH, or each of $U^1$ and $U^4$ represents N, $U^2$ represents $CR^2$ and each of $U^3$, $V^1$, $V^2$, $V^3$ and $V^4$ represents CH, or each of $U^2$ and $U^3$ represents N and each of $U^1$, $U^4$, $V^1$, $V^2$, $V^3$ and $V^4$ represents CH, or each of $U^2$ and $U^4$ represents N and each of $U^1$, $U^3$, $V^1$, $V^2$, $V^3$ and $V^4$ represents CH, or $V^1$ represents N, $U^1$ represents $CR^1$ and each of $U^2$, $U^3$, $U^4$, $V^2$, $V^3$ and $V^4$ represents CH, or $V^2$ represents N and each of $U^1$, $U^2$, $U^3$, $U^4$, $V^1$, $V^3$ and $V^4$ represents CH, or $V^3$ represents N and each of $U^1$, $U^2$, $U^3$, $U^4$, $V^1$, $V^2$ and $V^4$ represents CH, or $V^4$ represents N and each of $U^1$, $U^2$, $U^3$, $U^4$, $V^1$, $V^2$ and $V^3$ represents CH, or each of $U^4$ and $V^1$ represents N and each of $U^1$, $U^2$, $U^3$, $V^2$, $V^3$ and $V^4$ represents CH, or each of $V^2$ and $V^4$ represents N and each of $U^1$, $U^2$, $U^3$, $U^4$, $V^1$ and $V^3$ represents CH, or each of $V^3$ and $V^4$ represents N and each of $U^1$, $U^2$, $U^3$, $U^4$, $V^1$ and $V^2$ represents CH, or each of $U^1$, $U^2$ and $V^3$ represents N and each of $U^3$, $U^4$, $V^1$, $V^2$ and $V^4$ represents CH, or each of $U^1$, $U^2$ and $V^4$ represents N and each of $U^3$, $U^4$, $V^1$, $V^2$ and $V^3$ represents CH;
$R^1$ represents H, cyano or hydroxy;
$R^2$ represents H, hydroxy or $(C_1-C_3)$alkoxy;
$R^3$ represents H, cyano, hydroxy or $(C_1-C_3)$alkoxy;
$R^4$ represents H;
$R^5$ represents H or hydroxy;
$R^6$ represents H or hydroxy;
$R^7$ represents H;
the dotted line "-----" represents a bond or is absent;
W represents CH or N when the dotted line "-----" is a bond, or W represents $CH_2$ when the dotted line "-----" is absent;
X represents CH or N; and
Q represents O or S.

51) More preferably, the compounds of formula I as defined in embodiment 1) or 4) will be such that:
R represents H, cyano or $(C_1-C_3)$alkoxy;
$U^1$ represents $CR^1$, $U^2$ represents $CR^2$, $U^3$ represents $CR^3$, $U^4$ represents $CR^4$, $V^1$ represents $CR^5$, $V^2$ represents $CR^6$, $V^3$ represents $CR^7$ and $V^4$ represents CH, or $U^1$ represents N, $U^2$ represents $CR^2$, $U^3$ represents $CR^3$, $V^1$ represents $CR^5$, $V^2$ represents $CR^6$ and each of $U^4$, $V^3$ and $V^4$ represents CH, or $U^2$ represents N, $U^1$ represents $CR^1$, $U^3$ represents $CR^3$, and each of $U^4$, $V^1$, $V^2$, $V^3$ and $V^4$ represents CH, or $U^4$ represents N, $U^1$ represents $CR^1$, $V^1$ represents $CR^5$, $V^2$ represents $CR^6$ and each of $U^2$, $U^3$, $V^3$ and $V^4$ represents CH, or each of $U^1$ and $U^2$ represents N, $U^3$ represents $CR^3$, $V^1$ represents $CR^5$ and each of $U^4$, $V^2$, $V^3$ and $V^4$ represents CH, or each of $U^1$ and $U^4$ represents N, $U^2$ represents $CR^2$ and each of $U^3$, $V^1$, $V^2$, $V^3$ and $V^4$ represents CH, or each of $U^2$ and $U^3$ represents N and each of $U^1$, $U^4$, $V^1$, $V^2$, $V^3$ and $V^4$ represents CH, or each of $U^2$ and $U^4$ represents N and each of $U^1$, $U^3$, $V^1$, $V^2$, $V^3$ and $V^4$ represents CH, or $V^1$ represents N, $U^1$ represents $CR^1$ and each of $U^2$, $U^3$, $U^4$, $V^2$, $V^3$ and $V^4$ represents CH, or each of $V^3$ and $V^4$ represents N and each of $U^1$, $U^2$, $U^3$, $U^4$, $V^1$ and $V^2$ represents CH, or each of $U^1$, $U^2$ and $V^3$ represents N and each of $U^3$, $U^4$, $V^1$, $V^2$ and $V^4$ represents CH, or each of $U^1$, $U^2$ and $V^4$ represents N and each of $U^3$, $U^4$, $V^1$, $V^2$ and $V^3$ represents CH;
$R^1$ represents H, cyano or hydroxy;
$R^2$ represents H or $(C_1-C_3)$alkoxy;
$R^3$ represents H or $(C_1-C_3)$alkoxy;
$R^4$ represents H;
$R^5$ represents H or hydroxy;
$R^6$ represents H or hydroxy;
$R^7$ represents H;

the dotted line "-----" represents a bond or is absent;
W represents CH or N when the dotted line "-----" is a bond, or W represents $CH_2$ when the dotted line "-----" is absent;
X represents CH or N; and
Q represents O or S.

52) Even more preferably, the compounds of formula I as defined in embodiment 1) or 4) will be such that:
R represents H, cyano or methoxy;
$U^1$ represents $CR^1$, $U^2$ represents $CR^2$, $U^3$ represents $CR^3$, $U^4$ represents $CR^4$, $V^1$ represents $CR^5$, $V^2$ represents $CR^6$, $V^3$ represents $CR^7$ and $V^4$ represents CH, or $U^1$ represents N, $U^2$ represents $CR^2$, $U^3$ represents $CR^3$, $V^1$ represents $CR^5$, $V^2$ represents $CR^6$ and each of $U^4$, $V^3$ and $V^4$ represents CH, or $U^2$ represents N, $U^1$ represents $CR^1$, $U^3$ represents $CR^3$, and each of $U^4$, $V^1$, $V^2$, $V^3$ and $V^4$ represents CH, or $U^4$ represents N, $U^1$ represents $CR^1$, $V^1$ represents $CR^5$, $V^2$ represents $CR^6$ and each of $U^2$, $U^3$, $V^3$ and $V^4$ represents CH, or each of $U^1$ and $U^2$ represents N, $U^3$ represents $CR^3$, $V^1$ represents $CR^5$ and each of $U^4$, $V^2$, $V^3$ and $V^4$ represents CH, or each of $U^2$ and $U^4$ represents N and each of $U^1$, $U^3$, $V^1$, $V^2$, $V^3$ and $V^4$ represents CH, or $V^1$ represents N, $U^1$ represents $CR^1$ and each of $U^2$, $U^3$, $U^4$, $V^2$, $V^3$ and $V^4$ represents CH, or each of $U^1$, $U^2$ and $V^3$ represents N and each of $U^3$, $U^4$, $V^1$, $V^2$ and $V^4$ represents CH;
$R^1$ represents H or hydroxy;
$R^2$ represents H;
$R^3$ represents H;
$R^4$ represents H;
$R^5$ represents H or hydroxy;
$R^6$ represents H or hydroxy;
$R^7$ represents H;
the dotted line "-----" represents a bond or is absent;
W represents CH when the dotted line "-----" is a bond, or W represents $CH_2$ when the dotted line "-----" is absent;
X represents CH or N; and
Q represents O or S.

53) In a particularly preferred manner, the compounds of formula I as defined in embodiment 1) or 4) will be such that:
R represents cyano or methoxy;
each of $U^1$, $U^2$, $U^3$, $U^4$, $V^1$, $V^2$, $V^3$ and $V^4$ represents CH, or $U^1$ represents N, $V^1$ represents $CR^5$ wherein $R^5$ is hydroxy, and each of $U^2$, $U^3$, $U^4$, $V^2$, $V^3$ and $V^4$ represents CH, or $U^4$ represents N, $V^1$ represents $CR^5$ wherein $R^5$ is hydroxy, and each of $U^1$, $U^2$, $U^3$, $V^2$, $V^3$ and $V^4$ represents CH, or $U^4$ represents N, $V^2$ represents $CR^6$ wherein $R^6$ is hydroxy, and each of $U^1$, $U^2$, $U^3$, $V^1$, $V^3$ and $V^4$ represents CH, or each of $U^1$ and $U^2$ represents N, $V^1$ represents $CR^5$ wherein $R^5$ is H or hydroxy, $V^1$ represents $CR^5$ and each of $U^3$, $U^4$, $V^2$, $V^3$ and $V^4$ represents CH, or $V^1$ represents N, $U^1$ represents $CR^1$ wherein $R^1$ is hydroxy and each of $U^2$, $U^3$, $U^4$, $V^2$, $V^3$ and $V^4$ represents CH, or each of $U^1$, $U^2$ and $V^3$ represents N and each of $U^3$, $U^4$, $V^1$, $V^2$ and $V^4$ represents CH;
the dotted line "-----" represents a bond or is absent;
W represents CH when the dotted line "-----" is a bond, or W represents $CH_2$ when the dotted line "-----" is absent;
X represents CH or N; and
Q represents O or S.

54) Another embodiment of this invention relates to compounds of formula I as defined in one of embodiments 1) to 53) as well as to isotopically labelled, especially $^2$H (deuterium) labelled compounds of formula I as defined in one of embodiments 1) to 53), which compounds are identical to the compounds of formula I as defined in one of embodiments 1) to 53) except that one or more atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium) may lead to greater metabolic stability, resulting e.g. in an increased in-vivo half-life, reduced dosage requirements, or an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

55) Particularly preferred are the following compounds of formula I as defined in embodiment 1) or 5):
6-((R)-5-{2-[(3'-methoxy-biphenyl-3-ylmethyl)-amino]-ethyl}-2-oxo-oxazolidin-3-yl)-4H-benzo[1,4]thiazin-3-one;
2-methoxy-6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-isonicotinonitrile;
3'-({2-[(S)-2-oxo-3-(3-oxo-3,4-dihydro-2H-benzo[1,4]thiazin-6-yl)-oxazolidin-5-yl]-ethylamino}-methyl)-biphenyl-3-carbonitrile;
6-((S)-5-{2-[(3'-methoxy-biphenyl-3-ylmethyl)-amino]-ethyl}-2-oxo-oxazolidin-3-yl)-4H-pyrido[3,2-b][1,4]oxazin-3-one;
3'-({2-[(R)-2-oxo-3-(3-oxo-3,4-dihydro-2H-benzo[1,4]thiazin-6-yl)-oxazolidin-5-yl]-ethylamino}-methyl)-biphenyl-3-carbonitrile;
6-((R)-5-{2-[(4'-methoxy-biphenyl-3-ylmethyl)-amino]-ethyl}-2-oxo-oxazolidin-3-yl)-4H-benzo[1,4]thiazin-3-one;
6-((R)-5-{2-[(4'-hydroxy-3'-methoxy-biphenyl-3-ylmethyl)-amino]-ethyl}-2-oxo-oxazolidin-3-yl)-4H-benzo[1,4]thiazin-3-one;
5-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-2-carbonitrile;
5-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-3-carbonitrile;
6-((R)-5-{2-[(3'-hydroxy-5'-methoxy-biphenyl-3-ylmethyl)-amino]-ethyl}-2-oxo-oxazolidin-3-yl)-4H-benzo[1,4]thiazin-3-one;
6-((R)-5-{2-[(6-fluoro-3'-methoxy-biphenyl-3-ylmethyl)-amino]-ethyl}-2-oxo-oxazolidin-3-yl)-4H-benzo[1,4]thiazin-3-one;
6-((R)-5-{2-[(2-fluoro-3'-methoxy-biphenyl-3-ylmethyl)-amino]-ethyl}-2-oxo-oxazolidin-3-yl)-4H-benzo[1,4]thiazin-3-one;
6-((R)-5-{2-[3-(5-methoxy-pyridin-3-yl)-benzylamino]-ethyl}-2-oxo-oxazolidin-3-yl)-4H-benzo[1,4]thiazin-3-one;
6-((R)-5-{2-[3-(4-methoxy-pyridin-2-yl)-benzylamino]-ethyl}-2-oxo-oxazolidin-3-yl)-4H-benzo[1,4]thiazin-3-one;
6-((R)-5-{2-[3-(6-methoxy-pyridin-2-yl)-benzylamino]-ethyl}-2-oxo-oxazolidin-3-yl)-4H-benzo[1,4]thiazin-3-one;

6-((R)-5-{2-[3-(6-methoxy-pyridin-3-yl)-benzylamino]-ethyl}-2-oxo-oxazolidin-3-yl)-4H-benzo[1,4]thiazin-3-one;

5-[3-({2-[(R)-2-oxo-3-(3-oxo-3,4-dihydro-2H-benzo[1,4]thiazin-6-yl)-oxazolidin-5-yl]-ethylamino}-methyl)-phenyl]-nicotinonitrile;

6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-pyridine-2-carbonitrile;

6-hydroxy-5-[3-({2-[(R)-2-oxo-3-(3-oxo-3,4-dihydro-2H-benzo[1,4]thiazin-6-yl)-oxazolidin-5-yl]-ethylamino}-methyl)-phenyl]-nicotinonitrile;

6-[(R)-5-(2-{[6-(3-methoxy-phenyl)-pyridin-2-ylmethyl]-amino}-ethyl)-2-oxo-oxazolidin-3-yl]-4H-benzo[1,4]thiazin-3-one;

6-[(R)-5-(2-{[4-(3-methoxy-phenyl)-pyridin-2-ylmethyl]-amino}-ethyl)-2-oxo-oxazolidin-3-yl]-4H-benzo[1,4]thiazin-3-one;

6-((R)-5-{2-[(6'-methoxy-[2,2]bipyridinyl-6-ylmethyl)-amino]-ethyl}-2-oxo-oxazolidin-3-yl)-4H-benzo[1,4]thiazin-3-one;

6-((R)-5-{2-[3-(4-methoxy-pyrimidin-2-yl)-benzylamino]-ethyl}-2-oxo-oxazolidin-3-yl)-4H-benzo[1,4]thiazin-3-one;

6-((R)-5-{2-[3-(6-methoxy-pyrimidin-4-yl)-benzylamino]-ethyl}-2-oxo-oxazolidin-3-yl)-4H-benzo[1,4]thiazin-3-one;

6-((R)-5-{2-[3-(6-methoxy-pyrazin-2-yl)-benzylamino]-ethyl}-2-oxo-oxazolidin-3-yl)-4H-benzo[1,4]thiazin-3-one;

6-((R)-5-{2-[3-(2,6-dimethoxy-pyrimidin-4-yl)-benzylamino]-ethyl}-2-oxo-oxazolidin-3-yl)-4H-benzo[1,4]thiazin-3-one;

6-((R)-5-{2-[3-(4,6-dimethoxy-pyrimidin-2-yl)-benzylamino]-ethyl}-2-oxo-oxazolidin-3-yl)-4H-benzo[1,4]thiazin-3-one;

6-((R)-5-{2-[3-(4,6-dimethoxy-[1,3,5]triazin-2-yl)-benzylamino]-ethyl}-2-oxo-oxazolidin-3-yl)-4H-benzo[1,4]thiazin-3-one;

3-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-4-carboxylic acid amide;

6-((R)-5-{2-[3-(5-methoxy-pyridazin-3-yl)-benzylamino]-ethyl}-2-oxo-oxazolidin-3-yl)-4H-benzo[1,4]thiazin-3-one;

6-((R)-5-{2-[3-(6-methoxy-pyridin-2-yl)-benzylamino]-ethyl}-2-oxo-oxazolidin-3-yl)-4H-pyrido[3,2-b][1,4]oxazin-3-one;

5-methoxy-3'-({2-[(R)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile;

3'-({2-[(R)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

6-(5-{2-[(3'-methoxy-biphenyl-3-ylmethyl)-amino]-ethyl}-2-oxo-oxazol-3-yl)-4H-pyrido[3,2-b][1,4]oxazin-3-one;

6-(5-{2-[3-(6-methoxy-pyridin-2-yl)-benzylamino]-ethyl}-2-oxo-oxazol-3-yl)-4H-pyrido[3,2-b][1,4]oxazin-3-one;

3'-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-biphenyl-3-carbonitrile;

5-methoxy-3'-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-biphenyl-2-carbonitrile;

4-hydroxy-3-[4-({2-[(R)-2-oxo-3-(3-oxo-3,4-dihydro-2H-benzo[1,4]thiazin-6-yl)-oxazolidin-5-yl]-ethylamino}-methyl)-pyridin-2-yl]-benzonitrile;

6-[(R)-5-(2-{[2-(3-methoxy-phenyl)-pyridin-4-ylmethyl]-amino}-ethyl)-2-oxo-oxazolidin-3-yl]-4H-benzo[1,4]thiazin-3-one;

6-((S)-5-{2-[3-(6-methoxy-pyridin-2-yl)-benzylamino]-ethyl}-2-oxo-oxazolidin-3-yl)-4H-pyrido[3,2-b][1,4]oxazin-3-one;

5-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile;

3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

6-((S)-5-{2-[3-(6-methoxy-pyridin-2-yl)-benzylamino]-ethyl}-2-oxo-oxazolidin-3-yl)-4H-benzo[1,4]thiazin-3-one;

6-((S)-5-{2-[3-(5-methoxy-pyridazin-3-yl)-benzylamino]-ethyl}-2-oxo-oxazolidin-3-yl)-4H-pyrido[3,2-b][1,4]oxazin-3-one;

6-hydroxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

3-[4-({2-[(S)-2-oxo-3-(3-oxo-3,4-dihydro-2H-pyrido[3,2-b][1,4]oxazin-6-yl)-oxazolidin-5-yl]-ethylamino}-methyl)-pyridin-2-yl]-benzonitrile;

as well as the salts (in particular the pharmaceutically acceptable salts) thereof.

56) Also particularly preferred are the following compounds of formula I as defined in embodiment 1):

2-hydroxy-6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-isonicotinonitrile;

6-((S)-5-{2-[(3',4'-dimethoxy-biphenyl-3-ylmethyl)-amino]-ethyl}-2-oxo-oxazolidin-3-yl)-4H-pyrido[3,2-b][1,4]oxazin-3-one;

3-[4-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-pyridin-2-yl]-benzonitrile;

6-((S)-5-{2-[(3'-cyclobutylmethoxy-biphenyl-3-ylmethyl)-amino]-ethyl}-2-oxo-oxazolidin-3-yl)-4H-pyrido[3,2-b][1,4]oxazin-3-one;

6-(5-{2-[3-(6-methoxy-pyridin-2-yl)-benzylamino]-ethyl}-2-oxo-[1,3,4]oxadiazol-3-yl)-4H-pyrido[3,2-b][1,4]oxazin-3-one;

5-methoxy-3'-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-biphenyl-2-carbonitrile;

6-[(S)-5-(2-{[3'-(3-hydroxy-propoxy)-biphenyl-3-ylmethyl]-amino}-ethyl)-2-oxo-oxazolidin-3-yl]-4H-pyrido[3,2-b][1,4]oxazin-3-one;

6-[(S)-5-(2-{[3'-(2-methoxy-ethoxy)-biphenyl-3-ylmethyl]-amino}-ethyl)-2-oxo-oxazolidin-3-yl]-4H-pyrido[3,2-b][1,4]oxazin-3-one;

6-((S)-5-{2-[3-(2-methoxy-pyridin-4-yl)-benzylamino]-ethyl}-2-oxo-oxazolidin-3-yl)-4H-pyrido[3,2-b][1,4]oxazin-3-one;

3'-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-biphenyl-3-carbonitrile;

6-[(S)-5-(2-{3-[6-((RS)-3-hydroxy-pyrrolidin-1-yl)-pyridin-2-yl]-benzylamino}-ethyl)-2-oxo-oxazolidin-3-yl]-4H-pyrido[3,2-b][1,4]oxazin-3-one;

6-((S)-5-{2-[(3'-cyclopropylmethoxy-biphenyl-3-ylmethyl)-amino]-ethyl}-2-oxo-oxazolidin-3-yl)-4H-pyrido[3,2-b][1,4]oxazin-3-one;

6-((S)-5-{2-[3-(6-methoxy-pyridazin-4-yl)-benzylamino]-ethyl}-2-oxo-oxazolidin-3-yl)-4H-pyrido[3,2-b][1,4]oxazin-3-one;

5-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridazine-3-carbonitrile;

6-[2-hydroxy-3-({2-[5-oxo-4-(3-oxo-3,4-dihydro-2H-pyrido[3,2-b][1,4]oxadi-azol-2-yl]-ethylamino}-methyl)-phenyl]-pyridine-2-carbonitrile;

2-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-nicotinonitrile;

6-((S)-5-{2-[(3'-hydroxy-biphenyl-3-ylmethyl)-amino]-ethyl}-2-oxo-oxazolidin-3-yl)-4H-pyrido[3,2-b][1,4]oxazin-3-one;

6-((S)-5-{2-[(2',5'-dimethoxy-biphenyl-3-ylmethyl)-amino]-ethyl}-2-oxo-oxazolidin-3-yl)-4H-pyrido[3,2-b][1,4]oxazin-3-one;

[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-acetonitrile;

3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-4-carbonitrile;

6-[(S)-5-(2-{[3'-(4-hydroxy-butoxy)-biphenyl-3-ylmethyl]-amino}-ethyl)-2-oxo-oxazolidin-3-yl]-4H-pyrido[3,2-b][1,4]oxazin-3-one;

[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-acetic acid ethyl ester;

6-[(S)-5-(2-{3-[6-((3R,4S)-3,4-dihydroxy-cyclopentyl-methoxy)-pyridin-2-yl]-benzylamino}-ethyl)-2-oxo-oxazolidin-3-yl]-4H-pyrido[3,2-b][1,4]oxazin-3-one;

6-((S)-5-{2-[(3'-ethoxy-biphenyl-3-ylmethyl)-amino]-ethyl}-2-oxo-oxazolidin-3-yl)-4H-pyrido[3,2-b][1,4]oxazin-3-one;

1-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxymethyl]-cyclobutanecarbonitrile;

6-[(R)-5-(2-{[5-(3-methoxy-phenyl)-pyridin-3-ylmethyl]-amino}-ethyl)-2-oxo-oxazolidin-3-yl]-4H-benzo[1,4]thiazin-3-one;

3-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridine-2-carbonitrile;

6-(5-{2-[2-hydroxy-3-(6-methoxy-pyridin-2-yl)-benzylamino]-ethyl}-2-oxo-[1,3,4]oxadiazol-3-yl)-4H-pyrido[3,2-b][1,4]oxazin-3-one;

3-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-4-carbonitrile;

6-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carboxylic acid methyl ester;

N-methyl-2-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-acetamide;

6-((S)-5-{2-[3-(6-methoxy-pyridazin-3-yl)-benzylamino]-ethyl}-2-oxo-oxazolidin-3-yl)-4H-pyrido[3,2-b][1,4]oxazin-3-one;

6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridazine-4-carbonitrile;

6-((S)-5-{2-[3-(5-methoxy-pyridazin-3-yl)-benzylamino]-ethyl}-2-oxo-oxazolidin-3-yl)-4H-benzo[1,4]oxazin-3-one;

3'-({2-[(S)-2-oxo-3-(3-oxo-3,4-dihydro-2H-benzo[1,4]oxazin-6-yl)-oxazolidin-5-yl]-ethylamino}-methyl)-biphenyl-3-carbonitrile;

6-(5-{2-[3-(5-methoxy-pyridazin-3-yl)-benzylamino]-ethyl}-2-oxo-oxazol-3-yl)-4H-pyrido[3,2-b][1,4]oxazin-3-one;

6-((S)-5-{2-[3-(5-ethoxy-pyridin-3-yl)-benzylamino]-ethyl}-2-oxo-oxazolidin-3-yl)-4H-pyrido[3,2-b][1,4]oxazin-3-one;

6-(5-{2-[2-hydroxy-3-(6-methoxy-pyridin-2-yl)-benzylamino]-ethyl}-2-oxo-oxazol-3-yl)-4H-pyrido[3,2-b][1,4]oxazin-3-one;

3-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile;

6-((S)-5-{2-[(6'-methoxy-[2,2']bipyridinyl-4-ylmethyl)-amino]-ethyl}-2-oxo-oxazolidin-3-yl)-4H-pyrido[3,2-b][1,4]oxazin-3-one;

6-[2-hydroxy-3-({2-[(S)-2-oxo-3-(3-oxo-3,4-dihydro-2H-benzo[1,4]oxazin-6-yl)-oxazolidin-5-yl]-ethylamino}-methyl)-phenyl]-pyridine-2-carbonitrile;

6-((S)-5-{2-[4-hydroxy-3-(5-methoxy-pyridazin-3-yl)-benzylamino]-ethyl}-2-oxo-oxazolidin-3-yl)-4H-pyrido[3,2-b][1,4]oxazin-3-one;

6-((S)-5-{2-[2-hydroxy-3-(6-methoxy-pyridin-2-yl)-benzylamino]-ethyl}-2-oxo-oxazolidin-3-yl)-4H-benzo[1,4]oxazin-3-one;

6-((S)-5-{2-[3-(6-methoxy-pyrazin-2-yl)-benzylamino]-ethyl}-2-oxo-oxazolidin-3-yl)-4H-pyrido[3,2-b][1,4]oxazin-3-one;

6-[2-hydroxy-3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridine-2-carbonitrile;

6-((S)-5-{2-[2-hydroxy-3-(6-methoxy-pyridin-2-yl)-benzylamino]-ethyl}-2-oxo-oxazolidin-3-yl)-4H-pyrido[3,2-b][1,4]oxazin-3-one;

6-[2-hydroxy-3-({2-[(S)-2-oxo-3-(3-oxo-3,4-dihydro-2H-pyrido[3,2-b][1,4]thiazin-6-yl)-oxazolidin-5-yl]-ethylamino}-methyl)-phenyl]-pyridine-2-carbonitrile;

6-((S)-5-{2-[2-hydroxy-3-(6-methoxy-pyridin-2-yl)-benzylamino]-ethyl}-2-oxo-oxazolidin-3-yl)-4H-pyrido[3,2-b][1,4]thiazin-3-one;

6-[2-hydroxy-3-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-phenyl]-pyridine-2-carbonitrile;

6-((R)-5-{2-[3-(5-methoxy-pyridazin-3-yl)-benzylamino]-ethyl}-2-oxo-oxazolidin-3-yl)-4H-pyrido[3,2-b][1,4]oxazin-3-one;

6-((R)-5-{2-[3-(5-methoxy-pyridazin-3-yl)-benzylamino]-ethyl}-2-oxo-oxazolidin-3-yl)-4H-pyrido[3,2-b][1,4]thiazin-3-one;

6-((S)-5-{2-[3-(5-methoxy-pyridazin-3-yl)-benzylamino]-ethyl}-2-oxo-oxazolidin-3-yl)-4H-pyrido[3,2-b][1,4]thiazin-3-one;

3'-({2-[(S)-2-oxo-3-(3-oxo-3,4-dihydro-2H-pyrido[3,2-b][1,4]thiazin-6-yl)-oxazolidin-5-yl]-ethylamino}-methyl)-biphenyl-3-carbonitrile;

6-((S)-5-{2-[4-hydroxy-3-(4-methoxy-pyridin-2-yl)-benzylamino]-ethyl}-2-oxo-oxazolidin-3-yl)-4H-pyrido[3,2-b][1,4]oxazin-3-one;

6-[(S)-5-(2-{[2-(3-methoxy-phenyl)-pyrimidin-4-ylmethyl]-amino}-ethyl)-2-oxo-oxazolidin-3-yl]-4H-pyrido[3,2-b][1,4]oxazin-3-one;

6-[(S)-5-(2-{[5-(3-methoxy-phenyl)-pyridazin-3-ylmethyl]-amino}-ethyl)-2-oxo-oxazolidin-3-yl]-4H-pyrido[3,2-b][1,4]oxazin-3-one;

6-[(S)-5-(2-{[6-(3-methoxy-phenyl)-pyrazin-2-ylmethyl]-amino}-ethyl)-2-oxo-oxazolidin-3-yl]-4H-pyrido[3,2-b][1,4]oxazin-3-one;

6-[(S)-5-(2-{[6-(3-methoxy-phenyl)-pyridazin-4-ylmethyl]-amino}-ethyl)-2-oxo-oxazolidin-3-yl]-4H-pyrido[3,2-b][1,4]oxazin-3-one;

6-((S)-5-{2-[2-hydroxy-3-(4-methoxy-pyridin-2-yl)-benzylamino]-ethyl}-2-oxo-oxazolidin-3-yl)-4H-pyrido[3,2-b][1,4]oxazin-3-one;

6-(5-{2-[(3'-methoxy-biphenyl-3-ylmethyl)-amino]-ethyl}-2-oxo-[1,3,4]oxadiazol-3-yl)-4H-pyrido[3,2-b][1,4]oxazin-3-one;

6-(5-{2-[3-(5-methoxy-pyridazin-3-yl)-benzylamino]-ethyl}-2-oxo-[1,3,4]oxadiazol-3-yl)-4H-pyrido[3,2-b][1,4]oxazin-3-one;

(S)-6-(5-(2-((4-hydroxy-3-(6-methoxypyridin-2-yl)benzyl)amino)ethyl)-2-oxooxazolidin-3-yl)-2H-pyrido[3,2-b][1,4]oxazin-3(4H)-one;

(S)-6-(5-(2-(((5-(5-methoxypyridazin-3-yl)pyridin-3-yl)methyl)amino)ethyl)-2-oxooxazolidin-3-yl)-2H-pyrido[3,2-b][1,4]oxazin-3(4H)-one;

(S)-6-(5-(2-(((4-(5-methoxypyridazin-3-yl)pyridin-2-yl)methyl)amino)ethyl)-2-oxooxazolidin-3-yl)-2H-pyrido[3,2-b][1,4]oxazin-3(4H)-one;

as well as the salts (in particular the pharmaceutically acceptable salts) thereof.

57) The invention further relates to the compounds of formula I as defined in embodiment 1) which are selected from the group consisting of the compounds listed in embodiment 55) and the compounds listed in embodiment 56). In particular, it also relates to the groups of compounds of formula I selected from the group consisting of the compounds listed in embodiment 55) and the compounds listed in embodiment 56), which groups of compounds furthermore correspond to one of embodiments 2) to 53), as well as to the salts (in particular the pharmaceutically acceptable salts) of such compounds. The invention moreover relates to any individual compound of formula I selected from the group consisting of the compounds listed in embodiment 55) and the compounds listed in embodiment 56), and to the salts (in particular the pharmaceutically acceptable salts) of such individual compound.

The compounds of formula I according to the invention, i.e. according to one of embodiments 1) to 57) above, are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They may therefore be particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, Enterococcus faecium, Enterococcus casseliflavus, Staphylococcus epidermidis, Staphylococcus haemolyticus,* or *Peptostreptococcus* spp.; pharyngitis, rheumatic fever, and glomerulonephritis related to infection by *Streptococcus pyogenes*, Groups C and G streptococci, *Corynebacterium diphtherias*, or *Actinobacillus haemolyticum*; respiratory tract infections related to infection by *Mycoplasma pneumoniae, Legionella pneumophila, S. pneumoniae, H. influenzae,* or *Chlamydia pneumoniae*; blood and tissue infections, including endocarditis and osteomyelitis, caused by *S. aureus, S. haemolyticus, E. faecalis, E. faecium, Enterococcus durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *S. aureus*, coagulase-negative staphylococci (i.e., *S. epidermidis, S. haemolyticus*, etc.), *S. pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *S. aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; infections caused by *Mycobacterium tuberculosis, Mycobacterium leprae, Mycobacterium paratuberculosis, Mycobacterium kansasii,* or *Mycobacterium chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *H. pylori* or *C. pneumoniae*.

The preceding lists of infections and pathogens are to be interpreted merely as examples and in no way as limiting.

The compounds of formula I according to this invention, or the pharmaceutically acceptable salt thereof, may thus be used for the preparation of a medicament, and are suitable, for the prevention or treatment of a bacterial infection (notably for the prevention or treatment of a bacterial infection mediated by *Staphylococcus aureus* bacteria or *Acinetobacter baumannii* bacteria, especially for the prevention or treatment of a bacterial infection mediated by quinolone-resistant *Staphylococcus aureus* bacteria or *Acinetobacter baumannii* quinolone-resistant bacteria).

Accordingly, the compounds of formula I according to any one of embodiments 1) to 57), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, Lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

The compounds of formula I according to any one of embodiments 1) to 57), and the pharmaceutically acceptable salts thereof, may further be useful for the preparation of a medicament, and are suitable, for the treatment of infections that are mediated by Gram positive bacteria (such as *Staphylococcus aureus, Bacillus cereus, Bacillus anthracis, Clostridium difficile, Corynebacterium* spp. and *Propionibacterium acnes*), notably by Gram positive bacteria selected from the group consisting of *Bacillus cereus, Bacillus anthracis, Clostridium difficile* and *Propionibacterium acnes*. In particular, the compounds of formula I according to any one of embodiments 1) to 57), and the pharmaceutically acceptable salts thereof, can be used for the preparation of a medicament, and are suitable, for the treatment of a bacterial infection mediated by *Staphylococcus aureus* bacteria (especially quinolone-resistant *Staphylococcus aureus* bacteria).

The compounds of formula I according to any one of embodiments 1) to 57), and the pharmaceutically acceptable salts thereof, may further be useful for the preparation of a medicament, and are suitable, for the treatment of infections that are mediated by Gram negative bacteria (such as *E. coli, Klebsiella pneumoniae* and other Enterobacteriaceae, *Acinetobacter* spp. including *Acinetobacter baumannii, Pseudomonas aeruginosa, Stenotrophomonas maltophilia, Neisseria meningitidis, Moraxella catarrhalis* and *Bacteroides* spp), notably by Gram negative bacteria selected from the group consisting of *Escherichia coli, Klebsiella pneumoniae, Acinetobacter baumannii, Pseudomonas aeruginosa, Stenotrophomonas maltophilia, Moraxella catarrhalis* and *Neisseria meningitidis*. In particular, the compounds of formula I according to any one of embodiments 1) to 57), and the pharmaceutically acceptable salts thereof, can be used for the preparation of a medicament, and are suitable, for the treatment of a bacterial infection mediated by *Acinetobacter baumannii* bacteria (especially quinolone-resistant *Acinetobacter baumannii* bacteria).

The compounds of formula I according to any one of embodiments 1) to 57), and the pharmaceutically acceptable salts thereof, may further be useful for the preparation of a medicament, and are suitable, for the treatment of protozoal infections caused by *Plasmodium malaria, Plasmodium falciparum, Toxoplasma gondii, Pneumocystis carinii, Trypanosoma brucei* and *Leishmania* spp.

One aspect of this invention therefore relates to the use of a compound of formula I according to one of embodiments 1) to 57), or of a pharmaceutically acceptable salt thereof, for the manufacture of a medicament for the prevention or treatment of a bacterial infection (in particular one of the previously mentioned infections mediated by Gram negative bacteria or one of the previously mentioned infections mediated by Gram positive bacteria). Another aspect of this invention relates to a compound of formula I according to one of embodiments 1) to 57), or a pharmaceutically acceptable salt thereof, for the prevention or treatment of a bacterial infection (in particular for the prevention or treatment of one of the previously mentioned infections mediated by Gram negative bacteria or of one of the previously mentioned infections mediated by Gram positive bacteria). Yet another aspect of this invention relates to a compound of formula I according to one of embodiments 1) to 57), or a pharmaceutically acceptable salt thereof, as a medicament. Yet a further aspect of this invention relates to a pharmaceutical composition containing, as active principle, a compound of formula I according to one of embodiments 1) to 57), or a pharmaceutically acceptable salt thereof, and at least one therapeutically inert excipient.

As well as in humans, bacterial infections can also be treated using compounds of formula I, $I_{E1}$, $I_{E2}$, $I_{CE}$, $I_P$, $I_{PE1}$ or $I_{PE2}$ (or pharmaceutically acceptable salts thereof) in other species like pigs, ruminants, horses, dogs, cats and poultry.

The present invention also relates to pharmacologically acceptable salts and to compositions and formulations of compounds of formula I, $I_{E1}$, $I_{E2}$, $I_{CE}$, $I_P$, $I_{PE1}$ or $I_{PE2}$.

Any reference to a compound of formula I, $I_{E1}$, $I_{E2}$, $I_P$, $I_{PE1}$ or $I_{PE2}$ in this text is to be understood as referring also to the salts (and especially the pharmaceutically acceptable salts) of such compounds, as appropriate and expedient.

A pharmaceutical composition according to the present invention contains at least one compound of formula I, $I_{E1}$, $I_{E2}$, $I_{CE}$, $I_P$, $I_{PE1}$ or $I_{PE2}$ (or a pharmaceutically acceptable salt thereof) as the active agent and optionally carriers and/or diluents and/or adjuvants, and may also contain additional known antibiotics.

The compounds of formula I, $I_{E1}$, $I_{E2}$, $I_{CE}$, $I_P$, $I_{PE1}$ or $I_{PE2}$ and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient, comprising the administration to said patient of a pharmaceutically active amount of a compound of formula I according to one of embodiments 1) to 57) or a pharmaceutically acceptable salt thereof. Accordingly, the invention provides a method for the prevention or the treatment of a bacterial infection mediated by Gram negative bacteria (in particular a bacterial infection mediated by *Acinetobacter baumannii* bacteria, and especially by quinolone-resistant *Acinetobacter baumannii* bacteria) in a patient, comprising the administration to said patient of a pharmaceutically active amount of a compound of formula I according to one of embodiments 1) to 57) or a pharmaceutically acceptable salt thereof. The invention further provides a method for the prevention or the treatment of a bacterial infection mediated by Gram positive bacteria (in particular a bacterial infection mediated by *Staphylococcus aureus* bacteria, especially by quinolone-resistant *Staphylococcus aureus* bacteria) in a patient, comprising the administration to said patient of a pharmaceutically active amount of a compound of formula I according to one of embodiments 1) to 57) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 57), and to pharmaceutically acceptable salts thereof. It relates furthermore to the use of such compounds as medicaments, especially for the prevention or treatment of a bacterial infection, in particular for the prevention or treatment of a bacterial infection mediated by Gram positive bacteria (in particular a bacterial infection mediated by *Staphylococcus aureus* bacteria, especially by quinolone-resistant *Staphylococcus aureus* bacteria) or for the prevention or treatment of a bacterial infection mediated by Gram negative bacteria (in particular a bacterial infection mediated by *Acinetobacter baumannii* bacteria, and especially by quinolone-resistant *Acinetobacter baumannii* bacteria), and notably for the prevention or treatment of a bacterial infection mediated by quinolone-resistant *Staphylococcus aureus* or *Acinetobacter baumannii* bacteria. The following embodiments relating to the compounds of formula I according to embodiment 1) are thus possible and intended and herewith specifically disclosed in individualised form:

1, 2+1, 3+1, 4+1, 5+1, 6+5+1, 7+5+1, 8+1, 8+4+1, 8+5+1, 9+1, 9+4+1, 9+5+1, 10+9+1, 10+9+4+1, 10+9+5+1, 11+9+1, 11+9+4+1, 11+9+5+1, 12+1, 12+2+1, 12+3+1, 12+4+1, 12+5+1, 12+6+5+1, 12+7+5+1, 12+8+1, 12+8+4+1, 12+8+5+1, 12+9+1, 12+9+4+1, 12+9+5+1, 12+10+9+1, 12+10+9+4+1, 12+10+9+5+1, 12+11+9+1, 12+11+9+4+1, 12+11+9+5+1, 13+12+1, 13+12+2+1, 13+12+3+1, 13+12+4+1, 13+12+5+1, 13+12+6+5+1, 13+12+7+5+1, 13+12+8+1, 13+12+8+4+1, 13+12+8+5+1, 13+12+9+1, 13+12+9+4+1, 13+12+9+5+1, 13+12+10+9+1, 13+12+10+9+4+1, 13+12+10+9+5+1, 13+12+11+9+1, 13+12+11+9+4+1, 13+12+11+9+5+1, 14+1, 14+2+1, 14+3+1, 14+4+1, 14+5+1, 14+6+5+1, 14+7+5+1, 14+8+1, 14+8+4+1, 14+8+5+1, 14+9+1, 14+9+4+1, 14+9+5+1, 14+10+9+1, 14+10+9+4+1, 14+10+9+5+1, 14+11+9+1, 14+11+9+4+1, 14+11+9+5+1, 15+14+1, 15+14+2+1, 15+14+3+1, 15+14+4+1, 15+14+5+1, 15+14+6+5+1, 15+14+7+5+1, 15+14+8+1, 15+14+8+4+1, 15+14+8+5+1, 15+14+9+1, 15+14+9+4+1, 15+14+9+5+1, 15+14+10+9+1, 15+14+10+9+4+1, 15+14+10+9+5+1, 15+14+11+9+1, 15+14+11+9+4+1, 15+14+11+9+5+1, 16+1, 16+2+1, 16+3+1, 16+4+1, 16+5+1, 16+6+5+1, 16+7+5+1, 16+8+1, 16+8+4+1, 16+8+5+1, 16+9+1, 16+9+4+1, 16+9+5+1, 16+10+9+1, 16+10+9+4+1, 16+10+9+5+1, 16+11+9+1, 16+11+9+4+1, 16+11+9+5+1, 17+1, 17+2+1, 17+3+1, 17+4+1, 17+5+1, 17+6+5+1, 17+7+5+1, 17+8+1, 17+8+4+1, 17+8+5+1, 17+9+1, 17+9+4+1, 17+9+5+1, 17+10+9+1, 17+10+9+4+1, 17+10+9+5+1, 17+11+9+1, 17+11+9+4+1, 17+11+9+5+1, 17+12+1, 17+12+2+1, 17+12+3+1, 17+12+4+1, 17+12+5+1, 17+12+6+5+1, 17+12+7+5+1, 17+12+8+1, 17+12+8+4+1, 17+12+8+5+1, 17+12+9+1, 17+12+9+4+1, 17+12+9+5+1, 17+12+10+9+1, 17+12+10+9+4+1, 17+12+10+9+5+1, 17+12+11+9+1, 17+12+11+9+4+1, 17+12+11+9+5+1, 17+14+1, 17+14+2+1, 17+14+3+1, 17+14+4+1, 17+14+5+1, 17+14+6+5+1, 17+14+7+5+1, 17+14+8+1, 17+14+8+4+1, 17+14+8+5+1, 17+14+9+1, 17+14+9+4+1, 17+14+9+5+1, 17+14+10+9+1, 17+14+10+9+4+1, 17+14+10+9+5+1, 17+14+11+9+1, 17+14+11+9+4+1, 17+14+11+9+5+1, 17+16+1, 17+16+2+1, 17+16+3+1, 17+16+4+1, 17+16+5+1, 17+16+6+5+1, 17+16+7+5+1, 17+16+8+1, 17+16+8+4+1, 17+16+8+5+1, 17+16+9+1, 17+16+9+4+1, 17+16+9+5+1, 17+16+10+9+1, 17+16+10+9+4+1, 17+16+10+9+5+1, 17+16+11+9+1, 17+16+11+9+4+1, 17+16+11+9+5+1, 18+17+1, 18+17+2+1, 18+17+3+1, 18+17+4+1, 18+17+5+1, 18+17+6+5+1, 18+17+7+5+1, 18+17+8+1, 18+17+8+4+1, 18+17+8+5+1, 18+17+9+1, 18+17+9+4+1, 18+17+9+5+1, 18+17+10+9+1, 18+17+10+9+4+1, 18+17+10+9+5+1, 18+17+11+9+1, 18+17+11+9+4+1, 18+17+11+9+5+1, 18+17+12+1, 18+17+12+2+1, 18+17+12+3+1, 18+17+12+4+1, 18+17+12+5+1, 18+17+12+6+5+1, 18+17+12+7+5+1, 18+17+12+8+1, 18+17+12+8+4+1, 18+17+12+8+5+1, 18+17+12+9+1, 18+17+12+9+4+1, 18+17+12+9+5+1, 18+17+12+10+9+1, 18+17+12+10+9+4+1, 18+17+12+10+9+5+1, 18+17+12+11+9+1, 18+17+12+11+9+4+1, 18+17+12+11+9+5+1, 18+17+14+1, 18+17+14+2+1, 18+17+14+3+1, 18+17+14+4+1, 18+17+14+5+1, 18+17+14+6+5+1, 18+17+14+7+5+1, 18+17+14+8+1, 18+17+14+8+4+1, 18+17+14+8+5+1, 18+17+14+9+1, 18+17+14+9+4+1, 18+17+14+9+5+1, 18+17+14+10+9+1, 18+17+14+10+9+4+1, 18+17+14+10+9+5+1, 18+17+14+11+9+1, 18+17+14+11+9+4+1, 18+17+14+11+9+5+1, 18+17+16+1, 18+17+16+2+1, 18+17+16+3+1, 18+17+16+4+1, 18+17+16+5+1, 18+17+16+6+5+1, 18+17+16+7+5+1, 18+17+16+8+1, 18+17+16+8+4+1, 18+17+16+8+5+1, 18+17+16+9+1, 18+17+16+9+4+1, 18+17+16+9+5+1, 18+17+16+10+9+1, 18+17+16+10+9+4+1, 18+17+16+10+9+5+1, 18+17+16+11+9+1, 18+17+16+11+9+4+1, 18+17+16+11+9+5+1, 19+17+1, 19+17+2+1, 19+17+3+1, 19+17+4+1, 19+17+5+1, 19+17+6+5+1, 19+17+7+5+1, 19+17+8+1, 19+17+8+4+1, 19+17+8+5+1, 19+17+9+1, 19+17+9+4+1, 19+17+9+5+1, 19+17+10+9+1, 19+17+10+9+4+1, 19+17+10+9+5+1, 19+17+11+9+1, 19+17+11+9+4+1, 19+17+11+9+5+1, 19+17+12+1, 19+17+12+2+1, 19+17+12+3+1, 19+17+12+4+1, 19+17+12+5+1, 19+17+12+6+5+1, 19+17+12+7+5+1, 19+17+12+8+1, 19+17+12+8+4+1, 19+17+12+8+5+1, 19+17+12+9+1, 19+17+12+9+4+1, 19+17+12+9+5+1, 19+17+12+10+9+1, 19+17+12+10+9+4+1, 19+17+12+10+9+5+1, 19+17+12+11+9+1, 19+17+12+11+9+4+1, 19+17+12+11+9+5+1, 19+17+14+1, 19+17+14+2+1, 19+17+14+3+1, 19+17+14+4+1, 19+17+14+5+1, 19+17+14+6+5+1, 19+17+14+7+5+1, 19+17+14+8+1, 19+17+14+8+4+1, 19+17+14+8+5+1, 19+17+14+9+1, 19+17+14+9+4+1, 19+17+14+9+5+1, 19+17+14+10+9+1, 19+17+14+10+9+4+1, 19+17+14+10+9+5+1, 19+17+14+11+9+1, 19+17+14+11+9+4+1, 19+17+14+11+9+5+1, 19+17+16+1, 19+17+16+2+1, 19+17+16+3+1, 19+17+16+4+1, 19+17+16+5+1, 19+17+16+6+5+1, 19+17+16+7+5+1, 19+17+16+8+1, 19+17+16+8+4+1, 19+17+16+8+5+1, 19+17+16+9+1, 19+17+16+9+4+1, 19+17+16+9+5+1, 19+17+16+10+9+1, 19+17+16+10+9+4+1, 19+17+16+10+9+5+1, 19+17+16+11+9+1, 19+17+16+11+9+4+1, 19+17+16+11+9+5+1, 20+17+1, 20+17+2+1, 20+17+3+1, 20+17+4+1, 20+17+5+1, 20+17+6+5+1, 20+17+7+5+1, 20+17+8+1, 20+17+8+4+1, 20+17+8+5+1, 20+17+9+1, 20+17+9+4+1, 20+17+9+5+1, 20+17+10+9+1, 20+17+10+9+4+1, 20+17+10+9+5+1, 20+17+11+9+1, 20+17+11+9+4+1, 20+17+11+9+5+1, 20+17+12+1, 20+17+12+2+1, 20+17+12+3+1, 20+17+12+4+1, 20+17+12+5+1, 20+17+12+6+5+1, 20+17+12+7+5+1, 20+17+12+8+1, 20+17+12+8+4+1, 20+17+12+8+5+1, 20+17+12+9+1, 20+17+12+9+4+1, 20+17+12+9+5+1, 20+17+12+10+9+1, 20+17+12+10+9+4+1, 20+17+12+10+9+5+1, 20+17+12+11+9+1, 20+17+12+11+9+4+1, 20+17+12+11+9+5+1, 20+17+14+1, 20+17+14+2+1, 20+17+14+3+1, 20+17+14+4+1, 20+17+14+5+1, 20+17+14+6+5+1, 20+17+14+7+5+1, 20+17+14+8+1, 20+17+14+8+4+1, 20+17+14+8+5+1,

20+17+14+9+1, 20+17+14+9+4+1, 20+17+14+9+5+1, 20+17+14+10+9+1, 20+17+14+10+9+4+1, 20+17+14+10+9+5+1, 20+17+14+11+9+1, 20+17+14+11+9+4+1, 20+17+14+11+9+5+1, 20+17+16+1, 20+17+16+2+1, 20+17+16+3+1, 20+17+16+4+1, 20+17+16+5+1, 20+17+16+6+5+1, 20+17+16+7+5+1, 20+17+16+8+1, 20+17+16+8+4+1, 20+17+16+8+5+1, 20+17+16+9+1, 20+17+16+9+4+1, 20+17+16+9+5+1, 20+17+16+10+9+1, 20+17+16+10+9+4+1, 20+17+16+10+9+5+1, 20+17+16+11+9+1, 20+17+16+11+9+4+1, 20+17+16+11+9+5+1, 21+17+1, 21+17+2+1, 21+17+3+1, 21+17+4+1, 21+17+5+1, 21+17+6+5+1, 21+17+7+5+1, 21+17+8+1, 21+17+8+4+1, 21+17+8+5+1, 21+17+9+1, 21+17+9+4+1, 21+17+9+5+1, 21+17+10+9+1, 21+17+10+9+4+1, 21+17+10+9+5+1, 21+17+11+9+1, 21+17+11+9+4+1, 21+17+11+9+5+1, 21+17+12+1, 21+17+12+2+1, 21+17+12+3+1, 21+17+12+4+1, 21+17+12+5+1, 21+17+12+6+5+1, 21+17+12+7+5+1, 21+17+12+8+1, 21+17+12+8+4+1, 21+17+12+8+5+1, 21+17+12+9+1, 21+17+12+9+4+1, 21+17+12+9+5+1, 21+17+12+10+9+1, 21+17+12+10+9+4+1, 21+17+12+10+9+5+1, 21+17+12+11+9+1, 21+17+12+11+9+4+1, 21+17+12+11+9+5+1, 21+17+14+1, 21+17+14+2+1, 21+17+14+3+1, 21+17+14+4+1, 21+17+14+5+1, 21+17+14+6+5+1, 21+17+14+7+5+1, 21+17+14+8+1, 21+17+14+8+4+1, 21+17+14+8+5+1, 21+17+14+9+1, 21+17+14+9+4+1, 21+17+14+9+5+1, 21+17+14+10+9+1, 21+17+14+10+9+4+1, 21+17+14+10+9+5+1, 21+17+14+11+9+1, 21+17+14+11+9+4+1, 21+17+14+11+9+5+1, 21+17+16+1, 21+17+16+2+1, 21+17+16+3+1, 21+17+16+4+1, 21+17+16+5+1, 21+17+16+6+5+1, 21+17+16+7+5+1, 21+17+16+8+1, 21+17+16+8+4+1, 21+17+16+8+5+1, 21+17+16+9+1, 21+17+16+9+4+1, 21+17+16+9+5+1, 21+17+16+10+9+1, 21+17+16+10+9+4+1, 21+17+16+10+9+5+1, 21+17+16+11+9+1, 21+17+16+11+9+4+1, 21+17+16+11+9+5+1, 22+1, 22+2+1, 22+3+1, 22+4+1, 22+5+1, 22+6+5+1, 22+7+5+1, 22+8+1, 22+8+4+1, 22+8+5+1, 22+9+1, 22+9+4+1, 22+9+5+1, 22+10+9+1, 22+10+9+4+1, 22+10+9+5+1, 22+11+9+1, 22+11+9+4+1, 22+11+9+5+1, 22+12+1, 22+12+2+1, 22+12+3+1, 22+12+4+1, 22+12+5+1, 22+12+6+5+1, 22+12+7+5+1, 22+12+8+1, 22+12+8+4+1, 22+12+8+5+1, 22+12+9+1, 22+12+9+4+1, 22+12+9+5+1, 22+12+10+9+1, 22+12+10+9+4+1, 22+12+10+9+5+1, 22+12+11+9+1, 22+12+11+9+4+1, 22+12+11+9+5+1, 22+14+1, 22+14+2+1, 22+14+3+1, 22+14+4+1, 22+14+5+1, 22+14+6+5+1, 22+14+7+5+1, 22+14+8+1, 22+14+8+4+1, 22+14+8+5+1, 22+14+9+1, 22+14+9+4+1, 22+14+9+5+1, 22+14+10+9+1, 22+14+10+9+4+1, 22+14+10+9+5+1, 22+14+11+9+1, 22+14+11+9+4+1, 22+14+11+9+5+1, 22+16+1, 22+16+2+1, 22+16+3+1, 22+16+4+1, 22+16+5+1, 22+16+6+5+1, 22+16+7+5+1, 22+16+8+1, 22+16+8+4+1, 22+16+8+5+1, 22+16+9+1, 22+16+9+4+1, 22+16+9+5+1, 22+16+10+9+1, 22+16+10+9+4+1, 22+16+10+9+5+1, 22+16+11+9+1, 22+16+11+9+4+1, 22+16+11+9+5+1, 23+22+1, 23+22+2+1, 23+22+3+1, 23+22+4+1, 23+22+5+1, 23+22+6+5+1, 23+22+7+5+1, 23+22+8+1, 23+22+8+4+1, 23+22+8+5+1, 23+22+9+1, 23+22+9+4+1, 23+22+9+5+1, 23+22+10+9+1, 23+22+10+9+4+1, 23+22+10+9+5+1, 23+22+11+9+1, 23+22+11+9+4+1, 23+22+11+9+5+1, 23+22+12+1, 23+22+12+2+1, 23+22+12+3+1, 23+22+12+4+1, 23+22+12+5+1, 23+22+12+6+5+1, 23+22+12+7+5+1, 23+22+12+8+1, 23+22+12+8+4+1, 23+22+12+8+5+1, 23+22+12+9+1, 23+22+12+9+4+1, 23+22+12+9+5+1, 23+22+12+10+9+1, 23+22+12+10+9+4+1, 23+22+12+10+9+5+1, 23+22+12+11+9+1, 23+22+12+11+9+4+1, 23+22+12+11+9+5+1, 23+22+14+1, 23+22+14+2+1, 23+22+14+3+1, 23+22+14+4+1, 23+22+14+5+1, 23+22+14+6+5+1, 23+22+14+7+5+1, 23+22+14+8+1, 23+22+14+8+4+1, 23+22+14+8+5+1, 23+22+14+9+1, 23+22+14+9+4+1, 23+22+14+9+5+1, 23+22+14+10+9+1, 23+22+14+10+9+4+1, 23+22+14+10+9+5+1, 23+22+14+11+9+1, 23+22+14+11+9+4+1, 23+22+14+11+9+5+1, 23+22+16+1, 23+22+16+2+1, 23+22+16+3+1, 23+22+16+4+1, 23+22+16+5+1, 23+22+16+6+5+1, 23+22+16+7+5+1, 23+22+16+8+1, 23+22+16+8+4+1, 23+22+16+8+5+1, 23+22+16+9+1, 23+22+16+9+4+1, 23+22+16+9+5+1, 23+22+16+10+9+1, 23+22+16+10+9+4+1, 23+22+16+10+9+5+1, 23+22+16+11+9+1, 23+22+16+11+9+4+1, 23+22+16+11+9+5+1, 24+22+1, 24+22+2+1, 24+22+3+1, 24+22+4+1, 24+22+5+1, 24+22+6+5+1, 24+22+7+5+1, 24+22+8+1, 24+22+8+4+1, 24+22+8+5+1, 24+22+9+1, 24+22+9+4+1, 24+22+9+5+1, 24+22+10+9+1, 24+22+10+9+4+1, 24+22+10+9+5+1, 24+22+11+9+1, 24+22+11+9+4+1, 24+22+11+9+5+1, 24+22+12+1, 24+22+12+2+1, 24+22+12+3+1, 24+22+12+4+1, 24+22+12+5+1, 24+22+12+6+5+1, 24+22+12+7+5+1, 24+22+12+8+1, 24+22+12+8+4+1, 24+22+12+8+5+1, 24+22+12+9+1, 24+22+12+9+4+1, 24+22+12+9+5+1, 24+22+12+10+9+1, 24+22+12+10+9+4+1, 24+22+12+10+9+5+1, 24+22+12+11+9+1, 24+22+12+11+9+4+1, 24+22+12+11+9+5+1, 24+22+14+1, 24+22+14+2+1, 24+22+14+3+1, 24+22+14+4+1, 24+22+14+5+1, 24+22+14+6+5+1, 24+22+14+7+5+1, 24+22+14+8+1, 24+22+14+8+4+1, 24+22+14+8+5+1, 24+22+14+9+1, 24+22+14+9+4+1, 24+22+14+9+5+1, 24+22+14+10+9+1, 24+22+14+10+9+4+1, 24+22+14+10+9+5+1, 24+22+14+11+9+1, 24+22+14+11+9+4+1, 24+22+14+11+9+5+1, 24+22+16+1, 24+22+16+2+1, 24+22+16+3+1, 24+22+16+4+1, 24+22+16+5+1, 24+22+16+6+5+1, 24+22+16+7+5+1, 24+22+16+8+1, 24+22+16+8+4+1, 24+22+16+8+5+1, 24+22+16+9+1, 24+22+16+9+4+1, 24+22+16+9+5+1, 24+22+16+10+9+1, 24+22+16+10+9+4+1, 24+22+16+10+9+5+1, 24+22+16+11+9+1, 24+22+16+11+9+4+1, 24+22+16+11+9+5+1, 25+1, 25+2+1, 25+3+1, 25+4+1, 25+5+1, 25+6+5+1, 25+7+5+1, 25+8+1, 25+8+4+1, 25+8+5+1, 25+9+1, 25+9+4+1, 25+9+5+1, 25+10+9+1, 25+10+9+4+1, 25+10+9+5+1, 25+11+9+1, 25+11+9+4+1, 25+11+9+5+1, 25+12+1, 25+12+2+1, 25+12+3+1, 25+12+4+1, 25+12+5+1, 25+12+6+5+1, 25+12+7+5+1, 25+12+8+1, 25+12+8+4+1, 25+12+8+5+1, 25+12+9+1, 25+12+9+4+1, 25+12+9+5+1, 25+12+10+9+1, 25+12+10+9+4+1, 25+12+10+9+5+1, 25+12+11+9+1, 25+12+11+9+4+1, 25+12+11+9+5+1, 25+14+1, 25+14+2+1, 25+14+3+1, 25+14+4+1, 25+14+5+1, 25+14+6+5+1, 25+14+7+5+1, 25+14+8+1, 25+14+8+4+1, 25+14+8+5+1, 25+14+9+1, 25+14+9+4+1, 25+14+9+5+1, 25+14+10+9+1, 25+14+10+9+4+1, 25+14+10+9+5+1, 25+14+11+9+1, 25+14+11+9+4+1, 25+14+11+9+5+1, 25+16+1, 25+16+2+1, 25+16+3+1, 25+16+4+1, 25+16+5+1, 25+16+6+5+1, 25+16+7+5+1, 25+16+8+1, 25+16+8+4+1, 25+16+8+5+1, 25+16+9+1, 25+16+9+4+1, 25+16+9+5+1, 25+16+10+9+1, 25+16+10+9+4+1, 25+16+10+9+5+1, 25+16+11+9+1, 25+16+11+9+4+1, 25+16+11+9+5+1, 26+25+1, 26+25+2+1, 26+25+3+1, 26+25+4+1, 26+25+5+1, 26+25+6+5+1, 26+25+7+5+1, 26+25+8+1, 26+25+8+4+1, 26+25+8+5+1, 26+25+9+1, 26+25+9+4+1, 26+25+9+5+1, 26+25+10+9+1, 26+25+10+9+4+1, 26+25+10+9+5+1, 26+25+11+9+1, 26+25+11+9+4+1, 26+25+11+9+5+1, 26+25+12+1, 26+25+12+2+1, 26+25+12+3+1, 26+25+12+4+1, 26+25+12+5+1, 26+25+12+6+5+1, 26+25+12+7+5+1, 26+25+12+8+1, 26+25+12+8+4+1, 26+25+12+8+5+1, 26+25+12+9+1, 26+25+12+9+4+1, 26+25+12+9+5+1, 26+25+12+10+9+1, 26+25+12+10+9+4+1, 26+25+12+10+9+5+1, 26+25+12+11+9+1, 26+25+12+11+9+4+1, 26+25+12+11+9+5+1, 26+25+14+1, 26+25+14+2+1, 26+25+14+3+1, 26+25+14+4+1, 26+25+14+5+1, 26+25+14+6+5+1, 26+25+14+7+5+1, 26+25+14+8+1, 26+25+14+8+4+1, 26+25+14+8+5+1, 26+25+14+9+1, 26+25+14+9+4+1,

26+25+14+9+5+1, 26+25+14+10+9+1, 26+25+14+10+9+4+1, 26+25+14+10+9+5+1, 26+25+14+11+9+1, 26+25+14+11+9+4+1, 26+25+14+11+9+5+1, 26+25+16+1, 26+25+16+2+1, 26+25+16+3+1, 26+25+16+4+1, 26+25+16+5+1, 26+25+16+6+5+1, 26+25+16+7+5+1, 26+25+16+8+1, 26+25+16+8+4+1, 26+25+16+8+5+1, 26+25+16+9+1, 26+25+16+9+4+1, 26+25+16+9+5+1, 26+25+16+10+9+1, 26+25+16+10+9+4+1, 26+25+16+10+9+5+1, 26+25+16+11+9+1, 26+25+16+11+9+4+1, 26+25+16+11+9+5+1, 27+25+1, 27+25+2+1, 27+25+3+1, 27+25+4+1, 27+25+5+1, 27+25+6+5+1, 27+25+7+5+1, 27+25+8+1, 27+25+8+4+1, 27+25+8+5+1, 27+25+9+1, 27+25+9+4+1, 27+25+9+5+1, 27+25+10+9+1, 27+25+10+9+4+1, 27+25+10+9+5+1, 27+25+11+9+1, 27+25+11+9+4+1, 27+25+11+9+5+1, 27+25+12+1, 27+25+12+2+1, 27+25+12+3+1, 27+25+12+4+1, 27+25+12+5+1, 27+25+12+6+5+1, 27+25+12+7+5+1, 27+25+12+8+1, 27+25+12+8+4+1, 27+25+12+8+5+1, 27+25+12+9+1, 27+25+12+9+4+1, 27+25+12+9+5+1, 27+25+12+10+9+1, 27+25+12+10+9+4+1, 27+25+12+10+9+5+1, 27+25+12+11+9+1, 27+25+12+11+9+4+1, 27+25+12+11+9+5+1, 27+25+14+1, 27+25+14+2+1, 27+25+14+3+1, 27+25+14+4+1, 27+25+14+5+1, 27+25+14+6+5+1, 27+25+14+7+5+1, 27+25+14+8+1, 27+25+14+8+4+1, 27+25+14+8+5+1, 27+25+14+9+1, 27+25+14+9+4+1, 27+25+14+9+5+1, 27+25+14+10+9+1, 27+25+14+10+9+4+1, 27+25+14+10+9+5+1, 27+25+14+11+9+1, 27+25+14+11+9+4+1, 27+25+14+11+9+5+1, 27+25+16+1, 27+25+16+2+1, 27+25+16+3+1, 27+25+16+4+1, 27+25+16+5+1, 27+25+16+6+5+1, 27+25+16+7+5+1, 27+25+16+8+1, 27+25+16+8+4+1, 27+25+16+8+5+1, 27+25+16+9+1, 27+25+16+9+4+1, 27+25+16+9+5+1, 27+25+16+10+9+1, 27+25+16+10+9+4+1, 27+25+16+10+9+5+1, 27+25+16+11+9+1, 27+25+16+11+9+4+1, 27+25+16+11+9+5+1, 28+25+1, 28+25+2+1, 28+25+3+1, 28+25+4+1, 28+25+5+1, 28+25+6+5+1, 28+25+7+5+1, 28+25+8+1, 28+25+8+4+1, 28+25+8+5+1, 28+25+9+1, 28+25+9+4+1, 28+25+9+5+1, 28+25+10+9+1, 28+25+10+9+4+1, 28+25+10+9+5+1, 28+25+11+9+1, 28+25+11+9+4+1, 28+25+11+9+5+1, 28+25+12+1, 28+25+12+2+1, 28+25+12+3+1, 28+25+12+4+1, 28+25+12+5+1, 28+25+12+6+5+1, 28+25+12+7+5+1, 28+25+12+8+1, 28+25+12+8+4+1, 28+25+12+8+5+1, 28+25+12+9+1, 28+25+12+9+4+1, 28+25+12+9+5+1, 28+25+12+10+9+1, 28+25+12+10+9+4+1, 28+25+12+10+9+5+1, 28+25+12+11+9+1, 28+25+12+11+9+4+1, 28+25+12+11+9+5+1, 28+25+14+1, 28+25+14+2+1, 28+25+14+3+1, 28+25+14+4+1, 28+25+14+5+1, 28+25+14+6+5+1, 28+25+14+7+5+1, 28+25+14+8+1, 28+25+14+8+4+1, 28+25+14+8+5+1, 28+25+14+9+1, 28+25+14+9+4+1, 28+25+14+9+5+1, 28+25+14+10+9+1, 28+25+14+10+9+4+1, 28+25+14+10+9+5+1, 28+25+14+11+9+1, 28+25+14+11+9+4+1, 28+25+14+11+9+5+1, 28+25+16+1, 28+25+16+2+1, 28+25+16+3+1, 28+25+16+4+1, 28+25+16+5+1, 28+25+16+6+5+1, 28+25+16+7+5+1, 28+25+16+8+1, 28+25+16+8+4+1, 28+25+16+8+5+1, 28+25+16+9+1, 28+25+16+9+4+1, 28+25+16+9+5+1, 28+25+16+10+9+1, 28+25+16+10+9+4+1, 28+25+16+10+9+5+1, 28+25+16+11+9+1, 28+25+16+11+9+4+1, 28+25+16+11+9+5+1, 29+28+25+1, 29+28+25+2+1, 29+28+25+3+1, 29+28+25+4+1, 29+28+25+5+1, 29+28+25+6+5+1, 29+28+25+7+5+1, 29+28+25+8+1, 29+28+25+8+4+1, 29+28+25+8+5+1, 29+28+25+9+1, 29+28+25+9+4+1, 29+28+25+9+5+1, 29+28+25+10+9+1, 29+28+25+10+9+4+1, 29+28+25+10+9+5+1, 29+28+25+11+9+1, 29+28+25+11+9+4+1, 29+28+25+11+9+5+1, 29+28+25+12+1, 29+28+25+12+2+1, 29+28+25+12+3+1, 29+28+25+12+4+1, 29+28+25+12+5+1, 29+28+25+12+6+5+1, 29+28+25+12+7+5+1, 29+28+25+12+8+1, 29+28+25+12+8+4+1, 29+28+25+12+8+5+1, 29+28+25+12+9+1, 29+28+25+12+9+4+1, 29+28+25+12+9+5+1, 29+28+25+12+10+9+1, 29+28+25+12+10+9+4+1, 29+28+25+12+10+9+5+1, 29+28+25+12+11+9+1, 29+28+25+12+11+9+4+1, 29+28+25+12+11+9+5+1, 29+28+25+14+1, 29+28+25+14+2+1, 29+28+25+14+3+1, 29+28+25+14+4+1, 29+28+25+14+5+1, 29+28+25+14+6+5+1, 29+28+25+14+7+5+1, 29+28+25+14+8+1, 29+28+25+14+8+4+1, 29+28+25+14+8+5+1, 29+28+25+14+9+1, 29+28+25+14+9+4+1, 29+28+25+14+9+5+1, 29+28+25+14+10+9+1, 29+28+25+14+10+9+4+1, 29+28+25+14+10+9+5+1, 29+28+25+14+11+9+1, 29+28+25+14+11+9+4+1, 29+28+25+14+11+9+5+1, 29+28+25+16+1, 29+28+25+16+2+1, 29+28+25+16+3+1, 29+28+25+16+4+1, 29+28+25+16+5+1, 29+28+25+16+6+5+1, 29+28+25+16+7+5+1, 29+28+25+16+8+1, 29+28+25+16+8+4+1, 29+28+25+16+8+5+1, 29+28+25+16+9+1, 29+28+25+16+9+4+1, 29+28+25+16+9+5+1, 29+28+25+16+10+9+1, 29+28+25+16+10+9+4+1, 29+28+25+16+10+9+5+1, 29+28+25+16+11+9+1, 29+28+25+16+11+9+4+1, 29+28+25+16+11+9+5+1, 30+1, 30+2+1, 30+3+1, 30+4+1, 30+5+1, 30+6+5+1, 30+7+5+1, 30+8+1, 30+8+4+1, 30+8+5+1, 30+9+1, 30+9+4+1, 30+9+5+1, 30+10+9+1, 30+10+9+4+1, 30+10+9+5+1, 30+11+9+1, 30+11+9+4+1, 30+11+9+5+1, 30+12+1, 30+12+2+1, 30+12+3+1, 30+12+4+1, 30+12+5+1, 30+12+6+5+1, 30+12+7+5+1, 30+12+8+1, 30+12+8+4+1, 30+12+8+5+1, 30+12+9+1, 30+12+9+4+1, 30+12+9+5+1, 30+12+10+9+1, 30+12+10+9+4+1, 30+12+10+9+5+1, 30+12+11+9+1, 30+12+11+9+4+1, 30+12+11+9+5+1, 30+14+1, 30+14+2+1, 30+14+3+1, 30+14+4+1, 30+14+5+1, 30+14+6+5+1, 30+14+7+5+1, 30+14+8+1, 30+14+8+4+1, 30+14+8+5+1, 30+14+9+1, 30+14+9+4+1, 30+14+9+5+1, 30+14+10+9+1, 30+14+10+9+4+1, 30+14+10+9+5+1, 30+14+11+9+1, 30+14+11+9+4+1, 30+14+11+9+5+1, 30+16+1, 30+16+2+1, 30+16+3+1, 30+16+4+1, 30+16+5+1, 30+16+6+5+1, 30+16+7+5+1, 30+16+8+1, 30+16+8+4+1, 30+16+8+5+1, 30+16+9+1, 30+16+9+4+1, 30+16+9+5+1, 30+16+10+9+1, 30+16+10+9+4+1, 30+16+10+9+5+1, 30+16+11+9+1, 30+16+11+9+4+1, 30+16+11+9+5+1, 31+30+1, 31+30+2+1, 31+30+3+1, 31+30+4+1, 31+30+5+1, 31+30+6+5+1, 31+30+7+5+1, 31+30+8+1, 31+30+8+4+1, 31+30+8+5+1, 31+30+9+1, 31+30+9+4+1, 31+30+9+5+1, 31+30+10+9+1, 31+30+10+9+4+1, 31+30+10+9+5+1, 31+30+11+9+1, 31+30+11+9+4+1, 31+30+11+9+5+1, 31+30+12+1, 31+30+12+2+1, 31+30+12+3+1, 31+30+12+4+1, 31+30+12+5+1, 31+30+12+6+5+1, 31+30+12+7+5+1, 31+30+12+8+1, 31+30+12+8+4+1, 31+30+12+8+5+1, 31+30+12+9+1, 31+30+12+9+4+1, 31+30+12+9+5+1, 31+30+12+10+9+1, 31+30+12+10+9+4+1, 31+30+12+10+9+5+1, 31+30+12+11+9+1, 31+30+12+11+9+4+1, 31+30+12+11+9+5+1, 31+30+14+1, 31+30+14+2+1, 31+30+14+3+1, 31+30+14+4+1, 31+30+14+5+1, 31+30+14+6+5+1, 31+30+14+7+5+1, 31+30+14+8+1, 31+30+14+8+4+1, 31+30+14+8+5+1, 31+30+14+9+1, 31+30+14+9+4+1, 31+30+14+9+5+1, 31+30+14+10+9+1, 31+30+14+10+9+4+1, 31+30+14+10+9+5+1, 31+30+14+11+9+1, 31+30+14+11+9+4+1, 31+30+14+11+9+5+1, 31+30+16+1, 31+30+16+2+1, 31+30+16+3+1, 31+30+16+4+1, 31+30+16+5+1, 31+30+16+6+5+1, 31+30+16+7+5+1, 31+30+16+8+1, 31+30+16+8+4+1, 31+30+16+8+5+1, 31+30+16+9+1, 31+30+16+9+4+1, 31+30+16+9+5+1, 31+30+16+10+9+1, 31+30+16+10+9+4+1, 31+30+16+10+9+5+1, 31+30+16+11+9+1, 31+30+16+11+9+4+1, 31+30+16+11+9+5+1, 32+1, 32+2+1, 32+3+1, 32+4+1, 32+5+1, 32+6+5+1, 32+7+5+1, 32+8+1, 32+8+4+1, 32+8+5+1, 32+9+1, 32+9+4+1, 32+9+5+1, 32+10+9+1, 32+10+9+4+1, 32+10+9+5+1, 32+11+9+1, 32+11+9+4+1, 32+11+9+5+1, 32+12+1, 32+12+2+1, 32+12+3+1, 32+12+4+1, 32+12+5+1, 32+12+6+5+1, 32+12+7+5+1,

32+12+8+1, 32+12+8+4+1, 32+12+8+5+1, 32+12+9+1, 32+12+9+4+1, 32+12+9+5+1, 32+12+10+9+1, 32+12+10+9+4+1, 32+12+10+9+5+1, 32+12+11+9+1, 32+12+11+9+4+1, 32+12+11+9+5+1, 32+14+1, 32+14+2+1, 32+14+3+1, 32+14+4+1, 32+14+5+1, 32+14+6+5+1, 32+14+7+5+1, 32+14+8+1, 32+14+8+4+1, 32+14+8+5+1, 32+14+9+1, 32+14+9+4+1, 32+14+9+5+1, 32+14+10+9+1, 32+14+10+9+4+1, 32+14+10+9+5+1, 32+14+11+9+1, 32+14+11+9+4+1, 32+14+11+9+5+1, 32+16+1, 32+16+2+1, 32+16+3+1, 32+16+4+1, 32+16+5+1, 32+16+6+5+1, 32+16+7+5+1, 32+16+8+1, 32+16+8+4+1, 32+16+8+5+1, 32+16+9+1, 32+16+9+4+1, 32+16+9+5+1, 32+16+10+9+1, 32+16+10+9+4+1, 32+16+10+9+5+1, 32+16+11+9+1, 32+16+11+9+4+1, 32+16+11+9+5+1, 32+17+1, 32+17+2+1, 32+17+3+1, 32+17+4+1, 32+17+5+1, 32+17+6+5+1, 32+17+7+5+1, 32+17+8+1, 32+17+8+4+1, 32+17+8+5+1, 32+17+9+1, 32+17+9+4+1, 32+17+9+5+1, 32+17+10+9+1, 32+17+10+9+4+1, 32+17+10+9+5+1, 32+17+11+9+1, 32+17+11+9+4+1, 32+17+11+9+5+1, 32+17+12+1, 32+17+12+2+1, 32+17+12+3+1, 32+17+12+4+1, 32+17+12+5+1, 32+17+12+6+5+1, 32+17+12+7+5+1, 32+17+12+8+1, 32+17+12+8+4+1, 32+17+12+8+5+1, 32+17+12+9+1, 32+17+12+9+4+1, 32+17+12+9+5+1, 32+17+12+10+9+1, 32+17+12+10+9+4+1, 32+17+12+10+9+5+1, 32+17+12+11+9+1, 32+17+12+11+9+4+1, 32+17+12+11+9+5+1, 32+17+14+1, 32+17+14+2+1, 32+17+14+3+1, 32+17+14+4+1, 32+17+14+5+1, 32+17+14+6+5+1, 32+17+14+7+5+1, 32+17+14+8+1, 32+17+14+8+4+1, 32+17+14+8+5+1, 32+17+14+9+1, 32+17+14+9+4+1, 32+17+14+9+5+1, 32+17+14+10+9+1, 32+17+14+10+9+4+1, 32+17+14+10+9+5+1, 32+17+14+11+9+1, 32+17+14+11+9+4+1, 32+17+14+11+9+5+1, 32+17+16+1, 32+17+16+2+1, 32+17+16+3+1, 32+17+16+4+1, 32+17+16+5+1, 32+17+16+6+5+1, 32+17+16+7+5+1, 32+17+16+8+1, 32+17+16+8+4+1, 32+17+16+8+5+1, 32+17+16+9+1, 32+17+16+9+4+1, 32+17+16+9+5+1, 32+17+16+10+9+1, 32+17+16+10+9+4+1, 32+17+16+10+9+5+1, 32+17+16+11+9+1, 32+17+16+11+9+4+1, 32+17+16+11+9+5+1, 32+22+1, 32+22+2+1, 32+22+3+1, 32+22+4+1, 32+22+5+1, 32+22+6+5+1, 32+22+7+5+1, 32+22+8+1, 32+22+8+4+1, 32+22+8+5+1, 32+22+9+1, 32+22+9+4+1, 32+22+9+5+1, 32+22+10+9+1, 32+22+10+9+4+1, 32+22+10+9+5+1, 32+22+11+9+1, 32+22+11+9+4+1, 32+22+11+9+5+1, 32+22+12+1, 32+22+12+2+1, 32+22+12+3+1, 32+22+12+4+1, 32+22+12+5+1, 32+22+12+6+5+1, 32+22+12+7+5+1, 32+22+12+8+1, 32+22+12+8+4+1, 32+22+12+8+5+1, 32+22+12+9+1, 32+22+12+9+4+1, 32+22+12+9+5+1, 32+22+12+10+9+1, 32+22+12+10+9+4+1, 32+22+12+10+9+5+1, 32+22+12+11+9+1, 32+22+12+11+9+4+1, 32+22+12+11+9+5+1, 32+22+14+1, 32+22+14+2+1, 32+22+14+3+1, 32+22+14+4+1, 32+22+14+5+1, 32+22+14+6+5+1, 32+22+14+7+5+1, 32+22+14+8+1, 32+22+14+8+4+1, 32+22+14+8+5+1, 32+22+14+9+1, 32+22+14+9+4+1, 32+22+14+9+5+1, 32+22+14+10+9+1, 32+22+14+10+9+4+1, 32+22+14+10+9+5+1, 32+22+14+11+9+1, 32+22+14+11+9+4+1, 32+22+14+11+9+5+1, 32+22+16+1, 32+22+16+2+1, 32+22+16+3+1, 32+22+16+4+1, 32+22+16+5+1, 32+22+16+6+5+1, 32+22+16+7+5+1, 32+22+16+8+1, 32+22+16+8+4+1, 32+22+16+8+5+1, 32+22+16+9+1, 32+22+16+9+4+1, 32+22+16+9+5+1, 32+22+16+10+9+1, 32+22+16+10+9+4+1, 32+22+16+10+9+5+1, 32+22+16+11+9+1, 32+22+16+11+9+4+1, 32+22+16+11+9+5+1, 32+30+1, 32+30+2+1, 32+30+3+1, 32+30+4+1, 32+30+5+1, 32+30+6+5+1, 32+30+7+5+1, 32+30+8+1, 32+30+8+4+1, 32+30+8+5+1, 32+30+9+1, 32+30+9+4+1, 32+30+9+5+1, 32+30+10+9+1, 32+30+10+9+4+1, 32+30+10+9+5+1, 32+30+11+9+1, 32+30+11+9+4+1, 32+30+11+9+5+1, 32+30+12+1, 32+30+12+2+1, 32+30+12+3+1, 32+30+12+4+1, 32+30+12+5+1, 32+30+12+6+5+1, 32+30+12+7+5+1, 32+30+12+8+1, 32+30+12+8+4+1, 32+30+12+8+5+1, 32+30+12+9+1, 32+30+12+9+4+1, 32+30+12+9+5+1, 32+30+12+10+9+1, 32+30+12+10+9+4+1, 32+30+12+10+9+5+1, 32+30+12+11+9+1, 32+30+12+11+9+4+1, 32+30+12+11+9+5+1, 32+30+14+1, 32+30+14+2+1, 32+30+14+3+1, 32+30+14+4+1, 32+30+14+5+1, 32+30+14+6+5+1, 32+30+14+7+5+1, 32+30+14+8+1, 32+30+14+8+4+1, 32+30+14+8+5+1, 32+30+14+9+1, 32+30+14+9+4+1, 32+30+14+9+5+1, 32+30+14+10+9+1, 32+30+14+10+9+4+1, 32+30+14+10+9+5+1, 32+30+14+11+9+1, 32+30+14+11+9+4+1, 32+30+14+11+9+5+1, 32+30+16+1, 32+30+16+2+1, 32+30+16+3+1, 32+30+16+4+1, 32+30+16+5+1, 32+30+16+6+5+1, 32+30+16+7+5+1, 32+30+16+8+1, 32+30+16+8+4+1, 32+30+16+8+5+1, 32+30+16+9+1, 32+30+16+9+4+1, 32+30+16+9+5+1, 32+30+16+10+9+1, 32+30+16+10+9+4+1, 32+30+16+10+9+5+1, 32+30+16+11+9+1, 32+30+16+11+9+4+1, 32+30+16+11+9+5+1, 33+1, 33+2+1, 33+3+1, 33+4+1, 33+5+1, 33+6+5+1, 33+7+5+1, 33+8+1, 33+8+4+1, 33+8+5+1, 33+9+1, 33+9+4+1, 33+9+5+1, 33+10+9+1, 33+10+9+4+1, 33+10+9+5+1, 33+11+9+1, 33+11+9+4+1, 33+11+9+5+1, 33+12+1, 33+12+2+1, 33+12+3+1, 33+12+4+1, 33+12+5+1, 33+12+6+5+1, 33+12+7+5+1, 33+12+8+1, 33+12+8+4+1, 33+12+8+5+1, 33+12+9+1, 33+12+9+4+1, 33+12+9+5+1, 33+12+10+9+1, 33+12+10+9+4+1, 33+12+10+9+5+1, 33+12+11+9+1, 33+12+11+9+4+1, 33+12+11+9+5+1, 33+14+1, 33+14+2+1, 33+14+3+1, 33+14+4+1, 33+14+5+1, 33+14+6+5+1, 33+14+7+5+1, 33+14+8+1, 33+14+8+4+1, 33+14+8+5+1, 33+14+9+1, 33+14+9+4+1, 33+14+9+5+1, 33+14+10+9+1, 33+14+10+9+4+1, 33+14+10+9+5+1, 33+14+11+9+1, 33+14+11+9+4+1, 33+14+11+9+5+1, 33+16+1, 33+16+2+1, 33+16+3+1, 33+16+4+1, 33+16+5+1, 33+16+6+5+1, 33+16+7+5+1, 33+16+8+1, 33+16+8+4+1, 33+16+8+5+1, 33+16+9+1, 33+16+9+4+1, 33+16+9+5+1, 33+16+10+9+1, 33+16+10+9+4+1, 33+16+10+9+5+1, 33+16+11+9+1, 33+16+11+9+4+1, 33+16+11+9+5+1, 33+17+1, 33+17+2+1, 33+17+3+1, 33+17+4+1, 33+17+5+1, 33+17+6+5+1, 33+17+7+5+1, 33+17+8+1, 33+17+8+4+1, 33+17+8+5+1, 33+17+9+1, 33+17+9+4+1, 33+17+9+5+1, 33+17+10+9+1, 33+17+10+9+4+1, 33+17+10+9+5+1, 33+17+11+9+1, 33+17+11+9+4+1, 33+17+11+9+5+1, 33+17+12+1, 33+17+12+2+1, 33+17+12+3+1, 33+17+12+4+1, 33+17+12+5+1, 33+17+12+6+5+1, 33+17+12+7+5+1, 33+17+12+8+1, 33+17+12+8+4+1, 33+17+12+8+5+1, 33+17+12+9+1, 33+17+12+9+4+1, 33+17+12+9+5+1, 33+17+12+10+9+1, 33+17+12+10+9+4+1, 33+17+12+10+9+5+1, 33+17+12+11+9+1, 33+17+12+11+9+4+1, 33+17+12+11+9+5+1, 33+17+14+1, 33+17+14+2+1, 33+17+14+3+1, 33+17+14+4+1, 33+17+14+5+1, 33+17+14+6+5+1, 33+17+14+7+5+1, 33+17+14+8+1, 33+17+14+8+4+1, 33+17+14+8+5+1, 33+17+14+9+1, 33+17+14+9+4+1, 33+17+14+9+5+1, 33+17+14+10+9+1, 33+17+14+10+9+4+1, 33+17+14+10+9+5+1, 33+17+14+11+9+1, 33+17+14+11+9+4+1, 33+17+14+11+9+5+1, 33+17+16+1, 33+17+16+2+1, 33+17+16+3+1, 33+17+16+4+1, 33+17+16+5+1, 33+17+16+6+5+1, 33+17+16+7+5+1, 33+17+16+8+1, 33+17+16+8+4+1, 33+17+16+8+5+1, 33+17+16+9+1, 33+17+16+9+4+1, 33+17+16+9+5+1, 33+17+16+10+9+1, 33+17+16+10+9+4+1, 33+17+16+10+9+5+1, 33+17+16+11+9+1, 33+17+16+11+9+4+1, 33+17+16+11+9+5+1, 33+22+1, 33+22+2+1, 33+22+3+1, 33+22+4+1, 33+22+5+1, 33+22+6+5+1, 33+22+7+5+1, 33+22+8+1, 33+22+8+4+1, 33+22+8+5+1, 33+22+9+1, 33+22+9+4+1, 33+22+9+5+1, 33+22+10+9+1, 33+22+10+9+4+1, 33+22+10+9+5+1, 33+22+11+9+1, 33+22+11+9+4+1, 33+22+11+9+5+1, 33+22+12+1, 33+22+12+2+1, 33+22+12+3+1, 33+22+12+

4+1, 33+22+12+5+1, 33+22+12+6+5+1, 33+22+12+7+5+1, 33+22+12+8+1, 33+22+12+8+4+1, 33+22+12+8+5+1, 33+22+12+9+1, 33+22+12+9+4+1, 33+22+12+9+5+1, 33+22+12+10+9+1, 33+22+12+10+9+4+1, 33+22+12+10+9+5+1, 33+22+12+11+9+1, 33+22+12+11+9+4+1, 33+22+12+11+9+5+1, 33+22+14+1, 33+22+14+2+1, 33+22+14+3+1, 33+22+14+4+1, 33+22+14+5+1, 33+22+14+6+5+1, 33+22+14+7+5+1, 33+22+14+8+1, 33+22+14+8+4+1, 33+22+14+8+5+1, 33+22+14+9+1, 33+22+14+9+4+1, 33+22+14+9+5+1, 33+22+14+10+9+1, 33+22+14+10+9+4+1, 33+22+14+10+9+5+1, 33+22+14+11+9+1, 33+22+14+11+9+4+1, 33+22+14+11+9+5+1, 33+22+16+1, 33+22+16+2+1, 33+22+16+3+1, 33+22+16+4+1, 33+22+16+5+1, 33+22+16+6+5+1, 33+22+16+7+5+1, 33+22+16+8+1, 33+22+16+8+4+1, 33+22+16+8+5+1, 33+22+16+9+1, 33+22+16+9+4+1, 33+22+16+9+5+1, 33+22+16+10+9+1, 33+22+16+10+9+4+1, 33+22+16+10+9+5+1, 33+22+16+11+9+1, 33+22+16+11+9+4+1, 33+22+16+11+9+5+1, 33+30+1, 33+30+2+1, 33+30+3+1, 33+30+4+1, 33+30+5+1, 33+30+6+5+1, 33+30+7+5+1, 33+30+8+1, 33+30+8+4+1, 33+30+8+5+1, 33+30+9+1, 33+30+9+4+1, 33+30+9+5+1, 33+30+10+9+1, 33+30+10+9+4+1, 33+30+10+9+5+1, 33+30+11+9+1, 33+30+11+9+4+1, 33+30+11+9+5+1, 33+30+12+1, 33+30+12+2+1, 33+30+12+3+1, 33+30+12+4+1, 33+30+12+5+1, 33+30+12+6+5+1, 33+30+12+7+5+1, 33+30+12+8+1, 33+30+12+8+4+1, 33+30+12+8+5+1, 33+30+12+9+1, 33+30+12+9+4+1, 33+30+12+9+5+1, 33+30+12+10+9+1, 33+30+12+10+9+4+1, 33+30+12+10+9+5+1, 33+30+12+11+9+1, 33+30+12+11+9+4+1, 33+30+12+11+9+5+1, 33+30+14+1, 33+30+14+2+1, 33+30+14+3+1, 33+30+14+4+1, 33+30+14+5+1, 33+30+14+6+5+1, 33+30+14+7+5+1, 33+30+14+8+1, 33+30+14+8+4+1, 33+30+14+8+5+1, 33+30+14+9+1, 33+30+14+9+4+1, 33+30+14+9+5+1, 33+30+14+10+9+1, 33+30+14+10+9+4+1, 33+30+14+10+9+5+1, 33+30+14+11+9+1, 33+30+14+11+9+4+1, 33+30+14+11+9+5+1, 33+30+16+1, 33+30+16+2+1, 33+30+16+3+1, 33+30+16+4+1, 33+30+16+5+1, 33+30+16+6+5+1, 33+30+16+7+5+1, 33+30+16+8+1, 33+30+16+8+4+1, 33+30+16+8+5+1, 33+30+16+9+1, 33+30+16+9+4+1, 33+30+16+9+5+1, 33+30+16+10+9+1, 33+30+16+10+9+4+1, 33+30+16+10+9+5+1, 33+30+16+11+9+1, 33+30+16+11+9+4+1, 33+30+16+11+9+5+1, 34+33+1, 34+33+2+1, 34+33+3+1, 34+33+4+1, 34+33+5+1, 34+33+6+5+1, 34+33+7+5+1, 34+33+8+1, 34+33+8+4+1, 34+33+8+5+1, 34+33+9+1, 34+33+9+4+1, 34+33+9+5+1, 34+33+10+9+1, 34+33+10+9+4+1, 34+33+10+9+5+1, 34+33+11+9+1, 34+33+11+9+4+1, 34+33+11+9+5+1, 34+33+12+1, 34+33+12+2+1, 34+33+12+3+1, 34+33+12+4+1, 34+33+12+5+1, 34+33+12+6+5+1, 34+33+12+7+5+1, 34+33+12+8+1, 34+33+12+8+4+1, 34+33+12+8+5+1, 34+33+12+9+1, 34+33+12+9+4+1, 34+33+12+9+5+1, 34+33+12+10+9+1, 34+33+12+10+9+4+1, 34+33+12+10+9+5+1, 34+33+12+11+9+1, 34+33+12+11+9+4+1, 34+33+12+11+9+5+1, 34+33+14+1, 34+33+14+2+1, 34+33+14+3+1, 34+33+14+4+1, 34+33+14+5+1, 34+33+14+6+5+1, 34+33+14+7+5+1, 34+33+14+8+1, 34+33+14+8+4+1, 34+33+14+8+5+1, 34+33+14+9+1, 34+33+14+9+4+1, 34+33+14+9+5+1, 34+33+14+10+9+1, 34+33+14+10+9+4+1, 34+33+14+10+9+5+1, 34+33+14+11+9+1, 34+33+14+11+9+4+1, 34+33+14+11+9+5+1, 34+33+16+1, 34+33+16+2+1, 34+33+16+3+1, 34+33+16+4+1, 34+33+16+5+1, 34+33+16+6+5+1, 34+33+16+7+5+1, 34+33+16+8+1, 34+33+16+8+4+1, 34+33+16+8+5+1, 34+33+16+9+1, 34+33+16+9+4+1, 34+33+16+9+5+1, 34+33+16+10+9+1, 34+33+16+10+9+4+1, 34+33+16+10+9+5+1, 34+33+16+11+9+1, 34+33+16+11+9+4+1, 34+33+16+11+9+5+1, 34+33+17+1, 34+33+17+2+1, 34+33+17+3+1, 34+33+17+4+1, 34+33+17+5+1, 34+33+17+6+5+1, 34+33+17+7+5+1, 34+33+17+8+1, 34+33+17+8+4+1, 34+33+17+8+5+1, 34+33+17+9+1, 34+33+17+9+4+1, 34+33+17+9+5+1, 34+33+17+10+9+1, 34+33+17+10+9+4+1, 34+33+17+10+9+5+1, 34+33+17+11+9+1, 34+33+17+11+9+4+1, 34+33+17+11+9+5+1, 34+33+17+12+1, 34+33+17+12+2+1, 34+33+17+12+3+1, 34+33+17+12+4+1, 34+33+17+12+5+1, 34+33+17+12+6+5+1, 34+33+17+12+7+5+1, 34+33+17+12+8+1, 34+33+17+12+8+4+1, 34+33+17+12+8+5+1, 34+33+17+12+9+1, 34+33+17+12+9+4+1, 34+33+17+12+9+5+1, 34+33+17+12+10+9+1, 34+33+17+12+10+9+4+1, 34+33+17+12+10+9+5+1, 34+33+17+12+11+9+1, 34+33+17+12+11+9+4+1, 34+33+17+12+11+9+5+1, 34+33+17+14+1, 34+33+17+14+2+1, 34+33+17+14+3+1, 34+33+17+14+4+1, 34+33+17+14+5+1, 34+33+17+14+6+5+1, 34+33+17+14+7+5+1, 34+33+17+14+8+1, 34+33+17+14+8+4+1, 34+33+17+14+8+5+1, 34+33+17+14+9+1, 34+33+17+14+9+4+1, 34+33+17+14+9+5+1, 34+33+17+14+10+9+1, 34+33+17+14+10+9+4+1, 34+33+17+14+10+9+5+1, 34+33+17+14+11+9+1, 34+33+17+14+11+9+4+1, 34+33+17+14+11+9+5+1, 34+33+17+16+1, 34+33+17+16+2+1, 34+33+17+16+3+1, 34+33+17+16+4+1, 34+33+17+16+5+1, 34+33+17+16+6+5+1, 34+33+17+16+7+5+1, 34+33+17+16+8+1, 34+33+17+16+8+4+1, 34+33+17+16+8+5+1, 34+33+17+16+9+1, 34+33+17+16+9+4+1, 34+33+17+16+9+5+1, 34+33+17+16+10+9+1, 34+33+17+16+10+9+4+1, 34+33+17+16+10+9+5+1, 34+33+17+16+11+9+1, 34+33+17+16+11+9+4+1, 34+33+17+16+11+9+5+1, 34+33+22+1, 34+33+22+2+1, 34+33+22+3+1, 34+33+22+4+1, 34+33+22+5+1, 34+33+22+6+5+1, 34+33+22+7+5+1, 34+33+22+8+1, 34+33+22+8+4+1, 34+33+22+8+5+1, 34+33+22+9+1, 34+33+22+9+4+1, 34+33+22+9+5+1, 34+33+22+10+9+1, 34+33+22+10+9+4+1, 34+33+22+10+9+5+1, 34+33+22+11+9+1, 34+33+22+11+9+4+1, 34+33+22+11+9+5+1, 34+33+22+12+1, 34+33+22+12+2+1, 34+33+22+12+3+1, 34+33+22+12+4+1, 34+33+22+12+5+1, 34+33+22+12+6+5+1, 34+33+22+12+7+5+1, 34+33+22+12+8+1, 34+33+22+12+8+4+1, 34+33+22+12+8+5+1, 34+33+22+12+9+1, 34+33+22+12+9+4+1, 34+33+22+12+9+5+1, 34+33+22+12+10+9+1, 34+33+22+12+10+9+4+1, 34+33+22+12+10+9+5+1, 34+33+22+12+11+9+1, 34+33+22+12+11+9+4+1, 34+33+22+12+11+9+5+1, 34+33+22+14+1, 34+33+22+14+2+1, 34+33+22+14+3+1, 34+33+22+14+4+1, 34+33+22+14+5+1, 34+33+22+14+6+5+1, 34+33+22+14+7+5+1, 34+33+22+14+8+1, 34+33+22+14+8+4+1, 34+33+22+14+8+5+1, 34+33+22+14+9+1, 34+33+22+14+9+4+1, 34+33+22+14+9+5+1, 34+33+22+14+10+9+1, 34+33+22+14+10+9+4+1, 34+33+22+14+10+9+5+1, 34+33+22+14+11+9+1, 34+33+22+14+11+9+4+1, 34+33+22+14+11+9+5+1, 34+33+22+16+1, 34+33+22+16+2+1, 34+33+22+16+3+1, 34+33+22+16+4+1, 34+33+22+16+5+1, 34+33+22+16+6+5+1, 34+33+22+16+7+5+1, 34+33+22+16+8+1, 34+33+22+16+8+4+1, 34+33+22+16+8+5+1, 34+33+22+16+9+1, 34+33+22+16+9+4+1, 34+33+22+16+9+5+1, 34+33+22+16+10+9+1, 34+33+22+16+10+9+4+1, 34+33+22+16+10+9+5+1, 34+33+22+16+11+9+1, 34+33+22+16+11+9+4+1, 34+33+22+16+11+9+5+1, 34+33+30+1, 34+33+30+2+1, 34+33+30+3+1, 34+33+30+4+1, 34+33+30+5+1, 34+33+30+6+5+1, 34+33+30+7+5+1, 34+33+30+8+1, 34+33+30+8+4+1, 34+33+30+8+5+1, 34+33+30+9+1, 34+33+30+9+4+1, 34+33+30+9+5+1, 34+33+30+10+9+1, 34+33+30+10+9+4+1, 34+33+30+10+9+5+1, 34+33+30+11+9+1, 34+33+30+11+9+4+1, 34+33+30+11+9+5+1, 34+33+30+12+1, 34+33+30+12+2+1, 34+33+30+12+3+1, 34+33+30+12+4+1, 34+33+30+12+5+1, 34+33+30+12+6+5+1, 34+33+30+12+7+5+1, 34+33+30+12+8+1, 34+33+30+12+8+4+1, 34+33+30+12+8+5+1, 34+33+30+12+9+1, 34+33+

30+12+9+4+1, 34+33+30+12+9+5+1, 34+33+30+12+10+ 9+1, 34+33+30+12+10+9+4+1, 34+33+30+12+10+9+5+1, 34+33+30+12+11+9+1, 34+33+30+12+11+9+4+1, 34+33+ 30+12+11+9+5+1, 34+33+30+14+1, 34+33+30+14+2+1, 34+33+30+14+3+1, 34+33+30+14+4+1, 34+33+30+14+5+ 1, 34+33+30+14+6+5+1, 34+33+30+14+7+5+1, 34+33+ 30+14+8+1, 34+33+30+14+8+4+1, 34+33+30+14+8+5+1, 34+33+30+14+9+1, 34+33+30+14+9+4+1, 34+33+30+14+ 9+5+1, 34+33+30+14+10+9+1, 34+33+30+14+10+9+4+1, 34+33+30+14+10+9+5+1, 34+33+30+14+11+9+1, 34+33+ 30+14+11+9+4+1, 34+33+30+14+11+9+5+1, 34+33+30+ 16+1, 34+33+30+16+2+1, 34+33+30+16+3+1, 34+33+30+ 16+4+1, 34+33+30+16+5+1, 34+33+30+16+6+5+1, 34+33+30+16+7+5+1, 34+33+30+16+8+1, 34+33+30+16+ 8+4+1, 34+33+30+16+8+5+1, 34+33+30+16+9+1, 34+33+ 30+16+9+4+1, 34+33+30+16+9+5+1, 34+33+30+16+10+ 9+1, 34+33+30+16+10+9+4+1, 34+33+30+16+10+9+5+1, 34+33+30+16+11+9+1, 34+33+30+16+11+9+4+1, 34+33+ 30+16+11+9+5+1, 35+34+33+1, 35+34+33+2+1, 35+34+ 33+3+1, 35+34+33+4+1, 35+34+33+5+1, 35+34+33+6+5+ 1, 35+34+33+7+5+1, 35+34+33+8+1, 35+34+33+8+4+1, 35+34+33+8+5+1, 35+34+33+9+1, 35+34+33+9+4+1, 35+34+33+9+5+1, 35+34+33+10+9+1, 35+34+33+10+9+ 4+1, 35+34+33+10+9+5+1, 35+34+33+11+9+1, 35+34+ 33+11+9+4+1, 35+34+33+11+9+5+1, 35+34+33+12+1, 35+34+33+12+2+1, 35+34+33+12+3+1, 35+34+33+12+4+ 1, 35+34+33+12+5+1, 35+34+33+12+6+5+1, 35+34+33+ 12+7+5+1, 35+34+33+12+8+1, 35+34+33+12+8+4+1, 35+34+33+12+8+5+1, 35+34+33+12+9+1, 35+34+33+12+ 9+4+1, 35+34+33+12+9+5+1, 35+34+33+12+10+9+1, 35+34+33+12+10+9+4+1, 35+34+33+12+10+9+5+1, 35+34+33+12+11+9+1, 35+34+33+12+11+9+4+1, 35+34+ 33+12+11+9+5+1, 35+34+33+14+1, 35+34+33+14+2+1, 35+34+33+14+3+1, 35+34+33+14+4+1, 35+34+33+14+5+ 1, 35+34+33+14+6+5+1, 35+34+33+14+7+5+1, 35+34+ 33+14+8+1, 35+34+33+14+8+4+1, 35+34+33+14+8+5+1, 35+34+33+14+9+1, 35+34+33+14+9+4+1, 35+34+33+14+ 9+5+1, 35+34+33+14+10+9+1, 35+34+33+14+10+9+4+1, 35+34+33+14+10+9+5+1, 35+34+33+14+11+9+1, 35+34+ 33+14+11+9+4+1, 35+34+33+14+11+9+5+1, 35+34+33+ 16+1, 35+34+33+16+2+1, 35+34+33+16+3+1, 35+34+33+ 16+4+1, 35+34+33+16+5+1, 35+34+33+16+6+5+1, 35+34+33+16+7+5+1, 35+34+33+16+8+1, 35+34+33+16+ 8+4+1, 35+34+33+16+8+5+1, 35+34+33+16+9+1, 35+34+ 33+16+9+4+1, 35+34+33+16+9+5+1, 35+34+33+16+10+ 9+1, 35+34+33+16+10+9+4+1, 35+34+33+16+10+9+5+1, 35+34+33+16+11+9+1, 35+34+33+16+11+9+4+1, 35+34+ 33+16+11+9+5+1, 35+34+33+17+1, 35+34+33+17+2+1, 35+34+33+17+3+1, 35+34+33+17+4+1, 35+34+33+17+5+ 1, 35+34+33+17+6+5+1, 35+34+33+17+7+5+1, 35+34+ 33+17+8+1, 35+34+33+17+8+4+1, 35+34+33+17+8+5+1, 35+34+33+17+9+1, 35+34+33+17+9+4+1, 35+34+33+17+ 9+5+1, 35+34+33+17+10+9+1, 35+34+33+17+10+9+4+1, 35+34+33+17+10+9+5+1, 35+34+33+17+11+9+1, 35+34+ 33+17+11+9+4+1, 35+34+33+17+11+9+5+1, 35+34+33+ 17+12+1, 35+34+33+17+12+2+1, 35+34+33+17+12+3+1, 35+34+33+17+12+4+1, 35+34+33+17+12+5+1, 35+34+ 33+17+12+6+5+1, 35+34+33+17+12+7+5+1, 35+34+33+ 17+12+8+1, 35+34+33+17+12+8+4+1, 35+34+33+17+12+ 8+5+1, 35+34+33+17+12+9+1, 35+34+33+17+12+9+4+1, 35+34+33+17+12+9+5+1, 35+34+33+17+12+10+9+1, 35+34+33+17+12+10+9+4+1, 35+34+33+17+12+10+9+5+ 1, 35+34+33+17+12+11+9+1, 35+34+33+17+12+11+9+4+ 1, 35+34+33+17+12+11+9+5+1, 35+34+33+17+14+1, 35+34+33+17+14+2+1, 35+34+33+17+14+3+1, 35+34+ 33+17+14+4+1, 35+34+33+17+14+5+1, 35+34+33+17+ 14+6+5+1, 35+34+33+17+14+7+5+1, 35+34+33+17+14+ 8+1, 35+34+33+17+14+8+4+1, 35+34+33+17+14+8+5+1, 35+34+33+17+14+9+1, 35+34+33+17+14+9+4+1, 35+34+ 33+17+14+9+5+1, 35+34+33+17+14+10+9+1, 35+34+33+ 17+14+10+9+4+1, 35+34+33+17+14+10+9+5+1, 35+34+ 33+17+14+11+9+1, 35+34+33+17+14+11+9+4+1, 35+34+ 33+17+14+11+9+5+1, 35+34+33+17+16+1, 35+34+33+ 17+16+2+1, 35+34+33+17+16+3+1, 35+34+33+17+16+4+ 1, 35+34+33+17+16+5+1, 35+34+33+17+16+6+5+1, 35+34+33+17+16+7+5+1, 35+34+33+17+16+8+1, 35+34+ 33+17+16+8+4+1, 35+34+33+17+16+8+5+1, 35+34+33+ 17+16+9+1, 35+34+33+17+16+9+4+1, 35+34+33+17+16+ 9+5+1, 35+34+33+17+16+10+9+1, 35+34+33+17+16+10+ 9+4+1, 35+34+33+17+16+10+9+5+1, 35+34+33+17+16+ 11+9+1, 35+34+33+17+16+11+9+4+1, 35+34+33+17+16+ 11+9+5+1, 35+34+33+22+1, 35+34+33+22+2+1, 35+34+ 33+22+3+1, 35+34+33+22+4+1, 35+34+33+22+5+1, 35+34+33+22+6+5+1, 35+34+33+22+7+5+1, 35+34+33+ 22+8+1, 35+34+33+22+8+4+1, 35+34+33+22+8+5+1, 35+34+33+22+9+1, 35+34+33+22+9+4+1, 35+34+33+22+ 9+5+1, 35+34+33+22+10+9+1, 35+34+33+22+10+9+4+1, 35+34+33+22+10+9+5+1, 35+34+33+22+11+9+1, 35+34+ 33+22+11+9+4+1, 35+34+33+22+11+9+5+1, 35+34+33+ 22+12+1, 35+34+33+22+12+2+1, 35+34+33+22+12+3+1, 35+34+33+22+12+4+1, 35+34+33+22+12+5+1, 35+34+ 33+22+12+6+5+1, 35+34+33+22+12+7+5+1, 35+34+33+ 22+12+8+1, 35+34+33+22+12+8+4+1, 35+34+33+22+12+ 8+5+1, 35+34+33+22+12+9+1, 35+34+33+22+12+9+4+1, 35+34+33+22+12+9+5+1, 35+34+33+22+12+10+9+1, 35+34+33+22+12+10+9+4+1, 35+34+33+22+12+10+9+5+ 1, 35+34+33+22+12+11+9+1, 35+34+33+22+12+11+9+4+ 1, 35+34+33+22+12+11+9+5+1, 35+34+33+22+14+1, 35+34+33+22+14+2+1, 35+34+33+22+14+3+1, 35+34+ 33+22+14+4+1, 35+34+33+22+14+5+1, 35+34+33+22+ 14+6+5+1, 35+34+33+22+14+7+5+1, 35+34+33+22+14+ 8+1, 35+34+33+22+14+8+4+1, 35+34+33+22+14+8+5+1, 35+34+33+22+14+9+1, 35+34+33+22+14+9+4+1, 35+34+ 33+22+14+9+5+1, 35+34+33+22+14+10+9+1, 35+34+33+ 22+14+10+9+4+1, 35+34+33+22+14+10+9+5+1, 35+34+ 33+22+14+11+9+1, 35+34+33+22+14+11+9+4+1, 35+34+ 33+22+14+11+9+5+1, 35+34+33+22+16+1, 35+34+33+ 22+16+2+1, 35+34+33+22+16+3+1, 35+34+33+22+16+4+ 1, 35+34+33+22+16+5+1, 35+34+33+22+16+6+5+1, 35+34+33+22+16+7+5+1, 35+34+33+22+16+8+1, 35+34+ 33+22+16+8+4+1, 35+34+33+22+16+8+5+1, 35+34+33+ 22+16+9+1, 35+34+33+22+16+9+4+1, 35+34+33+22+16+ 9+5+1, 35+34+33+22+16+10+9+1, 35+34+33+22+16+10+ 9+4+1, 35+34+33+22+16+10+9+5+1, 35+34+33+22+16+ 11+9+1, 35+34+33+22+16+11+9+4+1, 35+34+33+22+16+ 11+9+5+1, 35+34+33+30+1, 35+34+33+30+2+1, 35+34+ 33+30+3+1, 35+34+33+30+4+1, 35+34+33+30+5+1, 35+34+33+30+6+5+1, 35+34+33+30+7+5+1, 35+34+33+ 30+8+1, 35+34+33+30+8+4+1, 35+34+33+30+8+5+1, 35+34+33+30+9+1, 35+34+33+30+9+4+1, 35+34+33+30+ 9+5+1, 35+34+33+30+10+9+1, 35+34+33+30+10+9+4+1, 35+34+33+30+10+9+5+1, 35+34+33+30+11+9+1, 35+34+ 33+30+11+9+4+1, 35+34+33+30+11+9+5+1, 35+34+33+ 30+12+1, 35+34+33+30+12+2+1, 35+34+33+30+12+3+1, 35+34+33+30+12+4+1, 35+34+33+30+12+5+1, 35+34+ 33+30+12+6+5+1, 35+34+33+30+12+7+5+1, 35+34+33+ 30+12+8+1, 35+34+33+30+12+8+4+1, 35+34+33+30+12+ 8+5+1, 35+34+33+30+12+9+1, 35+34+33+30+12+9+4+1, 35+34+33+30+12+9+5+1, 35+34+33+30+12+10+9+1, 35+34+33+30+12+10+9+4+1, 35+34+33+30+12+10+9+5+ 1, 35+34+33+30+12+11+9+1, 35+34+33+30+12+11+9+4+ 1, 35+34+33+30+12+11+9+5+1, 35+34+33+30+14+1, 35+34+33+30+14+2+1, 35+34+33+30+14+3+1, 35+34+ 33+30+14+4+1, 35+34+33+30+14+5+1, 35+34+33+30+

14+6+5+1, 35+34+33+30+14+7+5+1, 35+34+33+30+14+ 8+1, 35+34+33+30+14+8+4+1, 35+34+33+30+14+8+5+1, 35+34+33+30+14+9+1, 35+34+33+30+14+9+4+1, 35+34+ 33+30+14+9+5+1, 35+34+33+30+14+10+9+1, 35+34+33+ 30+14+10+9+4+1, 35+34+33+30+14+10+9+5+1, 35+34+ 33+30+14+11+9+1, 35+34+33+30+14+11+9+4+1, 35+34+ 33+30+14+11+9+5+1, 35+34+33+30+16+1, 35+34+33+ 30+16+2+1, 35+34+33+30+16+3+1, 35+34+33+30+16+4+ 1, 35+34+33+30+16+5+1, 35+34+33+30+16+6+5+1, 35+34+33+30+16+7+5+1, 35+34+33+30+16+8+1, 35+34+ 33+30+16+8+4+1, 35+34+33+30+16+8+5+1, 35+34+33+ 30+16+9+1, 35+34+33+30+16+9+4+1, 35+34+33+30+16+ 9+5+1, 35+34+33+30+16+10+9+1, 35+34+33+30+16+10+ 9+4+1, 35+34+33+30+16+10+9+5+1, 35+34+33+30+16+ 11+9+1, 35+34+33+30+16+11+9+4+1, 35+34+33+30+16+ 11+9+5+1, 36+34+33+1, 36+34+33+2+1, 36+34+33+3+1, 36+34+33+4+1, 36+34+33+5+1, 36+34+33+6+5+1, 36+34+33+7+5+1, 36+34+33+8+1, 36+34+33+8+4+1, 36+34+33+8+5+1, 36+34+33+9+1, 36+34+33+9+4+1, 36+34+33+9+5+1, 36+34+33+10+9+1, 36+34+33+10+9+ 4+1, 36+34+33+10+9+5+1, 36+34+33+11+9+1, 36+34+ 33+11+9+4+1, 36+34+33+11+9+5+1, 36+34+33+12+1, 36+34+33+12+2+1, 36+34+33+12+3+1, 36+34+33+12+4+ 1, 36+34+33+12+5+1, 36+34+33+12+6+5+1, 36+34+33+ 12+7+5+1, 36+34+33+12+8+1, 36+34+33+12+8+4+1, 36+34+33+12+8+5+1, 36+34+33+12+9+1, 36+34+33+12+ 9+4+1, 36+34+33+12+9+5+1, 36+34+33+12+10+9+1, 36+34+33+12+10+9+4+1, 36+34+33+12+10+9+5+1, 36+34+33+12+11+9+1, 36+34+33+12+11+9+4+1, 36+34+ 33+12+11+9+5+1, 36+34+33+14+1, 36+34+33+14+2+1, 36+34+33+14+3+1, 36+34+33+14+4+1, 36+34+33+14+5+ 1, 36+34+33+14+6+5+1, 36+34+33+14+7+5+1, 36+34+ 33+14+8+1, 36+34+33+14+8+4+1, 36+34+33+14+8+5+1, 36+34+33+14+9+1, 36+34+33+14+9+4+1, 36+34+33+14+ 9+5+1, 36+34+33+14+10+9+1, 36+34+33+14+10+9+4+1, 36+34+33+14+10+9+5+1, 36+34+33+14+11+9+1, 36+34+ 33+14+11+9+4+1, 36+34+33+14+11+9+5+1, 36+34+33+ 16+1, 36+34+33+16+2+1, 36+34+33+16+3+1, 36+34+33+ 16+4+1, 36+34+33+16+5+1, 36+34+33+16+6+5+1, 36+34+33+16+7+5+1, 36+34+33+16+8+1, 36+34+33+16+ 8+4+1, 36+34+33+16+8+5+1, 36+34+33+16+9+1, 36+34+ 33+16+9+4+1, 36+34+33+16+9+5+1, 36+34+33+16+10+ 9+1, 36+34+33+16+10+9+4+1, 36+34+33+16+10+9+5+1, 36+34+33+16+11+9+1, 36+34+33+16+11+9+4+1, 36+34+ 33+16+11+9+5+1, 36+34+33+17+1, 36+34+33+17+2+1, 36+34+33+17+3+1, 36+34+33+17+4+1, 36+34+33+17+5+ 1, 36+34+33+17+6+5+1, 36+34+33+17+7+5+1, 36+34+ 33+17+8+1, 36+34+33+17+8+4+1, 36+34+33+17+8+5+1, 36+34+33+17+9+1, 36+34+33+17+9+4+1, 36+34+33+17+ 9+5+1, 36+34+33+17+10+9+1, 36+34+33+17+10+9+4+1, 36+34+33+17+10+9+5+1, 36+34+33+17+11+9+1, 36+34+ 33+17+11+9+4+1, 36+34+33+17+11+9+5+1, 36+34+33+ 17+12+1, 36+34+33+17+12+2+1, 36+34+33+17+12+3+1, 36+34+33+17+12+4+1, 36+34+33+17+12+5+1, 36+34+ 33+17+12+6+5+1, 36+34+33+17+12+7+5+1, 36+34+33+ 17+12+8+1, 36+34+33+17+12+8+4+1, 36+34+33+17+12+ 8+5+1, 36+34+33+17+12+9+1, 36+34+33+17+12+9+4+1, 36+34+33+17+12+9+5+1, 36+34+33+17+12+10+9+1, 36+34+33+17+12+10+9+4+1, 36+34+33+17+12+10+9+5+ 1, 36+34+33+17+12+11+9+1, 36+34+33+17+12+11+9+4+ 1, 36+34+33+17+12+11+9+5+1, 36+34+33+17+14+1, 36+34+33+17+14+2+1, 36+34+33+17+14+3+1, 36+34+ 33+17+14+4+1, 36+34+33+17+14+5+1, 36+34+33+17+ 14+6+5+1, 36+34+33+17+14+7+5+1, 36+34+33+17+14+ 8+1, 36+34+33+17+14+8+4+1, 36+34+33+17+14+8+5+1, 36+34+33+17+14+9+1, 36+34+33+17+14+9+4+1, 36+34+ 33+17+14+9+5+1, 36+34+33+17+14+10+9+1, 36+34+33+ 17+14+10+9+4+1, 36+34+33+17+14+10+9+5+1, 36+34+ 33+17+14+11+9+1, 36+34+33+17+14+11+9+4+1, 36+34+ 33+17+14+11+9+5+1, 36+34+33+17+16+1, 36+34+33+ 17+16+2+1, 36+34+33+17+16+3+1, 36+34+33+17+16+4+ 1, 36+34+33+17+16+5+1, 36+34+33+17+16+6+5+1, 36+34+33+17+16+7+5+1, 36+34+33+17+16+8+1, 36+34+ 33+17+16+8+4+1, 36+34+33+17+16+8+5+1, 36+34+33+ 17+16+9+1, 36+34+33+17+16+9+4+1, 36+34+33+17+16+ 9+5+1, 36+34+33+17+16+10+9+1, 36+34+33+17+16+10+ 9+4+1, 36+34+33+17+16+10+9+5+1, 36+34+33+17+16+ 11+9+1, 36+34+33+17+16+11+9+4+1, 36+34+33+17+16+ 11+9+5+1, 36+34+33+22+1, 36+34+33+22+2+1, 36+34+ 33+22+3+1, 36+34+33+22+4+1, 36+34+33+22+5+1, 36+34+33+22+6+5+1, 36+34+33+22+7+5+1, 36+34+33+ 22+8+1, 36+34+33+22+8+4+1, 36+34+33+22+8+5+1, 36+34+33+22+9+1, 36+34+33+22+9+4+1, 36+34+33+22+ 9+5+1, 36+34+33+22+10+9+1, 36+34+33+22+10+9+4+1, 36+34+33+22+10+9+5+1, 36+34+33+22+11+9+1, 36+34+ 33+22+11+9+4+1, 36+34+33+22+11+9+5+1, 36+34+33+ 22+12+1, 36+34+33+22+12+2+1, 36+34+33+22+12+3+1, 36+34+33+22+12+4+1, 36+34+33+22+12+5+1, 36+34+ 33+22+12+6+5+1, 36+34+33+22+12+7+5+1, 36+34+33+ 22+12+8+1, 36+34+33+22+12+8+4+1, 36+34+33+22+12+ 8+5+1, 36+34+33+22+12+9+1, 36+34+33+22+12+9+4+1, 36+34+33+22+12+9+5+1, 36+34+33+22+12+10+9+1, 36+34+33+22+12+10+9+4+1, 36+34+33+22+12+10+9+5+ 1, 36+34+33+22+12+11+9+1, 36+34+33+22+12+11+9+4+ 1, 36+34+33+22+12+11+9+5+1, 36+34+33+22+14+1, 36+34+33+22+14+2+1, 36+34+33+22+14+3+1, 36+34+ 33+22+14+4+1, 36+34+33+22+14+5+1, 36+34+33+22+ 14+6+5+1, 36+34+33+22+14+7+5+1, 36+34+33+22+14+ 8+1, 36+34+33+22+14+8+4+1, 36+34+33+22+14+8+5+1, 36+34+33+22+14+9+1, 36+34+33+22+14+9+4+1, 36+34+ 33+22+14+9+5+1, 36+34+33+22+14+10+9+1, 36+34+33+ 22+14+10+9+4+1, 36+34+33+22+14+10+9+5+1, 36+34+ 33+22+14+11+9+1, 36+34+33+22+14+11+9+4+1, 36+34+ 33+22+14+11+9+5+1, 36+34+33+22+16+1, 36+34+33+ 22+16+2+1, 36+34+33+22+16+3+1, 36+34+33+22+16+4+ 1, 36+34+33+22+16+5+1, 36+34+33+22+16+6+5+1, 36+34+33+22+16+7+5+1, 36+34+33+22+16+8+1, 36+34+ 33+22+16+8+4+1, 36+34+33+22+16+8+5+1, 36+34+33+ 22+16+9+1, 36+34+33+22+16+9+4+1, 36+34+33+22+16+ 9+5+1, 36+34+33+22+16+10+9+1, 36+34+33+22+16+10+ 9+4+1, 36+34+33+22+16+10+9+5+1, 36+34+33+22+16+ 11+9+1, 36+34+33+22+16+11+9+4+1, 36+34+33+22+16+ 11+9+5+1, 36+34+33+30+1, 36+34+33+30+2+1, 36+34+ 33+30+3+1, 36+34+33+30+4+1, 36+34+33+30+5+1, 36+34+33+30+6+5+1, 36+34+33+30+7+5+1, 36+34+33+ 30+8+1, 36+34+33+30+8+4+1, 36+34+33+30+8+5+1, 36+34+33+30+9+1, 36+34+33+30+9+4+1, 36+34+33+30+ 9+5+1, 36+34+33+30+10+9+1, 36+34+33+30+10+9+4+1, 36+34+33+30+10+9+5+1, 36+34+33+30+11+9+1, 36+34+ 33+30+11+9+4+1, 36+34+33+30+11+9+5+1, 36+34+33+ 30+12+1, 36+34+33+30+12+2+1, 36+34+33+30+12+3+1, 36+34+33+30+12+4+1, 36+34+33+30+12+5+1, 36+34+ 33+30+12+6+5+1, 36+34+33+30+12+7+5+1, 36+34+33+ 30+12+8+1, 36+34+33+30+12+8+4+1, 36+34+33+30+12+ 8+5+1, 36+34+33+30+12+9+1, 36+34+33+30+12+9+4+1, 36+34+33+30+12+9+5+1, 36+34+33+30+12+10+9+1, 36+34+33+30+12+10+9+4+1, 36+34+33+30+12+10+9+5+ 1, 36+34+33+30+12+11+9+1, 36+34+33+30+12+11+9+4+ 1, 36+34+33+30+12+11+9+5+1, 36+34+33+30+14+1, 36+34+33+30+14+2+1, 36+34+33+30+14+3+1, 36+34+ 33+30+14+4+1, 36+34+33+30+14+5+1, 36+34+33+30+ 14+6+5+1, 36+34+33+30+14+7+5+1, 36+34+33+30+14+ 8+1, 36+34+33+30+14+8+4+1, 36+34+33+30+14+8+5+1, 36+34+33+30+14+9+1, 36+34+33+30+14+9+4+1, 36+34+

33+30+14+9+5+1, 36+34+33+30+14+10+9+1, 36+34+33+30+14+10+9+4+1, 36+34+33+30+14+10+9+5+1, 36+34+33+30+14+11+9+1, 36+34+33+30+14+11+9+4+1, 36+34+33+30+14+11+9+5+1, 36+34+33+30+16+1, 36+34+33+30+16+2+1, 36+34+33+30+16+3+1, 36+34+33+30+16+4+1, 36+34+33+30+16+5+1, 36+34+33+30+16+6+5+1, 36+34+33+30+16+7+5+1, 36+34+33+30+16+8+1, 36+34+33+30+16+8+4+1, 36+34+33+30+16+8+5+1, 36+34+33+30+16+9+1, 36+34+33+30+16+9+4+1, 36+34+33+30+16+9+5+1, 36+34+33+30+16+10+9+1, 36+34+33+30+16+10+9+4+1, 36+34+33+30+16+10+9+5+1, 36+34+33+30+16+11+9+1, 36+34+33+30+16+11+9+4+1, 36+34+33+30+16+11+9+5+1, 37+33+1, 37+33+2+1, 37+33+3+1, 37+33+4+1, 37+33+5+1, 37+33+6+5+1, 37+33+7+5+1, 37+33+8+1, 37+33+8+4+1, 37+33+8+5+1, 37+33+9+1, 37+33+9+4+1, 37+33+9+5+1, 37+33+10+9+1, 37+33+10+9+4+1, 37+33+10+9+5+1, 37+33+11+9+1, 37+33+11+9+4+1, 37+33+11+9+5+1, 37+33+12+1, 37+33+12+2+1, 37+33+12+3+1, 37+33+12+4+1, 37+33+12+5+1, 37+33+12+6+5+1, 37+33+12+7+5+1, 37+33+12+8+1, 37+33+12+8+4+1, 37+33+12+8+5+1, 37+33+12+9+1, 37+33+12+9+4+1, 37+33+12+9+5+1, 37+33+12+10+9+1, 37+33+12+10+9+4+1, 37+33+12+10+9+5+1, 37+33+12+11+9+1, 37+33+12+11+9+4+1, 37+33+12+11+9+5+1, 37+33+14+1, 37+33+14+2+1, 37+33+14+3+1, 37+33+14+4+1, 37+33+14+5+1, 37+33+14+6+5+1, 37+33+14+7+5+1, 37+33+14+8+1, 37+33+14+8+4+1, 37+33+14+8+5+1, 37+33+14+9+1, 37+33+14+9+4+1, 37+33+14+9+5+1, 37+33+14+10+9+1, 37+33+14+10+9+4+1, 37+33+14+10+9+5+1, 37+33+14+11+9+1, 37+33+14+11+9+4+1, 37+33+14+11+9+5+1, 37+33+16+1, 37+33+16+2+1, 37+33+16+3+1, 37+33+16+4+1, 37+33+16+5+1, 37+33+16+6+5+1, 37+33+16+7+5+1, 37+33+16+8+1, 37+33+16+8+4+1, 37+33+16+8+5+1, 37+33+16+9+1, 37+33+16+9+4+1, 37+33+16+9+5+1, 37+33+16+10+9+1, 37+33+16+10+9+4+1, 37+33+16+10+9+5+1, 37+33+16+11+9+1, 37+33+16+11+9+4+1, 37+33+16+11+9+5+1, 37+33+17+1, 37+33+17+2+1, 37+33+17+3+1, 37+33+17+4+1, 37+33+17+5+1, 37+33+17+6+5+1, 37+33+17+7+5+1, 37+33+17+8+1, 37+33+17+8+4+1, 37+33+17+8+5+1, 37+33+17+9+1, 37+33+17+9+4+1, 37+33+17+9+5+1, 37+33+17+10+9+1, 37+33+17+10+9+4+1, 37+33+17+10+9+5+1, 37+33+17+11+9+1, 37+33+17+11+9+4+1, 37+33+17+11+9+5+1, 37+33+17+12+1, 37+33+17+12+2+1, 37+33+17+12+3+1, 37+33+17+12+4+1, 37+33+17+12+5+1, 37+33+17+12+6+5+1, 37+33+17+12+7+5+1, 37+33+17+12+8+1, 37+33+17+12+8+4+1, 37+33+17+12+8+5+1, 37+33+17+12+9+1, 37+33+17+12+9+4+1, 37+33+17+12+9+5+1, 37+33+17+12+10+9+1, 37+33+17+12+10+9+4+1, 37+33+17+12+10+9+5+1, 37+33+17+12+11+9+1, 37+33+17+12+11+9+4+1, 37+33+17+12+11+9+5+1, 37+33+17+14+1, 37+33+17+14+2+1, 37+33+17+14+3+1, 37+33+17+14+4+1, 37+33+17+14+5+1, 37+33+17+14+6+5+1, 37+33+17+14+7+5+1, 37+33+17+14+8+1, 37+33+17+14+8+4+1, 37+33+17+14+8+5+1, 37+33+17+14+9+1, 37+33+17+14+9+4+1, 37+33+17+14+9+5+1, 37+33+17+14+10+9+1, 37+33+17+14+10+9+4+1, 37+33+17+14+10+9+5+1, 37+33+17+14+11+9+1, 37+33+17+14+11+9+4+1, 37+33+17+14+11+9+5+1, 37+33+17+16+1, 37+33+17+16+2+1, 37+33+17+16+3+1, 37+33+17+16+4+1, 37+33+17+16+5+1, 37+33+17+16+6+5+1, 37+33+17+16+7+5+1, 37+33+17+16+8+1, 37+33+17+16+8+4+1, 37+33+17+16+8+5+1, 37+33+17+16+9+1, 37+33+17+16+9+4+1, 37+33+17+16+9+5+1, 37+33+17+16+10+9+1, 37+33+17+16+10+9+4+1, 37+33+17+16+10+9+5+1, 37+33+17+16+11+9+1, 37+33+17+16+11+9+4+1, 37+33+17+16+11+9+5+1, 37+33+22+1, 37+33+22+2+1, 37+33+22+3+1, 37+33+22+4+1, 37+33+22+5+1, 37+33+22+6+5+1, 37+33+22+7+5+1, 37+33+22+8+1, 37+33+22+8+4+1, 37+33+22+8+5+1, 37+33+22+9+1, 37+33+22+9+4+1, 37+33+22+9+5+1, 37+33+22+10+9+1, 37+33+22+10+9+4+1, 37+33+22+10+9+5+1, 37+33+22+11+9+1, 37+33+22+11+9+4+1, 37+33+22+11+9+5+1, 37+33+22+12+1, 37+33+22+12+2+1, 37+33+22+12+3+1, 37+33+22+12+4+1, 37+33+22+12+5+1, 37+33+22+12+6+5+1, 37+33+22+12+7+5+1, 37+33+22+12+8+1, 37+33+22+12+8+4+1, 37+33+22+12+8+5+1, 37+33+22+12+9+1, 37+33+22+12+9+4+1, 37+33+22+12+9+5+1, 37+33+22+12+10+9+1, 37+33+22+12+10+9+4+1, 37+33+22+12+10+9+5+1, 37+33+22+12+11+9+1, 37+33+22+12+11+9+4+1, 37+33+22+12+11+9+5+1, 37+33+22+14+1, 37+33+22+14+2+1, 37+33+22+14+3+1, 37+33+22+14+4+1, 37+33+22+14+5+1, 37+33+22+14+6+5+1, 37+33+22+14+7+5+1, 37+33+22+14+8+1, 37+33+22+14+8+4+1, 37+33+22+14+8+5+1, 37+33+22+14+9+1, 37+33+22+14+9+4+1, 37+33+22+14+9+5+1, 37+33+22+14+10+9+1, 37+33+22+14+10+9+4+1, 37+33+22+14+10+9+5+1, 37+33+22+14+11+9+1, 37+33+22+14+11+9+4+1, 37+33+22+14+11+9+5+1, 37+33+22+16+1, 37+33+22+16+2+1, 37+33+22+16+3+1, 37+33+22+16+4+1, 37+33+22+16+5+1, 37+33+22+16+6+5+1, 37+33+22+16+7+5+1, 37+33+22+16+8+1, 37+33+22+16+8+4+1, 37+33+22+16+8+5+1, 37+33+22+16+9+1, 37+33+22+16+9+4+1, 37+33+22+16+9+5+1, 37+33+22+16+10+9+1, 37+33+22+16+10+9+4+1, 37+33+22+16+10+9+5+1, 37+33+22+16+11+9+1, 37+33+22+16+11+9+4+1, 37+33+22+16+11+9+5+1, 37+33+30+1, 37+33+30+2+1, 37+33+30+3+1, 37+33+30+4+1, 37+33+30+5+1, 37+33+30+6+5+1, 37+33+30+7+5+1, 37+33+30+8+1, 37+33+30+8+4+1, 37+33+30+8+5+1, 37+33+30+9+1, 37+33+30+9+4+1, 37+33+30+9+5+1, 37+33+30+10+9+1, 37+33+30+10+9+4+1, 37+33+30+10+9+5+1, 37+33+30+11+9+1, 37+33+30+11+9+4+1, 37+33+30+11+9+5+1, 37+33+30+12+1, 37+33+30+12+2+1, 37+33+30+12+3+1, 37+33+30+12+4+1, 37+33+30+12+5+1, 37+33+30+12+6+5+1, 37+33+30+12+7+5+1, 37+33+30+12+8+1, 37+33+30+12+8+4+1, 37+33+30+12+8+5+1, 37+33+30+12+9+1, 37+33+30+12+9+4+1, 37+33+30+12+9+5+1, 37+33+30+12+10+9+1, 37+33+30+12+10+9+4+1, 37+33+30+12+10+9+5+1, 37+33+30+12+11+9+1, 37+33+30+12+11+9+4+1, 37+33+30+12+11+9+5+1, 37+33+30+14+1, 37+33+30+14+2+1, 37+33+30+14+3+1, 37+33+30+14+4+1, 37+33+30+14+5+1, 37+33+30+14+6+5+1, 37+33+30+14+7+5+1, 37+33+30+14+8+1, 37+33+30+14+8+4+1, 37+33+30+14+8+5+1, 37+33+30+14+9+1, 37+33+30+14+9+4+1, 37+33+30+14+9+5+1, 37+33+30+14+10+9+1, 37+33+30+14+10+9+4+1, 37+33+30+14+10+9+5+1, 37+33+30+14+11+9+1, 37+33+30+14+11+9+4+1, 37+33+30+14+11+9+5+1, 37+33+30+16+1, 37+33+30+16+2+1, 37+33+30+16+3+1, 37+33+30+16+4+1, 37+33+30+16+5+1, 37+33+30+16+6+5+1, 37+33+30+16+7+5+1, 37+33+30+16+8+1, 37+33+30+16+8+4+1, 37+33+30+16+8+5+1, 37+33+30+16+9+1, 37+33+30+16+9+4+1, 37+33+30+16+9+5+1, 37+33+30+16+10+9+1, 37+33+30+16+10+9+4+1, 37+33+30+16+10+9+5+1, 37+33+30+16+11+9+1, 37+33+30+16+11+9+4+1, 37+33+30+16+11+9+5+1, 38+33+1, 38+33+2+1, 38+33+3+1, 38+33+4+1, 38+33+5+1, 38+33+6+5+1, 38+33+7+5+1, 38+33+8+1, 38+33+8+4+1, 38+33+8+5+1, 38+33+9+1, 38+33+9+4+1, 38+33+9+5+1, 38+33+10+9+1, 38+33+10+9+4+1, 38+33+10+9+5+1, 38+33+11+9+1, 38+33+11+9+4+1, 38+33+11+9+5+1, 38+33+12+1, 38+33+12+2+1, 38+33+12+3+1, 38+33+12+4+1, 38+33+12+5+1, 38+33+12+6+5+1, 38+33+12+7+5+1, 38+33+12+8+1, 38+33+12+8+4+1, 38+33+12+8+5+1, 38+33+12+9+1, 38+33+12+9+4+1, 38+33+12+9+5+1, 38+33+12+10+9+1, 38+33+12+10+9+4+1, 38+33+12+10+9+5+1, 38+33+12+11+9+1,

38+33+12+11+9+4+1, 38+33+12+11+9+5+1, 38+33+14+1, 38+33+14+2+1, 38+33+14+3+1, 38+33+14+4+1, 38+33+14+5+1, 38+33+14+6+5+1, 38+33+14+7+5+1, 38+33+14+8+1, 38+33+14+8+4+1, 38+33+14+8+5+1, 38+33+14+9+1, 38+33+14+9+4+1, 38+33+14+9+5+1, 38+33+14+10+9+1, 38+33+14+10+9+4+1, 38+33+14+10+9+5+1, 38+33+14+11+9+1, 38+33+14+11+9+4+1, 38+33+14+11+9+5+1, 38+33+16+1, 38+33+16+2+1, 38+33+16+3+1, 38+33+16+4+1, 38+33+16+5+1, 38+33+16+6+5+1, 38+33+16+7+5+1, 38+33+16+8+1, 38+33+16+8+4+1, 38+33+16+8+5+1, 38+33+16+9+1, 38+33+16+9+4+1, 38+33+16+9+5+1, 38+33+16+10+9+1, 38+33+16+10+9+4+1, 38+33+16+10+9+5+1, 38+33+16+11+9+1, 38+33+16+11+9+4+1, 38+33+16+11+9+5+1, 38+33+17+1, 38+33+17+2+1, 38+33+17+3+1, 38+33+17+4+1, 38+33+17+5+1, 38+33+17+6+5+1, 38+33+17+7+5+1, 38+33+17+8+1, 38+33+17+8+4+1, 38+33+17+8+5+1, 38+33+17+9+1, 38+33+17+9+4+1, 38+33+17+9+5+1, 38+33+17+10+9+1, 38+33+17+10+9+4+1, 38+33+17+10+9+5+1, 38+33+17+11+9+1, 38+33+17+11+9+4+1, 38+33+17+11+9+5+1, 38+33+17+12+1, 38+33+17+12+2+1, 38+33+17+12+3+1, 38+33+17+12+4+1, 38+33+17+12+5+1, 38+33+17+12+6+5+1, 38+33+17+12+7+5+1, 38+33+17+12+8+1, 38+33+17+12+8+4+1, 38+33+17+12+8+5+1, 38+33+17+12+9+1, 38+33+17+12+9+4+1, 38+33+17+12+9+5+1, 38+33+17+12+10+9+1, 38+33+17+12+10+9+4+1, 38+33+17+12+10+9+5+1, 38+33+17+12+11+9+1, 38+33+17+12+11+9+4+1, 38+33+17+12+11+9+5+1, 38+33+17+14+1, 38+33+17+14+2+1, 38+33+17+14+3+1, 38+33+17+14+4+1, 38+33+17+14+5+1, 38+33+17+14+6+5+1, 38+33+17+14+7+5+1, 38+33+17+14+8+1, 38+33+17+14+8+4+1, 38+33+17+14+8+5+1, 38+33+17+14+9+1, 38+33+17+14+9+4+1, 38+33+17+14+9+5+1, 38+33+17+14+10+9+1, 38+33+17+14+10+9+4+1, 38+33+17+14+10+9+5+1, 38+33+17+14+11+9+1, 38+33+17+14+11+9+4+1, 38+33+17+14+11+9+5+1, 38+33+17+16+1, 38+33+17+16+2+1, 38+33+17+16+3+1, 38+33+17+16+4+1, 38+33+17+16+5+1, 38+33+17+16+6+5+1, 38+33+17+16+7+5+1, 38+33+17+16+8+1, 38+33+17+16+8+4+1, 38+33+17+16+8+5+1, 38+33+17+16+9+1, 38+33+17+16+9+4+1, 38+33+17+16+9+5+1, 38+33+17+16+10+9+1, 38+33+17+16+10+9+4+1, 38+33+17+16+10+9+5+1, 38+33+17+16+11+9+1, 38+33+17+16+11+9+4+1, 38+33+17+16+11+9+5+1, 38+33+22+1, 38+33+22+2+1, 38+33+22+3+1, 38+33+22+4+1, 38+33+22+5+1, 38+33+22+6+5+1, 38+33+22+7+5+1, 38+33+22+8+1, 38+33+22+8+4+1, 38+33+22+8+5+1, 38+33+22+9+1, 38+33+22+9+4+1, 38+33+22+9+5+1, 38+33+22+10+9+1, 38+33+22+10+9+4+1, 38+33+22+10+9+5+1, 38+33+22+11+9+1, 38+33+22+11+9+4+1, 38+33+22+11+9+5+1, 38+33+22+12+1, 38+33+22+12+2+1, 38+33+22+12+3+1, 38+33+22+12+4+1, 38+33+22+12+5+1, 38+33+22+12+6+5+1, 38+33+22+12+7+5+1, 38+33+22+12+8+1, 38+33+22+12+8+4+1, 38+33+22+12+8+5+1, 38+33+22+12+9+1, 38+33+22+12+9+4+1, 38+33+22+12+9+5+1, 38+33+22+12+10+9+1, 38+33+22+12+10+9+4+1, 38+33+22+12+10+9+5+1, 38+33+22+12+11+9+1, 38+33+22+12+11+9+4+1, 38+33+22+12+11+9+5+1, 38+33+22+14+1, 38+33+22+14+2+1, 38+33+22+14+3+1, 38+33+22+14+4+1, 38+33+22+14+5+1, 38+33+22+14+6+5+1, 38+33+22+14+7+5+1, 38+33+22+14+8+1, 38+33+22+14+8+4+1, 38+33+22+14+8+5+1, 38+33+22+14+9+1, 38+33+22+14+9+4+1, 38+33+22+14+9+5+1, 38+33+22+14+10+9+1, 38+33+22+14+10+9+4+1, 38+33+22+14+10+9+5+1, 38+33+22+14+11+9+1, 38+33+22+14+11+9+4+1, 38+33+22+14+11+9+5+1, 38+33+22+16+1, 38+33+22+16+2+1, 38+33+22+16+3+1, 38+33+22+16+4+1, 38+33+22+16+5+1, 38+33+22+16+6+5+1, 38+33+22+16+7+5+1, 38+33+22+16+8+1, 38+33+22+16+8+4+1, 38+33+22+16+8+5+1, 38+33+22+16+9+1, 38+33+22+16+9+4+1, 38+33+22+16+9+5+1, 38+33+22+16+10+9+1, 38+33+22+16+10+9+4+1, 38+33+22+16+10+9+5+1, 38+33+22+16+11+9+1, 38+33+22+16+11+9+4+1, 38+33+22+16+11+9+5+1, 38+33+30+1, 38+33+30+2+1, 38+33+30+3+1, 38+33+30+4+1, 38+33+30+5+1, 38+33+30+6+5+1, 38+33+30+7+5+1, 38+33+30+8+1, 38+33+30+8+4+1, 38+33+30+8+5+1, 38+33+30+9+1, 38+33+30+9+4+1, 38+33+30+9+5+1, 38+33+30+10+9+1, 38+33+30+10+9+4+1, 38+33+30+10+9+5+1, 38+33+30+11+9+1, 38+33+30+11+9+4+1, 38+33+30+11+9+5+1, 38+33+30+12+1, 38+33+30+12+2+1, 38+33+30+12+3+1, 38+33+30+12+4+1, 38+33+30+12+5+1, 38+33+30+12+6+5+1, 38+33+30+12+7+5+1, 38+33+30+12+8+1, 38+33+30+12+8+4+1, 38+33+30+12+8+5+1, 38+33+30+12+9+1, 38+33+30+12+9+4+1, 38+33+30+12+9+5+1, 38+33+30+12+10+9+1, 38+33+30+12+10+9+4+1, 38+33+30+12+10+9+5+1, 38+33+30+12+11+9+1, 38+33+30+12+11+9+4+1, 38+33+30+12+11+9+5+1, 38+33+30+14+1, 38+33+30+14+2+1, 38+33+30+14+3+1, 38+33+30+14+4+1, 38+33+30+14+5+1, 38+33+30+14+6+5+1, 38+33+30+14+7+5+1, 38+33+30+14+8+1, 38+33+30+14+8+4+1, 38+33+30+14+8+5+1, 38+33+30+14+9+1, 38+33+30+14+9+4+1, 38+33+30+14+9+5+1, 38+33+30+14+10+9+1, 38+33+30+14+10+9+4+1, 38+33+30+14+10+9+5+1, 38+33+30+14+11+9+1, 38+33+30+14+11+9+4+1, 38+33+30+14+11+9+5+1, 38+33+30+16+1, 38+33+30+16+2+1, 38+33+30+16+3+1, 38+33+30+16+4+1, 38+33+30+16+5+1, 38+33+30+16+6+5+1, 38+33+30+16+7+5+1, 38+33+30+16+8+1, 38+33+30+16+8+4+1, 38+33+30+16+8+5+1, 38+33+30+16+9+1, 38+33+30+16+9+4+1, 38+33+30+16+9+5+1, 38+33+30+16+10+9+1, 38+33+30+16+10+9+4+1, 38+33+30+16+10+9+5+1, 38+33+30+16+11+9+1, 38+33+30+16+11+9+4+1, 38+33+30+16+11+9+5+1, 39+33+1, 39+33+2+1, 39+33+3+1, 39+33+4+1, 39+33+5+1, 39+33+6+5+1, 39+33+7+5+1, 39+33+8+1, 39+33+8+4+1, 39+33+8+5+1, 39+33+9+1, 39+33+9+4+1, 39+33+9+5+1, 39+33+10+9+1, 39+33+10+9+4+1, 39+33+10+9+5+1, 39+33+11+9+1, 39+33+11+9+4+1, 39+33+11+9+5+1, 39+33+12+1, 39+33+12+2+1, 39+33+12+3+1, 39+33+12+4+1, 39+33+12+5+1, 39+33+12+6+5+1, 39+33+12+7+5+1, 39+33+12+8+1, 39+33+12+8+4+1, 39+33+12+8+5+1, 39+33+12+9+1, 39+33+12+9+4+1, 39+33+12+9+5+1, 39+33+12+10+9+1, 39+33+12+10+9+4+1, 39+33+12+10+9+5+1, 39+33+12+11+9+1, 39+33+12+11+9+4+1, 39+33+12+11+9+5+1, 39+33+14+1, 39+33+14+2+1, 39+33+14+3+1, 39+33+14+4+1, 39+33+14+5+1, 39+33+14+6+5+1, 39+33+14+7+5+1, 39+33+14+8+1, 39+33+14+8+4+1, 39+33+14+8+5+1, 39+33+14+9+1, 39+33+14+9+4+1, 39+33+14+9+5+1, 39+33+14+10+9+1, 39+33+14+10+9+4+1, 39+33+14+10+9+5+1, 39+33+14+11+9+1, 39+33+14+11+9+4+1, 39+33+14+11+9+5+1, 39+33+16+1, 39+33+16+2+1, 39+33+16+3+1, 39+33+16+4+1, 39+33+16+5+1, 39+33+16+6+5+1, 39+33+16+7+5+1, 39+33+16+8+1, 39+33+16+8+4+1, 39+33+16+8+5+1, 39+33+16+9+1, 39+33+16+9+4+1, 39+33+16+9+5+1, 39+33+16+10+9+1, 39+33+16+10+9+4+1, 39+33+16+10+9+5+1, 39+33+16+11+9+1, 39+33+16+11+9+4+1, 39+33+16+11+9+5+1, 39+33+17+1, 39+33+17+2+1, 39+33+17+3+1, 39+33+17+4+1, 39+33+17+5+1, 39+33+17+6+5+1, 39+33+17+7+5+1, 39+33+17+8+1, 39+33+17+8+4+1, 39+33+17+8+5+1, 39+33+17+9+1, 39+33+17+9+4+1, 39+33+17+9+5+1, 39+33+17+10+9+1, 39+33+17+10+9+4+1, 39+33+17+10+9+5+1, 39+33+17+11+9+1, 39+33+17+11+9+4+1, 39+33+17+11+9+5+1, 39+33+17+12+1, 39+33+17+12+2+1, 39+33+17+12+3+1, 39+33+17+12+4+1, 39+33+17+12+5+1, 39+33+17+12+6+5+1, 39+33+17+12+7+5+1, 39+33+17+12+8+1, 39+33+17+12+8+4+1,

39+33+17+12+8+5+1, 39+33+17+12+9+1, 39+33+17+12+9+4+1, 39+33+17+12+9+5+1, 39+33+17+12+10+9+1, 39+33+17+12+10+9+4+1, 39+33+17+12+10+9+5+1, 39+33+17+12+11+9+1, 39+33+17+12+11+9+4+1, 39+33+17+12+11+9+5+1, 39+33+17+14+1, 39+33+17+14+2+1, 39+33+17+14+3+1, 39+33+17+14+4+1, 39+33+17+14+5+1, 39+33+17+14+6+5+1, 39+33+17+14+7+5+1, 39+33+17+14+8+1, 39+33+17+14+8+4+1, 39+33+17+14+8+5+1, 39+33+17+14+9+1, 39+33+17+14+9+4+1, 39+33+17+14+9+5+1, 39+33+17+14+10+9+1, 39+33+17+14+10+9+4+1, 39+33+17+14+10+9+5+1, 39+33+17+14+11+9+1, 39+33+17+14+11+9+4+1, 39+33+17+14+11+9+5+1, 39+33+17+16+1, 39+33+17+16+2+1, 39+33+17+16+3+1, 39+33+17+16+4+1, 39+33+17+16+5+1, 39+33+17+16+6+5+1, 39+33+17+16+7+5+1, 39+33+17+16+8+1, 39+33+17+16+8+4+1, 39+33+17+16+8+5+1, 39+33+17+16+9+1, 39+33+17+16+9+4+1, 39+33+17+16+9+5+1, 39+33+17+16+10+9+1, 39+33+17+16+10+9+4+1, 39+33+17+16+10+9+5+1, 39+33+17+16+11+9+1, 39+33+17+16+11+9+4+1, 39+33+17+16+11+9+5+1, 39+33+22+1, 39+33+22+2+1, 39+33+22+3+1, 39+33+22+4+1, 39+33+22+5+1, 39+33+22+6+5+1, 39+33+22+7+5+1, 39+33+22+8+1, 39+33+22+8+4+1, 39+33+22+8+5+1, 39+33+22+9+1, 39+33+22+9+4+1, 39+33+22+9+5+1, 39+33+22+10+9+1, 39+33+22+10+9+4+1, 39+33+22+10+9+5+1, 39+33+22+11+9+1, 39+33+22+11+9+4+1, 39+33+22+11+9+5+1, 39+33+22+12+1, 39+33+22+12+2+1, 39+33+22+12+3+1, 39+33+22+12+4+1, 39+33+22+12+5+1, 39+33+22+12+6+5+1, 39+33+22+12+7+5+1, 39+33+22+12+8+1, 39+33+22+12+8+4+1, 39+33+22+12+8+5+1, 39+33+22+12+9+1, 39+33+22+12+9+4+1, 39+33+22+12+9+5+1, 39+33+22+12+10+9+1, 39+33+22+12+10+9+4+1, 39+33+22+12+10+9+5+1, 39+33+22+12+11+9+1, 39+33+22+12+11+9+4+1, 39+33+22+12+11+9+5+1, 39+33+22+14+1, 39+33+22+14+2+1, 39+33+22+14+3+1, 39+33+22+14+4+1, 39+33+22+14+5+1, 39+33+22+14+6+5+1, 39+33+22+14+7+5+1, 39+33+22+14+8+1, 39+33+22+14+8+4+1, 39+33+22+14+8+5+1, 39+33+22+14+9+1, 39+33+22+14+9+4+1, 39+33+22+14+9+5+1, 39+33+22+14+10+9+1, 39+33+22+14+10+9+4+1, 39+33+22+14+10+9+5+1, 39+33+22+14+11+9+1, 39+33+22+14+11+9+4+1, 39+33+22+14+11+9+5+1, 39+33+22+16+1, 39+33+22+16+2+1, 39+33+22+16+3+1, 39+33+22+16+4+1, 39+33+22+16+5+1, 39+33+22+16+6+5+1, 39+33+22+16+7+5+1, 39+33+22+16+8+1, 39+33+22+16+8+4+1, 39+33+22+16+8+5+1, 39+33+22+16+9+1, 39+33+22+16+9+4+1, 39+33+22+16+9+5+1, 39+33+22+16+10+9+1, 39+33+22+16+10+9+4+1, 39+33+22+16+10+9+5+1, 39+33+22+16+11+9+1, 39+33+22+16+11+9+4+1, 39+33+22+16+11+9+5+1, 39+33+30+1, 39+33+30+2+1, 39+33+30+3+1, 39+33+30+4+1, 39+33+30+5+1, 39+33+30+6+5+1, 39+33+30+7+5+1, 39+33+30+8+1, 39+33+30+8+4+1, 39+33+30+8+5+1, 39+33+30+9+1, 39+33+30+9+4+1, 39+33+30+9+5+1, 39+33+30+10+9+1, 39+33+30+10+9+4+1, 39+33+30+10+9+5+1, 39+33+30+11+9+1, 39+33+30+11+9+4+1, 39+33+30+11+9+5+1, 39+33+30+12+1, 39+33+30+12+2+1, 39+33+30+12+3+1, 39+33+30+12+4+1, 39+33+30+12+5+1, 39+33+30+12+6+5+1, 39+33+30+12+7+5+1, 39+33+30+12+8+1, 39+33+30+12+8+4+1, 39+33+30+12+8+5+1, 39+33+30+12+9+1, 39+33+30+12+9+4+1, 39+33+30+12+9+5+1, 39+33+30+12+10+9+1, 39+33+30+12+10+9+4+1, 39+33+30+12+10+9+5+1, 39+33+30+12+11+9+1, 39+33+30+12+11+9+4+1, 39+33+30+12+11+9+5+1, 39+33+30+14+1, 39+33+30+14+2+1, 39+33+30+14+3+1, 39+33+30+14+4+1, 39+33+30+14+5+1, 39+33+30+14+6+5+1, 39+33+30+14+7+5+1, 39+33+30+14+8+1, 39+33+30+14+8+4+1, 39+33+30+14+8+5+1, 39+33+30+14+9+1, 39+33+30+14+9+4+1, 39+33+30+14+9+5+1, 39+33+30+14+10+9+1, 39+33+30+14+10+9+4+1, 39+33+30+14+10+9+5+1, 39+33+30+14+11+9+1, 39+33+30+14+11+9+4+1, 39+33+30+14+11+9+5+1, 39+33+30+16+1, 39+33+30+16+2+1, 39+33+30+16+3+1, 39+33+30+16+4+1, 39+33+30+16+5+1, 39+33+30+16+6+5+1, 39+33+30+16+7+5+1, 39+33+30+16+8+1, 39+33+30+16+8+4+1, 39+33+30+16+8+5+1, 39+33+30+16+9+1, 39+33+30+16+9+4+1, 39+33+30+16+9+5+1, 39+33+30+16+10+9+1, 39+33+30+16+10+9+4+1, 39+33+30+16+10+9+5+1, 39+33+30+16+11+9+1, 39+33+30+16+11+9+4+1, 39+33+30+16+11+9+5+1, 40+33+1, 40+33+2+1, 40+33+3+1, 40+33+4+1, 40+33+5+1, 40+33+6+5+1, 40+33+7+5+1, 40+33+8+1, 40+33+8+4+1, 40+33+8+5+1, 40+33+9+1, 40+33+9+4+1, 40+33+9+5+1, 40+33+10+9+1, 40+33+10+9+4+1, 40+33+10+9+5+1, 40+33+11+9+1, 40+33+11+9+4+1, 40+33+11+9+5+1, 40+33+12+1, 40+33+12+2+1, 40+33+12+3+1, 40+33+12+4+1, 40+33+12+5+1, 40+33+12+6+5+1, 40+33+12+7+5+1, 40+33+12+8+1, 40+33+12+8+4+1, 40+33+12+8+5+1, 40+33+12+9+1, 40+33+12+9+4+1, 40+33+12+9+5+1, 40+33+12+10+9+1, 40+33+12+10+9+4+1, 40+33+12+10+9+5+1, 40+33+12+11+9+1, 40+33+12+11+9+4+1, 40+33+12+11+9+5+1, 40+33+14+1, 40+33+14+2+1, 40+33+14+3+1, 40+33+14+4+1, 40+33+14+5+1, 40+33+14+6+5+1, 40+33+14+7+5+1, 40+33+14+8+1, 40+33+14+8+4+1, 40+33+14+8+5+1, 40+33+14+9+1, 40+33+14+9+4+1, 40+33+14+9+5+1, 40+33+14+10+9+1, 40+33+14+10+9+4+1, 40+33+14+10+9+5+1, 40+33+14+11+9+1, 40+33+14+11+9+4+1, 40+33+14+11+9+5+1, 40+33+16+1, 40+33+16+2+1, 40+33+16+3+1, 40+33+16+4+1, 40+33+16+5+1, 40+33+16+6+5+1, 40+33+16+7+5+1, 40+33+16+8+1, 40+33+16+8+4+1, 40+33+16+8+5+1, 40+33+16+9+1, 40+33+16+9+4+1, 40+33+16+9+5+1, 40+33+16+10+9+1, 40+33+16+10+9+4+1, 40+33+16+10+9+5+1, 40+33+16+11+9+1, 40+33+16+11+9+4+1, 40+33+16+11+9+5+1, 40+33+17+1, 40+33+17+2+1, 40+33+17+3+1, 40+33+17+4+1, 40+33+17+5+1, 40+33+17+6+5+1, 40+33+17+7+5+1, 40+33+17+8+1, 40+33+17+8+4+1, 40+33+17+8+5+1, 40+33+17+9+1, 40+33+17+9+4+1, 40+33+17+9+5+1, 40+33+17+10+9+1, 40+33+17+10+9+4+1, 40+33+17+10+9+5+1, 40+33+17+11+9+1, 40+33+17+11+9+4+1, 40+33+17+11+9+5+1, 40+33+17+12+1, 40+33+17+12+2+1, 40+33+17+12+3+1, 40+33+17+12+4+1, 40+33+17+12+5+1, 40+33+17+12+6+5+1, 40+33+17+12+7+5+1, 40+33+17+12+8+1, 40+33+17+12+8+4+1, 40+33+17+12+8+5+1, 40+33+17+12+9+1, 40+33+17+12+9+4+1, 40+33+17+12+9+5+1, 40+33+17+12+10+9+1, 40+33+17+12+10+9+4+1, 40+33+17+12+10+9+5+1, 40+33+17+12+11+9+1, 40+33+17+12+11+9+4+1, 40+33+17+12+11+9+5+1, 40+33+17+14+1, 40+33+17+14+2+1, 40+33+17+14+3+1, 40+33+17+14+4+1, 40+33+17+14+5+1, 40+33+17+14+6+5+1, 40+33+17+14+7+5+1, 40+33+17+14+8+1, 40+33+17+14+8+4+1, 40+33+17+14+8+5+1, 40+33+17+14+9+1, 40+33+17+14+9+4+1, 40+33+17+14+9+5+1, 40+33+17+14+10+9+1, 40+33+17+14+10+9+4+1, 40+33+17+14+10+9+5+1, 40+33+17+14+11+9+1, 40+33+17+14+11+9+4+1, 40+33+17+14+11+9+5+1, 40+33+17+16+1, 40+33+17+16+2+1, 40+33+17+16+3+1, 40+33+17+16+4+1, 40+33+17+16+5+1, 40+33+17+16+6+5+1, 40+33+17+16+7+5+1, 40+33+17+16+8+1, 40+33+17+16+8+4+1, 40+33+17+16+8+5+1, 40+33+17+16+9+1, 40+33+17+16+9+4+1, 40+33+17+16+9+5+1, 40+33+17+16+10+9+1, 40+33+17+16+10+9+4+1, 40+33+17+16+10+9+5+1, 40+33+17+16+11+9+1, 40+33+17+16+11+9+4+1, 40+33+17+16+11+9+5+1, 40+33+22+1, 40+33+22+2+1, 40+33+22+3+1, 40+33+22+4+1, 40+33+22+5+1, 40+33+22+6+5+1, 40+33+22+7+5+1, 40+33+22+8+1, 40+33+22+8+4+1, 40+33+22+8+5+1, 40+33+22+9+1, 40+33+22+9+4+1,

40+33+22+9+5+1, 40+33+22+10+9+1, 40+33+22+10+9+4+1, 40+33+22+10+9+5+1, 40+33+22+11+9+1, 40+33+22+11+9+4+1, 40+33+22+11+9+5+1, 40+33+22+12+1, 40+33+22+12+2+1, 40+33+22+12+3+1, 40+33+22+12+4+1, 40+33+22+12+5+1, 40+33+22+12+6+5+1, 40+33+22+12+7+5+1, 40+33+22+12+8+1, 40+33+22+12+8+4+1, 40+33+22+12+8+5+1, 40+33+22+12+9+1, 40+33+22+12+9+4+1, 40+33+22+12+9+5+1, 40+33+22+12+10+9+1, 40+33+22+12+10+9+4+1, 40+33+22+12+10+9+5+1, 40+33+22+12+11+9+1, 40+33+22+12+11+9+4+1, 40+33+22+12+11+9+5+1, 40+33+22+14+1, 40+33+22+14+2+1, 40+33+22+14+3+1, 40+33+22+14+4+1, 40+33+22+14+5+1, 40+33+22+14+6+5+1, 40+33+22+14+7+5+1, 40+33+22+14+8+1, 40+33+22+14+8+4+1, 40+33+22+14+8+5+1, 40+33+22+14+9+1, 40+33+22+14+9+4+1, 40+33+22+14+9+5+1, 40+33+22+14+10+9+1, 40+33+22+14+10+9+4+1, 40+33+22+14+10+9+5+1, 40+33+22+14+11+9+1, 40+33+22+14+11+9+4+1, 40+33+22+14+11+9+5+1, 40+33+22+16+1, 40+33+22+16+2+1, 40+33+22+16+3+1, 40+33+22+16+4+1, 40+33+22+16+5+1, 40+33+22+16+6+5+1, 40+33+22+16+7+5+1, 40+33+22+16+8+1, 40+33+22+16+8+4+1, 40+33+22+16+8+5+1, 40+33+22+16+9+1, 40+33+22+16+9+4+1, 40+33+22+16+9+5+1, 40+33+22+16+10+9+1, 40+33+22+16+10+9+4+1, 40+33+22+16+10+9+5+1, 40+33+22+16+11+9+1, 40+33+22+16+11+9+4+1, 40+33+22+16+11+9+5+1, 40+33+30+1, 40+33+30+2+1, 40+33+30+3+1, 40+33+30+4+1, 40+33+30+5+1, 40+33+30+6+5+1, 40+33+30+7+5+1, 40+33+30+8+1, 40+33+30+8+4+1, 40+33+30+8+5+1, 40+33+30+9+1, 40+33+30+9+4+1, 40+33+30+9+5+1, 40+33+30+10+9+1, 40+33+30+10+9+4+1, 40+33+30+10+9+5+1, 40+33+30+11+9+1, 40+33+30+11+9+4+1, 40+33+30+11+9+5+1, 40+33+30+12+1, 40+33+30+12+2+1, 40+33+30+12+3+1, 40+33+30+12+4+1, 40+33+30+12+5+1, 40+33+30+12+6+5+1, 40+33+30+12+7+5+1, 40+33+30+12+8+1, 40+33+30+12+8+4+1, 40+33+30+12+8+5+1, 40+33+30+12+9+1, 40+33+30+12+9+4+1, 40+33+30+12+9+5+1, 40+33+30+12+10+9+1, 40+33+30+12+10+9+4+1, 40+33+30+12+10+9+5+1, 40+33+30+12+11+9+1, 40+33+30+12+11+9+4+1, 40+33+30+12+11+9+5+1, 40+33+30+14+1, 40+33+30+14+2+1, 40+33+30+14+3+1, 40+33+30+14+4+1, 40+33+30+14+5+1, 40+33+30+14+6+5+1, 40+33+30+14+7+5+1, 40+33+30+14+8+1, 40+33+30+14+8+4+1, 40+33+30+14+8+5+1, 40+33+30+14+9+1, 40+33+30+14+9+4+1, 40+33+30+14+9+5+1, 40+33+30+14+10+9+1, 40+33+30+14+10+9+4+1, 40+33+30+14+10+9+5+1, 40+33+30+14+11+9+1, 40+33+30+14+11+9+4+1, 40+33+30+14+11+9+5+1, 40+33+30+16+1, 40+33+30+16+2+1, 40+33+30+16+3+1, 40+33+30+16+4+1, 40+33+30+16+5+1, 40+33+30+16+6+5+1, 40+33+30+16+7+5+1, 40+33+30+16+8+1, 40+33+30+16+8+4+1, 40+33+30+16+8+5+1, 40+33+30+16+9+1, 40+33+30+16+9+4+1, 40+33+30+16+9+5+1, 40+33+30+16+10+9+1, 40+33+30+16+10+9+4+1, 40+33+30+16+10+9+5+1, 40+33+30+16+11+9+1, 40+33+30+16+11+9+4+1, 40+33+30+16+11+9+5+1, 41+1, 41+2+1, 41+3+1, 41+4+1, 41+5+1, 41+6+5+1, 41+7+5+1, 41+8+1, 41+8+4+1, 41+8+5+1, 41+9+1, 41+9+4+1, 41+9+5+1, 41+10+9+1, 41+10+9+4+1, 41+10+9+5+1, 41+11+9+1, 41+11+9+4+1, 41+11+9+5+1, 41+12+1, 41+12+2+1, 41+12+3+1, 41+12+4+1, 41+12+5+1, 41+12+6+5+1, 41+12+7+5+1, 41+12+8+1, 41+12+8+4+1, 41+12+8+5+1, 41+12+9+1, 41+12+9+4+1, 41+12+9+5+1, 41+12+10+9+1, 41+12+10+9+4+1, 41+12+10+9+5+1, 41+12+11+9+1, 41+12+11+9+4+1, 41+12+11+9+5+1, 41+14+1, 41+14+2+1, 41+14+3+1, 41+14+4+1, 41+14+5+1, 41+14+6+5+1, 41+14+7+5+1, 41+14+8+1, 41+14+8+4+1, 41+14+8+5+1, 41+14+9+1, 41+14+9+4+1, 41+14+9+5+1, 41+14+10+9+1, 41+14+10+9+4+1, 41+14+10+9+5+1, 41+14+11+9+1, 41+14+11+9+4+1, 41+14+11+9+5+1, 41+16+1, 41+16+2+1, 41+16+3+1, 41+16+4+1, 41+16+5+1, 41+16+6+5+1, 41+16+7+5+1, 41+16+8+1, 41+16+8+4+1, 41+16+8+5+1, 41+16+9+1, 41+16+9+4+1, 41+16+9+5+1, 41+16+10+9+1, 41+16+10+9+4+1, 41+16+10+9+5+1, 41+16+11+9+1, 41+16+11+9+4+1, 41+16+11+9+5+1, 42+41+1, 42+41+2+1, 42+41+3+1, 42+41+4+1, 42+41+5+1, 42+41+6+5+1, 42+41+7+5+1, 42+41+8+1, 42+41+8+4+1, 42+41+8+5+1, 42+41+9+1, 42+41+9+4+1, 42+41+9+5+1, 42+41+10+9+1, 42+41+10+9+4+1, 42+41+10+9+5+1, 42+41+11+9+1, 42+41+11+9+4+1, 42+41+11+9+5+1, 42+41+12+1, 42+41+12+2+1, 42+41+12+3+1, 42+41+12+4+1, 42+41+12+5+1, 42+41+12+6+5+1, 42+41+12+7+5+1, 42+41+12+8+1, 42+41+12+8+4+1, 42+41+12+8+5+1, 42+41+12+9+1, 42+41+12+9+4+1, 42+41+12+9+5+1, 42+41+12+10+9+1, 42+41+12+10+9+4+1, 42+41+12+10+9+5+1, 42+41+12+11+9+1, 42+41+12+11+9+4+1, 42+41+12+11+9+5+1, 42+41+14+1, 42+41+14+2+1, 42+41+14+3+1, 42+41+14+4+1, 42+41+14+5+1, 42+41+14+6+5+1, 42+41+14+7+5+1, 42+41+14+8+1, 42+41+14+8+4+1, 42+41+14+8+5+1, 42+41+14+9+1, 42+41+14+9+4+1, 42+41+14+9+5+1, 42+41+14+10+9+1, 42+41+14+10+9+4+1, 42+41+14+10+9+5+1, 42+41+14+11+9+1, 42+41+14+11+9+4+1, 42+41+14+11+9+5+1, 42+41+16+1, 42+41+16+2+1, 42+41+16+3+1, 42+41+16+4+1, 42+41+16+5+1, 42+41+16+6+5+1, 42+41+16+7+5+1, 42+41+16+8+1, 42+41+16+8+4+1, 42+41+16+8+5+1, 42+41+16+9+1, 42+41+16+9+4+1, 42+41+16+9+5+1, 42+41+16+10+9+1, 42+41+16+10+9+4+1, 42+41+16+10+9+5+1, 42+41+16+11+9+1, 42+41+16+11+9+4+1, 42+41+16+11+9+5+1, 43+5+1, 44+43+5+1, 45+43+5+1, 46+43+5+1, 47+43+5+1, 48+43+5+1, 49+1, 49+2+1, 49+3+1, 49+4+1, 49+5+1, 49+6+5+1, 49+7+5+1, 49+8+1, 49+8+4+1, 49+8+5+1, 49+9+1, 49+9+4+1, 49+9+5+1, 49+10+9+1, 49+10+9+4+1, 49+10+9+5+1, 49+11+9+1, 49+11+9+4+1, 49+11+9+5+1, 49+12+1, 49+12+2+1, 49+12+3+1, 49+12+4+1, 49+12+5+1, 49+12+6+5+1, 49+12+7+5+1, 49+12+8+1, 49+12+8+4+1, 49+12+8+5+1, 49+12+9+1, 49+12+9+4+1, 49+12+9+5+1, 49+12+10+9+1, 49+12+10+9+4+1, 49+12+10+9+5+1, 49+12+11+9+1, 49+12+11+9+4+1, 49+12+11+9+5+1, 49+14+1, 49+14+2+1, 49+14+3+1, 49+14+4+1, 49+14+5+1, 49+14+6+5+1, 49+14+7+5+1, 49+14+8+1, 49+14+8+4+1, 49+14+8+5+1, 49+14+9+1, 49+14+9+4+1, 49+14+9+5+1, 49+14+10+9+1, 49+14+10+9+4+1, 49+14+10+9+5+1, 49+14+11+9+1, 49+14+11+9+4+1, 49+14+11+9+5+1, 49+16+1, 49+16+2+1, 49+16+3+1, 49+16+4+1, 49+16+5+1, 49+16+6+5+1, 49+16+7+5+1, 49+16+8+1, 49+16+8+4+1, 49+16+8+5+1, 49+16+9+1, 49+16+9+4+1, 49+16+9+5+1, 49+16+10+9+1, 49+16+10+9+4+1, 49+16+10+9+5+1, 49+16+11+9+1, 49+16+11+9+4+1, 49+16+11+9+5+1, 49+17+1, 49+17+2+1, 49+17+3+1, 49+17+4+1, 49+17+5+1, 49+17+6+5+1, 49+17+7+5+1, 49+17+8+1, 49+17+8+4+1, 49+17+8+5+1, 49+17+9+1, 49+17+9+4+1, 49+17+9+5+1, 49+17+10+9+1, 49+17+10+9+4+1, 49+17+10+9+5+1, 49+17+11+9+1, 49+17+11+9+4+1, 49+17+11+9+5+1, 49+17+12+1, 49+17+12+2+1, 49+17+12+3+1, 49+17+12+4+1, 49+17+12+5+1, 49+17+12+6+5+1, 49+17+12+7+5+1, 49+17+12+8+1, 49+17+12+8+4+1, 49+17+12+8+5+1, 49+17+12+9+1, 49+17+12+9+4+1, 49+17+12+9+5+1, 49+17+12+10+9+1, 49+17+12+10+9+4+1, 49+17+12+10+9+5+1, 49+17+12+11+9+1, 49+17+12+11+9+4+1, 49+17+12+11+9+5+1, 49+17+14+1, 49+17+14+2+1, 49+17+14+3+1, 49+17+14+4+1, 49+17+14+5+1, 49+17+14+6+5+1, 49+17+14+7+5+1, 49+17+14+8+1, 49+17+14+8+4+1, 49+17+14+8+5+1, 49+17+14+9+1, 49+17+14+9+4+1, 49+17+14+9+5+1, 49+17+14+10+9+1, 49+17+14+10+9+4+1, 49+17+14+10+9+5+1, 49+17+14+11+9+1, 49+17+

14+11+9+4+1, 49+17+14+11+9+5+1, 49+17+16+1, 49+17+16+2+1, 49+17+16+3+1, 49+17+16+4+1, 49+17+16+5+1, 49+17+16+6+5+1, 49+17+16+7+5+1, 49+17+16+8+1, 49+17+16+8+4+1, 49+17+16+8+5+1, 49+17+16+9+1, 49+17+16+9+4+1, 49+17+16+9+5+1, 49+17+16+10+9+1, 49+17+16+10+9+4+1, 49+17+16+10+9+5+1, 49+17+16+11+9+1, 49+17+16+11+9+4+1, 49+17+16+11+9+5+1, 49+22+1, 49+22+2+1, 49+22+3+1, 49+22+4+1, 49+22+5+1, 49+22+6+5+1, 49+22+7+5+1, 49+22+8+1, 49+22+8+4+1, 49+22+8+5+1, 49+22+9+1, 49+22+9+4+1, 49+22+9+5+1, 49+22+10+9+1, 49+22+10+9+4+1, 49+22+10+9+5+1, 49+22+11+9+1, 49+22+11+9+4+1, 49+22+11+9+5+1, 49+22+12+1, 49+22+12+2+1, 49+22+12+3+1, 49+22+12+4+1, 49+22+12+5+1, 49+22+12+6+5+1, 49+22+12+7+5+1, 49+22+12+8+1, 49+22+12+8+4+1, 49+22+12+8+5+1, 49+22+12+9+1, 49+22+12+9+4+1, 49+22+12+9+5+1, 49+22+12+10+9+1, 49+22+12+10+9+4+1, 49+22+12+10+9+5+1, 49+22+12+11+9+1, 49+22+12+11+9+4+1, 49+22+12+11+9+5+1, 49+22+14+1, 49+22+14+2+1, 49+22+14+3+1, 49+22+14+4+1, 49+22+14+5+1, 49+22+14+6+5+1, 49+22+14+7+5+1, 49+22+14+8+1, 49+22+14+8+4+1, 49+22+14+8+5+1, 49+22+14+9+1, 49+22+14+9+4+1, 49+22+14+9+5+1, 49+22+14+10+9+1, 49+22+14+10+9+4+1, 49+22+14+10+9+5+1, 49+22+14+11+9+1, 49+22+14+11+9+4+1, 49+22+14+11+9+5+1, 49+22+16+1, 49+22+16+2+1, 49+22+16+3+1, 49+22+16+4+1, 49+22+16+5+1, 49+22+16+6+5+1, 49+22+16+7+5+1, 49+22+16+8+1, 49+22+16+8+4+1, 49+22+16+8+5+1, 49+22+16+9+1, 49+22+16+9+4+1, 49+22+16+9+5+1, 49+22+16+10+9+1, 49+22+16+10+9+4+1, 49+22+16+10+9+5+1, 49+22+16+11+9+1, 49+22+16+11+9+4+1, 49+22+16+11+9+5+1, 49+30+1, 49+30+2+1, 49+30+3+1, 49+30+4+1, 49+30+5+1, 49+30+6+5+1, 49+30+7+5+1, 49+30+8+1, 49+30+8+4+1, 49+30+8+5+1, 49+30+9+1, 49+30+9+4+1, 49+30+9+5+1, 49+30+10+9+1, 49+30+10+9+4+1, 49+30+10+9+5+1, 49+30+11+9+1, 49+30+11+9+4+1, 49+30+11+9+5+1, 49+30+12+1, 49+30+12+2+1, 49+30+12+3+1, 49+30+12+4+1, 49+30+12+5+1, 49+30+12+6+5+1, 49+30+12+7+5+1, 49+30+12+8+1, 49+30+12+8+4+1, 49+30+12+8+5+1, 49+30+12+9+1, 49+30+12+9+4+1, 49+30+12+9+5+1, 49+30+12+10+9+1, 49+30+12+10+9+4+1, 49+30+12+10+9+5+1, 49+30+12+11+9+1, 49+30+12+11+9+4+1, 49+30+12+11+9+5+1, 49+30+14+1, 49+30+14+2+1, 49+30+14+3+1, 49+30+14+4+1, 49+30+14+5+1, 49+30+14+6+5+1, 49+30+14+7+5+1, 49+30+14+8+1, 49+30+14+8+4+1, 49+30+14+8+5+1, 49+30+14+9+1, 49+30+14+9+4+1, 49+30+14+9+5+1, 49+30+14+10+9+1, 49+30+14+10+9+4+1, 49+30+14+10+9+5+1, 49+30+14+11+9+1, 49+30+14+11+9+4+1, 49+30+14+11+9+5+1, 49+30+16+1, 49+30+16+2+1, 49+30+16+3+1, 49+30+16+4+1, 49+30+16+5+1, 49+30+16+6+5+1, 49+30+16+7+5+1, 49+30+16+8+1, 49+30+16+8+4+1, 49+30+16+8+5+1, 49+30+16+9+1, 49+30+16+9+4+1, 49+30+16+9+5+1, 49+30+16+10+9+1, 49+30+16+10+9+4+1, 49+30+16+10+9+5+1, 49+30+16+11+9+1, 49+30+16+11+9+4+1, 49+30+16+11+9+5+1, 50+1, 50+4+1, 51+1, 51+4+1, 52+1, 52+4+1, 53+1, 53+4+1, 54+1, 54+2+1, 54+3+1, 54+4+1, 54+5+1, 54+6+5+1, 54+7+5+1, 55+1, 55+5+1 and 56+1.

In the list above, the numbers refer to the embodiments according to their numbering provided hereinabove whereas "+" indicates the dependency from another embodiment. The different individualised embodiments are separated by commas. In other words, "8+4+1" for example refers to embodiment 8) depending on embodiment 4), depending on embodiment 1), i.e. embodiment "8+4+1" corresponds to embodiment 1) further limited by the features of embodiments 4) and 8). Likewise, "10+9+4+1" refers to embodiment 10) depending mutatis mutandis on embodiments 9) and 4), depending on embodiment 1), i.e. embodiment "10+9+4+1" corresponds to embodiment 1) further limited by the features of embodiment 4), further limited by the features of embodiments 9) and 10).

The compounds of formula I can be manufactured in accordance with the present invention using the procedures described hereafter.

Preparation of the Compounds of Formula I

Abbreviations

The following abbreviations are used throughout the specification and the examples:

Ac acetyl
AcOH acetic acid
Alloc allyloxycarbonyl
aq. aqueous
Boc tert-butoxycarbonyl
Bs 4-bromobenzenesulfonyl (brosylate)
Cbz benzyloxycarbonyl
CC column chromatography over silica gel
CDI 1,1'-carbonyldiimidazole
Cipro ciprofloxacin
Cy cyclohexyl
DAD diode array detection
dba dibenzylideneacetone
DCE 1,2-dichloroethane
DCM dichloromethane
DMAP 4-dimethylaminopyridine
DME 1,2-dimethoxyethane
DMF N,N-di methylformamide
DMSO dimethylsulfoxide
DPPA diphenylphosphoryl azide
DPPF 1,1'-bis(diphenylphosphino)ferrocene
EA ethyl acetate
EDC N-(3-dimethylaminopropyl)-N'-ethylcarbodiimide hydrochloride
ELSD evaporative light scattering detector
ESI electron spray ionisation
eq. equivalent
Et ethyl
EtOH ethanol
Hept heptane
Hex hexane
HPLC high pressure liquid chromatography
HV high vacuum conditions
IT internal temperature
LC liquid chromatography
Me methyl
MeCN acetonitrile
MeOH methanol
MS mass spectroscopy
Ms methanesulfonyl (mesyl)
Nf nonafluorobutanesulfonyl
NMR Nuclear Magnetic Resonance
Ns 4-nitrobenzenesulfonyl (nosylate)
org. organic
PCy$_3$ tricyclohexylphosphine
Pd/C palladium on carbon
Pd(OH)$_2$/C palladium dihydroxide on carbon
PEPPSI™-IPr [1,3-bis(2,6-diisopropylphenyl)imidazol-2-ylidene](3-chloropyridyl)palladium(II) dichloride
Ph phenyl
PMB 4-methoxybenzyl
prep-HPLC preparative high pressure liquid chromatography
Pyr pyridine Q-phos 1,2,3,4,5-pentaphenyl-1'-(di-tert-butylphosphino) ferrocene
rt room temperature
sat. saturated
SK-CC01-A 2'-(dimethylamino)-2-biphenylyl-palladium(II) chloride dinornbornylphosphine complex
S-Phos 2-dicyclohexylphosphino-2',6'-dimethoxybiphenyl
TBAF tetra-n-butylammonium fluoride
TBDMS tert-butyldimethylsilyl
TBDPS tert-butyldiphenylsilyl
TBME tert-butyl methyl ether
tBu tert-butyl
TEA triethylamine
Tf trifluoromethanesulfonyl (triflyl)
TFA trifluoroacetic acid
THF tetrahydrofuran
TLC thin layer chromatography
$t_R$ retention time
Ts para-toluenesulfonyl
XantPhos 4,5-bis(diphenylphosphino)-9,9-dimethylxanthene General Reaction Techniques:

General Reaction Technique 1 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, $MgSO_4$ or $Na_2SO_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. $NaBH_4$, $NaBH_3CN$, or $NaBH(OAc)_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (Sato et al., *Tetrahedron* (2004), 60, 7899-7906).

General Reaction Technique 2 (Removal of Amino Protecting Groups):

The Cbz protecting groups are removed by hydrogenolysis over a noble metal catalyst (e.g. Pd/C or $Pd(OH)_2/C$). The Boc group is removed under acidic conditions such as HCl in an org. solvent such as MeOH or dioxane, or TFA neat or diluted in a solvent such DCM. The Alloc group is removed in the presence of tetrakis(triphenylphosphine) palladium(0) in presence of an allyl cation scavenger such as morpholine, dimedone or tributyltin hydride between 0° C. and 50° C. in a solvent such as THF. The 4-methoxybenzyl group is removed using TFA neat or diluted in a solvent such as DCM. Further general methods to remove amine protecting groups have been described in T. W. Greene, P. G. M. Wuts, *Protecting Groups in Organic Synthesis*, 3$^{rd}$ Ed (1999), 494-653 (Publisher: John Wiley and Sons, Inc., New York, N.Y.).

General Reaction Technique 3 (Suzuki Coupling):

The aromatic halide (typically a bromide) is reacted with the required boronic acid derivative or its boronate ester equivalent (e.g. pinacol ester) in the presence of a palladium catalyst and a base such as $K_2CO_3$, $Cs_2CO_3$, $K_3PO_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as $Pd(PPh_3)_4$. These catalysts can also be prepared in situ from a common palladium source such as $Pd(OAc)_2$ or $Pd_2(dba)_3$ and a ligand such as trialkylphosphines (e.g. $PCy_3$ or $P(tBu)_3$), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in Miyaura and Suzuki, *Chem. Rev.* (1995), 95, 2457-2483, Bellina et al., *Synthesis* (2004), 2419-2440, Mauger and Mignani, *Aldrichimica Acta* (2006), 39, 17-24, Kantchev et al., *Aldrichimica Acta* (2006), 39, 97-111, Fu, *Acc. Chem. Res.* (2008), 41, 1555-1564, and references cited therein.

General Reaction Technique 4 (Removal of Hydroxy Protecting Groups):

The silyl ether groups are removed either using fluoride anion sources such as TBAF in THF between 0° C. and +40° C. or HF in MeCN between 0° C. and +40° C. or using acidic conditions such as AcOH in THF/MeOH or HCl in MeOH. Further methods to remove the TBDMS and TBDPS groups are given in T. W. Greene, P. G. M. Wuts, *Protecting Groups in Organic Synthesis*, 3$^{rd}$ Ed (1999), 133-139 and 142-143 respectively (Publisher: John Wiley and Sons, Inc., New York, N.Y.). Further general methods to remove alcohol protecting groups are described in T. W. Greene, P. G. M. Wuts, *Protecting Groups in Organic Synthesis*, 3$^{rd}$ Ed (1999), 23-147 (Publisher: John Wiley and Sons, Inc., New York, N.Y.).

General Reaction Technique 5 (Alcohol Activation):

The alcohol is reacted with MsCl, TfCl, BsCl, NfCl, NsCl or TsCl in the presence of a base such as TEA in a dry aprotic solvent such as Pyr, THF or DCM between −30° C. and +50° C. In the case of the triflate or mesylate, $Tf_2O$ or $Ms_2O$ can also be used.

General Reaction Technique 6 (Formation of Iodo, Chloro or Bromo Derivatives):

The sulfonates obtained using general reaction technique 5 can be reacted with a sodium halogenide such as NaI or NaBr in MeCN or DMF between 40° C. and 120° C., delivering the corresponding iodide derivatives. Alternatively the corresponding bromides or chlorides can also be obtained by reaction of the corresponding alcohol derivatives with $PBr_3$ or $PCl_3$ respectively.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sub-sections a) to e) hereafter describe general methods for preparing compounds of formula I. If not indicated otherwise, the generic groups R, $U^1$, $U^2$, $U^3$, $U^4$, $V^1$, $V^2$, $V^3$, $V^4$, W, X and Q are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formula I can be obtained by:

a) reacting a compound of formula II

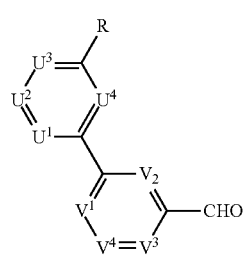

II wherein R, $U^1$, $U^2$, $U^3$, $U^4$, $V^1$, $V^2$, $V^3$ and $V^4$ are as defined in formula I, with a compound of formula III

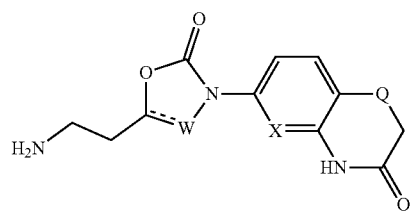

III wherein W, X and Q are as defined in formula I, using general reaction technique 1; or b) reacting a compound of formula IV

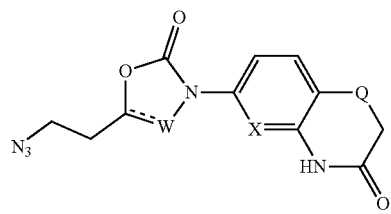

IV wherein W, X and Q are as defined in formula I, with $PPh_3$ followed by reaction with a compound of formula II as defined in section a), using general reaction technique 1; or c) reacting a compound of formula V

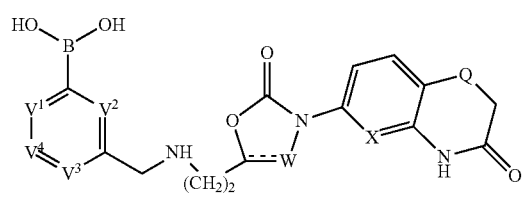

V wherein $V^1$, $V^2$, $V^3$, $V^4$, W, X and Q are as defined in formula I, with a compound of formula VI

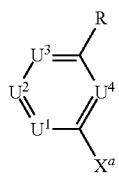

VI wherein $U^1$, $U^2$, $U^3$, $U^4$ and R have the same respective meanings as in formula I and $X^a$ represents either a halogen such as bromine or OTf, using general reaction technique 3; or d) hydrogenating, using general reaction technique 4, a compound of formula VII

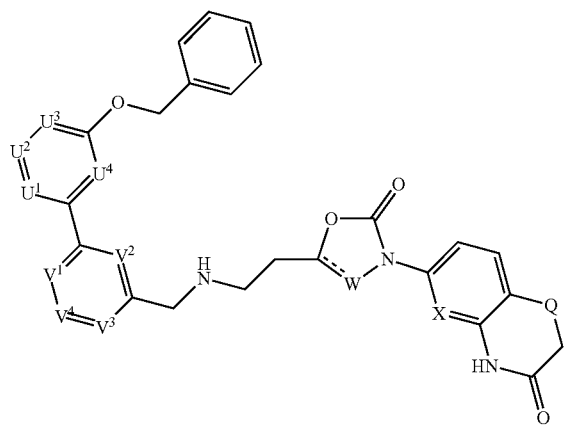

VII wherein $U^1$, $U^2$, $U^3$, $U^4$, $V^1$, $V^2$, $V^3$, $V^4$, W, X and Q are as defined in formula I, or a compound of formula VIIa

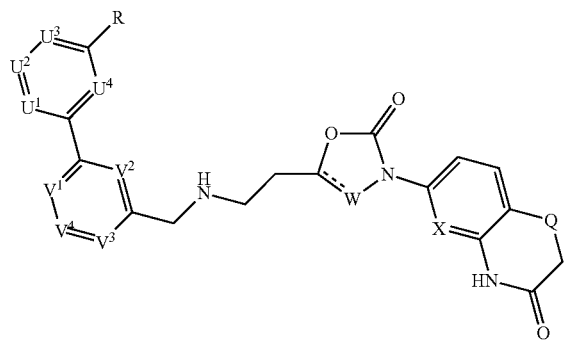

VIIa wherein one of $U^1$, $U^2$, $U^3$, $U^4$, $V^1$ and $V^2$ represents a carbon atom bearing a benzyloxy group (the others of $U^1$, $U^2$, $U^3$, $U^4$, $V^1$ and $V^2$ being as defined in formula I) and R, $V^3$, $V^4$, W, X and Q are as defined in formula I, in order to obtain the corresponding hydroxy derivatives of formula I; or e) reacting a compound of formula VIII

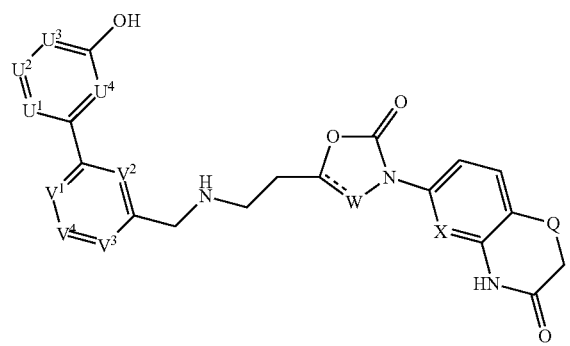

VIII wherein $U^1$, $U^2$, $U^3$, $U^4$, $V^1$, $V^2$, $V^3$, $V^4$, W, X and Q are as defined in formula I with an alkylating such as methyl iodide or dimethylsulphate in the presence of a base such as $Na_2CO_3$, $K_2CO_3$, DBU, NaH or in the presence of triethylchlorosilane between 20° C. and 100° C., in order to obtain compounds of formula I wherein R is methoxy, whereby the basic amine can optionally be protected before and deprotected after the alkylation reaction by generally known methods.

The compounds of formula I thus obtained may, if desired, be converted into their salts, and notably into their pharmaceutically acceptable salts using standard methods.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA, diethylamine) and eluent B (Hex), at a flow rate of 0.8 to 150 ml/min.

Preparation of the Synthesis Intermediates of Formulae II, III, IV, V, VI, VII, VIIa and VIII:

Compounds of Formula II:

The compounds of formula II are commercially available or can be prepared as summarised in Scheme 1 hereafter.

Scheme 1

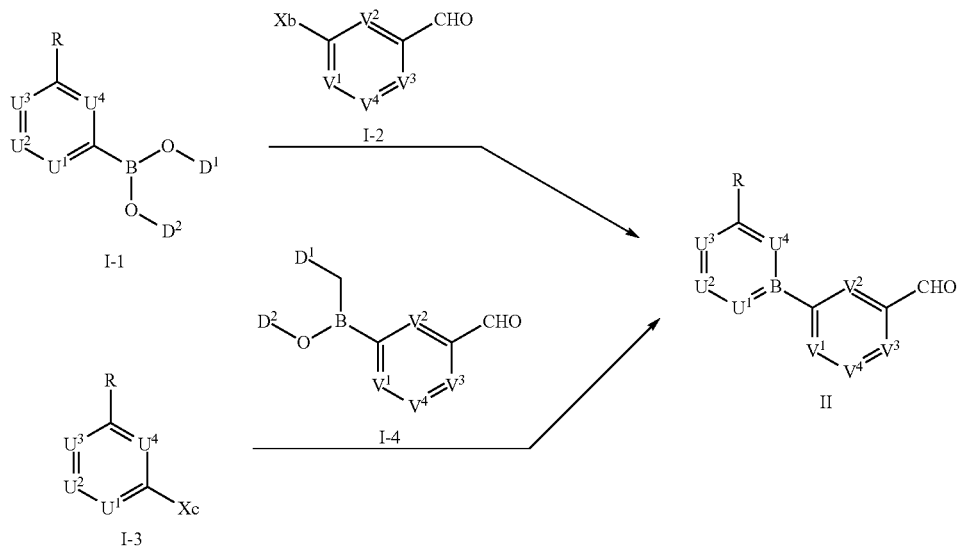

In Scheme 1, R, $U^1$, $U^2$, $U^3$, $U^4$, $V^1$, $V^2$, $V^3$ and $V^4$ are as defined in formula I, Xb and Xc represent a halogen such as bromine or chlorine and $D^1$ and $D^2$ represent H, methyl or ethyl or $D^1$ and $D^2$ together represent $CH_2C(Me)_2CH_2$ or $C(Me)_2C(Me)_2$.

The boronic esters or acids of formula I-1 can be reacted with the aldehydes of formula I-2 using general reaction technique 3. Alternatively, the boronic esters or acids of formula I-4 can be reacted with the halogenated derivatives of formula I-3 using general reaction technique 3.

Compounds of Formulae III and IV:

The compounds of formulae III and IV wherein the dotted line does not represent a bond can be prepared either as described in or in analogy to WO 2008/126024, WO 2009/104147 or WO 2010/041194, or as summarised in Scheme 2 hereafter.

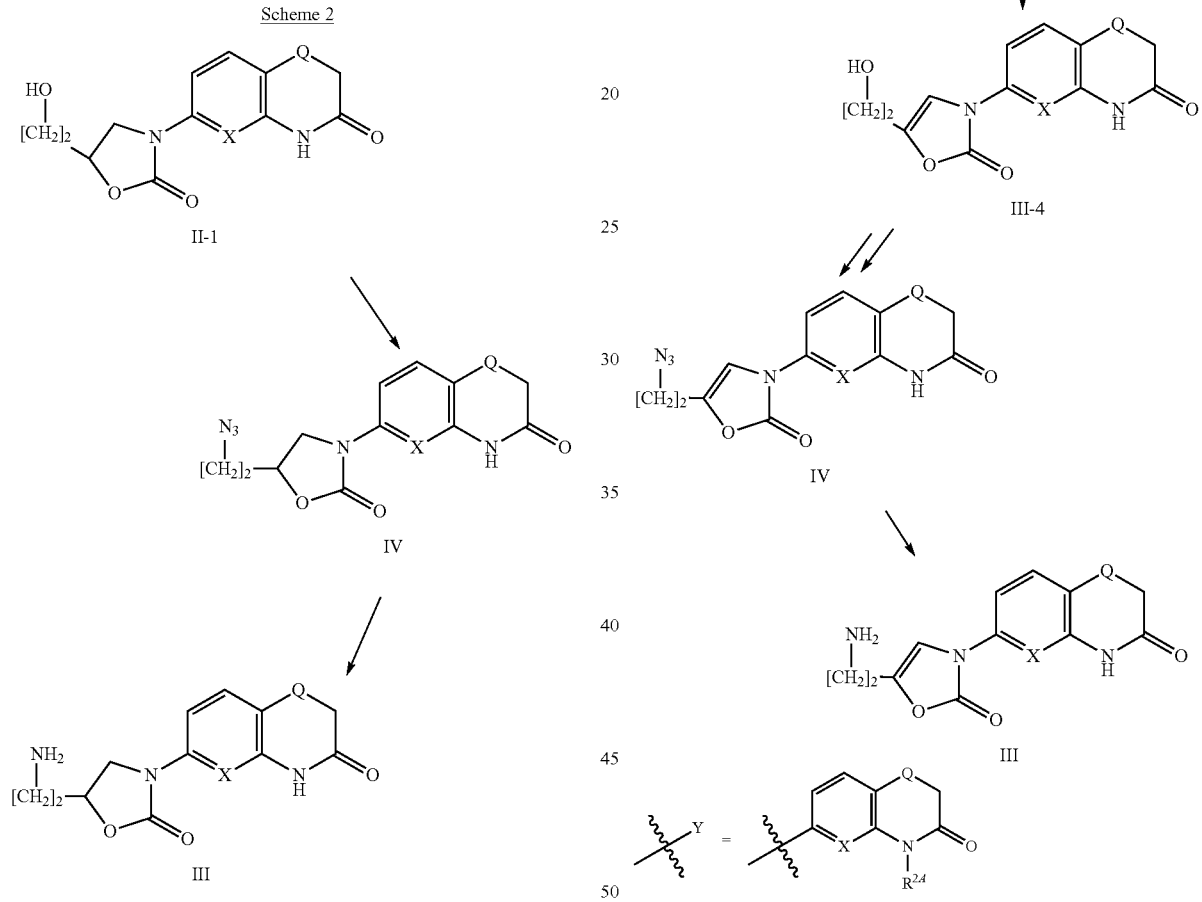

In Scheme 2, X and Q are as defined in formula I.

The alcohol derivatives of formula II-1 can be reacted with a compound of formula Cl—$SO_2R^A$ wherein $R^A$ represents methyl, trifluoromethyl or tolyl using general reaction technique 5. The resulting sulfonates can be optionally reacted with NaI using general reaction technique 6, and the resulting intermediates (sulfonates or iodides) can then be reacted with $NaN_3$. The compounds of formula IV thus obtained can be transformed into the derivatives of formula III by hydrogenolysis over a noble metal catalyst or by reaction with $PPh_3$ in the presence of water. The chiral compounds of formula III can be obtained starting from the chiral molecules of formula II-1 or through chiral separation at any stage of the synthesis.

The compounds of formula III wherein the dotted line represents a bond and W represents CH can be prepared as summarised in Scheme 3 hereafter.

In Scheme 3, X and Q are as defined in formula I, PG represents a hydroxy protecting group such as TBDMS or TBDPS and $R^{2A}$ represents an amide protecting group such as PMB.

The bromoalkyne derivatives of formula III-1 can be reacted (Scheme 3) with the secondary tert-butyloxycarbamate derivatives of formula III-2 under Cu(II)-catalyzed conditions affording the derivatives of formula III-3 which were transformed into the oxazolone derivatives of formula III-4 by a Au(I)-catalyzed cycloisomerization (see Istrate et al., Org. Lett. (2008), 10, 925-928) followed by removal of the alcohol protecting group using general reaction technique 4 (with loss of para-methoxy group). The alcohol derivatives of formula III-4 can be reacted with a compound of formula Cl—$SO_2R^A$ wherein $R^A$ represents methyl, trifluoromethyl or tolyl using general reaction technique 5. The resulting sulfonates can be optionally reacted with NaI using general reaction technique 6, and the resulting intermediates (sulfonates or iodides) can then be reacted with NaN₃. The compounds of formula IV thus obtained can be transformed into the derivatives of formula III by hydrogenolysis over a noble metal catalyst or by reaction with PPh₃ in presence of water.

The compounds of formula III wherein the dotted line represents a bond and W represents N can be prepared as summarised in Scheme 4 hereafter.

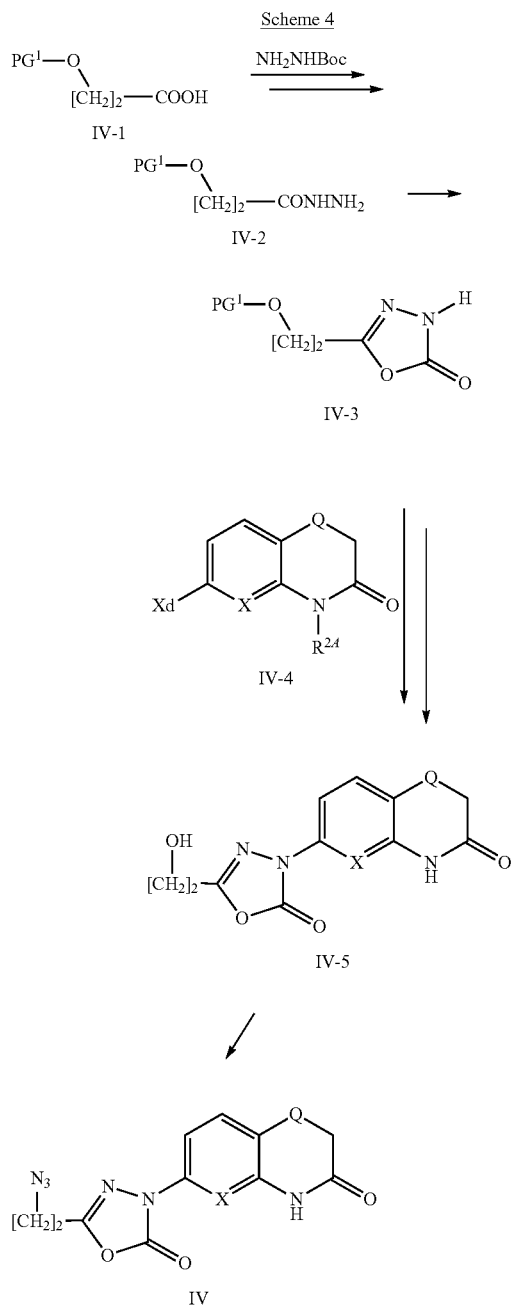

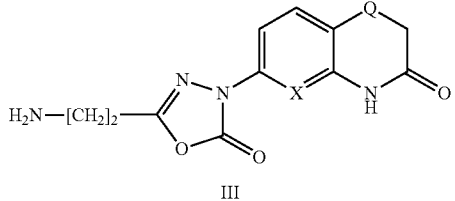

In Scheme 4, X, W and Q are as defined in formula I, PG¹ represents a hydroxy protecting group such as benzyl, TBDMS or TBDPS, Xd represents a halogen such as chlorine, bromine or iodine and $R^{2A}$ represents an amide protecting group such as PMB.

The carboxylic acids of formula IV-1 can be reacted (Scheme 4) with tert-butyl carbazate in the presence of a peptide coupling reagent such as EDC, followed by removal of the Boc protecting group using general reaction technique 2, affording the derivatives of formula IV-2. The compounds of formula IV-3 can be obtained by reacting the intermediates of formula IV-2 with CDI. The compounds of formula IV-3 can be further reacted with the derivatives of formula IV-4 in the presence of (trans)-N,N'-dimethyl-1,2-cyclohexanediamine and CuI, followed by the simultaneous removal of the protecting groups PG¹ and $R^{2A}$ with TFA, affording the derivatives of formula IV-5. The resulting alcohol derivatives of formula IV-5 can by reacted with a compound of formula Cl—SO₂$R^A$ wherein $R^A$ represents methyl, trifluoromethyl or tolyl using general reaction technique 5. The resulting sulfonates can be optionally reacted with NaI using general reaction technique 6, and the resulting intermediates (sulfonates or iodides) can then be reacted with NaN₃. The compounds of formula IV thus obtained can be transformed into the derivatives of formula III by hydrogenolysis over a noble metal catalyst or by reaction with PPh₃ in the presence of water.

Compounds of Formula V.

The compounds of formula V can be prepared as summarised in Scheme 5 hereafter.

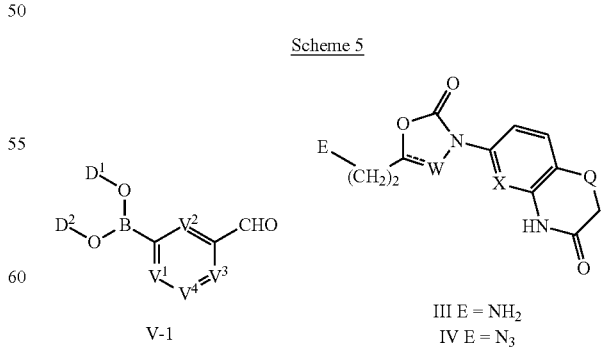

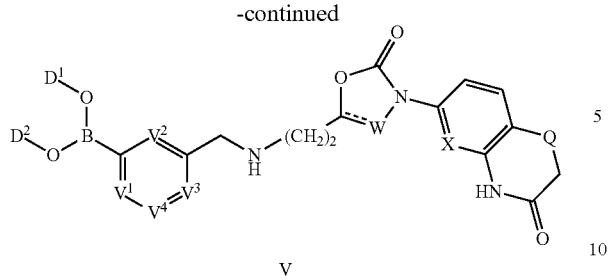

V

In Scheme 5, $V^1$, $V^2$, $V^3$, $V^4$, W, Q and X are as defined in formula I, $D^1$ and $D^2$ represent H, methyl or ethyl or $D^1$ and $D^2$ together represent $CH_2C(Me)_2CH_2$ or $C(Me)_2C(Me)_2$ and E represents $N_3$ or $NH_2$.

The boronic esters or acids of formula V-1 can be reacted (Scheme 5) with the compounds of formula III using general reaction technique 1. Alternatively the compounds of formula IV can be reacted with $PPh_3$ prior to reaction of the resulting intermediates with the boronic esters or acids of formula V-1 using general reaction technique 1.

Compounds of Formula VI:

The compounds of formula VI wherein $X^a$ represents a halogen are commercially available. The compounds of formula VI wherein $X^a$ represents OTf can be obtained from the corresponding compounds wherein $X^a$ represents OH (commercially available) through reaction with $Tf_2O$.

Compounds of Formulae VII and VIIa:

The compounds of formulae VII and VIIa can be prepared from the appropriate starting materials in analogy to the methods described in sub-sections a) to c) and e) of the section "Preparation of the compounds of formula I".

Compounds of Formula VIII:

The compounds of formula VIII can be prepared from the appropriate starting materials in analogy to the methods described in sub-sections a) to d) of the section "Preparation of the compounds of formula I".

Preparation of the Synthesis Intermediates of Formulae I-1, I-2, I-3, I-4, II-1, III-1, III-2, IV-1, IV-4 and V-1:

The compounds of formulae I-1, I-2, I-3 and I-4 are commercially available or can be prepared as described in the "EXAMPLES" section, in analogy thereto or by standard methods known to one skilled in the art.

The intermediates of formula II-1 can be prepared either as described in or in analogy to WO 2009/104147 or WO 2009/104159, or, in the case wherein X is N and Q is O, as summarised in Scheme 6 hereafter.

Scheme 6

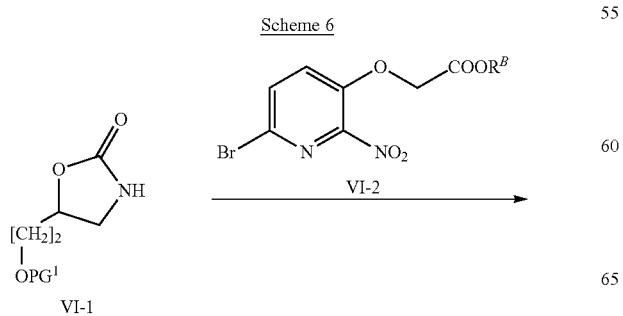

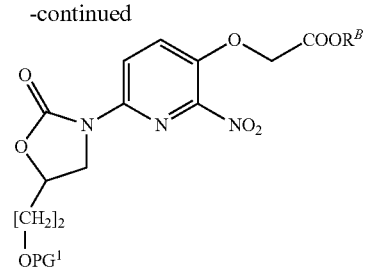

VI-3

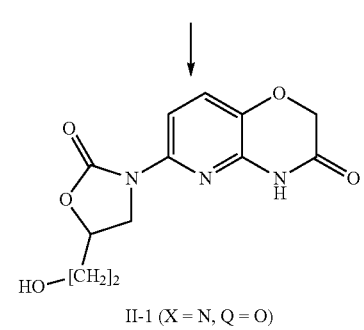

II-1 (X = N, Q = O)

In Scheme 6, $PG^1$ represents a hydroxy protecting group such as benzyl, TBDMS or TBDPS and $R^B$ represents $(C_1-C_4)$alkyl.

The compounds of formula VI-1 (prepared according to WO 2010/041194) can be reacted with the compounds of formula VI-2 (prepared according to WO 2004/002992) in the presence of CuI, an inorganic base such as $K_2CO_3$ and N,N-dimethyl-ethylenediamine, affording the compounds of formula VI-3. The latter can be heated between 50 and 70° C. in the presence of iron and ammonium chloride followed by reflux in AcOH, affording the compounds of formula II-1.

The intermediates of formula III-1 can be prepared according to Villeneuve et al., Org. Letters (2004), 6(24), 4543-4546.

The compounds of formula III-2 can be prepared as summarised in Scheme 7 hereafter.

Scheme 7

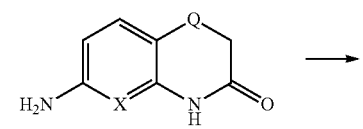

VII-1

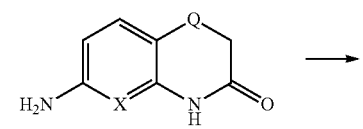

VII-2

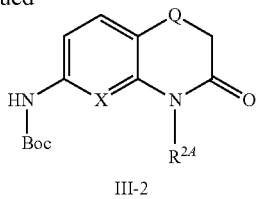

III-2

In Scheme 7, Q and X are as defined in formula I and $R^{2A}$ represents an amide protecting group such as PMB.

The derivatives of formula VII-1 (commercially available) can be reacted (Scheme 7) with 4-methoxybenzyl chloride in the presence of NaH followed by sequential reaction with (Boc)$_2$O in presence of DMAP and TEA and subsequent treatment with water dioxane, affording the derivatives of formula III-2.

The intermediates of formula IV-1 are either commercially available (PG$^1$=TBDPS) or can be prepared according to EP 297042.

The intermediates of formula IV-4 can be prepared as summarised in Scheme 8 hereafter.

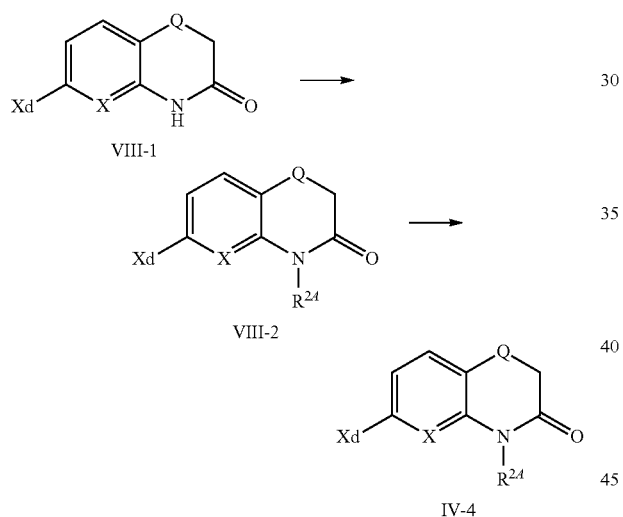

Scheme 8

In Scheme 8, Q and X are as defined in formula I, Xd represents a halogen such as chlorine, bromine or iodine and $R^{2A}$ represents PMB.

The derivatives of formula VIII-1 (either commercially available or prepared according to WO 01/30782, WO 2010/041194 or Ramesh et al., *Tetrahedron* (2011), 67, 1187-1192) can be reacted with 4-methoxybenzyl chloride in the presence of a base such as NaH, Cs$_2$CO$_3$ or Na$_2$CO$_3$, affording the intermediates of formula VIII-2. The latter can be further transformed into the derivatives of formula IV-4 by reaction with NaI in the presence of (trans)-N,N'-dimethyl-1,2-cyclohexanediamine and CuI.

The compounds of formula V-1 are commercially available or can be prepared as described in the "EXAMPLES" section, in analogy thereto or by standard methods known to one skilled in the art.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterisations were performed with 0.2 mm plates: Merck, Silica gel 60 F$_{254}$. Elution is performed with EA, Hept, DCM, MeOH or mixtures thereof. Detection was done with UV or with a solution of KMnO$_4$ (3 g), K$_2$CO$_3$ (20 g), 5% NaOH (3 mL) and H$_2$O (300 mL) with subsequent heating.

CCs were performed using Brunschwig 60A silica gel (0.032-0.63 mm), elution being carried out with EA, Hept, DCM, MeOH or mixtures thereof. When the compounds contained an acid function, 1% of AcOH was added to the eluent(s). NH$_4$OH as used for CC is 25% aq.

Compounds were characterized by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 F$_{254}$); or by melting point.

The analytical LC-MS data have been obtained using the following respective conditions:

MS1 data:
  Column: Zorbax SB-Aq, 3.5 µm, 4.6×50 mm;
  Injection volume: 1 µL;
  Column oven temperature: 40° C.;
  Pump: Agilent G4220A;
  Makeup pump: Dionex HPG-32005D;
  DAD: Agilent G4212A;
  MS: Thermo MSQ Plus;
  ELSD: Sedere Sedex 90;
  Detection: UV 210 nm, ELSD and MS;
  MS ionization mode: ESI+;
  Eluents: A: H$_2$O+0.04% TFA; and B: MeCN;
  Flow rate: 4.5 mL/min;
  Gradient: 5% B (0.00 min-0.08 min), 5% B to 95% B (0.08 min-1.07 min), 95% B (1.07 min-1.57 min).

MS2 data:
  Column: Waters Atlantis T3, 5 µm, 4.6×30 mm;
  Injection volume: 1 µL;
  Column oven temperature: 40° C.;
  Pump: Dionex HPG-3200RS;
  Makeup pump: Dionex ISO-3100SD;
  DAD: Dionex DAD-30000RS;
  MS: Thermo MSQ Plus;
  ELSD: Sedere Sedex 85;
  Detection: UV 210 nm, ELSD and MS;
  MS ionization mode: ESI+;
  Eluents: A: H$_2$O+0.04% TFA; and B: MeCN;
  Eluent flow rate: 4.5 mL/min;
  Gradient: 5% B (0.00 min-0.01 min), 5% B to 95% B (0.01 min-1.0 min), 95% B (1.0 min-1.45 min).

MS3 data:
  Column: Zorbax SB-Aq, 3.5 µm, 4.6×50 mm;
  otherwise same parameters as for obtaining MS2 data.

MS4 data:
  Makeup pump: Dionex ISO-3100A;
  otherwise same parameters as for obtaining MS2 data.

MS5 data:
  Column: Accucore C18 2.6 μm, 2.1×50 mm;
  Injection volume: 1 μL;
  Column oven temperature: 40° C.;
  Pump: Dionex HPG-3000;
  Makeup pump: Dionex ISO-31005D;
  DAD: Dionex TCC-3000 Column Compartment;
  MS: Thermo MSQ MS;
  ELSD: PolymerLab ELS 2100;
  Detection: UV 210 nm, ELSD and MS;
  MS ionization mode: ESI+;
  Eluents: A: $H_2O$+0.05% FA; and B: MeCN;
  Eluent flow rate: 1.2 mL/min;
  Gradient: 95% A-5% B to 5% A-95% B (2.6 min).
MS6 data:
  Column: Accucore C18 2.6 μm, 2.1×50 mm;
  Injection volume: 2 μL;
  Column oven temperature: 40° C.;
  Pump: Dionex HPG-3000;
  Makeup pump: Dionex ISO-3100SD;
  DAD: Dionex TCC-3000 Column Compartment;
  MS: Thermo MSQ MS;
  ELSD: PolymerLab ELS 2100;
  Detection: UV 210 nm, ELSD and MS;
  MS ionization mode: ESI+;
  Eluents: A: $H_2O$+0.05% $NH_4OH$+2% MeCN; and B: MeCN;
  Eluent flow rate: 1.2 mL/min;
  Gradient: 95% A-5% B to 5% A-95% B (2.6 min)
MS7 data:
  Column: Ascentis Express C18 2.7 μm, 2.1×50 mm;
  HPLC-System: Thermo Scientific Ultimate 3000;
  MS: Thermo Dionex Surveyor MSQ Plus;
  Detection: UV 254 and 220 nm;
  MS ionization mode: ESI+;
  Eluents: A: $H_2O$+0.1% TFA; and B: MeCN+0.085% TFA;
  Flow rate: 1.4 mL/min;
  Gradient: 97% A-3% B (0.00 to 0.05 min), then in 2.75 min to 3% A-97% B, then 3% A-97% B for 0.38 min.
MS8 data:
  Column: Ascentis Express C18 2.7 μm, 3.0×50 mm;
  HPLC-System: Agilent 1100 Series;
  MS: Thermo Dionex Surveyor MSQ Plus;
  Detection: UV 254 and 220 nm;
  MS ionization mode: ESI+;
  Eluents: A: $H_2O$+0.1% TFA; and B: MeCN+0.085% TFA;
  Flow rate: 1.3 mL/min;
  Gradient: 97% A-3% B (0.00 to 0.05 min), then in 2.90 min to 3% A-97% B, then 3% A-97% B for 0.20 min.

The number of decimals given for the corresponding [M+H$^+$] peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
  Method 1:
    Column: Waters Atlantis T3 OBD, 10 μm, 30×75 mm;
    Flow rate: 75 mL/min;
    Eluents: A: $H_2O$+0.5% HCOOH; B: MeCN;
    Gradient: 90% A to 5% A (0.0 min-4.0 min), 5% A (4.0 min-6.0 min).
  Method 2:
    Column: Waters Atlantis T3 OBD, 10 μm, 30×75 mm;
    Flow rate: 75 mL/min;
    Eluents: A: $H_2O$+0.5% HCOOH; B: MeCN;
    Gradient: 80% A to 5% A (0.0 min-4.0 min), 5% A (4.0 min-6.0 min).
  Method 3:
    Column: Waters XBridge C18, 10 μm, 30×75 mm;
    Flow rate: 75 mL/min;
    Eluents: A: $H_2O$+0.5% HCOOH; B: MeCN;
    Gradient: 90% A to 5% A (0.0 min-4.0 min), 5% A (4.0 min-6.0 min).
  Method 4:
    Column: Xbridge Prep C18 5 μm, OBD 19×50 mm;
    Flow rate: 40 mL/min;
    Eluents: A: $H_2O$+0.1% HCOOH; B: MeCN+0.1% HCOOH;
  Method 5:
    Column: Xbridge Prep C18 5 μm, OBD 19×50 mm;
    Flow rate: 40 mL/min;
    Eluents: A: $H_2O$+0.1% $NH_4OH$; B: MeCN+0.1% $NH_4OH$;
  Method 6:
    Column: Waters XBridge C18, 10 μm, 30×75 mm;
    Flow rate: 75 mL/min;
    Eluents: A: $H_2O$+0.5% $NH_4OH$; B: MeCN;
    Gradient: 90% A to 5% A (0.0 min-4.0 min), 5% A (4.0 min-6.0 min).
  Method 7:
    Column: Waters Atlantis T3 OBD, 10 μm, 30×75 mm;
    Flow rate: 75 mL/min;
    Eluents: A: $H_2O$+0.5% HCOOH; B: MeCN;
    Gradient: 95% A to 5% A (0.0 min-4.0 min), 5% A (4.0 min-6.0 min).

The following other purification methods were furthermore used:
  Filtration over Si-carbonate: silica bound equivalent of tetramethyl ammonium carbonate, SiliaPrep SPE cartridges Carbonate, 200 mg, 3 mL (Silicycle SPE-R66030B-03G).
  Filtration over Alumina cartridges: polar sorbent basic character, SiliaPrep SPE Cartridges Alumina Neutral, 1 g, 6 mL (Silicycle SPE-AUT-0054-06S).

PREPARATIONS

Preparation A

3'-formyl-[1,1'-biphenyl]-3-carbonitrile

A suspension of 3-bromobenzaldehyde (200 mg; commercial) and (3-cyanophenyl)boronic acid neopentyl glycol ester (325 mg; commercial) in toluene/EtOH (2.3 mL; 1:1) was treated with sat. aq. $Na_2CO_3$ (2.3 mL) and degassed by bubbling with nitrogen for 5 min. The suspension was treated with Pd(PPh$_3$)$_4$ (28 mg) and refluxed overnight in a sealed tube. The reaction mixture was allowed to reach rt and diluted with water and EA. The aq. layer was extracted with EA and the combined org. layers were washed with brine, dried over $MgSO_4$, filtered and evaporated under reduced pressure. After purification by CC (Hept/EA 2:1 to 1:1), the title compound was obtained as an off-white solid (325 mg; quantitative yield).

$^1$H NMR (CDCl$_3$) δ: 10.11 (s, 1H); 8.08 (t, J=1.7 Hz, 1H); 7.88 (m, 4H); 7.69 (m, 2H); 7.61 (m, 1H).

Preparation B

3'-formyl-5-methoxy-[1,1'-biphenyl]-2-carbonitrile

Starting from 2-chloro-4-methoxybenzonitrile (223 mg; commercial) and 3-formylphenylboronic acid (200 mg; commercial) and proceeding in analogy to Preparation A, the title compound was obtained as a beige solid (325 mg; 100% yield as crude material).

$^1$H NMR (CDCl$_3$) δ: 10.10 (s, 1H); 8.03 (s, 1H); 7.98 (m, 1H); 7.85 (m, 1H); 7.69 (m, 3H); 6.98 (s, 1H); 3.91 (m, 3H).

Preparation C

3'-formyl-5-methoxy-[1,1'-biphenyl]-3-carbonitrile

Starting from 3-bromo-5-methoxybenzonitrile (113 mg; commercial) and 3-formylphenylboronic acid (80 mg; commercial) and proceeding in analogy to Preparation A, the title compound was obtained, after CC purification (Hept/EA 2:1 to 1:1), as a colourless solid (69 mg; 55% yield).

$^1$H NMR (CDCl$_3$) δ: 10.10 (s, 1H); 8.07 (m, 1H); 7.93 (m, 1H); 7.82 (m, 1H); 7.66 (m, 1H); 7.49 (m, 1H); 7.36 (m, 1H); 7.17 (m, 1H); 3.90 (m, 3H).

Preparation D

6-fluoro-3'-methoxy-[1,1'-biphenyl]-3-carboxaldehyde

Starting from 3-bromo-anisole (99 mg; commercial) and 2-fluoro-5-formylphenylboronic acid (125 mg; commercial) and proceeding in analogy to Preparation A, the title compound was obtained, after CC purification (Hept/EA 2:1 to 1:1), as a yellow oil (12 mg; 10% yield).

$^1$H NMR (CDCl$_3$) δ: 10.01 (s, 1H); 8.00 (m, 1H); 7.87 (m, 1H); 7.57 (m, 1H); 7.34 (m, 1H); 7.12 (m, 2H); 6.97 (m, 1H); 3.85 (m, 3H).

MS1 (ESI, m/z): $t_R$=0.45 min.

Preparation E

2-fluoro-3'-methoxy-[1,1'-biphenyl]-3-carbaldehyde

Starting from 3-bromo-anisole (99 mg; commercial) and 2-fluoro-3-formylphenylboronic acid (125 mg; commercial) and proceeding in analogy to Preparation A, the title compound was obtained, after CC purification (Hept/EA 2:1 to 1:1), as a yellow oil (19 mg; 15% yield).

$^1$H NMR (CDCl$_3$) δ: 10.45 (s, 1H); 7.86 (m, 1H); 7.70 (m, 1H); 7.59 (m, 1H); 7.35 (m, 2H); 7.12 (m, 1H); 6.96 (m, 1H); 3.85 (s, 3H).

Preparation F

3-(5-methoxypyridin-3-yl)benzaldehyde

Starting from 3-bromo-benzaldehyde (92 mg; commercial) and 3-methoxypyridine-5-boronic acid pinacol ester (117 mg; commercial) and proceeding in analogy to Preparation A, the title compound was obtained, after CC purification (Hept/EA 2:1 to 1:1), as a colourless solid (82 mg; 77% yield).

MS1 (ESI, m/z): 214.3 [M+H$^+$]; $t_R$=0.59 min.

Preparation G

3-(4-methoxypyridin-2-yl)benzaldehyde

Starting from 2-bromo-4-methoxypyridine (100 mg; commercial) and 3-formylphenylboronic acid (112 mg; commercial) and proceeding in analogy to Preparation A, the title compound was obtained, after CC purification (Hept/EA 2:1 to 1:1), as a colourless solid (57 mg; 50% yield).

MS1 (ESI, m/z): 214.3 [M+H$^+$]; $t_R$=0.50 min.

Preparation H

3-(6-methoxypyridin-2-yl)benzaldehyde

Starting from 3-bromo-benzaldehyde (256 mg; commercial) and 6-methoxypyridine-2-boronic acid pinacol ester (455 mg; commercial) and proceeding in analogy to Preparation A, the title compound was obtained, after CC purification (Hept/EA 2:1 to 1:1), as a colourless oil (200 mg; 67% yield).

MS1 (ESI, m/z): 214.3 [M+H$^+$]; $t_R$=0.89 min.

Preparation I

3-(6-methoxy-3-pyridinyl)-benzaldehyde

Starting from 3-bromobenzaldehyde (200 mg; commercial) and 2-methoxy-5-pyridineboronic acid (231 mg; commercial) and proceeding in analogy to Preparation A, the title compound was obtained, after CC purification (Hept/EA 2:1 to 1:1), as a colourless solid (101 mg; 44% yield).

MS1 (ESI, m/z): 214.3 [M+H$^+$]; $t_R$=0.81 min.

Preparation J

5-(3-formylphenyl)-3-pyridinecarbonitrile

Starting from 5-bromonicotinonitrile (97 mg; commercial) and 3-formylphenylboronic acid (80 mg; commercial) and proceeding in analogy to Preparation A, the title compound was obtained, after trituration in TBME and EA, as a dark green solid (80 mg; 72% yield).

MS1 (ESI, m/z): 250.3 [M+H$^+$]; $t_R$=0.77 min.

Preparation K

6-(3-formylphenyl)picolinonitrile

Starting from 6-bromopicolinonitrile (97 mg; commercial) and 3-formylphenylboronic acid (80 mg; commercial) and proceeding in analogy to Preparation A, the title compound was obtained, after trituration in TBME and EA, as an off-white solid (78 mg; 70% yield).

MS1 (ESI, m/z): 209.3 [M+H$^+$]; $t_R$=0.82 min.

Preparation L

5-(3-formylphenyl)-6-hydroxynicotinonitrile

Starting from 5-bromo-6-hydroxynicotinonitrile (106 mg; commercial) and 3-formylphenylboronic acid (80 mg; commercial) and proceeding in analogy to Preparation A, the title compound was obtained, after trituration in TBME and EA, as an off-white solid (48 mg; 40% yield).
MS1 (ESI, m/z): 225.2 [M+H$^+$]; $t_R$=0.64 min.

Preparation M 4-(3-methoxyphenyl)picolinaldehyde

Starting from 4-bromopyridine-2-carboxaldehyde (257 mg; commercial) and 3-methoxyphenylboronic acid (294 mg; commercial) and proceeding in analogy to Preparation A, the title compound was obtained, after trituration in TBME and EA, as an orange oil (234 mg; 79% yield).
MS1 (ESI, m/z): 214.3 [M+H$^+$]; $t_R$=0.81 min.

Preparation N

6'-methoxy-[2,2'-bipyridine]-6-carboxaldehyde

Starting from 6-bromo-2-pyridinecarboxaldehyde (257 mg; commercial) and 6-methoxypyridine-2-boronic acid pinacol ester (455 mg; commercial) and proceeding in analogy to Preparation A, the title compound was obtained, after CC purification (Hept/EA 2:1 to 1:1), as a colourless solid (43 mg; 14% yield).
MS1 (ESI, m/z): 215.3 [M+H$^+$]; $t_R$=0.87 min.

Preparation O 3-(4-methoxypyrimidin-2-yl)benzaldehyde

Starting from 2-chloro-4-methoxypyrimidine (77 mg; commercial) and 3-formylphenylboronic acid (112 mg; commercial) and proceeding in analogy to Preparation A, the title compound was obtained, after CC purification (Hept/EA 2:1 to 1:1), as a colourless solid (40 mg; 35% yield).
MS1 (ESI, m/z): 215.3 [M+H$^+$]; $t_R$=0.81 min.

Preparation P 3-(6-methoxypyrimidin-4-yl)benzaldehyde

Starting from 4-chloro-6-methoxypyrimidine (77 mg; commercial) and 3-formylphenylboronic acid (80 mg; commercial) and proceeding in analogy to Preparation A, the title compound was obtained, after trituration in TBME and EA, as a yellow solid (14 mg; 12% yield).
MS1 (ESI, m/z): 215.4 [M+H$^+$]; $t_R$=0.78 min.

Preparation Q 3-(6-methoxypyrazin-2-yl)benzaldehyde

Starting from 2-chloro-6-methoxypyrazine (77 mg; commercial) and 3-formylphenylboronic acid (80 mg; commercial) and proceeding in analogy to Preparation A, the title compound was obtained, after trituration in TBME and EA, as a beige solid (10 mg; 9% yield).
MS1 (ESI, m/z): 215.3 [M+H$^+$]; $t_R$=0.83 min.

Preparation R 3-(2,6-dimethoxypyrimidin-4-yl)benzaldehyde

Starting from 6-chloro-2,4-dimethoxypyrimidine (93 mg; commercial) and 3-formylphenylboronic acid (80 mg; commercial) and proceeding in analogy to Preparation A, the title compound was obtained, after CC purification (Hept/EA 2:1 to 1:1), as a colourless solid (134 mg; 100% yield).
MS1 (ESI, m/z): 245.3 [M+H$^+$]; $t_R$=0.86 min.

Preparation S 3-(4,6-dimethoxypyrimidin-2-yl)benzaldehyde

Starting from 2-chloro-4,6-dimethoxypyrimidine (93 mg; commercial) and 3-formylphenylboronic acid (80 mg; commercial) and proceeding in analogy to Preparation A, the title compound was obtained, after CC purification (Hept/EA 2:1 to 1:1), as a colourless solid (157 mg; quantitative yield).
MS1 (ESI, m/z): 245.3 [M+H$^+$]; $t_R$=0.91 min.

Preparation T 3-(4,6-dimethoxy-1,3,5-triazin-2-yl)benzaldehyde

Starting from 2-chloro-4,6-dimethoxy-1,3,5-triazine (93 mg; commercial) and 3-formylphenylboronic acid (80 mg; commercial) and proceeding in analogy to Preparation A, the title compound was obtained, after trituration in TBME and EA, as a dark solid (25 mg; 20% yield).
MS1 (ESI, m/z): 246.3 [M+H$^+$]; $t_R$=0.82 min.

Preparation U 3-(4-formyl-pyridin-2-yl)-4-hydroxy-benzonitrile

Starting from bromoisonicotinaldehyde (96 mg; commercial) and 5-cyano-2-hydroxyphenylboronic acid (70 mg; commercial) and proceeding in analogy to Preparation A, the title compound was obtained, after purification by CC (Hept/EA 100:0 to 50:50), as a dark solid (51 mg; 53% yield).
MS3 (ESI, m/z): 225.3 [M+H$^+$]; $t_R$=0.82 min.

Preparation V 2-(3-formyl-phenyl)-6-methoxy-isonicotinonitrile

Starting from 2-chloro-6-methoxy-isonicotinonitrile (1.49 g; commercial) and 3-formylphenylboronic acid (1.32 g; commercial) and proceeding in analogy to Preparation A, the title compound was obtained, after triturating in TBME/Hept, as a colourless powder (516 mg; 25% yield).
MS1 (ESI, m/z): 239.3 [M+H$^+$]; $t_R$=0.92 min.

Preparation W (R)-(3-(((2-(2-oxo-3-(3-oxo-3,4-dihydro-2H-benzo[b][1,4]thiazin-6-yl)oxazolidin-5-yl)ethyl)amino)methyl)phenyl)boronic acid A solution of 3-formylphenylboronic acid (154 mg; commercial) and (R)-5-(2-aminoethyl)-3-(3-oxo-3,4-dihydro-2H-benzo[b][1,4]thiazin-6-yl)oxazolidin-2-one (301 mg; prepared according to WO 2009/104147) in DCM/DMF (6 mL, 1:1) was treated with NaBH(OAc)$_3$ (653 mg) and stirred at rt overnight. The mixture was partitioned between sat. NaHCO$_3$ and DCM, the org. phase was separated, dried over MgSO$_4$, concentrated under reduced pressure and triturated in TBME/DCM, affording an off-white solid (329 mg; 75% yield).

MS1 (ESI, m/z): 428.2 [M+H$^+$]; $t_R$=0.55 min.

Preparation X (R)-(3-(((2-(2-oxo-3-(3-oxo-3,4-dihydro-2H-pyrido [3,2-b][1,4]oxazin-6-yl)oxazolidin-5-yl)ethyl)amino) methyl)phenyl)boronic acid X.i. (6-{(R)-5-[2-(tert-butyl-dimethyl-silanyloxy)-ethyl]-2-oxo-oxazolidin-3-yl}-2-nitro-pyridin-3-yloxy)-acetic acid ethyl ester A suspension of K$_2$CO$_3$ (11.26 g), CuI (388 mg), (R)-5-[2-(tert-butyl-dimethyl-silanyloxy)-ethyl]-oxazolidin-2-one (10.0 g; prepared according to WO 2009/104159), (6-bromo-2-nitro-pyridin-3-yloxy)-acetic acid ethyl ester (12.43 g; prepared according to WO 2004/002992) and N,N-dimethyl-ethylenediamine (0.92 mL) in dioxane (305 mL) was degassed by bubbling with argon and refluxed at 100° C. overnight. The resulting dark brown mixture was filtered over Celite, the filtrate was evaporated under reduced pressure and the residue was purified by CC (Hept/ EA 2:1 to 0:1), affording a beige solid (16.0 g; 84% yield).

MS3 (ESI, m/z): 470.3 [M+H$^+$]; $t_R$=1.04 min.

X.ii. 6-[(R)-5-(2-hydroxy-ethyl)-2-oxo-oxazolidin-3-yl]-4H-pyrido[3,2-b][1, 4]oxazin-3-one A suspension of ammonium chloride (13.67 g), iron (8.56 g) in MeOH/water (204 mL; 1:1) was heated to 50° C., treated dropwise with a solution of intermediate X.i (16.0 g) in MeOH (360 mL) and further stirred at 68° C. for 2.5 h. The hot suspension was filtered over a pad of Celite. The filtrate was diluted with AcOH (112 mL) and stirred at 95° C. for 2 h. The reaction mixture was allowed to reach rt and concentrated under reduced pressure. The suspension was cooled to 0° C., filtered and the solid was collected by filtration, affording a beige solid (9.45 g; 100% yield).

MS2 (ESI, m/z): 280.1 [M+H$^+$]; $t_R$=0.47 min.

X.iii. Methanesulfonic acid 2-[(R)-2-oxo-3-(3-oxo-3,4-dihydro-2H-pyrido[3,2-b][1,4]oxazin-6-yl)-oxazolidin-5-yl]-ethyl ester A suspension of intermediate X.ii (4.2 g) in DCM (65 mL) was cooled to −40° C. and treated with MsCl (1.6 mL) for 1 h. The reaction mixture was diluted with sat. aq. NaHCO$_3$ and the aq. layer was extracted with DCM. The combined org. layers were dried over MgSO$_4$, concentrated under reduced pressure and the residue was triturated in TBME/ DCM/MeOH, affording a salmon solid (732 mg; 17% yield).

MS1 (ESI, m/z): 358.2 [M+H$^+$]; $t_R$=0.65 min.

X.iv. 6-[(R)-5-(2-azido-ethyl)-2-oxo-oxazolidin-3-yl]-4H-pyrido[3,2-b][1,4]oxazin-3-one A solution of intermediate X.iii (2.5 g) in DMF (20 mL) was treated with NaN$_3$ (427 mg) and stirred at 80° C. for 3 h. The reaction mixture was partitioned between EA and water. The aq. layer was extracted with EA. The combined org. layers were dried over MgSO$_4$ and concentrated under reduced pressure, affording a salmon solid (976 mg; 59% yield).

MS1 (ESI, m/z): 305.2 [M+H$^+$]; $t_R$=0.72 min.

X.v. (R)-(3-(((2-(2-oxo-3-(3-oxo-3,4-dihydro-2H-pyrido[3,2-b][1,4]oxazin-6-yl)oxazolidin-5-yl)ethyl) amino)methyl)phenyl)boronic acid A solution of intermediate X.iv (950 mg) in DCM (23 mL) was treated with PPh$_3$ (983 mg) and stirred at rt for 3 h. The reaction mixture was treated with 3-formylphenyl-boronic acid (468 mg; commercial) and further stirred at rt overnight. The resulting reaction mixture was treated with NaBH(OAc)$_3$ (1.98 g) in MeOH (8 mL) and further stirred at rt for 20 min. The reaction mixture was diluted with water and sat. aq. NaHCO$_3$ solution and extracted with DCM/ MeOH. The aq. layer was extracted with three times with DCM/MeOH. The combined org. layers were dried over MgSO$_4$, concentrated under reduced pressure, affording after trituration in DCM/TBME, an off-white solid (1.28 g; 100% yield). An aliquot (200 mg) was purified by prep-HPLC, affording a colourless solid (22 mg).

MS1 (ESI, m/z): 413.3 [M+H$^+$]; $t_R$=0.53 min.

Preparation Y

6-[5-(2-azido-ethyl)-2-oxo-oxazol-3-yl]-4H-pyrido [3,2-b][1,4]oxazin-3-one

Y.i. [4-(4-methoxy-benzyl)-3-oxo-3,4-dihydro-2H-pyrido[3,2-b][1,4]oxazin-6-yl]-carbamic acid tert-butyl ester A solution of 6-bromo-4-(4-methoxy-benzyl)-4H-pyrido [3,2-b][1,4]oxazin-3-one (1.0 g; prepared according to WO 2009/104159) in dioxane (25 mL) was treated with tert-butyl carbamate (369 mg) and Cs$_2$CO$_3$ (1.21 g). The resulting solution was treated with tris(dibenzylideneacetone)dipalla-dium(0) (39.3 mg) and XantPhos (49.7 mg) under Ar. The reaction mixture was stirred at 90° C. for 4 days under Ar and filtered. The filtrate was concentrated under reduced pressure and purified by CC (EA/Hept 1:1), affording a yellow foam (1.1 g; 96% yield).

MS3 (ESI, m/z): 385.95 [M+H$^+$]; $t_R$=0.94 min.

Y.ii. [4-(tert-butyl-dimethyl-silanyloxy)-but-1-ynyl]-[4-(4-methoxy-benzyl)-3-oxo-3,4-dihydro-2H-pyrido[3,2-b][1,4]oxazin-6-yl]-carbamic acid tert-butyl ester K$_3$PO$_4$ (3.30 g), CuSO$_4$ (286 mg) and 1,10-phenanthro-line (711 mg) were added to a mixture of intermediate Y.i (3.15 g) and [(4-bromo-3-butyn-1-yl)oxy](1,1-dimethyl-ethyl)dimethyl-silane (2.36 g; prepared according to Ville-neuve et al., Organic Letters (2004), 6(24), 4543-4546) in toluene (20 mL) and heated at 85° C. for 2 days. The reaction mixture was cooled to rt, filtered through glass fiber paper, washed with EA, and the filtrate was concentrated under reduced pressure. The residue was purified by CC (Hept/EA 4:1) affording a colourless oil (2.0 g; 59% yield).

MS3 (ESI, m/z): 568.1 [M+H$^+$]; $t_R$=1.15 min.

Y.iii. 6-{5-[2-(tert-butyl-dimethyl-silanyloxy)-ethyl]-2-oxo-oxazol-3-yl}-4-(4-methoxy-benzyl)-4H-pyrido[3,2-b][1,4]oxazin-3-one:

A suspension of AuPh$_3$PCl (157 mg) and AgSbF$_6$ (109 mg) in MeCN (1 mL) was treated with a solution of intermediate Y.ii (1.8 g) in dry DCM (8 mL). The resulting mixture was stirred at 40° C. for 5 h, concentrated under reduced pressure and the residue was purified by CC (Hept/EA, 1:0 to 4:6), affording an off-white solid (1.0 g; 61% yield).

MS3 (ESI, m/z): 512.2 [M+H$^+$]; $t_R$=1.09 min.

Y.iv. 6-[5-(2-hydroxy-ethyl)-2-oxo-oxazol-3-yl]-4H-pyrido[3,2-b][1,4]oxazin-3-one A solution of intermediate Y.iii (0.99 g) in DCM (60 mL) was treated at rt with TFA (7.4 mL) and trifluoromethanesulfonic acid (1.7 mL). The mixture was stirred at rt for 30 min, cooled to 0° C., quenched with TEA/MeOH (40 mL; 1:1) and further stirred at 0° C. for 1 h. The reaction mixture was filtered and the solid was washed with DCM. The filtrate was diluted with DCM and water. The aq. layer was extracted with DCM and the combined org. layers were sequentially washed with 0.1N HCl, water and brine, dried over MgSO$_4$ and concentrated under reduced pressure. The residue and the solid resulting from the filtration were combined and stirred in TBME, affording, after filtration and drying, a grey solid (476 mg; 89% yield).

MS3 (ESI, m/z): 278.1 [M+H$^+$]; $t_R$=0.56 min.

Y.v. Methanesulfonic acid 2-[2-oxo-3-(3-oxo-3,4-dihydro-2H-pyrido[3,2-b][1,4]oxazin-6-yl)-2,3-dihydro-oxazol-5-yl]-ethyl ester:

A suspension of intermediate Y.iv (470 mg) in DCM (8 mL) was treated at 0° C. with TEA (0.48 mL) and MsCl (0.26 mL). The mixture was stirred at rt overnight. The reaction mixture was diluted with sat. aq. NaHCO$_3$ and DCM. The aq. layer was extracted with DCM and the combined org. layers were dried over MgSO$_4$ and concentrated under reduced pressure. The residue was purified by CC (Hept/EA, 1:0 to 1:4), affording an off-white solid (144 mg; 24% yield).

MS3 (ESI, m/z): 356.0 [M+H$^+$]; $t_R$=0.66 min.

Y.vi. 6-[5-(2-azido-ethyl)-2-oxo-oxazol-3-yl]-4H-pyrido[3,2-b][1,4]oxazin-3-one A suspension of intermediate Y.v (140 mg) in DMF (2 mL) was treated with NaN$_3$ (30 mg) and heated at 80° C. for 3 h. The reaction mixture was diluted with water and EA. The aq. layer was extracted with EA and the combined org. layers were dried over MgSO$_4$ and concentrated under reduced pressure, affording a beige solid (70 mg; 59% yield).

MS1 (ESI, m/z): 303.2 [M+H$^+$]; $t_R$=0.73 min.

Preparation Z

6-[(S)-5-(2-amino-ethyl)-2-oxo-oxazolidin-3-yl]-4H-pyrido[3,2-b][1,4]oxazin-3-one

Z.i. 3-[(S)-2-oxo-3-(3-oxo-3,4-dihydro-2H-pyrido[3,2-b][1,4]oxazin-6-yl)-oxazolidin-5-yl]-propionic acid A solution of 3-[(S)-2-oxo-3-(3-oxo-3,4-dihydro-2H-pyrido[3,2-b][1,4]oxazin-6-yl)-oxazolidin-5-yl]-propionaldehyde (8.0 g; prepared according to WO 2010/041194) in water (46 mL) and acetone (240 mL) was treated with KMnO$_4$ (9.8 g) and further stirred at rt for 2 h. The reaction mixture was treated with sodium bisulfite (9.0 g), further stirred for 15 min, filtered through a pad of Celite and the volatiles were removed under reduced pressure. The pH of the aq. layer was adjusted to 5 and the solid was collected by filtration. The crude product was dissolved with EA and extracted twice with 0.1M NaOH. The combined aq. layers were washed with EA, acidified (pH 3) with 1M HCl, the precipitate was filtered off, affording 4 g of title compound as a colourless solid. The aq. phase was extracted three times with DCM/MeOH. The combined org. layers were washed with brine, dried over MgSO$_4$ and concentrated under reduced pressure, affording another 670 mg of title compound as a colourless solid (total: 4.67 g; 62% yield).

MS4 (ESI, m/z): 507.9 [M+H$^+$]; $t_R$=0.58 min.

Z.ii. {2-[(S)-2-oxo-3-(3-oxo-3,4-dihydro-2H-pyrido[3,2-b][1,4]oxazin-6-yl)-oxazolidin-5-yl]-ethyl}-carbamic acid benzyl ester A solution of intermediate Z.i (1.60 g), benzyl alcohol (5.39 mL) and TEA (3.8 mL) in DMF (4.8 mL) was heated to 100° C. and treated dropwise with DPPA (1.26 mL) and further stirred at 100° C. for 4 h. The reaction mixture was diluted with EA, sequentially washed with sat. aq. NH$_4$Cl, sat. aq. NaHCO$_3$ and brine, dried over MgSO$_4$, filtered and concentrated to dryness. Water was added and the azetrope was removed under reduced pressure. The crude product was purified by CC (EA/Hept 2:1), affording an off-white solid (0.8 g; 37% yield).

MS1 (ESI, m/z): 413.4 [M+H$^+$]; $t_R$=0.78 min.

Z.iii. 6-[(S)-5-(2-amino-ethyl)-2-oxo-oxazolidin-3-yl]-4H-pyrido[3,2-b][1,4]oxazin-3-one A solution of intermediate Z.ii (750 mg) in MeOH (30 mL) was hydrogenated over Pd(OH)$_2$/C (121 mg) for 1 h. The catalyst was filtered off and the filtrate was concentrated under reduced pressure, affording an off-white foam (530 mg; 100% yield).

MS1 (ESI, m/z): 279.32 [M+H$^+$]; $t_R$=0.45 min.

Preparation AA

3'-formyl-6-hydroxy-[1,1'-biphenyl]-3-carbonitrile

Starting from 3-bromo-benzaldehyde (124 mg; commercial) and 5-cyano-2-hydroxyphenylboronic acid (105 mg; commercial) and proceeding in analogy to Preparation A, the title compound was obtained as a yellow solid (145 mg; 100% yield).

$^1$H NMR (CDCl$_3$) δ: 10.03 (m, 1H); 8.04 (m, 1H); 7.84 (m, 1H); 7.77 (m, 1H); 7.57 (m, 1H); 7.46 (m, 1H); 7.26 (m, 1H); 6.95 (m, 1H); 2.73 (m, 1H).

Preparation AB

3-(4-formylpyridine-2-yl)benzonitrile

Starting from 2-bromo-4-pyridinecarboxaldehyde (144 mg; commercial) and 3-(5,5-dimethyl-1,3,2-dioxaborinan-2-yl)-benzonitrile (139 mg; commercial) and proceeding in analogy to Preparation A, the title compound was obtained as a yellow solid (177 mg; quantitative yield).

MS1 (ESI, m/z): 209.2 [M+H$^+$]; $t_R$=0.79 min.

Preparation AC

4-hydroxy-3-(4-methoxypyridin-2-yl)benzaldehyde

AC.i. 4-(benzyloxy)-3-(4-methoxypyridin-2-yl)benzaldehyde

A suspension of 2-chloro-4-methoxypyridine (250 mg; commercial), 2-benzyloxy-5-formylphenylboronic acid (455 mg; commercial), $K_2CO_3$ (1.65 g) in water (3 mL) and DMF (12 mL) was degassed with nitrogen, treated with bis(triphenylphosphine)palladium(II) dichloride (48 mg) and heated for 3 h at 100° C. The reaction mixture was evaporated under reduced pressure and the residue was partitioned between water and EA. The aq. layer was extracted with EA. The combined org. layers were washed with water and brine, dried over $MgSO_4$, evaporated under reduced pressure and purified by CC (Hept to Hept/EA 2:3) to yield a light yellow solid (309 mg; 60% yield).
MS1 (ESI, m/z): 320.1 [M+H$^+$]; $t_R$=0.66 min.

AC.ii. 4-(hydroxymethyl)-2-(4-methoxypyridin-2-yl)phenol

To a solution of intermediate AC.i (309 mg) in MeOH (7 mL) degassed three times and purged with $N_2$, was added 5% Pd/C (103 mg). The resulting suspension was stirred at rt under an $H_2$ atmosphere for 4 h. The catalyst was removed by filtration. The solvent was evaporated to dryness, affording the title compound, contaminated with some aldehyde, as a yellow oil (170 mg). The latter was not further purified.
MS1 (ESI, m/z): 232.2 [M+H$^+$]; $t_R$=0.46 min.

AC.iii. 4-hydroxy-3-(4-methoxypyridin-2-yl)benzaldehyde

To a suspension of intermediate AC.ii (170 mg) in MeCN (2.3 mL) was added $MnO_2$ (396 mg). The mixture was stirred overnight at rt. The mixture was filtered through a pad of Celite which was then washed with DCM. The filtrate was concentrated under reduced pressure, yielding the desired compound as a light yellow solid (154 mg; 91% yield).
MS1 (ESI, m/z): 230.2 [M+H$^+$]; $t_R$=0.57 min.

Preparation AD

5-(3-methoxyphenyl)pyridazine-3-carbaldehyde

AD.i. 3-chloro-5-(3-methoxyphenyl)pyridazine

A mixture of 3,5-dichloropyridazine (157 mg), 3-methoxybenzeneboronic acid (157 mg) and KF (147 mg) in toluene (4 mL) and water (1 mL) was degassed with $N_2$. Palladium(II) acetate (11 mg) and Q-phos (42 mg) were added and the mixture was further degassed with $N_2$ and stirred in a sealed tube at 70° C. for 20 h. The mixture was cooled to rt, diluted with EA, filtered through a glass fibre filter and concentrated under reduced pressure. The crude residue was purified by CC (CombiFlash, EA-Hept 2-8), affording a white solid (127 mg; 58% yield).
MS1 (ESI, m/z): 221.1 [M+H$^+$]; $t_R$=0.79 min.

AD.ii. 5-(3-methoxyphenyl)-3-vinylpyridazine

A mixture of intermediate AD.i (22 mg), 2,4,6-trivinyl-cyclotriboroxane pyridine complex (24 mg), $K_2CO_3$ (24 mg), PCy$_3$ (4 mg) and Pd$_2$(dba)$_3$ (5 mg) in dioxane (0.5 mL) and water (0.2 mL) was degassed with $N_2$ and stirred at 80° C. for 1 h. The mixture was diluted with EA, filtered through a glass fibre filter and purified by CC (CombiFlash, EA-Hept 25-75), affording a brown oil (19 mg; 90% yield).
MS1 (ESI, m/z): 213.2 [M+H$^+$]; $t_R$=0.80 min.

AD.iii. 5-(3-methoxyphenyl)pyridazine-3-carbaldehyde

A solution of intermediate AD.ii (19 mg) in dioxane (1 mL) and water (0.3 mL) was treated at 0° C. with an $OsO_4$ solution in water (4%; 0.1 mL). The suspension was stirred at 0° C. for 1 h then at rt for 1 h. $NaIO_4$ (54 mg) was added and the suspension was stirred at rt for 15 h. The reaction mixture was diluted with water and EA. The aq layer was extracted with EA. The combined org. layers were dried over $MgSO_4$, filtered and concentrated under reduced pressure, affording a brown oil (24 mg).
MS1 (ESI, m/z): 215.2 [M+H$^+$]; $t_R$=0.55 min.

Preparation AE

6-(3-methoxyphenyl)pyrazine-2-carbaldehyde

AE.i. 2-chloro-6-dimethoxymethyl-pyrazine

A solution of 6-chloropyrazine-2-carbaldehyde (309 mg), trimethyl orthoformate (0.3 mL) and TsOH monohydrate (12 mg) in MeOH (5 mL) was stirred at rt overnight. Sat. aq. $NaHCO_3$ and $Et_2O$ were added. The org. layer was separated, dried over $MgSO_4$, filtered, concentrated under reduced pressure and purified by CC (CombiFlash EA-Hept 1-9), affording a colourless liquid (407 mg; quantitative).
MS1 (ESI, m/z): 189.2 [M+H$^+$]; $t_R$=0.62 min.

AE.ii. 2-dimethoxymethyl-6-(3-methoxy-phenyl)-pyrazine

A mixture of intermediate AE.i (38 mg), 3-methoxybenzeneboronic acid (31 mg, commercial), palladium(II) acetate (2.25 mg), 1,1'-bis(diphenylphosphino)ferrocene (5.7 mg) and caesium carbonate (163 mg) in dioxane (0.8 mL) and water (0.2 mL) was degassed for 10 min with $N_2$ and sealed in a glass vial. The resulting dark brown suspension was stirred at 70° C. for 15 h. The mixture was cooled down to rt, diluted with EA, filtered through a glass fibre filter and concentrated under reduced pressure. The crude residue was purified by CC (Hept to Hept-EA 3-1), affording a yellow oil (41 mg; 79% yield).
MS1 (ESI, m/z): 261.2 [M+H$^+$]; $t_R$=0.82 min.

AE.iii. 6-(3-methoxyphenyl)pyrazine-2-carbaldehyde

Intermediate AE.ii (41 mg) was stirred in 1N HCl (1 mL) at 80° C. for 90 min. The mixture was cooled to rt, diluted with EA and basified with 1N NaOH until pH>10. The org. layer was separated, dried over $MgSO_4$, filtered and concentrated under reduced pressure, affording a pale yellow solid (43 mg).
MS1 (ESI, m/z): 215.2 [M+H$^+$]; $t_R$=0.79 min.

Preparation AF

3-(6-methoxypyridazin-4-yl)benzaldehyde

AF.i. 3-(6-hydroxy-pyridazin-4-yl)-benzaldehyde

A suspension of 5-chloropyridazin-3 (2H)-one (400 mg; commercial), 3-formylphenylboronic acid (597 mg; commercial), K₂CO₃ (2.96 g) in water (5.2 mL) and DMF (22 mL) was degassed with nitrogen, treated with bis(triphenyl-phosphine)palladium(II) dichloride (194 mg) and heated overnight at 100° C. The reaction mixture was evaporated under reduced pressure and the residue was partitioned between water and EA. The aq. layer was extracted with EA. The combined org. layers were washed with water, brine, dried over MgSO₄ and evaporated under reduced pressure. The resulting solid was suspended in DCM and filtered, affording a beige solid (150 mg; 24% yield).

MS1 (ESI, m/z): 201.2 [M+H⁺]; $t_R$=0.56 min.

AF.ii. 3-(6-methoxypyridazin-4-yl)benzaldehyde

A suspension of intermediate AF.i (120 mg) in DMF (1 mL) was treated with K₂CO₃ (166 mg) and methyl iodide (0.0561 mL) and the mixture was stirred at rt for 2 h. Water was added and the mixture was extracted twice with EA. The combined org. layers were washed with water, dried over MgSO₄, filtered and concentrated under reduced pressure. The crude product was purified by prep-HPLC (Method 1), affording a yellowish solid (45 mg; 35% yield).

MS1 (ESI, m/z): 215.1 [M+H⁺]; $t_R$=0.65 min.

Preparation AG 5-(3-formyl-phenyl)-pyridazine-3-carbonitrile

AG.i. 5-(3-formylphenyl)pyridazin-3-yl trifluoromethanesulfonate

To a solution of intermediate AF.i (90 mg) in DCM (1.5 mL) was added Pyr (0.04 mL) and the solution was cooled to 0° C. Tf₂O (0.0837 mL) was added dropwise and the mixture was stirred at rt for 30 min. Water was added and the mixture was extracted with DCM. The org. layer was dried over MgSO₄ and concentrated under reduced pressure, affording an orange oil (135 mg; 90% yield).

MS1 (ESI, m/z): 373.8 [M+MeCN]; $t_R$=0.88 min.

AG.ii. 5-(3-formyl-phenyl)-pyridazine-3-carbonitrile

A mixture of intermediate AG.i (120 mg), Zn(CN)₂ (43.4 mg), Pd₂(dba)₃ (49.8 mg) and DPPF (30.1 mg) in DMF (1.5 mL) was stirred for 5 min under N₂. The suspension was then heated at 85° C. in a closed vessel overnight. The solvent was evaporated under reduced pressure. Water was added and the mixture was extracted twice with DCM. The combined org. layers were dried over MgSO₄, filtered and concentrated under reduced pressure. The residue was purified by CC (Combi Flash System; gradient Hept to Hept-EA 40-60), affording an orange solid (48 mg; 63% yield).

MS1 (ESI, m/z): 210.1 [M+H⁺]; $t_R$=0.70 min.

Preparation AH 6-(3-methoxyphenyl)pyridazine-4-carbaldehyde

AH.i. 5-chloro-3-(3-methoxyphenyl)pyridazine

Starting from 3,5-dichloropyridazine (157 mg) and 3-methoxybenzeneboronic acid (157 mg) and proceeding in analogy to Preparation AE, step AE.ii, the title compound was obtained as a pale yellow oil (135 mg; 61% yield).

MS1 (ESI, m/z): 221.1 [M+H⁺]; $t_R$=0.79 min.

AH.ii. 3-(3-methoxyphenyl)-5-vinylpyridazine

Starting from intermediate AH.i (113 mg) and proceeding in analogy to Preparation AD, step AD.ii, the title compound was obtained, after purification by CC (CombiFlash, EA-Hept 25-75), as a yellow oil (80 mg, 74% yield).

MS1 (ESI, m/z): 213.2 [M+H⁺]; $t_R$=0.77 min.

AH.iii. 6-(3-methoxyphenyl)pyridazine-4-carbaldehyde

Starting from intermediate AH.ii (377 mg) and proceeding in analogy to Preparation AD, step AD.iii, the title compound was obtained as a dark orange solid (91 mg; quantitative).

MS1 (ESI, m/z): 233.2 [M+H⁺+H₂O]; $t_R$=0.54 min.

Preparation AI

3'-(4-hydroxy-butoxy)-biphenyl-3-carbaldehyde

Starting from 4-(3-bromophenoxy)butan-1-ol (153 mg; commercial) and 3-formylphenylboronic acid (112 mg) and proceeding in analogy to Preparation A, the title compound was obtained as a brown oil (228 mg; quantitative).

MS1 (ESI, m/z): 311.2 [M+MeCN]; $t_R$=0.78 min.

Preparation AJ

3-[6-((3aS,5rs,6aR)-2,2-dimethyl-tetrahydro-cyclo-penta[1,3]dioxol-5-ylmethoxy)-pyridin-2-yl]-benzal-dehyde AJ.i. (1rs,3R,4S)-3,4-dihydroxy-cyclopentanecarboxylic acid methyl ester To a solution of N-methylmorpholine-N-oxide (2786 mg) in H₂O (7 mL) and THF (19 mL) were added potassium osmate (VI) dihydrate (43.8 mg) in tBuOH (8 mL) and methyl 3-cyclopentenecarboxylate (1500 mg) under N₂. The resulting mixture was stirred at rt overnight. The reaction mixture was treated with sodium bisulphite and extracted with DCM. The org. layer was washed with brine, dried over MgSO₄, filtered and concentrated under reduced pressure, affording a crude orange oil (1.39 g; 73% yield) which was used directly in the next step.

¹H NMR (CDCl₃) δ: 4.15-4.27 (m, 1H); 3.95-4.11 (m, 1H); 3.67 (s, 3H); 3.07-3.25 (m, 1H); 1.87-2.32 (m, 4H).

AJ.ii. (3aS,5rs,6aR)-2,2-dimethyl-tetrahydro-cyclo-penta[1,3]dioxole-5-carboxylic acid methyl ester To a solution of intermediate AJ.i (1313 mg) and 2,2-dimethoxypropane (0.791 mL) in acetone (27 mL) was added TsOH monohydrate (108 mg). The mixture was stirred at rt for 3 h. The mixture was concentrated and the residue was diluted with sat. aq. NaHCO₃ (10 mL). The aq. layer was then extracted 3 times with EA. The combined org. layers were extracted with water and brine, dried over MgSO₄, filtered and concentrated, affording a yellow liquid (1.15 g; 91% yield).

¹H NMR (CDCl₃) δ: 4.67 (dd, J=1.2, 3.7 Hz, 2H); 3.68 (s, 3H); 2.94-3.11 (m, 1H); 2.13 (dd, J=6.0, 14.2 Hz, 2H); 1.64-1.80 (m, 2H); 1.43 (s, 3H); 1.28 (s, 3H).

AJ.iii. ((3aS,5rs,6aR)-2,2-dimethyl-tetrahydro-cy-clopenta[1,3]dioxol-5-yl)-methanol To an ice cooled 0° C. suspension of LiAlH₄ (322 mg) in THF (3 mL) was added a solution of intermediate AJ.ii (1100 mg) in THF (2.5 mL). This mixture was then stirred at 0° C. for 1.5 h. The reaction was quenched at 0° C. with water and 10% aq. NaOH. The resulting suspension was filtered and the filtrate was concentrated. The crude product was purified by CC (Combi Flash; gradient Hept to Hept-EA 1-1), affording a yellowish oil (845 mg; 89% yield).

$^1$H NMR (CDCl$_3$) δ: 4.65 (dd, J=1.3, 3.7 Hz, 2H); 3.63 (d, J=6.0 Hz, 2H); 2.33-2.52 (m, 1H); 1.94 (dd, J=5.8, 14.0 Hz, 2H); 1.44 (s, 3H); 1.29 (s, 3H), 1.18-1.34 (overlapped m, 2H).

AJ.iv. 2-bromo-6-((3aS,5rs,6aR)-2,2-dimethyl-tetrahydro-cyclopenta[1,3]dioxol-5-ylmethoxy)-pyridine and 2-chloro-6-((3aS,5rs,6aR)-2,2-dimethyl-tetrahydro-cyclopenta[1,3]dioxol-5-ylmethoxy)-pyridine To a solution of intermediate AJ.iii (300 mg) and 2-bromo-6-chloropyridine (352 mg) in DMF (5 mL) at 0° C. was added NaH (60% suspension in oil, 105 mg). The reaction was stirred at rt overnight. The mixture was quenched with brine and extracted with EA. The org. layer was washed with water (3×), dried over MgSO$_4$, filtered and concentrated under reduced pressure. The residue was purified by CC (Combi Flash; gradient Hept to Hept-EA 80-20), affording a colourless oil (345 mg; 60% yield).

MS1 (ESI, m/z): 328.0 [M+H$^+$]; t$_R$=0.92 min.

AJ.v. 3-[6-((3aS,5rs,6aR)-2,2-dimethyl-tetrahydrocyclopenta[1,3]dioxol-5-ylmethoxy)-pyridin-2-yl]-benzaldehyde Starting from intermediate AJ.iv (310 mg) and 3-formylphenylboronic acid (149 mg) and proceeding in analogy to Preparation A, the title compound was obtained, after purification by CC (Combi Flash; gradient Hept to Hept-EA 70-30), as a colourless oil (199 mg; 60% yield).

MS1 (ESI, m/z): 354.0 [M+H$^+$]; t$_R$=0.97 min.

Preparation AK 1-(((03'-formyl-[1,1'-biphenyl]-3-yl)oxy)methyl)cyclobutane-1-carbonitrile Starting from 1-[(3-bromophenoxy)methyl]-cyclobutanecarbonitrile, (66 mg; commercial) and 3-formylphenylboronic acid (75 mg; commercial) and proceeding in analogy to Preparation A, the title compound was purified by filtration over Si-carbonate then over alumina cartridges, affording 23 mg (32% yield) of material which was not further purified.

MS5 (ESI, m/z): 292.0 [M+H$^+$]; t$_R$=1.10 min.

Preparation AL 2-(benzyloxy)-3-(4-methoxypyridin-2-yl)benzaldehyde

Starting from 2-chloro-4-methoxypyridine (200 mg) and 2-benzyloxy-3-formylphenylboronic acid (364 mg; commercial) and proceeding in analogy to Preparation A, the title compound was obtained, after purification by CC (CombiFlash, gradient EA-Hept 1-2), as a yellow oil (177 mg, 41% yield).

MS1 (ESI, m/z): 320.1 [M+H+]; t$_R$=0.64 min.

Preparation AM 2-(3-methoxyphenyl)pyrimidine-4-carbaldehyde

AM.i.
4-(dimethoxymethyl)-2-(3-methoxyphenyl)pyrimidine

A mixture of 2-chloro-4-(dimethoxymethyl)-pyrimidine (38 mg; commercial), 3-methoxybenzeneboronic acid (31 mg; commercial), palladium(II) acetate (2.25 mg), DPPF (5.7 mg) and caesium carbonate (163 mg) in dioxane (0.8 mL) and water (0.2 mL) was degassed for 10 min with N$_2$ and sealed in a glass vial. The resulting dark brown suspension was stirred at 70° C. for 15 h. The mixture was cooled down to rt, diluted with EA, filtered through a glass fibre filter and concentrated under reduced pressure. The crude residue was purified by CC (Hept to Hept-EA 3-1), affording a colourless oil (43 mg; 82% yield).

MS1 (ESI, m/z): 261.3 [M+H$^+$]; t$_R$=0.82 min.

AM.ii.
2-(3-methoxyphenyl)pyrimidine-4-carbaldehyde

Intermediate AM.i (42.6 mg) was stirred in 1N HCl (2.1 mL) at 80° C. for 90 min. The mixture was cooled to rt, diluted with EA and basified with 1N NaOH until pH>10. The layers were separated, the org. layer was dried over MgSO$_4$, filtered and concentrated under reduced pressure, affording an orange oil (29 mg; 83% yield).

MS1 (ESI, m/z): 215.2 [M+H$^+$]; t$_R$=0.59 min.

Preparation AN 2-(3'-formyl-biphenyl-3-yloxy)-N-methyl-acetamide

Starting from 2-(3-bromophenoxy)-N-methyl-acetamide (178 mg, commercial) and 3-formylphenylboronic acid (112 mg) and proceeding in analogy to Preparation A, the title compound was obtained as a brown oil (117 mg; 70% yield).

MS1 (ESI, m/z): 312.2 [M+MeCN]; t$_R$=0.83 min.

Preparation AO 3-(6-methoxy-pyridazin-3-yl)-benzaldehyde

Starting from 3-chloro-6-methoxypyridazine (150 mg) and 3-formylphenylboronic acid (202 mg) and proceeding in analogy to Preparation A, the title compound was obtained, after purification by CC (CombiFlash-System; gradient Hept to Hept-EA 60-40), as a colourless solid (211 mg; 95% yield).

MS1 (ESI, m/z): 215.0 [M+H$^+$]; t$_R$=0.71 min.

Preparation AP 6-(3-formyl-phenyl)-pyridazine-4-carbonitrile

AP.i. 3-(5-chloro-pyridazin-3-yl)-benzaldehyde

Starting from 3,5-dichloropyridazine (1.00 g) and 3-formylphenylboronic acid (1.06 g) and proceeding in analogy to Preparation A, the title compound was obtained, after purification by CC (Combi Flash System; gradient Hept to Hept-EA 1-1), as a yellowish solid (661 mg; 45% yield).
MS1 (ESI, m/z): 219.1 [M+H$^+$]; $t_R$=0.74 min.

AP.ii. 6-(3-formyl-phenyl)-pyridazine-4-carbonitrile

A mixture of intermediate AP.i (200 mg), zinc cyanide (113 mg) and Pd(PPh$_3$)$_4$ (106 mg) in DMF (1.5 mL) was heated in a sealed vial under N$_2$ at 110° C. for 2 h. The reaction mixture was cooled to rt and washed with sat. aq. NH$_4$Cl. The aq. layer was washed twice with EA and the combined org. were dried over MgSO$_4$, filtered and concentrated. The residue was purified by CC (CombiFlash; gradient Hept to Hept-EA 40-60), affording a yellow solid (87 mg; 45% yield).
MS1 (ESI, m/z): 251.0 [M+H$^+$]; $t_R$=0.69 min.

Preparation AQ

6-[(S)-5-(2-amino-ethyl)-2-oxo-oxazolidin-3-yl]-4H-benzo[1,4]oxazin-3-one

AQ.i. Methanesulfonic acid 2-[(S)-2-oxo-3-(3-oxo-3,4-dihydro-2H-benzo[1,4]oxazin-6-yl)-oxazolidin-5-yl]-ethyl ester A suspension of 6-[(S)-5-(2-hydroxy-ethyl)-2-oxo-oxazolidin-3-yl]-4H-benzo[1,4]oxazin-3-one (6.24 g; prepared according to WO 2009/104159) in DCM (150 mL) was treated with TEA (6.2 mL) and MsCl (2.1 mL) at 0° C. The mixture was stirred at rt for 2 h, partitioned between water and DCM. The org layer was dried over MgSO$_4$ and concentrated. The residue was taken up with EA and the resulting crystals were collected by filtration, affording a beige solid (6.8 g; 85% yield).
MS1 (ESI, m/z): 357.2 [M+H$^+$]; $t_R$=0.63 min.

AQ.ii. 6-[(S)-5-(2-azido-ethyl)-2-oxo-oxazolidin-3-yl]-4H-benzol[1,4]oxazin-3-one Intermediate AQ.i (500 mg) was dissolved in DMF (8 mL) and treated with sodium azide (109 mg). The mixture was stirred at 60° C. for 3 h. Water was added and the mixture was extracted with EA. The org. layer was washed twice with water and once with brine, dried over MgSO$_4$, filtered and concentrated under reduced pressure. The residue was then purified by CC (Combi Flash; gradient Hept to Hept-EA 30-70), affording a yellowish solid (301 mg; 71% yield).
MS1 (ESI, m/z): 344.9 [M+H$^+$]; $t_R$=0.69 min.

AQ.iii. 6-[(S)-5-(2-amino-ethyl)-2-oxo-oxazolidin-3-yl]-4H-benzol[1,4]oxazin-3-one Intermediate AQ.ii (270 mg) was dissolved in THF-MeOH 1-1 (8 mL), then 10% Pd/C (47.2 mg) was added and the mixture was stirred under a H$_2$ atmosphere for 2 h. The suspension was filtered over Celite, washed with THF-MeOH 1-1 and the filtrate was concentrated under reduced pressure, affording a yellow solid (231 mg; 94% yield).
MS1 (ESI, m/z): 278.0 [M+H$^+$]; $t_R$=0.43 min.

Preparation AR 3-(5-methoxy-pyridazin-3-yl)-benzaldehyde

Starting from 3-chloro-5-methoxypyridazine (500 mg; commercial) and 3-formylphenylboronic acid (674 mg; commercial) and proceeding in analogy to Preparation AF, the title compound was obtained, after purification by CC (CombiFlash; gradient Hept to Hept-EA 1-2), as a light yellow solid (420 mg; 57% yield).
MS1 (ESI, m/z): 215.2 [M+H$^+$]; $t_R$=0.63 min.

Preparation AS

6'-methoxy-[2,2]bipyridinyl-4-carbaldehyde

AS.i. 4-dimethoxymethyl-6'-methoxy-[2,2']bipyridinyl

A mixture of 2-bromo-4-(dimethoxymethyl)-pyridine (23 mg, prepared according to Thaler et al., *J. Med. Chem.* (2010), 53(2), 822-839), 6-methoxypyridine-2-boronic acid pinacol ester (48 mg, commercial), palladium(II) acetate (1.12 mg), DPPF (5.7 mg), CuCl (11 mg) and caesium carbonate (130 mg) in DMF (1 mL) was degassed for 10 min with N$_2$ and sealed in a glass vial. The resulting dark brown suspension was stirred at 100° C. for 1.5 h. The mixture was cooled down to rt, diluted with EA, washed with brine, dried over MgSO$_4$, filtered and concentrated under reduced pressure. The crude residue was purified by CC (CombiFlash, 4 g; 0-10% EA in Hept), affording a colourless oil (43 mg; 82% yield).
MS1 (ESI, m/z): 261.2 [M+H$^+$]; $t_R$=0.66 min.

AS.ii. 6'-Methoxy-[2,2']bipyridinyl-4-carbaldehyde

Intermediate AS.i (21 mg) was stirred in 1N HCl (1 mL) at 80° C. for 90 min. The mixture was cooled to rt, diluted with EA and treated with conc. aq. NaOH (pH>10). The layers were separated and the org. layer was dried over MgSO$_4$, filtered and concentrated under reduced pressure, affording a pale yellow solid (22 mg).
MS1 (ESI, m/z): 215.2 [M+H$^+$]; $t_R$=0.80 min.

Preparation AT 6-(3-formyl-2-hydroxyphenyl)picolinonitrile

AT.i. 6-(2-(benzyloxy)-3-formylphenyl)picolinonitrile

Starting from 6-chloropyridine-2-carbonitrile (118 mg; commercial) and [2-(benzyloxy)-3-formylphenyl]boronic acid (259 mg; commercial) and proceeding in analogy to Preparation A, the title compound was obtained after purification by CC (Hex-EA 4-1) as an oil, which crystallised as a pale yellowish solid (197 mg; 74% yield).
MS7 (ESI, m/z): 315.0 [M+H$^+$]; $t_R$=1.75 min.

AT.ii. 6-(3-formyl-2-hydroxyphenyl)picolinonitrile

To a solution of intermediate AT.i (1.60 g) in EtOH (230 mL) was added 10% Pd/C (157 mg) under argon at rt. Argon was exchanged by H$_2$, EtOH (10 mL) was added and the mixture was stirred at rt for 23.5 h. The reaction mixture was filtered through a short pad of Celite (glass sinter filter) and the solid was thoroughly washed with DCM/EtOH/EA. The combined filtrates were concentrated under reduced pressure. The crude product was purified by two CC separations (Hex-EA 3-1 to 2-1 to 1-1 then DCM), affording a pale yellow, glossy fluffy solid (824.9 mg; 72% yield).
$^1$H-NMR (DMSO-d6): 12.30-12.90 (br. s, 1H); 10.30 (s, 1H); 8.46 (dd, J=0.9, 8.3 Hz, 1H); 8.26 (dd, J=1.8, 8.0 Hz, 1H); 8.23 (t-like signal, J=8.0 Hz, 1H); 8.09 (dd, J=1.0, 7.7 Hz, 1H); 7.89 (dd, J=1.8, 7.6 Hz, 1H); 7.20 (t, J=7.7 Hz, 1H).
MS8 (ESI, m/z): 225.0 [M+H$^+$]; $t_R$=1.89 min.

Preparation AU 4-hydroxy-3-(5-methoxy-pyridazin-3-yl)-benzaldehyde

AU.i. 4-benzyloxy-3-(5-methoxy-pyridazin-3-yl)-benzaldehyde

Starting from 3-chloro-5-methoxypyridazine (250 mg; commercial) and 2-benzyloxy-5-formylphenylboronic acid (443 mg; commercial) and proceeding in analogy to Preparation AF, the title compound was purified by CC (Hept-EA 20-80), affording a beige material (321 mg; 58% yield).
MS1 (ESI, m/z): 320.9 [M+H$^+$]; $t_R$=0.79 min.

AU.ii. 4-hydroxymethyl-2-(5-methoxy-pyridazin-3-yl)-phenol

A suspension of intermediate AU.i (320 mg) in MeOH (5 mL) was hydrogenated over 10% Pd/C (77.2 mg) for 4 h. The catalyst was filtered off and the filtrate was concentrated under reduced pressure. The crude product was purified by CC (Combi Flash System; gradient DCM to DCM-MeOH 19-1), affording a light yellow solid (82 mg; 51% yield).
MS1 (ESI, m/z): 233.1 [M+H$^+$]; $t_R$=0.54 min.

AU.iii. 4-hydroxy-3-(5-methoxy-pyridazin-3-yl)-benzaldehyde

To a suspension of intermediate AU.ii (75 mg) in MeCN (1 mL) was treated with MnO$_2$ (87 mg). The mixture was stirred at rt overnight. The mixture was filtered through a pad of Celite which was then washed with DCM. The solvent was evaporated and the solid was dried under HV, affording a yellow solid (73 mg; 98% yield).
MS1 (ESI, m/z): 231.1 [M+H$^+$]; $t_R$=0.72 min.

Preparation AV 2-hydroxy-3-(6-methoxypyridin-2-yl)benzaldehyde

Starting from 2-methoxypyridine-6-boronic acid hydrochloride (550 mg; commercial) and 3-bromo-2-hydroxybenzaldehyde (584 mg) and proceeding in analogy to Preparation A, the title compound was obtained, after purification by CC (toluene-EA 30-1 to 20-1 to 10-1), as a shiny yellow crystalline solid (797 mg; 30% yield).
$^1$H-NMR (DMSO-d6): 14.20-14.70 (br. s, 1H); 10.45 (s, 1H); 8.35 (dd, J=1.7, 7.9 Hz, 1H); 7.98 (t, J=8.0 Hz, 1H); 7.86 (d, J=7.7 Hz, 1H); 7.76 (dd, J=1.7, 7.7 Hz, 1H); 7.08 (dt, J=0.6, 7.7 Hz, 1H); 6.97 (dd, J=0.6, 8.2 Hz, 1H); 3.99 (s, 3H).

Preparation AW

6-[(S)-5-(2-amino-ethyl)-2-oxo-oxazolidin-3-yl]-4H-pyrido[3,2-b][1,4]thiazin-3-one Starting from 6-[(5S)-5-(2-hydroxyethyl)-2-oxo-3-oxazolidinyl]-2H-pyrido[3,2-b]-1,4-thiazin-3(4H)-one (prepared according to WO 2010/041194), and proceeding in analogy to Preparation AQ, the title compound was obtained as a yellowish solid (mesylate formation: beige solid, 84% yield; azide formation: yellowish solid, 67% yield; azide reduction: 93% yield).
MS1 (ESI, m/z): 295.0 [M+H$^+$]; $t_R$=0.48 min.

Preparation AX

6-[5-(2-amino-ethyl)-2-oxo-[1,3,4]oxadiazol-3-yl]-4H-pyrido[3,2-b][1,4]oxazin-3-one AX.i. N'-(4-benzyloxy-butyryl)-hydrazinecarboxylic acid tert-butyl ester 4-benzyloxybutyric acid (14.1 mL, commercial), tert-butyl carbazate (12.2 g) and EDC (23.9 g) in DCM (300 mL) were stirred at rt overnight under argon. The mixture was washed with sat. aq. NH$_4$Cl and brine, dried over MgSO$_4$ and concentrated under reduced pressure, affording a yellowish oil (27.9 g; quantitative).
MS1 (ESI, m/z): 309.2 [M+H$^+$]; $t_R$=0.67 min.

AX.ii. 4-benzyloxy-butyric acid hydrazide

A solution of intermediate AX.i (22.6 g) in DCM (200 mL) was treated with TFA (213 mL) and further stirred for 1 h at rt. The solution was concentrated to dryness, then diluted with DCM and treated with excess aq. NH$_4$OH. The aq. layer was extracted twice with DCM. The combined org. layers were washed with brine and dried over MgSO$_4$, filtered and concentrated to dryness, affording a yellowish oil (13.46 g; 93% yield).
MS1 (ESI, m/z): 209.3 [M+H$^+$]; $t_R$=0.43 min.

AX.iii. 5-(3-benzyloxy-propyl)-3H-[1,3,4]oxadiazol-2-one

A solution of intermediate AX.ii (13.45 g) in DCE (300 mL) was treated with CDI (20.94 g) and the mixture stirred for 1 h at 80° C. After cooling to rt, the mixture was concentrated under reduced pressure. The crude was purified by CC (DCM-MeOH—NH$_4$OH 1000-50-4), then by another CC (EA-Hept 1-1), affording a colourless oil (6.23 g; 41% yield).
MS1 (ESI, m/z): 235.3 [M+H$^+$]; $t_R$=0.71 min.

AX.iv. 6-[5-(3-benzyloxy-propyl)-2-oxo-[1,3,4]oxadiazol-3-yl]-4-(4-methoxy-benzyl)-4H-pyrido[3,2-b][1,4]oxazin-3-one K$_2$CO$_3$ (792 mg), CuI (109 mg) and (trans)-N,N'-dimethyl-1,2-cyclohexanediamine (0.0903 mL) were placed in a reaction vessel and purged with argon for 5 min. The reaction mixture was treated with intermediate AX.iii (1.00 g), 6-bromo-4-[(4-methoxyphenyl)methyl]-2H-pyrido[3,2-b]-1,4-oxazin-3(4H)-one (805 mg; prepared according to WO 2009/104159) and DMF (15 mL) and the mixture was stirred at 110° C. overnight. The mixture was cooled to rt and filtered over a glass-fibre filter. The solid was washed with EA and the filtrate was diluted with EA and washed with NH$_4$Cl. The aq. layer was twice extracted with EA. The combined org. layers were washed twice with water and brine, dried over MgSO$_4$ and concentrated under reduced pressure. The crude product was purified by CC (Combi Flash; gradient Hept to Hept-EA 60-40) affording 910 mg (63% yield) of a yellow oil.

MS1 (ESI, m/z): 503.2 [M+H$^+$]; $t_R$=0.99 min.

AX.v. 6-[5-(3-hydroxy-propyl)-2-oxo-[1,3,4]oxadi-azol-3-yl]-4-(4-methoxy-benzyl)-4H-pyrido[3,2-b][1,4]oxazin-3-one A solution of intermediate AX.iv (880 mg) in MeOH (22 mL) and THF (10 mL) was hydrogenated over 10% Pd/C (143 mg) for 4 h. The suspension was filtered over Celite and the filter cake was washed with DCM/MeOH. The filtrate was concentrated under reduced pressure and the oil was dried under HV, affording a light yellow oil (554 mg; 100% yield).

MS1 (ESI, m/z): 413.2 [M+H$^+$]; $t_R$=0.79 min.

AX.vi. 3-{4-[4-(4-methoxy-benzyl)-3-oxo-3,4-di-hydro-2H-pyrido[3,2-b][1,4]oxazin-6-yl]-5-oxo-4,5-dihydro-[1,3,4]oxadiazol-2-yl}-propionaldehyde A solution of intermediate AX.v (1220 mg) and DIPEA (1.52 mL) in DCM (20 mL) was cooled to 10° C. At this temperature a solution of SO$_3$.Pyr complex (1.04 g) in DMSO (4.2 mL) was added dropwise over 10 min and stirred at rt for 4 h. SO$_3$. Pyr complex (283 mg) was added again and the mixture was stirred at rt for 1.5 h. The reaction mixture was diluted with DCM and washed with HCl 1M (2.34 mL), water and brine, dried over MgSO$_4$ and concentrated under reduced pressure. The residue was purified by CC (Combi Flash; gradient Hept-EA 30-70), affording a yellowish foam (610 mg; 50% yield).

MS1 (ESI, m/z): 411.1 [M+H$^+$]; $t_R$=0.84 min.

AX.vii. 3-{4-[4-(4-methoxy-benzyl)-3-oxo-3,4-di-hydro-2H-pyrido[3,2-b][1,4]oxazin-6-yl]-5-oxo-4,5-dihydro-[1,3,4]oxadiazol-2-yl}-propionic acid Intermediate AX.vi (580 mg) was dissolved in water (4 mL) and acetone (14 mL). KMnO$_4$ (558 mg) was added. The reaction mixture was stirred at rt for 1 h. Sodium bisulphite (515 mg) was added. The mixture was stirred 15 min, filtered through Celite and the acetone was removed under reduced pressure. The residue was partitioned between EA and 0.1M NaOH. The org. layer was extracted with 0.1M NaOH. The combined aq. layers were washed with EA and acidified with 1M HCl. The acidic aq. phase was extracted twice with EA. The combined org. layers were dried over MgSO$_4$ and concentrated under reduced pressure and the solid was dried under HV, affording a yellowish foam (420 mg; 70% yield).

MS1 (ESI, m/z): 427.1 [M+H$^+$]; $t_R$=0.78 min.

AX.viii. (2-{4-[4-(4-methoxy-benzyl)-3-oxo-3,4-dihydro-2H-pyrido[3,2-b][1,4]oxazin-6-yl]-5-oxo-4,5-dihydro-[1,3,4]oxadiazol-2-yl}-ethyl)-carbamic acid benzyl ester To a solution of intermediate AX.vii (395 mg) in DMF (1.1 mL) and benzyl alcohol (0.767 mL) was added TEA (0.129 mL) at rt, the mixture was heated to 100° C. DPPA (0.225 mL) was added dropwise and the mixture was stirred at 100° C. for 3 h. EA was added. The resulting mixture was sequentially washed with NH$_4$Cl, NaHCO$_3$, water and brine, dried over MgSO$_4$, filtered and concentrated to dryness under vacuum. The residue was purified by prep-HPLC (Method 1), affording a colourless foam (69 mg; 14% yield).

MS1 (ESI, m/z): 532.2 [M+H$^+$]; $t_R$=0.93 min.

AX.ix. 6-[5-(2-amino-ethyl)-2-oxo-[1,3,4]oxadiazol-3-yl]-4H-pyrido[3,2-b][1, 4]oxazin-3-one To a solution of intermediate AX.viii (64 mg) in DCM (2 mL) was added TFA (0.461 mL) and TfOH (0.107 mL) at rt. The reaction mixture was stirred at rt for 40 min. After cooling to 0° C. TEA (1.68 mL) was carefully added to quench the reaction. Water and DCM were added and the phases were separated. The aq. layer was extracted twice with DCM and the org. layer was dried over MgSO$_4$ and concentrated. The yellow oil residue was purified by prep-HPLC (Method 6), affording a beige powder (11 mg; 33% yield).

MS1 (ESI, m/z): 278.2 [M+H$^+$]; $t_R$=0.43 min.

Preparation AY

6-[5-(2-amino-ethyl)-2-oxo-oxazol-3-yl]-4H-pyrido[3,2-b][1,4]oxazin-3-one formate salt AY.i. (4-bromo-but-3-ynyl)-carbamic acid tert-butyl ester Tert-butyl N-3-butyn-1-ylcarbamate (950 mg; commercial) was dissolved in acetone (5 mL), treated with N-bromosuccinimide (1.20 g) and AgNO$_3$ (24 mg) and stirred at rt for 1.5 h. The reaction mixture was poured on ice/water. The solid was filtered off and washed with water and EA. The aq. layer was extracted with EA. The combined org. phases were washed with water, dried over MgSO$_4$, filtered and concentrated. The crude product was purified by CC (Combi Flash; gradient Hept to Hept-EA 80-20), affording a light yellow oil (815 mg; 59% yield).

$^1$H NMR (CDCl$_3$) δ: 4.82 (br. s, 1H); 3.20-3.38 (m, 2H); 2.43 (t, J=6.4 Hz, 2H); 1.48 (s, 9H).

AY.ii. [4-(4-methoxy-benzyl)-3-oxo-3,4-dihydro-2H-pyrido[3,2-b][1,4]oxazin-6-yl]-carbamic acid tert-butyl ester Tert-butyl carbamate (369 mg), cesium carbonate (1.21 g) tris(dibenzylideneacetone)dipalladium(0) (39 mg) and XantPhos (50 mg). were added to a solution of 6-bromo-4-[(4-methoxyphenyl)methyl]-2H-pyrido[3,2-b]-1,4-oxazin-3 (4H)-one (1.00 g; prepared according to WO 2009/104159) in dioxane (15 mL). The reaction mixture was purged several times with N$_2$ and the mixture was stirred at 90° C. overnight. The reaction mixture was cooled to rt and the solid was filtered off. The filtrate was evaporated under reduced pressure and the residue was purified by CC (Combi Flash System; gradient Hept to Hept-EA 1-1), affording a yellowish foam (915 mg; 83% yield). MS1 (ESI, m/z): 386.1 [M+H$^+$]; $t_R$=0.95 min.

AY.iii. (4-{tert-butoxycarbonyl-[4-(4-methoxy-benzyl)-3-oxo-3,4-dihydro-2H-pyrido[3,2-b][1,4]oxazin-6-yl]-amino}-but-3-ynyl)-carbamic acid tert-butyl ester K$_3$PO$_4$ (716 mg), CuSO$_4$ (62.1 mg) and 1,10-phenanthroline monohydrate (154 mg) were added to a mixture of intermediate AY.ii (500 mg) and intermediate AY.i (386 mg) in toluene (15 mL) and heated at 85° C. for 3 days. The reaction mixture was cooled to rt, filtered and washed with EA. The filtrate was concentrated under reduced pressure and purified by CC (Combi Flash; gradient Hept to Hept-EA 1-1), affording a colourless foam (335 mg; 47% yield).
MS1 (ESI, m/z): 553.1 [M+H$^+$]; $t_R$=1.01 min.

AY.iv. (2-{3-[4-(4-methoxy-benzyl)-3-oxo-3,4-dihydro-2H-pyrido[3,2-b][1,4]oxazin-6-yl]-2-oxo-2,3-dihydro-oxazol-5-yl}-ethyl)-carbamic acid tert-butyl ester A solution of intermediate AY.iii (320 mg) in dry DCM (1.5 mL) was added to a suspension of chloro(triphenylphosphine)gold(I) (5.7 mg) and silver hexafluoroantimonate (V) (4.0 mg) in MeCN (0.15 mL). The resulting mixture was heated at 40° C. for 3 h. The mixture was concentrated under reduced pressure and the residue was purified by CC (Combi Flash; gradient Hept to Hept-EA 1-1), affording a yellowish foam (132 mg; 46% yield).
MS1 (ESI, m/z): 497.0 [M+H$^+$]; $t_R$=0.93 min.

AY.v. 6-[5-(2-amino-ethyl)-2-oxo-oxazol-3-yl]-4H-pyrido[3,2-b][1,4]oxazin-3-one formate salt TFA (2.08 mL) and TfOH (0.481 mL) were added at rt to a solution of intermediate AY.iv (270 mg) in DCM (6 mL). The reaction mixture was stirred at rt for 45 min. After cooling to 0° C., TEA (7.57 mL) was carefully added followed by water (20 mL) and DCM (40 mL). The phases were separated. The aq. layer was concentrated to a volume of 20 mL and purified by prep-HPLC (Method 7), affording a beige solid (125 mg; 71% yield).
MS1 (ESI, m/z): 277.0 [M+H$^+$]; $t_R$=0.45 min.

Preparation AZ

6-[(R)-5-(2-amino-ethyl)-2-oxo-oxazolidin-3-yl]-4H-pyrido[3,2-b][1,4]oxazin-3-one AZ.i. [(R)-4-(tert-butyl-dimethyl-silanyloxy)-2-hydroxy-butyl]-carbamic acid ethyl ester (S,S)-(+)-N,N'-bis(3,5-di-ter t-butylsalicylidene)-1,2-cyclohexanediaminocobalt(II) (8.5 g; commercial) in TBME (66.4 mL) was treated with 4-nitrobenzoic acid (4.7 g) and stirred for 20 min at rt. The suspension was sequentially treated with urethane (19.92 g) and 2-[2-[[(tert-butyl)dimethylsilyl]oxy]ethyl]oxirane (95 g; prepared according to WO 2009/080761) and further stirred at rt for 6 h. The solvent was removed under reduced pressure and the residue was purified by CC (Hex-EA 1-1), affording a brown oil (65.4 g; 48% yield).
$^1$H NMR (CDCl$_3$) δ: 5.11 (br. s, 1H); 4.11 (q, J=7.1 Hz, 2H); 3.74-3.99 (m, 4H); 3.25-3.43 (m, 1H); 3.03-3.20 (m, 1H); 1.58-1.76 (m, 2H); 1.16-1.29 (m, 3H); 0.89 (s, 9H); 0.08 (s, 6H).

AZ.ii. (R)-5-[2-(tert-butyl-dimethyl-silanyloxy)-ethyl]-oxazolidin-2-one

KOtBu (30.2 g) was added at 0° C. to a solution of intermediate AZ.i (65.4 g) in THF (800 mL) and the reaction mixture was further stirred at rt for 4 h. The reaction mixture was concentrated to about 200 mL, diluted with water and extracted with EA. The combined org. phases were dried over MgSO$_4$, filtered, concentrated and purified by CC (Hept/EA 1:1), affording a dark yellow oil (46.7 g; 85% yield) which crystallised on standing.
$^1$H NMR (CDCl$_3$) δ: 5.27 (br. s, 1H); 4.74-4.88 (m, 1H); 3.74-3.82 (m, 2H); 3.69 (t, J=8.4 Hz, 1H); 3.26-3.38 (m, 1H); 1.79-2.07 (m, 2H); 0.88 (s, 9H); 0.05 (s, 6H).

AZ.iii. (6-{(R)-5-[2-(tert-butyl-dimethyl-silanyloxy)-ethyl]-2-oxo-oxazolidin-3-yl}-2-nitro-pyridin-3-yloxy)-acetic acid ethyl ester K$_2$CO$_3$ (11.26 g), CuI (388 mg), intermediate AZ.ii (10.00 g) and (6-bromo-2-nitro-pyridin-3-yloxy)-acetic acid ethyl ester (12.43 g; commercial) were placed in a 3-necked 500 mL flask. Dioxane (305 mL) and N,N-dimethyl-ethylenediamine (0.921 mL) were added and the mixture was degassed with argon. The suspension was heated at 100° C. overnight. The reaction mixture was filtered over Celite and the filtrate was evaporated under reduced pressure. The residue was purified by CC (Hept-EA 2-1 to 0-1), affording a beige solid (16 g; 84% yield).
MS1 (ESI, m/z): 470.3 [M+H$^+$]; $t_R$=1.04 min.

AZ.iv. 6-[(R)-5-(2-hydroxy-ethyl)-2-oxo-oxazolidin-3-yl]-4H-pyrido[3,2-b][1,4]oxazin-3-one Iron (85.6 g) was added to a solution of NH$_4$Cl (13.7 g) in H$_2$O (102 mL) and MeOH (102 mL). The grey suspension was heated to 50° C. and treated dropwise with a solution of intermediate AZ.iii (16.0 g) in MeOH (360 mL). The suspension was further heated at 68° C. IT for 2.5 h and filtered over Celite. The filtrate was treated with AcOH (112 mL) and further refluxed at 95° C. for 2 h. The solvent was evaporated and the suspension was cooled to 0° C. The crystals were collected by filtration. The mother liquor was evaporated to dryness and the residue was stirred with the minimum of water affording a second crop of crystals. The total yield was 9.54 g (100% yield; beige crystals).
MS1 (ESI, m/z): 280.11 [M+H$^+$]; $t_R$=0.47 min.

AZ.v. Methanesulfonic acid 2-[(R)-2-oxo-3-(3-oxo-3,4-dihydro-2H-pyrido[3,2-b][1,4]oxazin-6-yl)-oxazolidin-5-yl]-ethyl ester TEA (4.19 mL) and MsCl (1.28 mL) were added at −60° C. to a suspension of intermediate AZ.iv (4.20 g) in DCM (65 mL). The reaction mixture was slowly allowed to reach −40° C. over 2 h. The reaction mixture was treated with sat. aq. NaHCO$_3$ and extracted with DCM. The combined org. layers were dried over MgSO$_4$, filtered and concentrated to dryness, affording, after stirring the residue in TBME-DCM-MeOH, a salmon solid (1.88 g; 35% yield).
MS1 (ESI, m/z): 358.2 [M+H$^+$]; $t_R$=0.65 min.

AZ.vi. 6-[(R)-5-(2-azido-ethyl)-2-oxo-oxazolidin-3-yl]-4H-pyrido[3,2-b][1,4]oxazin-3-one Starting from intermediate AZ.v and sodium azide and proceeding in analogy to Preparation AQ, step AQ.ii, the title compound was obtained as a salmon solid (950 mg; 61% yield).
MS1 (ESI, m/z): 305.2 [M+H$^+$]; $t_R$=0.71 min.

AZ.vii. 6-[(R)-5-(2-amino-ethyl)-2-oxo-oxazolidin-3-yl]-4H-pyrido[3,2-b][1,4]oxazin-3-one Starting from intermediate AZ.vi and proceeding in analogy to Preparation AQ, step AQ.iii, the title compound was obtained as a yellow solid (177 mg; 97% yield).
MS1 (ESI, m/z): 279.0 [M+H$^+$]; $t_R$=0.43 min.

Preparation BA

6-[(R)-5-(2-amino-ethyl)-2-oxo-oxazolidin-3-yl]-4H-pyrido[3,2-b][1,4]thiazin-3-one Starting from 6-[(5R)-5-(2-hydroxyethyl)-2-oxo-3-oxazolidinyl]-2H-pyrido[3,2-b]-1,4-thiazin-3(4H)-one (prepared according to WO 2010/041194), the title compound was prepared in analogy to Preparation AQ (mesylate formation: 84% yield, beige solid); azide formation: 81% yield, yellowish solid; azide reduction: 90% yield, yellowish solid).

MS1 (ESI, m/z): 294.9 [M+H$^+$]; $t_R$=0.47 min.

Preparation BB

4-(benzyloxy)-3-(6-methoxypyridin-2-yl)benzaldehyde

Starting from 2-chloro-6-methoxypyridine (200 mg; commercial) and 2-benzyloxy-5-formylphenylboronic acid (364 mg; commercial) and proceeding in analogy to Preparation A, the title compound was obtained as a light yellow oil (279 mg; 64% yield).

MS1 (ESI, m/z): 320.1 [M+H$^+$]; $t_R$=0.97 min.

Preparation BC

5-(5-methoxypyridazin-3-yl)nicotinaldehyde

BC.i. Ethyl 5-(5-methoxypyridazin-3-yl)nicotinate 3-chloro-5-methoxypyridazine (149 mg; commercial), 3-(ethoxycarbonyl)pyridine-5-boronic acid pinacol ester (289 mg; commercial), K$_2$CO$_3$ (276 mg) and Pd(PPh$_3$)$_4$ (173 mg) were suspended in DMF (3.4 mL). The sealed tube was evacuated and refilled with N$_2$ three times. The mixture was then stirred overnight at 85° C. The reaction mixture was cooled down to rt and diluted with EA and water. The layers were separated and the aq. phase was extracted twice with EA. The combined org. layers were dried over MgSO$_4$ and concentrated under reduced pressure. The crude was purified by prep-HPLC (Method 6) to afford the desired product as a white solid (156 mg; 60% yield).

MS1 (ESI, m/z): 260.2 [M+H$^+$]; $t_R$=0.72 min.

BC.ii. (5-(5-methoxypyridazin-3-yl)pyridin-3-yl)methanol

Starting from intermediate BC.i (50 mg) and proceeding in analogy to Preparation AJ, step AJ.iii, the title alcohol was obtained without purification, as a yellow sticky solid (42 mg; 95% yield).

MS1 (ESI, m/z): 218.2 [M+H$^+$]; $t_R$=0.41 min.

BC.iii. 5-(5-methoxypyridazin-3-yl)nicotinaldehyde

Starting from intermediate BC.ii (42 mg) and proceeding in analogy to Preparation AC, step AC.iii, the title compound was obtained as a yellow solid (33 mg; 78% yield).

$^1$H NMR (CDCl$_3$) δ: 10.27 (s, 1H); 9.58 (d, J=2.3 Hz, 1H); 9.24 (d, J=1.9 Hz, 1H); 9.03 (d, J=2.8 Hz, 1H); 8.88 (t, J=2.1 Hz, 1H); 7.37 (d, J=2.8 Hz, 1H); 4.08 (s, 3H).

Preparation BD

4-(5-methoxypyridazin-3-yl)picolinaldehyde

BD.i. Methyl 4-(5-methoxypyridazin-3-yl)picolinate 3-chloro-5-methoxypyridazine (253 mg; commercial), methyl 4-(4,4,5,5-tetramethyl-1,3,2-dioxaborolan-2-yl)picolinate (447 mg; commercial), K$_2$CO$_3$ (470 mg) and tetrakis(triphenylphosphine)palladium (295 mg) were suspended in DMF (5.78 mL). The sealed tube was evacuated and refilled with N$_2$ three times. The mixture was then heated to 85° C. and stirred at this temperature overnight. The reaction mixture was cooled to rt and partitioned between EA/MeOH 9:1 and diluted with sat. aq. NH$_4$OH. The two phases were separated and org. layer was washed twice with EA/MeOH 9:1 and with sat. aq. NaHCO$_3$, dried over MgSO$_4$ and concentrated. The aq. phases were combined and concentrated. The residue was purified by prep-HPLC (Method 7). The residue (from aq. phases) was triturated with DCM/MeOH 4:1, the solid (salt) was filtered, washed with DCM/MeOH 4:1 and the filtrate was concentrated. The residue was purified by prep-HPLC (Method 7) and a pink solid (87 mg; 22% yield) was obtained.

MS1 (ESI, m/z): 247.07 [M+H$^+$]; $t_R$=0.60 min.

BD.ii. (4-(5-methoxypyridazin-3-yl)pyridin-2-yl)methanol

A suspension of intermediate BD.i (34.3 mg) in THF (0.84 mL) was cooled down to 0° C. and treated with LiAlH$_4$ (1M in THF; 0.126 mL). The mixture was stirred at 0° C. for 5 min. The reaction mixture was quenched with water (0.007 mL), NaOH 1N (0.007 mL) and water (0.21 mL). The mixture was diluted with EA and filtered. The filtrate was evaporated under reduced pressure to afford a yellow foam (29 mg, 95% yield) which was not further purified.

MS1 (ESI, m/z): 218.15 [M+H$^+$]; $t_R$=0.40 min.

BD.iii. 4-(5-methoxypyridazin-3-yl)picolinaldehyde

A suspension of intermediate BD.ii (28.2 mg) in MeCN (1.56 mL) and DCM (0.8 mL) was treated at rt with activated MnO$_2$ (126 mg). After 15 h, the mixture was filtered over Celite, washed with DCM and the filtrate was evaporated to afford a whitish solid (16 mg; 58% yield).

MS1 (ESI, m/z): 216.15 [M+H$^+$]; $t_R$=0.59 min.

EXAMPLES OF COMPOUNDS ACCORDING TO THE INVENTION

Example 1

6-((R)-5-{2-[(3'-methoxy-biphenyl-3-ylmethyl)-amino]-ethyl}-2-oxo-oxazolidin-3-yl)-4H-benzo[1,4]thiazin-3-one 3'-methoxy-[1,1'-biphenyl]-3-carboxaldehyde (72 mg; commercial) and (R)-5-(2-aminoethyl)-3-(3-oxo-3,4-dihydro-2H-benzo[b][1,4]thiazin-6-yl)oxazolidin-2-one (79 mg; prepared according to WO 2009/104147) were dissolved in DCM (0.9 mL) and DMF (0.9 mL). The mixture was treated with NaBH(OAc)$_3$ (217 mg) and stirred at rt for 40 min. The residue was partitioned between sat. aq. NaHCO$_3$ and EA. The org. layer was separated, washed with brine, dried over MgSO$_4$, and concentrated under reduced pressure. After purification by prep-HPLC (Method 2), the title compound was obtained as a colourless foam (78 mg; 46% yield).
MS3 (ESI, m/z): 490.3 [M+H$^+$]; $t_R$=0.71 min.

Example 2

2-methoxy-6-[3-({2-[(R)-2-oxo-3-(3-oxo-3,4-di-hydro-2H-benzo[1,4]thiazin-6-yl)-oxazolidin-5-yl]-ethylamino}-methyl)-phenyl]-isonicotinonitrile Starting from the compound of Preparation V (89 mg) and (R)-5-(2-aminoethyl)-3-(3-oxo-3,4-dihydro-2H-benzo[b][1,4]thiazin-6-yl)oxazolidin-2-one (110 mg; prepared according to WO 2009/104147) and proceeding in analogy to Example 1, the title compound was obtained, after purification by prep-HPLC (Method 2), as a colourless foam (25 mg; 13% yield).
$^1$H NMR (CDCl$_3$) δ: 7.92 (m, 2H); 7.52 (m, 1H); 7.42 (m, 2H); 7.34 (m, 1H); 7.22 (m, 1H); 6.88 (m, 2H); 4.77 (m, 1H); 4.04 (m, 4H); 3.86 (m, 2H); 3.64 (m, 1H); 3.35 (m, 2H); 2.86 (m, 2H); 2.00 (m, 2H).
MS1 (ESI, m/z): 516.3 [M+H$^+$]; $t_R$=0.72 min.

Example 3

3'-({2-[(S)-2-oxo-3-(3-oxo-3,4-dihydro-2H-benzo[1,4]thiazin-6-yl)-oxazolidin-5-yl]-ethylamino}-methyl)-biphenyl-3-carbonitrile Starting from the compound of Preparation A (47 mg) and (S)-5-(2-aminoethyl)-3-(3-oxo-3,4-dihydro-2H-benzo[b][1,4]thiazin-6-yl)oxazolidin-2-one (101 mg; prepared according to WO 2010/041194) and proceeding in analogy to Example 1, the title compound was obtained, after purification by prep-HPLC (Method 2), as a colourless foam (12 mg; 13% yield).
MS1 (ESI, m/z): 485.2 [M+H$^+$]; $t_R$=0.70 min.

Example 4

6-((S)-5-{2-[(3'-methoxy-biphenyl-3-ylmethyl)-amino]-ethyl}-2-oxo-oxazolidin-3-yl)-4H-pyrido[3,2-b][1,4]oxazin-3-one Starting from 3'-methoxy-[1,1'-biphenyl]-3-carboxaldehyde (53 mg; commercial) and compound of Preparation Z (75 mg) and proceeding in analogy to Example 1, the title compound was obtained, after purification by prep-HPLC (Method 2), as a colourless powder (56 mg; 47% yield).
MS1 (ESI, m/z): 475.2 [M+H$^+$]; $t_R$=0.70 min.

Example 5

3'-({2-[(R)-2-oxo-3-(3-oxo-3,4-dihydro-2H-benzo[1,4]thiazin-6-yl)-oxazolidin-5-yl]-ethylamino}-methyl)-biphenyl-3-carbonitrile Starting from the compound of Preparation A (84 mg) and (R)-5-(2-aminoethyl)-3-(3-oxo-3,4-dihydro-2H-benzo[b][1,4]thiazin-6-yl)oxazolidin-2-one (83 mg; prepared according to WO 2009/104147) and proceeding in analogy to Example 1, the title compound was obtained, after purification by prep-HPLC (Method 1), as a colourless foam (71 mg; 52% yield).
MS1 (ESI, m/z): 485.2 [M+H$^+$]; $t_R$=0.71 min.

Example 6

6-((R)-5-{2-[(4'-methoxy-biphenyl-3-ylmethyl)-amino]-ethyl}-2-oxo-oxazolidin-3-yl)-4H-benzo[1,4]thiazin-3-one Starting from 4'-methoxy-[1,1'-biphenyl]-3-carboxaldehyde (40 mg; commercial) and (R)-5-(2-aminoethyl)-3-(3-oxo-3,4-dihydro-2H-benzo[b][1,4]thiazin-6-yl)oxazolidin-2-one (55 mg; prepared according to WO 2009/104147) and proceeding in analogy to Example 1, the title compound was obtained, after purification by prep-HPLC (Method 1), as a colourless foam (14 mg; 15% yield).
MS1 (ESI, m/z): 490.2 [M+H$^+$]; $t_R$=0.72 min.

Example 7

6-((R)-5-{2-[(4'-hydroxy-3'-methoxy-biphenyl-3-ylmethyl)-amino]-ethyl}-2-oxo-oxazolidin-3-yl)-4H-benzo[1,4]thiazin-3-one Starting from 4'-hydroxy-3'-methoxy-[1,1'-biphenyl]-3-carboxaldehyde (46 mg; commercial) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 1), as a colourless solid (34 mg; 34% yield).
MS1 (ESI, m/z): 506.1 [M+H$^+$]; $t_R$=0.66 min.

Example 8

5-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-2-carbonitrile Starting from the compound of Preparation B (67 mg) and (R)-5-(2-aminoethyl)-3-(3-oxo-3,4-dihydro-2H-benzo[b][1,4]thiazin-6-yl)oxazolidin-2-one (75 mg; prepared according to WO 2009/104147) and proceeding in analogy to Example 1, the title compound was obtained, after purification by prep-HPLC (Method 1), as a colourless foam (41 mg; 31% yield).
$^1$H NMR (CDCl$_3$) δ: 8.51 (m, 1H); 8.33 (m, 1H); 7.68 (m, 1H); 7.58 (m, 1H); 7.47 (m, 3H); 7.33 (m, 1H); 6.96 (m, 3H); 4.76 (m, 1H); 4.00 (m, 3H); 3.87 (m, 3H); 3.65 (m, 1H); 3.38 (m, 2H); 2.95 (m, 2H); 2.10 (m, 2H).
MS1 (ESI, m/z): 515.1 [M+H$^+$]; $t_R$=0.72 min.

Example 9

5-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-3-carbonitrile Starting from the compound of Preparation C (48 mg) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 2), as a colourless foam (56 mg; 54% yield).
MS3 (ESI, m/z): 515.2 [M+H$^+$]; $t_R$=0.72 min.

Example 10

6-((R)-5-{2-[(3'-hydroxy-5'-methoxy-biphenyl-3-ylmethyl)-amino]-ethyl}-2-oxo-oxazolidin-3-yl)-4H-benzo[1,4]thiazin-3-one Starting from 3'-hydroxy-5'-methoxy-[1,1'-biphenyl]-3-carboxaldehyde (46 mg; prepared according to WO 2007/058602) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 1), as a colourless foam (54 mg; 53% yield).

MS3 (ESI, m/z): 506.1 [M+H$^+$]; $t_R$=0.66 min.

Example 11

6-((R)-5-{2-[(6-fluoro-3'-methoxy-biphenyl-3-ylmethyl)-amino]-ethyl}-2-oxo-oxazolidin-3-yl)-4H-benzo[1,4]thiazin-3-one Starting from the compound of Preparation D (11 mg) and (R)-5-(2-aminoethyl)-3-(3-oxo-3,4-dihydro-2H-benzo[b][1,4]thiazin-6-yl)oxazolidin-2-one (8 mg; prepared according to WO 2009/104147) and proceeding in analogy to Example 1, the title compound was obtained, after purification by prep-HPLC (Method 1), as a colourless foam (3 mg; 18% yield).

MS1 (ESI, m/z): 508.2 [M+H$^+$]; $t_R$=0.73 min.

Example 12

6-((R)-5-{2-[(2-fluoro-3'-methoxy-biphenyl-3-ylmethyl)-amino]-ethyl}-2-oxo-oxazolidin-3-yl)-4H-benzo[1,4]thiazin-3-one Starting from the compound of Preparation E (16 mg) and (R)-5-(2-aminoethyl)-3-(3-oxo-3,4-dihydro-2H-benzo[b][1,4]thiazin-6-yl)oxazolidin-2-one (8 mg; prepared according to WO 2009/104147) and proceeding in analogy to Example 1, the title compound was obtained, after purification by prep-HPLC (Method 2), as a colourless foam (2 mg; 15% yield).

MS1 (ESI, m/z): 508.2 [M+H$^+$]; $t_R$=0.72 min.

Example 13

6-((R)-5-{2-[3-(5-methoxy-pyridin-3-yl)-benzylamino]-ethyl}-2-oxo-oxazolidin-3-yl)-4H-benzo[1,4]thiazin-3-one Starting from the compound of Preparation F (60 mg) and (R)-5-(2-aminoethyl)-3-(3-oxo-3,4-dihydro-2H-benzo[b][1,4]thiazin-6-yl)oxazolidin-2-one (83 mg; prepared according to WO 2009/104147) and proceeding in analogy to Example 1, the title compound was obtained, after purification by prep-HPLC (Method 1), as a colourless foam (55 mg; 40% yield).

MS1 (ESI, m/z): 491.2 [M+H$^+$]; $t_R$=0.57 min.

Example 14

6-((R)-5-{2-[3-(4-methoxy-pyridin-2-yl)-benzylamino]-ethyl}-2-oxo-oxazolidin-3-yl)-4H-benzo[1,4]thiazin-3-one Starting from the compound of Preparation G (50 mg) and (R)-5-(2-aminoethyl)-3-(3-oxo-3,4-dihydro-2H-benzo[b][1,4]thiazin-6-yl)oxazolidin-2-one (69 mg; prepared according to WO 2009/104147) and proceeding in analogy to Example 1, the title compound was obtained, after purification by prep-HPLC (Method 1), as a colourless foam (56 mg; 49% yield).

MS1 (ESI, m/z): 491.2 [M+H$^+$]; $t_R$=0.53 min.

Example 15

6-((R)-5-{2-[3-(6-methoxy-pyridin-2-yl)-benzylamino]-ethyl}-2-oxo-oxazolidin-3-yl)-4H-benzo[1,4]thiazin-3-one Starting from the compound of Preparation H (100 mg) and (R)-5-(2-aminoethyl)-3-(3-oxo-3,4-dihydro-2H-benzo[b][1,4]thiazin-6-yl)oxazolidin-2-one (83 mg; prepared according to WO 2009/104147) and proceeding in analogy to Example 1, the title compound was obtained, after purification by prep-HPLC (Method 2), as a colourless foam (10 mg; 7% yield).

MS1 (ESI, m/z): 491.2 [M+H$^+$]; $t_R$=0.71 min.

Example 16

6-((R)-5-{2-[3-(6-methoxy-pyridin-3-yl)-benzylamino]-ethyl}-2-oxo-oxazolidin-3-yl)-4H-benzo[1,4]thiazin-3-one Starting from the compound of Preparation I (60 mg) and (R)-5-(2-aminoethyl)-3-(3-oxo-3,4-dihydro-2H-benzo[b][1,4]thiazin-6-yl)oxazolidin-2-one (83 mg; prepared according to WO 2009/104147) and proceeding in analogy to Example 1, the title compound was obtained, after purification by prep-HPLC (Method 1), as a colourless foam (9 mg; 62% yield).

MS1 (ESI, m/z): 491.2 [M+H$^+$]; $t_R$=0.67 min.

Example 17

5-[3-({2-[(R)-2-oxo-3-(3-oxo-3,4-dihydro-2H-benzo[1,4]thiazin-6-yl)-oxazolidin-5-yl]-ethylamino}-methyl)-phenyl]-nicotinonitrile Starting from the compound of Preparation J (42 mg) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 1), as a colourless foam (44 mg; 45% yield).

$^1$H NMR (CDCl$_3$) δ: 8.34 (m, 1H); 8.08 (m, 1H); 7.92 (m, 3H); 7.61 (m, 1H); 7.46 (m, 2H); 7.22 (m, 2H); 6.95 (m, 1H); 4.75 (m, 1H); 4.04 (m, 3H); 3.66 (m, 1H); 3.34 (m, 2H); 3.00 (m, 2H); 2.09 (m, 2H).

MS1 (ESI, m/z): 486.1 [M+H$^+$]; $t_R$=0.67 min.

Example 18

6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-pyridine-2-carbonitrile Starting from the compound of Preparation K (42 mg) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 1), as a colourless foam (34 mg; 35% yield).

$^1$H NMR (CDCl$_3$) δ: 9.00 (m, 1H); 8.81 (d, J=1.8 Hz, 1H); 8.30 (m, 1H); 8.19 (t, J=2.0 Hz, 1H); 7.65 (m, 1H); 7.51 (m, 1H); 7.47 (m, 2H); 7.31 (m, 1H); 7.21 (m, 1H); 6.92 (m, 1H); 4.75 (m, 1H); 4.07 (m, 1H); 4.02 (s, 2H); 3.67 (m, 1H); 3.33 (s, 2H); 3.01 (m, 2H); 2.11 (m, 2H).

MS1 (ESI, m/z): 486.1 [M+H$^+$]; t$_R$=0.65 min.

Example 19

6-hydroxy-5-[3-({2-[(R)-2-oxo-3-(3-oxo-3,4-di-hydro-2H-benzo[1,4]thiazin-6-yl)-oxazolidin-5-yl]-ethylamino}-methyl)-phenyl]-nicotinonitrile Starting from the compound of Preparation L (45 mg) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 1), as a colourless foam (13 mg; 13% yield).

MS1 (ESI, m/z): 502.1 [M+H$^+$]; t$_R$=0.61 min.

Example 20

6-[(R)-5-(2-{[6-(3-methoxy-phenyl)-pyridin-2-ylm-ethyl]-amino}-ethyl)-2-oxo-oxazolidin-3-yl]-4H-benzo[1,4]thiazin-3-one Starting from 6-(3-methoxyphenyl)-2-pyridinecarboxal-dehyde (60 mg; prepared according to Jensen et al., J. Am. Chem. Soc. (2003), 125, 2113-2128) and (R)-5-(2-amino-ethyl)-3-(3-oxo-3,4-dihydro-2H-benzo[b][1,4]thiazin-6-yl) oxazolidin-2-one (83 mg; prepared according to WO 2009/104147) and proceeding in analogy to Example 1, the title compound was obtained, after purification by prep-HPLC (Method 1), as a colourless solid (76 mg; 55% yield).

MS1 (ESI, m/z): 491.2 [M+H$^+$]; t$_R$=0.70 min.

Example 21

6-[(R)-5-(2-{[4-(3-methoxy-phenyl)-pyridin-2-ylm-ethyl]-amino}-ethyl)-2-oxo-oxazolidin-3-yl]-4H-benzo[1,4]thiazin-3-one Starting from compound of Preparation M (86 mg) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 1), as a colourless foam (1 mg; 1% yield).

MS1 (ESI, m/z): 491.1 [M+H$^+$]; t$_R$=0.69 min.

Example 22

6-((R)-5-{2-[(6'-methoxy-[2,2']bipyridinyl-6-ylm-ethyl)-amino]-ethyl}-2-oxo-oxazolidin-3-yl)-4H-benzo[1,4]thiazin-3-one Starting from the compound of Preparation N (36 mg) and (R)-5-(2-aminoethyl)-3-(3-oxo-3,4-dihydro-2H-benzo[b][1,4]thiazin-6-yl)oxazolidin-2-one (50 mg; prepared according to WO 2009/104147) and proceeding in analogy to Example 1, the title compound was obtained, after purification by prep-HPLC (Method 2), as a colourless foam (62 mg; 74% yield).

MS1 (ESI, m/z): 492.2 [M+H$^+$]; t$_R$=0.69 min.

Example 23

6-((R)-5-{2-[3-(4-methoxy-pyrimidin-2-yl)-benzy-lamino]-ethyl}-2-oxo-oxazolidin-3-yl)-4H-benzo[1,4]thiazin-3-one Starting from the compound of Preparation O (35 mg) and (R)-5-(2-aminoethyl)-3-(3-oxo-3,4-dihydro-2H-benzo[b][1,4]thiazin-6-yl)oxazolidin-2-one (43 mg; prepared according to WO 2009/104147) and proceeding in analogy to Example 1, the title compound was obtained, after purification by prep-HPLC (Method 1), as a colourless foam (27 mg; 37% yield).

MS1 (ESI, m/z): 492.2 [M+H$^+$]; t$_R$=0.66 min.

Example 24

6-((R)-5-{2-[3-(6-methoxy-pyrimidin-4-yl)-benzy-lamino]-ethyl}-2-oxo-oxazolidin-3-yl)-4H-benzo[1,4]thiazin-3-one Starting from the compound of Preparation P (13 mg) and (R)-5-(2-aminoethyl)-3-(3-oxo-3,4-dihydro-2H-benzo[b][1,4]thiazin-6-yl)oxazolidin-2-one (18 mg; prepared according to WO 2009/104147) and proceeding in analogy to Example 1, the title compound was obtained, after purification by prep-HPLC (Method 1), as a colourless foam (16 mg; 53% yield).

MS1 (ESI, m/z): 492.1 [M+H$^+$]; t$_R$=0.65 min.

Example 25

6-((R)-5-{2-[3-(6-methoxy-pyrazin-2-yl)-benzy-lamino]-ethyl}-2-oxo-oxazolidin-3-yl)-4H-benzo[1,4]thiazin-3-one Starting from the compound of Preparation Q (9 mg) and (R)-5-(2-aminoethyl)-3-(3-oxo-3,4-dihydro-2H-benzo[b][1,4]thiazin-6-yl)oxazolidin-2-one (13 mg; prepared according to WO 2009/104147) and proceeding in analogy to Example 1, the title compound was obtained, after purification by prep-HPLC (Method 2), as a colourless foam (9 mg; 41% yield).

MS1 (ESI, m/z): 492.1 [M+H$^+$]; t$_R$=0.67 min.

Example 26

6-((R)-5-{2-[3-(2,6-dimethoxy-pyrimidin-4-yl)-ben-zylamino]-ethyl}-2-oxo-oxazolidin-3-yl)-4H-benzo[1,4]thiazin-3-one Starting from the compound of Preparation R (49 mg) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 2), as a colourless foam (66 mg; 63% yield).

MS3 (ESI, m/z): 522.1 [M+H$^+$]; $t_R$=0.68 min.

Example 27

6-((R)-5-{2-[3-(4,6-dimethoxy-pyrimidin-2-yl)-benzylamino]-ethyl}-2-oxo-oxazolidin-3-yl)-4H-benzo[1,4]thiazin-3-one Starting from the compound of Preparation S (49 mg) and (R)-5-(2-aminoethyl)-3-(3-oxo-3,4-dihydro-2H-benzo[b][1,4]thiazin-6-yl)oxazolidin-2-one (59 mg; prepared according to WO 2009/104147) and proceeding in analogy to Example 1, the title compound was obtained, after purification by prep-HPLC (Method 2), as a colourless foam (37 mg; 36% yield).

MS3 (ESI, m/z): 522.1 [M+H$^+$]; $t_R$=0.71 min.

Example 28

6-((R)-5-{2-[3-(4,6-dimethoxy-[1,3,5]triazin-2-yl)-benzylamino]-ethyl}-2-oxo-oxazolidin-3-yl)-4H-benzo[1,4]thiazin-3-one Starting from the compound of Preparation T (20 mg) and (R)-5-(2-aminoethyl)-3-(3-oxo-3,4-dihydro-2H-benzo[b][1,4]thiazin-6-yl)oxazolidin-2-one (24 mg; prepared according to WO 2009/104147) and proceeding in analogy to Example 1, the title compound was obtained, after purification by prep-HPLC (Method 1), as a colourless foam (18 mg; 42% yield).

MS1 (ESI, m/z): 523.2 [M+H$^+$]; $t_R$=0.66 min.

Example 29

3-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-4-carboxylic acid amide A suspension of 4-bromo-2-methoxybenzamide (48 mg; commercial) and the compound of Preparation W (60 mg) in toluene/EtOH (0.4 mL; 4:1) was treated with sat. aq. Na$_2$CO$_3$ (0.4 mL) and degassed by bubbling with nitrogen for 5 min. The suspension was treated with Pd(PPh$_3$)$_4$ (4 mg) and refluxed overnight in a sealed tube. The reaction mixture was allowed to reach rt and diluted with water and EA. The aq. layer was extracted with EA and the combined org. layers were washed with brine, dried over MgSO$_4$, filtered, evaporated under reduced pressure and purified by prep-HPLC (Method 2), affording a colourless foam (10 mg; 22% yield).

MS1 (ESI, m/z): 533.2 [M+H$^+$]; $t_R$=0.65 min.

Example 30

6-((R)-5-{2-[3-(5-methoxy-pyridazin-3-yl)-benzylamino]-ethyl}-2-oxo-oxazolidin-3-yl)-4H-benzo[1,4]thiazin-3-one Starting from 3-chloro-5-methoxypyridazine (46 mg; commercial) and the compound of Preparation W (76 mg) and proceeding in analogy to Example 29, the title compound was obtained, after purification by prep-HPLC (Method 2), as a colourless foam (6 mg; 11% yield).

MS1 (ESI, m/z): 492.1 [M+H$^+$]; $t_R$=0.60 min.

Example 31

6-((R)-5-{2-[3-(6-methoxy-pyridin-2-yl)-benzylamino]-ethyl}-2-oxo-oxazolidin-3-yl)-4H-pyrido[3,2-b][1,4]oxazin-3-one Starting from 2-bromo-6-methoxypyridine (33 mg; commercial) and the compound of Preparation X (80 mg) and proceeding in analogy to Example 29, the title compound was obtained, after purification by prep-HPLC (Method 1), as a colourless foam (2 mg; 2% yield).

MS1 (ESI, m/z): 477.2 [M+H$^+$]; $t_R$=0.59 min.

Example 32

5-methoxy-3'-({2-[(R)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile Starting from 2-chloro-4-methoxybenzonitrile (29 mg; commercial) and the compound of Preparation X (80 mg) and proceeding in analogy to Example 29, the title compound was obtained, after purification by prep-HPLC (Method 1), as a colourless foam (3 mg; 3% yield).

MS1 (ESI, m/z): 500.2 [M+H$^+$]; $t_R$=0.70 min.

Example 33

3'-({2-[(R)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile Starting from 3-bromobenzonitrile (32 mg; commercial) and the compound of Preparation X (80 mg) and proceeding in analogy to Example 29, the title compound was obtained, after purification by prep-HPLC (Method 1), as a colourless foam (13 mg; 16% yield).

$^1$H NMR (CDCl$_3$) δ: 8.24 (m, 1H), 7.77 (m, 2H), 7.61 (m, 1H), 7.51 (m, 2H), 7.36 (m, 3H), 7.15 (m, 1H), 4.68 (m, 1H), 4.47 (m, 2H), 4.16 (m, 1H), 3.86 (m, 2H), 3.74 (m, 1H), 2.82 (m, 2H), 1.97 (m, 2H).

MS1 (ESI, m/z): 470.2 [M+H$^+$]; $t_R$=0.69 min.

Example 34

6-(5-{2-[(3'-methoxy-biphenyl-3-ylmethyl)-amino]-ethyl}-2-oxo-oxazol-3-yl)-4H-pyrido[3,2-b][1,4]oxazin-3-one A solution of the compound of Preparation Y (70 mg) in DCM (1.8 mL) was treated with PPh$_3$ (67 mg) for 3 h at rt. The reaction mixture was treated with 3'-methoxy-[1,1'-biphenyl]-3-carboxaldehyde (49 mg; commercial) at 40° C. for 2 days followed by NaBH(OAc)$_3$ (200 mg) and MeOH (0.6 mL) at rt overnight. The mixture was partitioned between sat. aq. NaHCO$_3$ and DCM. The org. phase was separated, dried over MgSO$_4$, concentrated under reduced pressure and purified by CC (Hept/EA 1:0 to 0:1, then DCM/MeOH+1% NH$_4$OH 100:0 to 95:5), affording an off-white solid (49 mg; 45% yield).

MS3 (ESI, m/z): 513.9 [M+H$^+$]; $t_R$=0.69 min.

Example 35

6-(5-{2-[3-(6-methoxy-pyridin-2-yl)-benzylamino]-ethyl}-2-oxo-oxazol-3-yl)-4H-pyrido[3,2-b][1,4]oxazin-3-one A solution of the compound of Preparation Y (83 mg) in DCM (1.8 mL) was treated with PPh$_3$ (79 mg) for 3 h at rt. The reaction mixture was treated with the compound of Preparation H (59 mg) at 40° C. for 2 days followed by NaBH(OAc)$_3$ (174 mg) and MeOH (0.6 mL) at rt for 3 h. The mixture was partitioned between sat. aq. NaHCO$_3$ and DCM. The org. phase was separated, dried over MgSO$_4$, concentrated under reduced pressure and purified by prep-HPLC (Method 3), affording an off-white solid (28 mg; 22% yield).

MS1 (ESI, m/z): 474.2 [M+H$^+$]; $t_R$=0.69 min.

Example 36

3'-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-biphenyl-3-carbonitrile Starting from 3'-formyl-biphenyl-3-carbonitrile (77 mg; commercial) and the compound of Preparation Y (83 mg) and proceeding in analogy to Example 35, the title compound was obtained, after purification by prep-HPLC (Method 3), as a colourless powder (32 mg; 25% yield).

MS1 (ESI, m/z): 468.2 [M+H$^+$]; $t_R$=0.69 min.

Example 37

5-methoxy-3'-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-biphenyl-2-carbonitrile Starting from the compound of Preparation B (60 mg) and the compound of Preparation Y (83 mg) and proceeding in analogy to Example 35, the title compound was obtained, after purification by prep-HPLC (Method 3), as an off-white solid (7 mg; 5% yield).

MS1 (ESI, m/z): 498.1 [M+H$^+$]; $t_R$=0.70 min.

Example 38

4-hydroxy-3-[4-({2-[(R)-2-oxo-3-(3-oxo-3,4-dihydro-2H-benzo[1,4]thiazin-6-yl)-oxazolidin-5-yl]-ethylamino}-methyl)-pyridin-2-yl]-benzonitrile Starting from the compound of Preparation U (51 mg) and (R)-5-(2-aminoethyl)-3-(3-oxo-3,4-dihydro-2H-benzo[b][1,4]thiazin-6-yl)oxazolidin-2-one (67 mg; prepared according to WO 2009/104147) and proceeding in analogy to Example 1, the title compound was obtained, after purification by CC (DCM/MeOH 100:0 to 95:5), as a yellow solid (39 mg; 34% yield).

MS1 (ESI, m/z): 502.4 [M+H$^+$]; $t_R$=0.67 min.

Example 39

6-[(R)-5-(2-{[2-(3-methoxy-phenyl)-pyridin-4-ylmethyl]-amino}-ethyl)-2-oxo-oxazolidin-3-yl]-4H-benzo[1,4]thiazin-3-one Starting from 3-methoxyphenylboronic acid (50 mg), 2-bromoisonicotinaldehyde (61 mg), tetrakis-(triphenylphosphine)-palladium (15 mg) and K$_2$CO$_3$ (136 mg), and proceeding in analogy to Preparation A, 2-(3-methoxyphenyl)isonicotinaldehyde was obtained. The latter was reacted without purification with (R)-5-(2-aminoethyl)-3-(3-oxo-3,4-dihydro-2H-benzo[b][1,4]thiazin-6-yl)oxazolidin-2-one (77 mg; prepared according to WO 2009/104147), in analogy to Example 1, affording after purification by prep-HPLC (Method 1), the title compound as a colourless powder (39 mg; 24% yield).

MS1 (ESI, m/z): 491.2 [M+H$^+$]; $t_R$=0.63 min.

Example 40

3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile Starting from 3-formylphenylboronic acid (49 mg; commercial), 3-bromo-benzonitrile (60 mg; commercial), tetrakis-(triphenylphosphine)-palladium (15 mg) and K$_2$CO$_3$ (136 mg), and proceeding in analogy to Preparation A, 3'-formyl-[1,1'-biphenyl]-3-carbonitrile was obtained. Without purification, the latter was further reacted with the compound of Preparation Z (69 mg), in analogy to the procedure of Example 1, affording, after purification by prep-HPLC (Method 1), the title compound as a colourless powder (26 mg; 17% yield).

MS1 (ESI, m/z): 470.2 [M+H$^+$]; $t_R$=0.68 min.

Example 41

6-((S)-5-{2-[3-(6-methoxy-pyridin-2-yl)-benzylamino]-ethyl}-2-oxo-oxazolidin-3-yl)-4H-pyrido[3,2-b][1,4]oxazin-3-one Starting from 3-formylphenylboronic acid (49 mg; commercial), 2-bromo-6-methoxypyridine (62 mg; commercial), tetrakis-(triphenylphosphine)-palladium (15 mg) and K$_2$CO$_3$ (136 mg), and proceeding in analogy to Preparation A, 3'-formyl-[1,1'-biphenyl]-3-carbonitrile was obtained. Without purification, the latter was further reacted with the compound of Preparation Z (69 mg), in analogy to the procedure of Example 1, affording, after purification by prep-HPLC (Method 1), the title compound as a colourless powder (20 mg; 13% yield).

MS1 (ESI, m/z): 476.2 [M+H$^+$]; $t_R$=0.68 min.

Example 42

5-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile Starting from 3-formylphenylboronic acid (49 mg; commercial), 2-chloro-4-methoxybenzonitrile (55 mg; commercial), tetrakis-(triphenylphosphine)-palladium (15 mg) and K$_2$CO$_3$ (136 mg), and proceeding in analogy to Preparation A, 3-(6-methoxypyridin-2-yl)benzaldehyde was obtained. Without purification, the latter was further reacted without any purification with the compound of Preparation Z (69 mg), in analogy to the procedure of Example 1, affording, after purification by HPLC (Method 1), the title compound as a colourless powder (20 mg; 12% yield).

MS1 (ESI, m/z): 500.3 [M+H$^+$]; $t_R$=0.69 min.

Example 43

6-((S)-5-{2-[3-(6-methoxy-pyridin-2-yl)-benzylamino]-ethyl}-2-oxo-oxazolidin-3-yl)-4H-benzo[1,4]thiazin-3-one Starting from 3-formylphenylboronic acid (99 mg; commercial), 2-bromo-6-methoxypyridine, (124 mg; commercial), tetrakis-(triphenylphosphine)-palladium (30 mg) and K$_2$CO$_3$ (273 mg), and proceeding in analogy to Preparation A, 3-(6-methoxypyridin-2-yl)benzaldehyde was obtained. Without purification, the latter was further reacted with the compound of Preparation Z (154 mg), in analogy to the procedure of Example 1, affording, after purification by prep-HPLC (Method 3), the title compound as a colourless powder (1 mg; 0.3% yield).

MS1 (ESI, m/z): 491.1 [M+H$^+$]; $t_R$=0.71 min.

Example 44

6-((S)-5-{2-[3-(5-methoxy-pyridazin-3-yl)-benzylamino]-ethyl}-2-oxo-oxazolidin-3-yl)-4H-pyrido[3,2-b][1,4]oxazin-3-one Starting from 3-formylphenylboronic acid (59 mg; commercial), 3-chloro-5-methoxypyridazine, (57 mg; commercial), tetrakis-(triphenylphosphine)-palladium (18 mg) and K$_2$CO$_3$ (164 mg), and proceeding in analogy to Preparation A, 3-(5-methoxypyridazin-3-yl)benzaldehyde was obtained. Without purification, the latter was further reacted with the compound of Preparation Z (79 mg), in analogy to the procedure of Example 1, affording, after purification by prep-HPLC (Method 3), the title compound as a colourless powder (13 mg; 7% yield).

MS1 (ESI, m/z): 477.1 [M+H$^+$]; $t_R$=0.58 min.

Example 45

6-hydroxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile Starting from the compound of Preparation AA (60 mg) and the compound of Preparation Z (86 mg) and proceeding in analogy to Example 1, the title compound was obtained, after purification by prep-HPLC (Method 2), as a colourless powder (14 mg; 11% yield).

MS1 (ESI, m/z): 486.1 [M+H$^+$]; $t_R$=0.65 min.

Example 46

3-[4-({2-[(S)-2-oxo-3-(3-oxo-3,4-dihydro-2H-pyrido[3,2-b][1,4]oxazin-6-yl)-oxazolidin-5-yl]-ethylamino}-methyl)-pyridin-2-yl]-benzonitrile Starting from the compound of Preparation AB (5 mg) and the compound of Preparation Z (6 mg) and proceeding in analogy to Example 1, the title compound was obtained, after purification by HPLC (Method 2), as a colourless foam (0.3 mg; 3% yield).

MS1 (ESI, m/z): 471.1 [M+H$^+$]; $t_R$=0.63 min.

Example 47

2-hydroxy-6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-isonicotinonitrile To a solution of the compound of Example 2 (10 mg) in MeCN (0.2 mL) was added NaI (8.6 mg) and trimethylchlorosilane (6.3 mg). The resulting mixture was heated at 80° C. for 2.5 h. The mixture was diluted with DMF and acidified with AcOH. The mixture was filtered over a glass fibre filter and purified by prep-HPLC (Method 1) to afford the desired compound as a colourless powder (4.2 mg; 44% yield).

MS1 (ESI, m/z): 502.3 [M+H$^+$]; $t_R$=0.60 min.

Example 48

6-((S)-5-{2-[(3',4'-dimethoxy-biphenyl-3-ylmethyl)-amino]-ethyl}-2-oxo-oxazolidin-3-yl)-4H-pyrido[3,2-b][1,4]oxazin-3-one Starting from the compound of Preparation Z (33 mg) and 3',4'-dimethoxy-[1,1'-biphenyl]-3-carboxaldehyde (29 mg; commercial) and proceeding in analogy to the procedure of Example 1, the title compound was obtained, after purification by prep-HPLC (Method 4), as a colourless powder (4 mg; 8% yield).

MS5 (ESI, m/z): 505.1 [M+H$^+$]; $t_R$=0.78 min.

Example 49

3-[4-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-pyridin-2-yl]-benzonitrile Starting from the compound of Preparation AB (7 mg) and the compound of Preparation AY (9 mg) and proceeding in analogy to the procedure of Example 1, the title compound was obtained, after purification by prep-HPLC (Method 1), as a yellow powder (3 mg; 20% yield).

$^1$H NMR (d6-DMSO) δ: 11.36 (br. s, 1H); 8.64 (d, J=4.5 Hz, 1H); 8.48 (s, 1H); 8.42 (d, J=7.7 Hz, 1H); 8.07 (s, 1H); 7.90 (d, J=7.3 Hz, 1H); 7.69 (t, J=7.7 Hz, 1H); 7.59 (d, J=8.5 Hz, 1H); 7.51 (d, J=8.5 Hz, 1H); 7.42 (d, J=4.0 Hz, 1H); 7.26 (s, 1H); 4.67 (s, 2H); 3.90 (s, 2H); 2.75-2.91 (m, 2H); 2.65-2.75 (m, 2H).

MS1 (ESI, m/z): 469.0 [M+H$^+$]; $t_R$=0.62 min.

Example 50

6-((S)-5-{2-[(3'-cyclobutylmethoxy-biphenyl-3-ylmethyl)-amino]-ethyl}-2-oxo-oxazolidin-3-yl)-4H-pyrido[3,2-b][1,4]oxazin-3-one Starting from 1-bromo-3-cyclobutylmethoxybenzene (60 mg; commercial), 3-formylphenylboronic acid (75 mg; commercial) and DIPEA (0.171 mL) and proceeding in analogy to Preparation A, crude 3'-(cyclobutylmethoxy)[1,1'-biphenyl]-3-carbaldehyde was obtained, which was purified by filtration over Si-carbonate followed by filtration over alumina cartridges. Using the material thus obtained and the compound of Preparation Z (22 mg) and proceeding in analogy to the procedure of Example 1, the title compound was obtained, after purification by prep-HPLC (Method 5), as a colourless powder (1.1 mg; 3% yield).

$^1$H NMR (d6-DMSO) δ: 7.61 (s, 1H); 7.46-7.57 (m, 2H); 7.26-7.44 (m, 4H); 7.20 (d, J=7.5 Hz, 1H); 7.14 (s, 1H); 6.90 (d, J=7.9 Hz, 1H); 4.70-4.84 (m, 1H); 4.58 (s, 2H); 4.13-4.26 (m, 1H); 3.98 (d, J=6.6 Hz, 2H); 3.62-3.85 (m, 2H); 2.57-2.77 (m, 4H); 2.01-2.15 (m, 2H); 1.74-1.98 (m, 6H).

MS6 (ESI, m/z): 529.1 [M+H$^+$]; $t_R$=1.70 min.

Example 51

6-(5-{2-[3-(6-methoxy-pyridin-2-yl)-benzylamino]-ethyl}-2-oxo-[1,3,4]oxadiazol-3-yl)-4H-pyrido[3,2-b][1,4]oxazin-3-one Starting from the compound of Preparation H (15 mg) and the compound of Preparation AX (20 mg) and proceeding in analogy to the procedure of Example 1, the title compound was obtained, after purification by prep-HPLC (Method 1), as a light yellow powder (5 mg; 15% yield).

$^1$H NMR (d6-DMSO) δ: 8.17 (br. s, 1H); 8.04 (s, 1H); 7.97 (dt, J=1.3, 7.5 Hz, 1H); 7.72-7.79 (m, 1H); 7.49-7.56 (m, 2H); 7.38-7.46 (m, 2H); 7.31 (d, J=8.5 Hz, 1H); 6.77 (d, J=7.9 Hz, 1H); 4.68 (s, 2H); 3.95 (s, 3H); 3.84 (s, 2H); 2.87-2.94 (m, 2H); 2.81-2.87 (m, 2H).

MS1 (ESI, m/z): 475.0 [M+H$^+$]; $t_R$=0.66 min.

Example 52

5-methoxy-3'-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-biphenyl-2-carbonitrile Starting from the compound of Preparation B (15 mg) and the compound of Preparation AX (16 mg) and proceeding in analogy to the procedure of Example 1, the title compound was obtained, after purification by prep-HPLC (Method 1), as a light yellow powder (8 mg; 28% yield).

$^1$H NMR (d6-DMSO) δ: 8.16 (br. s, 1H); 7.85 (d, J=8.6 Hz, 1H); 7.54-7.57 (m, 1H); 7.51 (d, J=8.5 Hz, 1H); 7.43-7.48 (m, 3H); 7.30 (d, J=8.5 Hz, 1H); 7.08-7.14 (m, 2H); 4.68 (s, 2H); 3.89 (s, 3H); 3.82 (s, 2H); 2.85-2.91 (m, 2H); 2.80-2.85 (m, 2H).

MS1 (ESI, m/z): 498.9 [M+H$^+$]; $t_R$=0.67 min.

Example 53

6-[(S)-5-(2-{[3'-(3-hydroxy-propoxy)-biphenyl-3-ylmethyl]-amino}-ethyl)-2-oxo-oxazolidin-3-yl]-4H-pyrido[3,2-b][1,4]oxazin-3-one 53.i. 3'-(3-hydroxypropoxy)-[1,1'-biphenyl]-3-carbaldehyde A solution of 3-formylphenylboronic acid (90 mg; commercial) in iPrOH (1 mL) is treated with DIPEA (0.105 mL), flushed with nitrogen and added to a vial containing 3-(3-bromophenoxy)propan-1-ol (69 mg; commercial). The reaction mixture is treated with dibenzylideneacetone palladium (0) phosphaadamantane ethyl silica (100 mg; Aldrich) and further heated overnight at 65° C. After cooling to rt and filtration over Si-carbonate followed by filtration over alumina cartridges, the title compound was obtained.

53.ii. 6-[(S)-5-(2-{[3'-(3-hydroxy-propoxy)-biphenyl-3-ylmethyl]-amino}-ethyl)-2-oxo-oxazolidin-3-yl]-4H-pyrido[3,2-b][1,4]oxazin-3-one Starting from intermediate 53.i and the compound of Preparation Z (33 mg) and proceeding in analogy to the procedure of Example 1, the title compound was obtained, after purification by prep-HPLC (Method 4), as a colourless powder (3.5 mg; 7% yield). MS5 (ESI, m/z): 519.1 [M+H$^+$]; $t_R$=0.76 min.

Example 54

6-[(S)-5-(2-{[3'-(2-methoxy-ethoxy)-biphenyl-3-ylmethyl]-amino}-ethyl)-2-oxo-oxazolidin-3-yl]-4H-pyrido[3,2-b][1,4]oxazin-3-one Starting from 1-bromo-3-(2-methoxyethoxy)benzene (69 mg; commercial) and 3-formylphenylboronic acid (90 mg; commercial) and proceeding in analogy to Example 53, step 53.i, 3-(5-(2-methoxyethoxy)pyridin-3-yl)benzaldehyde was obtained. Using the latter and the compound of Preparation Z (33 mg) and proceeding in analogy to the procedure of Example 1, the title compound was obtained, after purification by prep-HPLC (Method 4), as a colourless powder (6 mg; 12% yield).

MS5 (ESI, m/z): 519.0 [M+H$^+$]; $t_R$=0.83 min.

Example 55

6-((S)-5-{2-[3-(2-methoxy-pyridin-4-yl)-benzylamino]-ethyl}-2-oxo-oxazolidin-3-yl)-4H-pyrido[3,2-b][1,4]oxazin-3-one Starting from 4-bromo-2-methoxypyridine (56 mg; commercial) and 3-formylphenylboronic acid (90 mg; commercial) and proceeding in analogy to Example 53, step 53.i, 3-(2-methoxypyridin-4-yl)benzaldehyde was obtained. Using the latter and the compound of Preparation Z (33 mg) and proceeding in analogy to the procedure of Example 1, the title compound was obtained, after purification by filtration over succinic acid ethyl sulfide silica (60-200 μm, 60 A, 0.6 mmol/g; Phosphonics STMA), as a colourless powder (7.5 mg; 13% yield).

MS5 (ESI, m/z): 476.0 [M+H$^+$]; $t_R$=0.87 min.

Example 56

3'-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-biphenyl-3-carbonitrile Starting from the compound of Preparation A (15 mg) and the compound of Preparation AX (20 mg) and proceeding in analogy to the procedure of Example 1, the title compound was obtained, after purification by prep-HPLC (Method 1), as a beige powder (12.5 mg; 37% yield).

$^1$H NMR (d6-DMSO) δ: 8.13-8.17 (m, 2H); 8.01-8.06 (m, 1H); 7.82-7.88 (m, 1H); 7.80 (br. s, 1H); 7.65-7.74 (m, 2H); 7.44-7.55 (m, 3H); 7.30 (d, J=8.5 Hz, 1H); 4.68 (s, 2H); 4.03 (s, 2H); 3.07 (t, J=6.8 Hz, 2H); 2.95 (t, J=6.6 Hz, 2H).

MS1 (ESI, m/z): 469.0 [M+H$^+$]; $t_R$=0.66 min.

Example 57

6-[(S)-5-(2-{3-[6-((RS)-3-hydroxy-pyrrolidin-1-yl)-pyridin-2-yl]-benzylamino}-ethyl)-2-oxo-oxazolidin-3-yl]-4H-pyrido[3,2-b][1,4]oxazin-3-one Starting from 1-(6-chloro-2-pyridinyl)-3-pyrrolidinol (50 mg; CAS 1219972-03-8; commercial) and 3-formylphenylboronic acid (75 mg; commercial) and proceeding in analogy to Preparation A, 3-(6-(3-hydroxypyrrolidin-1-yl)pyridin-2-yl)benzaldehyde was obtained, which was purified by filtration over Si-carbonate followed by filtration over alumina cartridges. Using the resulting material and the compound of Preparation Z (22 mg) and proceeding in analogy to the procedure of Example 1, the title compound was obtained, after purification by prep-HPLC (Method 5), as a colourless powder (3 mg; 7% yield).

MS6 (ESI, m/z): 531.1 [M+H$^+$]; $t_R$=1.17 min.

Example 58

6-((S)-5-{2-[(3'-cyclopropylmethoxy-biphenyl-3-ylmethyl)-amino]-ethyl}-2-oxo-oxazolidin-3-yl)-4H-pyrido[3,2-b][1,4]oxazin-3-one Starting from 1-bromo-3-cyclopropylmethoxybenzene (56 mg; commercial) and 3-formylphenylboronic acid (75 mg; commercial) and proceeding in analogy to Preparation A, 3'-(oxiran-2-ylmethoxy)-[1,1'-biphenyl]-3-carbaldehyde was obtained, which was purified by filtration over Si-carbonate followed by filtration over alumina cartridges. Using the resulting material and the compound of Preparation Z (22 mg) and proceeding in analogy to the procedure of Example 1, the title compound was obtained, after purification by prep-HPLC (Method 5), as a colourless powder (4.5 mg; 11% yield).

MS6 (ESI, m/z): 515.1 [M+H$^+$]; $t_R$=1.54 min.

Example 59

6-((S)-5-{2-[3-(6-methoxy-pyridazin-4-yl)-benzylamino]-ethyl}-2-oxo-oxazolidin-3-yl)-4H-pyrido[3,2-b][1,4]oxazin-3-one Starting from the compound of Preparation AF (40 mg) and the compound of Preparation Z (55 mg) and proceeding in analogy to the procedure of Example 1, the title compound was obtained, after purification by prep-HPLC (Method 1), as a colourless powder (43 mg; 48% yield).

$^1$H NMR (d6-DMSO) δ: 11.20 (br. s, 1H); 8.35 (d, J=2.2 Hz, 1H); 8.19 (s, 1H); 7.82 (s, 1H); 7.72 (d, J=6.9 Hz, 1H); 7.59 (d, J=8.7 Hz, 1H); 7.46-7.54 (m, 1H); 7.43 (d, J=8.7 Hz, 1H); 7.22 (d, J=2.2 Hz, 1H); 4.75-4.86 (m, 1H); 4.61 (s, 2H); 4.22 (t, J=10.0 Hz, 1H); 3.83 (s, 2H); 3.76 (dd, J=7.2, 10.0 Hz, 1H); 3.69 (s, 3H); 2.62-2.75 (m, 2H); 1.86-2.02 (m, 2H).

MS1 (ESI, m/z): 477.0 [M+H$^+$]; $t_R$=0.56 min.

Example 60

5-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridazine-3-carbonitrile Starting from the compound of Preparation AG (25 mg) and the compound of Preparation Z (35 mg) and proceeding in analogy to the procedure of Example 1, the title compound was obtained, after purification by prep-HPLC (Method 1), as a yellow powder (15 mg; 27% yield).

$^1$H NMR (d6-DMSO) δ: 11.19 (br. s, 1H); 9.95 (d, J=2.2 Hz, 1H); 8.76 (d, J=2.2 Hz, 1H); 8.21 (s, 1H); 8.03 (s, 1H); 7.94 (d, J=7.1 Hz, 1H); 7.54-7.64 (m, 2H); 7.42 (d, J=8.7 Hz, 1H); 4.76-4.87 (m, 1H); 4.61 (s, 2H); 4.22 (t, J=10.0 Hz, 1H); 3.87 (s, 2H); 3.76 (dd, J=7.2, 10.0 Hz, 1H); 2.63-2.77 (m, 2H); 1.89-2.03 (m, 2H).

MS1 (ESI, m/z): 472.0 [M+H$^+$]; $t_R$=0.59 min.

Example 61

6-[2-hydroxy-3-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-phenyl]-pyridine-2-carbonitrile Starting from the compound of Preparation AT (20 mg) and the compound of Preparation AX (24 mg) and proceeding in analogy to the procedure of Example 1, the title compound was obtained, after purification by prep-HPLC (Method 1), as a yellow powder (19 mg; 46% yield).

$^1$H NMR (d6-DMSO) δ: 11.49 (br. s, 1H); 8.39 (dd, J=0.6, 8.2 Hz, 1H); 8.14 (s, 1H); 8.03 (t, J=7.8 Hz, 1H); 7.97 (dd, J=0.7, 7.5 Hz, 1H); 7.84 (d, J=7.0 Hz, 1H); 7.52 (d, J=8.5 Hz, 1H); 7.26-7.33 (m, 2H); 6.94 (t, J=7.6 Hz, 1H); 4.68 (s, 2H); 4.03 (s, 2H); 2.95-3.02 (m, 2H); 2.88-2.95 (m, 2H).

MS1 (ESI, m/z): 486.0 [M+H$^+$]; $t_R$=0.63 min.

Example 62

2-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-nicotinonitrile Starting from 2-chloronicotinonitrile (55 mg; commercial) and 3-formylphenylboronic acid (30 mg; commercial) and proceeding in analogy to Example 53, step 53.i, 2-(3-formylphenyl)nicotinonitrile was obtained. Using the latter and the compound of Preparation Z (28 mg) and proceeding in analogy to the procedure of Example 1, the title compound was obtained, after purification by prep-HPLC (Method 5), as a colourless powder (3 mg; 6% yield).

MS6 (ESI, m/z): 471.0 [M+H$^+$]; $t_R$=1.06 min.

Example 63

6-((S)-5-{2-[(3'-hydroxy-biphenyl-3-ylmethyl)-amino]-ethyl}-2-oxo-oxazolidin-3-yl)-4H-pyrido[3,2-b][1,4]oxazin-3-one Starting from 3-bromo-phenol (69 mg; commercial) and 3-formylphenylboronic acid (30 mg; commercial) and proceeding in analogy to Example 53, step 53.i, 3'-hydroxy-[1,1'-biphenyl]-3-carbaldehyde was obtained. Using the latter and the compound of Preparation Z (28 mg) and proceeding in analogy to the procedure of Example 1, the title compound was obtained, after purification by prep-HPLC (Method 5), as a colourless powder (4.5 mg; 11% yield).

MS6 (ESI, m/z): 461.2 [M+H$^+$]; $t_R$=1.14 min.

Example 64

6-((S)-5-{2-[(2',5'-dimethoxy-biphenyl-3-ylmethyl)-amino]-ethyl}-2-oxo-oxazolidin-3-yl)-4H-pyrido[3,2-b][1,4]oxazin-3-one Starting from the compound of Preparation Z (28 mg) and 2',5'-dimethoxy-[1,1'-biphenyl]-3-carboxaldehyde (24 mg;

commercial) and proceeding in analogy to the procedure of Example 1, the title compound was obtained, after purification by prep-HPLC (Method 5), as a colourless powder (7 mg; 13% yield).

MS5 (ESI, m/z): 505.1 [M+H$^+$]; $t_R$=0.89 min.

Example 65

[3'-({2-[(S)-2-oxo-3-(3-oxo-3,4-dihydro-2H-pyrido [3,2-b][1,4]oxazin-6-yl)-oxazolidin-5-yl]-ethylamino}-methyl)-biphenyl-3-yloxy]-acetonitrile Starting from 2-(3-bromophenoxy)acetonitrile (127 mg; commercial) and 3-formylphenylboronic acid (45 mg; commercial) and proceeding in analogy to Example 53, step 53.i, 2-((3'-formyl-[1,1'-biphenyl]-3-yl)oxy)acetonitrile was obtained. Using the latter and the compound of Preparation Z (28 mg) and proceeding in analogy to the procedure of Example 1, the title compound was obtained, after purification by prep-HPLC (Method 5), as a colourless powder (16 mg; 32% yield).

MS6 (ESI, m/z): 500.1 [M+H$^+$]; $t_R$=1.30 min.

Example 66

3'-({2-[(S)-2-oxo-3-(3-oxo-3,4-dihydro-2H-pyrido[3, 2-b][1,4]oxazin-6-yl)-oxazolidin-5-yl]-ethylamino}-methyl)-biphenyl-4-carbonitrile Starting from the compound of Preparation Z (33 mg) and 3'-formyl-[1,1'-biphenyl]-4-carbonitrile (25 mg; commercial) and proceeding in analogy to the procedure of Example 1, the title compound was obtained, after purification by prep-HPLC (Method 4), as a colourless powder (1.3 mg; 3% yield).

MS5 (ESI, m/z): 470.0 [M+H$^+$]; $t_R$=0.80 min.

Example 67

6-[(S)-5-(2-{[3'-(4-hydroxy-butoxy)-biphenyl-3-ylmethyl]-amino}-ethyl)-2-oxo-oxazolidin-3-yl]-4H-pyrido[3,2-b][1,4]oxazin-3-one Starting from the compound of Preparation AI (9.4 mg) and the compound from Preparation Z (8.2 mg) and proceeding in analogy to the procedure of Example 1, the title compound was obtained, after purification by prep-HPLC (Method 2), as a colourless powder (3 mg; 21% yield).

$^1$H NMR (CDCl$_3$) δ: 7.73 (d, J=8.8 Hz, 1H), 7.44-7.55 (m, 2H), 7.22-7.42 (overlapped m, 4H), 7.08-7.20 (m, 2H), 6.82-6.91 (m, 1H), 4.66-4.81 (m, 1H), 4.58 (s, 2H), 4.15-4.27 (m, 1H), 4.05 (t, J=6.1 Hz, 2H), 3.86 (s, 2H), 3.73-3.82 (m, 1H), 3.69 (t, J=6.3 Hz, 2H), 2.79-2.93 (m, 2H), 1.60-2.12 (m, 6H).

MS1 (ESI, m/z): 533.0 [M+H$^+$]; $t_R$=0.68 min.

Example 68

[3'-({2-[(S)-2-oxo-3-(3-oxo-3,4-dihydro-2H-pyrido [3,2-b][1,4]oxazin-6-yl)-oxazolidin-5-yl]-ethylamino}-methyl)-biphenyl-3-yloxy]-acetic acid ethyl ester Starting from ethyl 2-(3-bromophenoxy)acetate (104 mg; commercial) and 3-formylphenylboronic acid (30 mg; commercial) and proceeding in analogy to Example 53, step 53.i, ethyl 2((3'-formyl-[1,1'-biphenyl]-3-yl)oxy)acetate was obtained. Using the latter and the compound of Preparation Z (33 mg) and proceeding in analogy to the procedure of Example 1, the title compound was obtained, after purification by filtration over succinic acid ethyl sulfide silica (60-200 μm, 60 A, 0.6 mmol/g; Phosphonics STMA), as a colourless powder (3 mg; 4% yield).

MS5 (ESI, m/z): 547.0 [M+H$^+$]; $t_R$=1.12 min.

Example 69

6-[(S)-5-(2-{3-[6-((1rs,3R,4S)-3,4-dihydroxy-cyclopentylmethoxy)-pyridin-2-yl]-benzylamino}-ethyl)-2-oxo-oxazolidin-3-yl]-4H-pyrido[3,2-b][1,4]oxazin-3-one Starting from the compound of Preparation AJ (100 mg) and the compound from Preparation Z (91 mg) and proceeding in analogy to the procedure of Example 1, the corresponding amine was obtained after purification by prep-HPLC (Method 1). This latter was further reacted with HCl (25% in water, 2 mL) to afford the title compound, after purification by prep-HPLC (Method 1), as a colourless powder (19 mg; 45% yield).

MS1 (ESI, m/z): 576.0 [M+H$^+$]; $t_R$=0.62 min.

Example 70

6-((S)-5-{2-[(3'-ethoxy-biphenyl-3-ylmethyl)-amino]-ethyl}-2-oxo-oxazolidin-3-yl)-4H-pyrido[3, 2-b][1,4]oxazin-3-one Starting from the compound of Preparation Z (22 mg) and 3'-ethoxy-[1,1'-biphenyl]-3-carboxaldehyde (18 mg; commercial) and proceeding in analogy to the procedure of Example 1, the title compound was obtained, after purification by prep-HPLC (Method 5), as a colourless powder (5.6 mg; 14% yield).

MS6 (ESI, m/z): 489.0 [M+H$^+$]; $t_R$=1.45 min.

Example 71

1-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxymethyl]-cyclobutanecarbonitrile Starting from the compound of Preparation Z (22 mg) and the compound of Preparation AK (23 mg) and proceeding in analogy to the procedure of Example 1, the title compound was obtained, after purification by prep-HPLC (Method 5), as a colourless powder (7 mg; 16% yield).

MS6 (ESI, m/z): 554.1 [M+H$^+$]; $t_R$=1.47 min.

Example 72

6-[(R)-5-(2-{[5-(3-methoxy-phenyl)-pyridin-3-ylmethyl]-amino}-ethyl)-2-oxo-oxazolidin-3-yl]-4H-benzo[1,4]thiazin-3-one Starting from 5-(3-methoxyphenyl)-3-pyridinecarboxaldehyde (70 mg; commercial) and (R)-5-(2-aminoethyl)-3-(3-oxo-3,4-dihydro-2H-benzo[b][1,4]thiazin-6-yl)oxazolidin-2-one (77 mg; prepared according to WO 2009/104147) and proceeding in analogy to the procedure of Example 1, the title compound was obtained, after purification by prep-HPLC (Method 1), as a colourless powder (19 mg; 12% yield).

¹H NMR (CDCl₃) δ: 8.76 (s, 1H); 8.58 (s, 1H); 8.31 (br. s, 1H); 7.93 (s, 1H); 7.33-7.42 (m, 2H); 7.22 (d, J=8.6 Hz, 1H); 7.15 (d, J=7.8 Hz, 1H); 7.07-7.12 (m, 1H); 6.86-6.97 (m, 2H); 4.71-4.86 (m, 1H); 3.99-4.07 (m, 1H); 3.97 (s, 2H); 3.85 (s, 3H); 3.62-3.72 (m, 1H); 3.37 (s, 2H); 2.90-3.04 (m, 2H); 1.92-2.19 (m, 2H).

MS1 (ESI, m/z): 491.2 [M+H⁺]; $t_R$=0.64 min.

Example 73

3-[3-({2-[(S)-2-oxo-3-(3-oxo-3,4-dihydro-2H-pyrido[3,2-b][1,4]oxazin-6-yl)-oxazolidin-5-yl]-ethyl-amino}-methyl)-phenyl]-pyridine-2-carbonitrile Starting from 3-bromopyridine-2-carbonitrile (110 mg; commercial) and 3-formylphenylboronic acid (45 mg; commercial) and proceeding in analogy to Example 53, step 53.i, 3-(3-formylphenyl)picolinonitrile was obtained. Using the latter and the compound of Preparation Z (28 mg) and proceeding in analogy to the procedure of Example 1, the title compound was obtained, after purification by prep-HPLC (Method 5), as a colourless powder (5 mg; 10% yield).

MS6 (ESI, m/z): 471.1 [M+H⁺]; $t_R$=0.80 min.

Example 74

6-(5-{2-[2-hydroxy-3-(6-methoxy-pyridin-2-yl)-benzylamino]-ethyl}-2-oxo-[1,3,4]oxadiazol-3-yl)-4H-pyrido[3,2-b][1,4]oxazin-3-one Starting from the compound of Preparation AV (20 mg) and the compound of Preparation AX (23 mg) and proceeding in analogy to the procedure of Example 1, the title compound was obtained, after purification by prep-HPLC (Method 1), as a yellow powder (6 mg; 14% yield).

¹H NMR (d6-DMSO) δ: 11.48 (br. s, 1H); 8.17 (s, 1H); 7.90 (dd, J=1.5, 8.0 Hz, 1H); 7.85 (t, J=7.9 Hz, 1H); 7.75 (d, J=7.5 Hz, 1H); 7.51 (d, J=8.5 Hz, 1H); 7.28-7.34 (m, 2H); 6.89 (t, J=7.7 Hz, 1H); 6.82-6.86 (m, 1H); 4.68 (s, 2H); 3.93 (s, 3H); 3.87 (s, 2H); 2.90-2.96 (m, 2H); 2.84-2.90 (m, 2H).

MS1 (ESI, m/z): 491.0 [M+H⁺]; $t_R$=0.66 min.

Example 75

3-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-4-carbonitrile Starting from 4-bromo-2-methoxybenzonitrile, (127 mg; commercial) and 3-formylphenylboronic acid (45 mg; commercial) and proceeding in analogy to Example 53, step 53.i, 3'-formyl-3-methoxy-[1,1'-biphenyl]-4-carbonitrile was obtained. Using the latter and the compound of Preparation Z (28 mg) and proceeding in analogy to the procedure of Example 1, the title compound was obtained, after purification by prep-HPLC (Method 5), as a colourless powder (9 mg; 19% yield).

MS6 (ESI, m/z): 500.1 [M+H⁺]; $t_R$=1.30 min.

Example 76

6-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile Starting from 3-bromo-4-methoxybenzonitrile (64 mg; commercial) and 3-formylphenylboronic acid (90 mg; commercial) and proceeding in analogy to Example 53, step 53.i, 3'-formyl-6-methoxy-[1,1'-biphenyl]-3-carbonitrile was obtained. Using the latter and the compound of Preparation Z (33 mg) and proceeding in analogy to the procedure of Example 1, the title compound was obtained, after purification by prep-HPLC (Method 4), as a colourless powder (4 mg; 7% yield).

MS5 (ESI, m/z): 500.1 [M+H⁺]; $t_R$=0.81 min.

Example 77

3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carboxylic acid methyl ester Starting from methyl 3-bromobenzoate (64 mg; commercial) and 3-formylphenylboronic acid (90 mg; commercial) and proceeding in analogy to Example 53, step 53.i, methyl 3'-formyl-[1,1'-biphenyl]-3-carboxylate was obtained. Using the latter and the compound of Preparation Z (33 mg) and proceeding in analogy to the procedure of Example 1, the title compound was obtained, after purification by prep-HPLC (Method 4), as a colourless powder (4 mg; 7% yield).

MS5 (ESI, m/z): 503.2 [M+H⁺]; $t_R$=0.83 min.

Example 78

N-methyl-2-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-acetamide Starting from the compound of Preparation AN (81 mg) and the compound of Preparation Z (62 mg) and proceeding in analogy to the procedure of Example 1, the title compound was obtained, after purification by prep-HPLC (Method 1), as a colourless powder (63 mg; 56% yield).

¹H NMR (CDCl₃) δ: 8.47 (br. s, 1H); 7.62 (d, J=8.7 Hz, 1H); 7.59 (s, 1H); 7.46-7.54 (m, 1H); 7.28-7.44 (m, 3H); 7.20 (d, J=8.7 Hz, 2H); 7.11 (s, 1H); 6.94 (br. s, 1H); 6.81-6.89 (m, 1H); 4.61-4.77 (m, 1H); 4.55 (s, 2H); 4.50 (s, 2H); 4.08-4.22 (m, 1H); 3.99 (s, 2H); 3.67-3.82 (m, 1H); 2.94-3.12 (m, 2H); 2.87 (m, 3H); 1.97-2.21 (m, 2H).

MS1 (ESI, m/z): 532.1 [M+H⁺]; $t_R$=0.65 min.

Example 79

6-((S)-5-{2-[3-(6-methoxy-pyridazin-3-yl)-benzylamino]-ethyl}-2-oxo-oxazolidin-3-yl)-4H-pyrido[3,2-b][1,4]oxazin-3-one Starting from the compound of Preparation AO (40 mg) and the compound of Preparation Z (55 mg) and proceeding in analogy to the procedure of Example 1, the title compound was obtained, after purification by prep-HPLC (Method 1), as a pale pink powder (28 mg; 31% yield).

¹H NMR (d6-DMSO) δ: 11.20 (br. s, 1H); 8.18 (s, 1H); 8.16 (d, J=9.3 Hz, 1H); 8.07 (s, 1H); 7.92-7.98 (m, 1H); 7.59 (m, 1H); 7.46-7.52 (m, 1H); 7.43 (d, J=8.7 Hz, 1H); 7.32 (d, J=9.3 Hz, 1H); 4.77-4.86 (m, 1H); 4.61 (s, 2H); 4.19-4.26

(m, 1H); 4.08 (s, 3H); 3.86 (s, 2H); 3.76 (dd, J=7.2, 10.0 Hz, 1H); 2.67-2.73 (m, 2H); 1.89-2.02 (m, 2H).
MS1 (ESI, m/z): 477.0 [M+H$^+$]; $t_R$=0.60 min.

Example 80

6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridazine-4-carbonitrile Starting from the compound of Preparation AP (40 mg) and the compound of Preparation Z (56 mg) and proceeding in analogy to the procedure of Example 1, the title compound was obtained, after purification by prep-HPLC (Method 1), as a yellow powder (41 mg; 45% yield).
$^1$H NMR (d6-DMSO) δ: 11.20 (br. s, 1H); 9.62 (d, J=1.8 Hz, 1H); 8.85 (d, J=1.8 Hz, 1H); 8.25 (s, 1H); 8.19 (s, 1H); 8.10 (dt, J=1.6, 7.2 Hz, 1H); 7.54-7.62 (m, 2H); 7.43 (d, J=8.7 Hz, 1H); 4.75-4.89 (m, 1H); 4.61 (s, 2H); 4.18-4.27 (m, 1H); 3.88 (s, 2H); 3.76 (dd, J=7.2, 10.1 Hz, 1H); 2.66-2.78 (m, 2H); 1.87-2.03 (m, 2H).
MS1 (ESI, m/z): 472.0 [M+H$^+$]; $t_R$=0.58 min.

Example 81

6-((S)-5-{2-[3-(5-methoxy-pyridazin-3-yl)-benzylamino]-ethyl}-2-oxo-oxazolidin-3-yl)-4H-benzo[1,4]oxazin-3-one Starting from the compound of Preparation AR (15 mg) and the compound of Preparation AQ (19 mg) and proceeding in analogy to the procedure of Example 1, the title compound was obtained, after purification by prep-HPLC (Method 1), as a colourless powder (9 mg; 27% yield).
$^1$H NMR (d6-DMSO) δ: 10.75 (s, 1H); 8.97 (d, J=2.8 Hz, 1H); 8.19 (s, 2H); 8.01-8.09 (m, 1H); 7.71 (d, J=2.8 Hz, 1H); 7.49-7.56 (m, 2H); 7.33 (d, J=2.5 Hz, 1H); 6.93-6.97 (m, 1H); 4.75-4.84 (m, 1H); 4.54 (s, 2H); 4.10 (t, J=8.7 Hz, 1H); 4.02 (s, 3H); 3.88 (s, 2H); 3.71 (dd, J=7.2, 8.7 Hz, 1H); 2.67-2.80 (m, 2H); 1.87-2.02 (m, 2H).
MS1 (ESI, m/z): 476.0 [M+H$^+$]; $t_R$=0.56 min.

Example 82

3'-({2-[(S)-2-oxo-3-(3-oxo-3,4-dihydro-2H-benzo[1,4]oxazin-6-yl)-oxazolidin-5-yl]-ethylamino}-methyl)-biphenyl-3-carbonitrile Starting from the compound of Preparation A (15 mg) and the compound of Preparation AQ (20 mg) and proceeding in analogy to the procedure of Example 1, the title compound was obtained, after purification by prep-HPLC (Method 1), as a colourless powder (9 mg; 27% yield).
$^1$H NMR (d6-DMSO) δ: 10.75 (br. s, 1H); 8.21-8.24 (m, 1H); 8.15-8.18 (m, 1H); 8.02-8.06 (m, 1H); 7.82-7.86 (m, 1H); 7.78 (s, 1H); 7.64-7.71 (m, 2H); 7.41-7.51 (m, 2H); 7.33 (d, J=2.5 Hz, 1H); 6.92-6.96 (m, 1H); 4.74-4.83 (m, 1H); 4.54 (s, 2H); 4.10 (t, J=8.7 Hz, 1H); 3.89 (s, 2H); 3.67-3.73 (m, 1H); 2.70-2.82 (m, 2H); 1.89-2.04 (m, 2H).
MS1 (ESI, m/z): 469.0 [M+H$^+$]; $t_R$=0.66 min.

Example 83

6-(5-{2-[3-(5-methoxy-pyridazin-3-yl)-benzylamino]-ethyl}-2-oxo-oxazol-3-yl)-4H-pyrido[3,2-b][1,4]oxazin-3-one Starting from the compound of Preparation AR (7 mg) and the compound of Preparation AY (9 mg) and proceeding in analogy to the procedure of Example 1, the title compound was obtained, after purification by prep-HPLC (Method 1), as a yellow powder (6 mg; 37% yield).
$^1$H NMR (d6-DMSO) δ: 11.36 (br. s, 1H); 8.96 (d, J=2.6 Hz, 1H); 8.19 (s, 1H); 8.02-8.09 (m, 1H); 7.69 (d, J=2.6 Hz, 1H); 7.56-7.62 (m, 1H); 7.49-7.56 (m, 3H); 7.25 (s, 1H); 4.67 (s, 2H); 4.00 (s, 3H); 3.91 (s, 2H); 2.78-2.91 (m, 2H); 2.66-2.76 (m, 2H).
MS1 (ESI, m/z): 475.0 [M+H$^+$]; $t_R$=0.58 min.

Example 84

6-((S)-5-{2-[3-(5-ethoxy-pyridin-3-yl)-benzylamino]-ethyl}-2-oxo-oxazolidin-3-yl)-4H-pyrido[3,2-b][1,4]oxazin-3-one Starting from 3-bromo-5-ethoxypyridine (121 mg; commercial) and 3-formylphenylboronic acid (45 mg; commercial) and proceeding in analogy to Example 53, step 53.i, 3-(5-ethoxypyridin-3-yl)benzaldehyde was obtained. Using the latter and the compound of Preparation Z (28 mg) and proceeding in analogy to the procedure of Example 1, the title compound was obtained, after purification by prep-HPLC (Method 5), as a colourless powder (8 mg; 17% yield).
MS6 (ESI, m/z): 490.1 [M+H$^+$]; $t_R$=1.22 min.

Example 85

6-(5-{2-[2-hydroxy-3-(6-methoxy-pyridin-2-yl)-benzylamino]-ethyl}-2-oxo-oxazol-3-yl)-4H-pyrido[3,2-b][1,4]oxazin-3-one Starting from the compound of Preparation AV (7.5 mg) and the compound of Preparation AY (9 mg) and proceeding in analogy to the procedure of Example 1, the title compound was obtained, after purification by prep-HPLC (Method 1), as a yellow powder (6.5 mg; 41% yield).
$^1$H NMR (d6-DMSO) δ: 8.18 (br. s, 1H); 7.96 (d, J=7.8 Hz, 1H); 7.86 (t, J=7.9 Hz, 1H); 7.77 (d, J=7.7 Hz, 1H); 7.58 (d, J=8.5 Hz, 1H); 7.51 (d, J=8.5 Hz, 1H); 7.36 (d, J=7.1 Hz, 1H); 7.28 (s, 1H); 6.93 (t, J=7.6 Hz, 1H); 6.86 (d, J=8.2 Hz, 1H); 4.68 (s, 2H); 4.00 (s, 2H); 3.93 (s, 3H); 2.89-3.02 (m, 2H); 2.73-2.84 (m, 2H).
MS1 (ESI, m/z): 490.0 [M+H$^+$]; $t_R$=0.67 min.

Example 86

3-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile Starting from 2-bromo-6-methoxybenzonitrile, (53 mg; 1245647-50-0; commercial) and 3-formylphenylboronic acid (75 mg; commercial) and proceeding in analogy to Preparation A, 3'-formyl-3-methoxy-[1,1'-biphenyl]-2-carbonitrile was obtained, which was purified by filtration over Si-carbonate followed by filtration over alumina cartridges. Using the purified material (19 mg) and the compound of Preparation Z (22 mg) and proceeding in analogy to the procedure of Example 1, the title compound was obtained, after purification by prep-HPLC (Method 5), as a colourless powder (4 mg; 9% yield).

MS6 (ESI, m/z): 500.0 [M+H$^+$]; $t_R$=1.25 min.

Example 87

6-((S)-5-{2-[(6'-methoxy-[2,2]bipyridinyl-4-ylmethyl)-amino]-ethyl}-2-oxo-oxazolidin-3-yl)-4H-pyrido[3,2-b][1,4]oxazin-3-one Starting from the compound of Preparation AS (17 mg) and the compound of Preparation Z (23 mg) and proceeding in analogy to the procedure of Example 1, the title compound was obtained, after purification by prep-HPLC (Method 6), as a white powder (7 mg; 18% yield).

$^1$H NMR (d6-DMSO) δ: 11.19 (br. s, 1H); 8.59 (dd, J=0.5, 4.9 Hz, 1H); 8.35 (d, J=0.7 Hz, 1H); 7.99 (dd, J=0.7, 7.4 Hz, 1H); 7.84 (dd, J=7.5, 8.1 Hz, 1H); 7.59 (m, 1H); 7.43 (d, J=8.7 Hz, 1H); 7.39-7.43 (overlapped m, 1H); 6.87 (dd, J=0.7, 8.2 Hz, 1H); 4.79-4.88 (m, 1H); 4.61 (s, 2H); 4.19-4.27 (m, 1H); 3.98 (s, 3H); 3.85 (s, 2H); 3.76 (dd, J=7.3, 10.1 Hz, 1H); 2.60-2.71 (m, 2H); 1.86-2.06 (m, 2H).

MS1 (ESI, m/z): 477.1 [M+H$^+$]; $t_R$=0.60 min.

Example 88

6-[2-hydroxy-3-({2-[(S)-2-oxo-3-(3-oxo-3,4-dihydro-2H-benzo[1,4]oxazin-6-yl)-oxazolidin-5-yl]-ethylamino}-methyl)-phenyl]-pyridine-2-carbonitrile Starting from the compound of Preparation AT (15 mg) and the compound of Preparation AQ (18 mg) and proceeding in analogy to the procedure of Example 1, the title compound was obtained, after purification by prep-HPLC (Method 6), as a yellow powder (15 mg; 49% yield).

$^1$H NMR (d6-DMSO) δ: 10.74 (s, 1H); 8.45 (dd, J=0.8, 8.2 Hz, 1H); 8.09 (t, J=7.8 Hz, 1H); 7.96 (dd, J=0.8, 7.6 Hz, 1H); 7.78 (dd, J=1.5, 7.9 Hz, 1H); 7.33 (d, J=2.5 Hz, 1H); 7.25 (dd, J=1.2, 7.3 Hz, 1H); 6.93-6.97 (m, 1H); 6.88-6.93 (m, 2H); 4.69-4.81 (m, 1H); 4.54 (s, 2H); 4.10 (t, J=8.6 Hz, 2H); 3.99 (s, 2H); 3.69 (dd, J=7.2, 8.7 Hz, 1H); 2.67-2.81 (m, 2H); 1.88-2.05 (m, 2H).

MS1 (ESI, m/z): 486.0 [M+H$^+$]; $t_R$=0.65 min.

Example 89

6-((S)-5-{2-[4-hydroxy-3-(5-methoxy-pyridazin-3-yl)-benzylamino]-ethyl}-2-oxo-oxazolidin-3-yl)-4H-pyrido[3,2-b][1,4]oxazin-3-one Starting from the compound of Preparation AU (30 mg) and the compound of Preparation Z (38 mg) and proceeding in analogy to the procedure of Example 1, the title compound was obtained, after purification by prep-HPLC (Method 1), as a light yellow powder (27 mg; 42% yield).

$^1$H NMR (d6-DMSO) δ: 11.20 (br. s, 1H); 8.97 (d, J=2.8 Hz, 1H); 8.27 (s, 1H); 8.11 (d, J=1.9 Hz, 1H); 7.92 (d, J=2.8 Hz, 1H); 7.58 (d, J=8.7 Hz, 1H); 7.38-7.46 (m, 2H); 6.98 (d, J=8.4 Hz, 1H); 4.75-4.89 (m, 1H); 4.61 (s, 2H); 4.17-4.29 (m, 1H); 4.05 (s, 3H); 3.84 (s, 2H); 3.75 (dd, J=7.1, 10.1 Hz, 1H); 2.68-2.83 (m, 2H); 1.92-2.05 (m, 2H).

MS1 (ESI, m/z): 493.0 [M+H$^+$]; $t_R$=0.59 min.

Example 90

6-((S)-5-{2-[2-hydroxy-3-(6-methoxy-pyridin-2-yl)-benzylamino]-ethyl}-2-oxo-oxazolidin-3-yl)-4H-benzo[1,4]oxazin-3-one Starting from the compound of Preparation AV (15 mg) and the compound of Preparation AQ (17 mg) and proceeding in analogy to the procedure of Example 1, the title compound was obtained, after purification by prep-HPLC (Method 6), as a colourless powder (11 mg; 36% yield).

$^1$H NMR (CDCl$_3$) δ: 8.50 (br. s, 1H); 7.79-7.83 (m, 1H); 7.73-7.79 (m, 1H); 7.49 (d, J=7.5 Hz, 1H); 7.39-7.44 (m, 1H); 7.31-7.34 (m, 1H); 6.87-6.99 (m, 3H); 6.76 (d, J=8.2 Hz, 1H); 4.82-4.90 (m, 1H); 4.58 (s, 2H); 4.10-4.22 (m, 2H); 4.03-4.10 (overlapped m, 1H); 4.05 (s, 3H); 3.68-3.75 (m, 1H); 3.02-3.17 (m, 2H); 2.26-2.41 (m, 2H).

MS1 (ESI, m/z): 491.0 [M+H$^+$]; $t_R$=0.68 min.

Example 91

6-((S)-5-{2-[3-(6-methoxy-pyrazin-2-yl)-benzylamino]-ethyl}-2-oxo-oxazolidin-3-yl)-4H-pyrido[3,2-b][1,4]oxazin-3-one Starting from the compound of Preparation Q (40 mg) and the compound of Preparation Z (55 mg) and proceeding in analogy the procedure of Example 1, the title compound was obtained, after purification by prep-HPLC (Method 1), as a yellow powder (46 mg; 52% yield).

$^1$H NMR (d6-DMSO) δ: 11.21 (s, 1H); 8.82 (s, 1H); 8.27 (s, 1H); 8.19 (s, 1H); 8.13 (s, 1H); 8.01-8.07 (m, 1H); 7.58 (d, J=8.7 Hz, 1H); 7.47-7.53 (m, 1H); 7.43 (d, J=8.7 Hz, 1H); 4.77-4.87 (m, 1H); 4.61 (s, 2H); 4.19-4.27 (m, 1H); 4.03 (s, 3H); 3.89 (s, 2H); 3.76 (dd, J=7.2, 10.0 Hz, 1H); 2.66-2.79 (m, 2H); 1.90-2.04 (m, 2H).

MS1 (ESI, m/z): 477.0 [M+H$^+$]; $t_R$=0.64 min.

Example 92

6-[2-hydroxy-3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridine-2-carbonitrile Starting from the compound of Preparation AT (40 mg) and the compound of Preparation Z (50 mg) and proceeding in analogy to the procedure of Example 1, the title compound was obtained, after purification by prep-HPLC (Method 1), as a light yellow powder (56 mg; 68% yield).

$^1$H NMR (d6-DMSO) δ: 11.20 (br. s, 1H); 8.46 (dd, J=0.7, 8.3 Hz, 1H); 8.18 (br. s, 1H); 8.11 (t, J=7.7 Hz, 1H); 7.98 (dd, J=0.8, 7.6 Hz, 1H); 7.83 (dd, J=1.5, 7.9 Hz, 1H); 7.59 (d, J=8.7 Hz, 1H); 7.43 (d, J=8.7 Hz, 1H); 7.29 (dd, J=1.3, 7.4 Hz, 1H); 6.92 (t, J=7.6 Hz, 1H); 4.73-4.82 (m, 1H); 4.61 (s, 2H); 4.19-4.27 (m, 1H); 4.02 (d, J=1.8 Hz, 2H); 3.74 (dd, J=7.2, 10.1 Hz, 1H); 2.70-2.83 (m, 2H); 1.94-2.04 (m, 2H).

MS1 (ESI, m/z): 486.9 [M+H$^+$]; $t_R$=0.65 min.

Example 93

6-((S)-5-{2-[2-hydroxy-3-(6-methoxy-pyridin-2-yl)-benzylamino]-ethyl}-2-oxo-oxazolidin-3-yl)-4H-pyrido[3,2-b][1,4]oxazin-3-one Starting from the compound of Preparation AV (40 mg) and the compound of Preparation Z (49 mg) and proceeding in analogy to the procedure of Example 1, the title compound was obtained, after purification by prep-HPLC (Method 1), as a beige powder (41 mg; 50% yield).

$^1$H NMR (d6-DMSO) δ: 11.21 (br. s, 1H); 8.23 (br. s, 1H); 7.96 (dd, J=1.3, 8.0 Hz, 1H); 7.91 (t, J=7.9 Hz, 1H); 7.80 (d, J=7.7 Hz, 1H); 7.58 (d, J=8.7 Hz, 1H); 7.43 (d, J=8.7 Hz, 1H); 7.35-7.40 (m, 1H); 6.94 (t, J=7.7 Hz, 1H); 6.89 (d, J=8.2 Hz, 1H); 4.74-4.85 (m, 1H); 4.61 (s, 2H); 4.18-4.28 (m, 1H); 3.98 (s, 2H); 3.96 (s, 3H); 3.76 (dd, J=7.1, 10.1 Hz, 1H); 2.77-2.92 (m, 2H); 1.96-2.10 (m, 2H).

MS1 (ESI, m/z): 492.0 [M+H$^+$]; t$_R$=0.69 min.

Example 94

6-[2-hydroxy-3-({2-[(S)-2-oxo-3-(3-oxo-3,4-dihydro-2H-pyrido[3,2-b][1,4]thiazin-6-yl)-oxazolidin-5-yl]-ethylamino}-methyl)-phenyl]-pyridine-2-carbonitrile Starting from the compound of Preparation AT (15 mg) and the compound of Preparation AW (19 mg) and proceeding in analogy to the procedure of Example 1, the title compound was obtained, after purification by prep-HPLC (Method 6), as a light yellow powder (12 mg; 38% yield).

$^1$H NMR (d6-DMSO) δ: 10.87 (br. s, 1H); 8.40-8.50 (m, 1H); 8.08 (t, J=7.8 Hz, 1H); 7.92-7.98 (m, 1H); 7.75-7.82 (m, 2H); 7.68 (d, J=8.5 Hz, 1H); 7.25 (d, J=6.7 Hz, 1H); 6.90 (t, J=7.6 Hz, 1H); 4.69-4.87 (m, 1H); 4.18-4.30 (m, 1H); 3.98 (s, 2H); 3.74 (dd, J=7.2, 10.2 Hz, 1H); 3.53 (s, 2H); 2.71 (d, J=5.0 Hz, 2H); 1.98 (m, 2H).

MS1 (ESI, m/z): 503.0 [M+H$^+$]; t$_R$=0.68 min.

Example 95

6-((S)-5-{2-[2-hydroxy-3-(6-methoxy-pyridin-2-yl)-benzylamino]-ethy}-2-oxo-oxazolidin-3-yl)-4H-pyrido[3,2-b][1,4]thiazin-3-one Starting from the compound of Preparation AV (15 mg) and the compound of Preparation AW (18 mg) and proceeding in analogy to the procedure of Example 1, the title compound was obtained, after purification by prep-HPLC (Method 6), as a colourless powder (9 mg; 29% yield).

$^1$H NMR (d6-DMSO) δ: 10.87 (br. s, 1H); 7.87 (t, J=8.0 Hz, 2H); 7.75-7.82 (m, 2H); 7.68 (d, J=8.5 Hz, 1H); 7.30 (d, J=6.5 Hz, 1H); 6.89 (t, J=7.6 Hz, 1H); 6.84 (d, J=8.2 Hz, 1H); 4.77-4.86 (m, 1H); 4.19-4.27 (m, 1H); 3.95 (s, 3H); 3.83 (s, 2H); 3.76 (dd, J=7.2, 10.2 Hz, 1H); 3.53 (s, 2H); 2.68 (m, 2H); 1.95 (m, 2H).

MS1 (ESI, m/z): 508.0 [M+H$^+$]; t$_R$=0.71 min.

Example 96

6-[2-hydroxy-3-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-phenyl]-pyridine-2-carbonitrile Starting from the compound of Preparation AT (18 mg) and the compound of Preparation AY (25 mg) and proceeding in analogy to the procedure of Example 1, the title compound was obtained, after purification by prep-HPLC (Method 6), as a yellow powder (18 mg; 49% yield).

$^1$H NMR (d6-DMSO) δ: 11.30 (br. s, 1H); 8.34 (dd, J=2.0, 7.3 Hz, 1H); 7.88-7.96 (m, 2H); 7.77 (dd, J=1.7, 7.9 Hz, 1H); 7.55-7.60 (m, 1H); 7.50-7.55 (m, 1H); 7.27 (s, 1H); 7.22 (dd, J=1.6, 7.3 Hz, 1H); 6.88 (t, J=7.6 Hz, 1H); 4.68 (s, 2H); 3.98 (s, 2H); 2.77-2.84 (m, 2H); 2.68-2.75 (m, 2H).

MS1 (ESI, m/z): 485.0 [M+H$^+$]; t$_R$=0.64 min.

Example 97

6-((R)-5-{2-[3-(5-methoxy-pyridazin-3-yl)-benzylamino]-ethyl}-2-oxo-oxazolidin-3-yl)-4H-pyrido[3,2-b][1,4]oxazin-3-one Starting from the compound of Preparation AR (18 mg) and the compound of Preparation AZ (39 mg) and proceeding in analogy to the procedure of Example 1, the title compound was obtained, after purification by prep-HPLC (Method 6), as a yellow foam (14 mg; 35% yield).

$^1$H NMR (d6-DMSO) δ: 11.21 (br. s, 1H); 8.97 (d, J=2.8 Hz, 1H); 8.16 (s, 1H); 7.99-8.06 (m, 1H); 7.70 (d, J=2.8 Hz, 1H); 7.59 (d, J=8.7 Hz, 1H); 7.47-7.53 (m, 2H); 7.43 (d, J=8.7 Hz, 1H); 4.76-4.86 (m, 1H); 4.61 (s, 2H); 4.17-4.26 (m, 1H); 4.01 (s, 3H); 3.83 (s, 2H); 3.76 (dd, J=7.3, 10.0 Hz, 1H); 2.58-2.73 (m, 2H); 1.83-2.02 (m, 2H).

MS1 (ESI, m/z): 477.0 [M+H$^+$]; t$_R$=0.57 min.

Example 98

6-((R)-5-{2-[3-(5-methoxy-pyridazin-3-yl)-benzylamino]-ethyl}-2-oxo-oxazolidin-3-yl)-4H-pyrido[3,2-b][1,4]thiazin-3-one Starting from the compound of Preparation AR (18 mg) and the compound of Preparation BA (28 mg) and proceeding in analogy to the procedure of Example 1, the title compound was obtained, after purification by prep-HPLC (Method 6), as a light yellow foam (26 mg; 63% yield).

$^1$H NMR (d6-DMSO) δ: 10.88 (br. s, 1H); 8.97 (d, J=2.8 Hz, 1H); 8.15 (s, 1H); 7.99-8.07 (m, 1H); 7.79 (d, J=8.5 Hz, 1H); 7.70 (d, J=2.8 Hz, 1H); 7.68 (d, J=8.5 Hz, 1H); 7.47-7.54 (m, 2H); 4.79-4.89 (m, 1H); 4.19-4.29 (m, 1H); 4.01 (s, 3H); 3.82 (s, 2H); 3.77 (dd, J=7.2, 10.2 Hz, 1H); 3.53 (s, 2H); 2.60-2.73 (m, 2H); 1.86-2.01 (m, 2H).

MS1 (ESI, m/z): 493.0 [M+H$^+$]; t$_R$=0.59 min.

Example 99

6-((S)-5-{2-[3-(5-methoxy-pyridazin-3-yl)-benzylamino]-ethyl}-2-oxo-oxazolidin-3-yl)-4H-pyrido[3,2-b][1,4]thiazin-3-one Starting from the compound of Preparation AR (15 mg) and the compound of Preparation AW (21 mg) and proceeding in analogy to the procedure of Example 1, the title compound was obtained, after purification by prep-HPLC (Method 6), as a yellow foam (16 mg; 46% yield).

$^1$H NMR (d6-DMSO) δ: 10.88 (br. s, 1H); 8.98 (d, J=2.8 Hz, 1H); 8.22 (s, 1H); 8.03-8.12 (m, 1H); 7.80 (d, J=8.5 Hz, 1H); 7.72 (d, J=2.8 Hz, 1H); 7.68 (d, J=8.5 Hz, 1H); 7.50-7.59 (m, 2H); 4.78-4.91 (m, 1H); 4.19-4.30 (m, 1H); 4.02 (s, 3H); 3.95 (s, 2H); 3.77 (dd, J=7.1, 10.3 Hz, 1H); 3.54 (s, 2H); 2.70-2.88 (m, 2H); 1.93-2.07 (m, 2H).

MS1 (ESI, m/z): 493.0 [M+H$^+$]; t$_R$=0.59 min.

Example 100

3'-({2-[(S)-2-oxo-3-(3-oxo-3,4-dihydro-2H-pyrido[3,2-b][1,4]thiazin-6-yl)-oxazolidin-5-yl]-ethylamino}-methyl)-biphenyl-3-carbonitrile Starting from the compound of Preparation A (15 mg) and the compound of Preparation AW (21 mg) and proceeding in analogy to the procedure of Example 1, the title compound was obtained, after purification by prep-HPLC (Method 1), as a colourless foam (14 mg; 40% yield).

$^1$H NMR (d6-DMSO) δ: 10.88 (br. s, 1H); 8.17 (s, 1H); 8.05 (d, J=7.8 Hz, 1H); 7.85 (d, J=7.6 Hz, 1H); 7.76-7.82 (m, 2H); 7.63-7.73 (m, 3H); 7.40-7.53 (m, 2H); 4.78-4.89 (m, 1H); 4.19-4.29 (m, 1H); 3.92 (s, 2H); 3.77 (dd, J=7.3, 9.7 Hz, 1H); 3.53 (s, 2H); 2.68-2.89 (m, 2H); 1.91-2.09 (m, 2H).

MS1 (ESI, m/z): 486.0 [M+H$^+$]; $t_R$=0.69 min.

Example 101

6-((S)-5-{2-[4-hydroxy-3-(4-methoxy-pyridin-2-yl)-benzylamino]-ethyl}-2-oxo-oxazolidin-3-yl)-4H-pyrido[3,2-b][1,4]oxazin-3-one Starting from the compound of Preparation AC (77 mg) and the compound of Preparation Z (94 mg) and proceeding in analogy to the procedure of Example 1, the title compound was obtained, after purification by prep-HPLC (Method 6), as a yellow solid (72 mg; 43% yield).

$^1$H NMR (d6-DMSO) δ: 14.39 (br. s, 1H); 8.45 (d, J=6.0 Hz, 1H); 7.97 (d, J=2.0 Hz, 1H); 7.68 (d, J=2.4 Hz, 1H); 7.59 (d, J=8.7 Hz, 1H); 7.43 (d, J=8.7 Hz, 1H); 7.27 (dd, J=2.0, 8.3 Hz, 1H); 7.03 (dd, J=2.4, 6.0 Hz, 1H); 6.85 (d, J=8.3 Hz, 1H); 4.75-4.86 (m, 1H); 4.61 (s, 2H); 4.18-4.26 (m, 1H); 3.96 (s, 3H); 3.76 (dd, J=7.2, 10.0 Hz, 1H); 3.69 (s, 2H); 2.57-2.69 (m, 2H); 1.82-1.99 (m, 2H).

MS1 (ESI, m/z): 492.1 [M+H$^+$]; $t_R$=0.53 min.

Example 102

6-[(S)-5-(2-{[2-(3-methoxy-phenyl)-pyrimidin-4-ylmethyl]-amino}-ethyl)-2-oxo-oxazolidin-3-yl]-4H-pyrido[3,2-b][1,4]oxazin-3-one Starting from the compound of Preparation AM (29 mg) and the compound of Preparation Z (40 mg) and proceeding in analogy to the procedure of Example 1, the title compound was obtained, after purification by prep-HPLC (Method 6), as a white solid (29 mg; 44% yield).

$^1$H NMR (d6-DMSO) δ: 11.20 (br. s, 1H); 8.84 (d, J=5.1 Hz, 1H); 7.99-8.06 (m, 1H); 7.93-7.98 (m, 1H); 7.60 (d, J=8.7 Hz, 1H); 7.50 (d, J=5.1 Hz, 1H); 7.41-7.48 (m, 2H); 7.10 (ddd, J=0.8, 2.7, 8.2 Hz, 1H); 4.79-4.91 (m, 1H); 4.61 (s, 2H); 4.18-4.29 (m, 1H); 3.90 (s, 2H); 3.85 (s, 3H); 3.78 (dd, J=7.3, 10.0 Hz, 1H); 2.68-2.80 (m, 2H); 1.89-2.06 (m, 2H).

MS1 (ESI, m/z): 477.0 [M+H$^+$]; $t_R$=0.64 min.

Example 103

6-[(S)-5-(2-{[5-(3-methoxy-phenyl)-pyridazin-3-ylmethyl]-amino}-ethyl)-2-oxo-oxazolidin-3-yl]-4H-pyrido[3,2-b][1,4]oxazin-3-one A suspension of the compound of Preparation AD (19 mg) and the compound of Preparation Z (26 mg) in MeOH (1 mL) was stirred at rt for 2 h. NaBH$_4$ (6 mg) was then added and the mixture was stirred at rt for 15 h. Water was added and the mixture was filtered. The filtrate was concentrated under reduced pressure and partitioned between water and EA. The layers were separated and the aq. layer was still extracted twice with EA. The combined org. layers were dried over MgSO$_4$, filtered and concentrated under reduced pressure. After purification by prep-HPLC (Method 6), the title compound was obtained as a light purple solid (4.5 mg; 11% yield).

$^1$H NMR (d6-DMSO) δ: 11.20 (br. s, 1H); 9.54 (d, J=2.3 Hz, 1H); 8.03 (d, J=2.3 Hz, 1H); 7.58 (d, J=8.7 Hz, 1H); 7.48-7.50 (m, 2H); 7.45-7.47 (m, 1H); 7.42 (d, J=8.7 Hz, 1H); 7.09-7.14 (m, 1H); 4.77-4.88 (m, 1H); 4.61 (s, 2H); 4.16-4.28 (m, 1H); 4.07 (s, 2H); 3.86 (s, 3H); 3.76 (dd, J=7.2, 10.0 Hz, 1H); 2.65-2.76 (m, 2H); 1.88-2.05 (m, 2H).

MS1 (ESI, m/z): 477.1 [M+H$^+$]; $t_R$=0.63 min.

Example 104

6-[(S)-5-(2-{[6-(3-methoxy-phenyl)-pyrazin-2-ylmethyl]-amino}-ethyl)-2-oxo-oxazolidin-3-yl]-4H-pyrido[3,2-b][1,4]oxazin-3-one Starting from the compound of Preparation AE (34 mg) and the compound of Preparation Z (48 mg) and proceeding in analogy to the procedure of Example 1, the title compound was obtained, after purification by prep-HPLC (Method 6), as a light brown solid (25 mg; 33% yield).

$^1$H NMR (d6-DMSO) δ: 9.13 (s, 1H); 8.66 (s, 1H); 7.72-7.76 (m, 1H); 7.70 (dd, J=1.8, 2.5 Hz, 1H); 7.57-7.61 (m, 1H); 7.45-7.48 (m, 1H); 7.43 (d, J=8.7 Hz, 1H); 7.08 (ddd, J=0.8, 2.6, 8.2 Hz, 1H); 4.78-4.89 (m, 1H); 4.61 (s, 2H); 4.19-4.27 (m, 1H); 3.95 (s, 2H); 3.85 (s, 3H); 3.77 (dd, J=7.2, 10.0 Hz, 1H); 2.67-2.81 (m, 2H); 1.89-2.03 (m, 2H).

MS1 (ESI, m/z): 477.1 [M+H$^+$]; $t_R$=0.63 min.

Example 105

6-[(S)-5-(2-{[6-(3-methoxy-phenyl)-pyridazin-4-ylmethyl]-amino}-ethyl)-2-oxo-oxazolidin-3-yl]-4H-pyrido[3,2-b][1,4]oxazin-3-one Starting from the compound of Preparation AH (21 mg) and the compound of Preparation Z (31 mg) and proceeding in analogy to the procedure of Example 1, the title compound was obtained, after purification by prep-HPLC (Method 6) and by CC (DCM-MeOH), as a light yellow solid (35 mg; 44% yield).

$^1$H NMR (d6-DMSO) δ: 11.20 (br. s, 1H); 9.20 (d, J=1.9 Hz, 1H); 8.15 (d, J=1.8 Hz, 1H); 7.69-7.75 (m, 2H); 7.57-7.62 (m, 1H); 7.48 (t, J=8.3 Hz, 1H); 7.43 (d, J=8.7 Hz, 1H); 7.11 (ddd, J=1.1, 2.4, 8.3 Hz, 1H); 4.79-4.88 (m, 1H); 4.61 (s, 2H); 4.19-4.27 (m, 1H); 3.87 (s, 3H); 3.83-3.86 (overlapped m, 2H); 3.77 (dd, J=7.2, 10.0 Hz, 1H); 2.60-2.74 (m, 2H); 1.88-1.98 (m, 2H).

MS1 (ESI, m/z): 476.9 [M+H$^+$]; $t_R$=0.60 min.

Example 106

6-((S)-5-{2-[2-hydroxy-3-(4-methoxy-pyridin-2-yl)-benzylamino]-ethyl}-2-oxo-oxazolidin-3-yl)-4H-pyrido[3,2-b][1,4]oxazin-3-one Starting from the compound of Preparation AL (90 mg) and the compound of Preparation Z (78 mg) and proceeding in analogy to the procedure of Example 1, the corresponding O-benzyl protected amine was obtained. The latter was dissolved in MeOH (3.6 mL) and placed in the presence of Pd/C (5%, 30 mg) under an H$_2$ atmosphere for 6 h. The catalysts were removed by filtration and the filtrate was concentrated to dryness. After purification by prep-HPLC (Method 6), the desired compound was obtained as a light yellow solid (40 mg; 29% yield).

¹H NMR (d6-DMSO) δ: 11.19 (br. s, 1H); 8.44 (d, J=6.0 Hz, 1H); 7.96 (dd, J=1.4, 8.1 Hz, 1H); 7.70 (d, J=2.3 Hz, 1H); 7.59 (d, J=8.7 Hz, 1H); 7.43 (d, J=8.7 Hz, 1H); 7.35 (dd, J=1.2, 7.3 Hz, 1H); 7.03 (dd, J=2.4, 6.0 Hz, 1H); 6.87 (t, J=7.6 Hz, 1H); 4.74-4.87 (m, 1H); 4.61 (s, 2H); 4.17-4.30 (m, 1H); 3.96 (s, 3H); 3.71-3.80 (m, 3H); 2.61-2.76 (m, 2H); 1.81-2.04 (m, 2H).
MS1 (ESI, m/z): 492.1 [M+H⁺]; $t_R$=0.67 min.

Example 107

6-(5-{2-[(3'-methoxy-biphenyl-3-ylmethyl)-amino]-ethyl}-2-oxo-[1,3,4]oxadiazol-3-yl)-4H-pyrido[3,2-b][1,4]oxazin-3-one Starting from 3'-methoxy-[1,1'-biphenyl]-3-carboxaldehyde (7.5 mg; commercial) and the compound of Preparation AX (10 mg) and proceeding in analogy to the procedure of Example 1, the title compound was obtained, after purification by prep-HPLC (Method 2), as a beige powder (3.5 mg; 21% yield).
¹H NMR (CDCl₃) δ: 8.18 (br. s, 1H); 7.53-7.58 (m, 1H); 7.45-7.53 (m, 2H); 7.27-7.43 (m, 4H); 7.11-7.18 (m, 1H); 7.06-7.11 (m, 1H); 6.83-6.93 (m, 1H); 4.65 (s, 2H); 3.93 (s, 2H); 3.84 (s, 3H); 3.07-3.18 (m, 2H); 2.89-3.00 (m, 2H).
MS1 (ESI, m/z): 474.1 [M+H⁺]; $t_R$=0.69 min.

Example 108

6-(5-{2-[3-(5-methoxy-pyridazin-3-yl)-benzylamino]-ethyl}-2-oxo-[1,3,4]oxadiazol-3-yl)-4H-pyrido[3,2-b][1,4]oxazin-3-one Starting from the compound of Preparation AR (15 mg) and the compound of Preparation AX (19 mg) and proceeding in analogy to the procedure of Example 1, the title compound was obtained, after purification by prep-HPLC (Method 1), as a yellow foam (7 mg; 21% yield).
¹H NMR (d6-DMSO) δ: 11.49 (br. s, 1H); 8.96 (d, J=2.8 Hz, 1H); 8.17 (s, 2H); 8.01-8.07 (m, 1H); 7.69 (d, J=2.8 Hz, 1H); 7.48-7.55 (m, 2H); 7.31 (d, J=8.5 Hz, 1H); 4.68 (s, 2H); 4.01 (s, 3H); 3.90 (s, 2H); 2.90-2.97 (m, 2H); 2.83-2.90 (m, 2H).
MS1 (ESI, m/z): 476.0 [M+H⁺]; $t_R$=0.56 min.

Example 109

(S)-6-(5-(24(4-hydroxy-3-(6-methoxypyridin-2-yl)benzyl)amino)ethyl)-2-oxooxazolidin-3-yl)-2H-pyrido[3,2-b][1,4]oxazin-3(4H)-one Starting from the compound of Preparation BB (111 mg) and the compound of Preparation Z (97 mg) and proceeding in analogy to the procedure of Example 1, the corresponding amine was obtained as a crude material. The latter was dissolved in MeOH (4.4 mL) and placed in the presence of Pd/C (5%; 37 mg) under an atmospheric H₂ atmosphere for 48 h. The catalyst was removed by filtration and the filtrate was concentrated to dryness. The residue was redissolved in THF (4.4 mL) and treated with Pd/C (5%, 37 mg) under an atmospheric H₂ pressure for 16 h. The catalyst was removed by filtration and the filtrate concentrated under reduced pressure. After purification by prep-HPLC (Method 6), the desired compound was obtained as a white solid (14 mg; 8% yield).
¹H NMR (d6-DMSO) δ: 12.80 (s, 1H); 11.18 (br. s, 1H); 7.86-7.94 (m, 2H); 7.76 (d, J=7.7 Hz, 1H); 7.59 (d, J=8.7 Hz, 1H); 7.43 (d, J=8.7 Hz, 1H); 7.26 (dd, J=1.9, 8.4 Hz, 1H); 6.87 (dd, J=3.6, 8.3 Hz, 2H); 4.75-4.89 (m, 1H); 4.61 (s, 2H); 4.16-4.27 (m, 1H); 3.94 (s, 3H); 3.75 (dd, J=7.3, 10.0 Hz, 1H); 3.68 (s, 2H); 2.57-2.67 (m, 2H); 1.81-2.04 (m, 2H).
MS1 (ESI, m/z): 492.0 [M+H⁺]; $t_R$=0.68 min.

Example 110

(S)-6-(5-(2-(((5-(5-methoxypyridazin-3-yl)pyridin-3-yl)methyl)amino)ethyl)-2-oxooxazolidin-3-yl)-2H-pyrido[3,2-b][1,4]oxazin-3(4H)-one Starting from the compound of Preparation BC (33 mg) and the compound of Preparation Z (42 mg) and proceeding in analogy to the procedure of Example 1, the title compound was obtained, after purification by prep-HPLC (Method 6), as a white solid (18 mg; 25% yield).
¹H NMR (d6-DMSO) δ: 11.19 (br s., 1H); 9.22 (d, J=2.0 Hz, 1H); 9.02 (d, J=2.8 Hz, 1H); 8.69 (d, J=1.7 Hz, 1H); 8.52 (s, 1H); 7.85 (d, J=2.8 Hz, 1H); 7.58 (d, J=8.7 Hz, 1H); 7.42 (d, J=8.7 Hz, 1H); 4.75-4.90 (m, 1H); 4.61 (s, 2H); 4.18-4.29 (m, 1H); 4.03 (s, 3H); 3.85 (s, 2H); 3.77 (dd, J=7.3, 10.0 Hz, 1H); 2.61-2.77 (m, 2H); 1.82-2.05 (m, 2H).
MS1 (ESI, m/z): 478.1 [M+H⁺]; $t_R$=0.54 min.

Example 111

(S)-6-(5-(2-(((4-(5-methoxypyridazin-3-yl)pyridin-2-yl)methyl)amino)ethyl)-2-oxooxazolidin-3-yl)-2H-pyrido[3,2-b][1,4]oxazin-3(4H)-one Starting from the compound of Preparation BD (16 mg) and the compound of Preparation Z (22 mg) and proceeding in analogy to the procedure of Example 1, the title compound was obtained, after purification by prep-HPLC (Method 7), as a white solid (24 mg; 67% yield).
MS1 (ESI, m/z): 478.0 [M+H⁺]; $t_R$=0.55 min.

Pharmacological Properties of the Invention Compounds

In Vitro Assays

Bacterial Growth Minimal Inhibitory Concentrations:

Experimental Methods:

Minimal Inhibitory Concentrations (MICs; mg/L) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA (2006).

Results:

All Example compounds were tested against several Gram positive and Gram negative bacteria.

All Example compounds were tested against several Gram positive and Gram negative bacteria. Typical antibacterial test results are given in Table 1 hereafter (MICs in mg/L). *Staphylococcus aureus* A798, *Enterococcus faecium* A949 and *Acinetobacter baumannii* T6474 are multiply-resistant strains (in particular quinolone-resistant), while *Moraxella catarrhalis* A894 is a quinolone-sensitive strain and *Staphylococcus aureus* ATCC29213 is a methicillin-sensitive and quinolone-sensitive strain.

TABLE 1

| Example No. | MIC for S. aureus ATCC29213 | MIC for S. aureus A798 | MIC for E. faecium A949 | MIC for M. catarrhalis A894 | MIC for A. baumannii T6474 |
| --- | --- | --- | --- | --- | --- |
| 1 | 0.25 | 0.25 | 2 | 0.031 | 0.5 |
| 2 | ≤0.016 | ≤0.016 | 0.5 | ≤0.016 | 0.25 |
| 3 | 0.063 | 0.063 | 0.5 | ≤0.016 | 0.125 |
| 4 | 0.25 | 0.25 | 4 | 0.031 | 0.5 |
| 5 | 0.063 | 0.063 | 1 | ≤0.016 | 0.125 |
| 6 | 1 | 1 | 4 | 0.063 | 4 |
| 7 | 0.5 | 0.5 | 4 | 0.063 | 1 |
| 8 | 0.063 | 0.063 | 1 | ≤0.016 | 0.25 |
| 9 | 0.031 | 0.031 | 1 | ≤0.016 | 0.25 |
| 10 | 0.5 | 0.5 | 8 | ≤0.016 | 0.5 |
| 11 | 1 | 1 | 8 | 0.125 | 2 |
| 12 | 0.5 | 0.5 | 2 | 0.063 | 2 |
| 13 | 0.063 | 0.063 | 1 | ≤0.016 | 0.125 |
| 14 | 0.125 | 0.125 | 2 | ≤0.016 | 0.25 |
| 15 | 0.063 | 0.031 | 0.5 | ≤0.016 | 0.125 |
| 16 | 0.5 | 0.5 | 2 | 0.063 | 1 |
| 17 | 0.063 | 0.125 | 1 | ≤0.016 | 0.125 |
| 18 | 0.25 | 0.25 | 4 | 0.031 | 0.25 |
| 19 | 1 | 1 | >8 | 0.125 | 1 |
| 20 | 0.125 | 0.25 | 1 | 0.063 | 0.5 |
| 21 | 0.125 | 0.125 | 1 | 0.031 | 0.25 |
| 22 | 0.25 | 0.5 | 2 | 0.063 | 1 |
| 23 | 0.063 | 0.063 | 1 | ≤0.016 | 0.25 |
| 24 | 0.5 | 0.5 | 4 | 0.063 | 1 |
| 25 | 0.031 | 0.031 | 1 | ≤0.016 | 0.25 |
| 26 | 0.5 | 0.25 | 4 | 0.063 | 2 |
| 27 | 0.063 | 0.031 | 1 | ≤0.016 | 0.5 |
| 28 | 0.25 | 0.25 | 4 | 0.063 | 1 |
| 29 | 1 | 2 | 8 | 0.063 | 2 |
| 30 | 0.125 | 0.125 | 4 | 0.031 | 0.25 |
| 31 | 0.25 | 0.25 | 2 | ≤0.016 | 0.5 |
| 32 | 0.125 | 0.125 | 2 | ≤0.016 | 0.5 |
| 33 | 0.125 | 0.25 | 2 | ≤0.016 | 0.125 |
| 34 | 0.125 | 0.125 | 1 | ≤0.016 | 0.25 |
| 35 | 0.063 | 0.063 | 1 | ≤0.016 | 0.125 |
| 36 | 0.063 | 0.063 | 0.5 | ≤0.016 | 0.063 |
| 37 | 0.063 | 0.063 | 1 | ≤0.016 | 0.25 |
| 38 | ≤0.016 | ≤0.016 | 0.125 | ≤0.016 | 0.063 |
| 39 | 1 | 1 | 4 | 0.125 | 2 |
| 40 | 0.125 | 0.125 | 2 | ≤0.016 | 0.25 |
| 41 | 0.063 | 0.063 | 1 | ≤0.016 | 0.25 |
| 42 | 0.063 | 0.125 | 1 | ≤0.016 | 0.5 |
| 43 | 0.125 | 0.063 | 2 | ≤0.016 | 0.5 |
| 44 | 0.25 | 0.125 | 8 | ≤0.016 | 0.25 |
| 45 | 2 | 4 | >8 | 0.125 | 2 |
| 46 | 0.5 | 0.5 | 2 | 0.031 | 0.25 |
| 47 | 4 | 4 | >8 | .25 | 8 |
| 48 | 4 | 4 | 16 | 0.125 | 16 |
| 49 | 1 | 2 | 8 | 0.031 | 0.5 |
| 50 | 4 | 2 | 8 | 0.5 | >8 |
| 51 | 0.5 | 1 | 2 | ≤0.016 | 0.5 |
| 52 | 0.5 | 1 | 4 | 0.031 | 2 |
| 53 | 2 | 1 | 16 | 0.125 | 4 |
| 54 | 2 | 2 | 16 | 0.125 | 8 |
| 55 | 2 | 2 | >8 | 0.031 | 1 |
| 56 | 0.5 | 2 | 4 | ≤0.016 | 1 |
| 57 | 2 | 1 | 8 | 0.25 | 2 |
| 58 | 2 | 1 | 8 | 0.125 | 8 |
| 59 | 2 | 4 | >8 | 0.125 | 2 |
| 60 | 2 | 4 | >8 | 0.063 | 1 |
| 61 | 0.25 | 0.5 | 2 | ≤0.016 | 0.5 |
| 62 | 1 | 2 | 16 | ≤0.063 | 1 |
| 63 | 1 | 1 | 16 | ≤0.063 | 0.5 |
| 64 | 1 | 2 | 16 | ≤0.063 | 16 |
| 65 | 1 | 1 | 16 | ≤0.063 | 2 |
| 66 | 1 | 2 | 16 | ≤0.063 | 2 |
| 67 | 1 | 0.5 | 8 | 0.063 | 2 |
| 68 | 1 | 1 | >8 | 0.125 | 8 |
| 69 | 1 | 0.25 | 8 | 0.063 | 1 |
| 70 | 1 | 0.5 | 8 | 0.063 | 2 |
| 71 | 1 | 1 | 8 | 0.25 | >8 |
| 72 | 0.5 | 1 | 4 | 0.063 | 1 |
| 73 | 0.5 | 2 | 16 | ≤0.063 | 1 |
| 74 | 0.125 | 0.063 | 0.5 | ≤0.016 | 0.25 |
| 75 | 0.5 | 0.5 | 8 | ≤0.063 | 1 |
| 76 | 0.5 | 1 | 8 | ≤0.063 | 2 |

TABLE 1-continued

| Example No. | MIC for S. aureus ATCC29213 | MIC for S. aureus A798 | MIC for E. faecium A949 | MIC for M. catarrhalis A894 | MIC for A. baumannii T6474 |
|---|---|---|---|---|---|
| 77 | 0.5 | 0.25 | 4 | ≤0.063 | 2 |
| 78 | 0.5 | 1 | 8 | 0.031 | 1 |
| 79 | 0.5 | 0.5 | 8 | 0.063 | 0.5 |
| 80 | 0.5 | 0.5 | >8 | 0.031 | 0.25 |
| 81 | 0.5 | 1 | >8 | 0.063 | 1 |
| 82 | 0.5 | 0.5 | 4 | ≤0.016 | 0.5 |
| 83 | 0.063 | 0.063 | 2 | ≤0.016 | 0.063 |
| 84 | 0.25 | 0.125 | 8 | ≤0.063 | 0.5 |
| 85 | ≤0.016 | ≤0.016 | 0.5 | ≤0.016 | 0.125 |
| 86 | 0.125 | 0.5 | 4 | ≤0.016 | 8 |
| 87 | 0.125 | 0.063 | 2 | ≤0.016 | 0.25 |
| 88 | 0.125 | 0.25 | 4 | ≤0.016 | 0.25 |
| 89 | 0.063 | 0.063 | 8 | ≤0.016 | 0.125 |
| 90 | 0.063 | 0.031 | 2 | ≤0.016 | 0.5 |
| 91 | 0.031 | 0.031 | 2 | ≤0.016 | 0.063 |
| 92 | 0.031 | ≤0.016 | 0.5 | ≤0.016 | 0.063 |
| 93 | ≤0.016 | ≤0.016 | 0.25 | ≤0.016 | 0.063 |
| 94 | ≤0.016 | ≤0.016 | 0.125 | ≤0.016 | 0.031 |
| 95 | ≤0.016 | ≤0.016 | 0.125 | ≤0.016 | 0.063 |
| 96 | 0.031 | 0.031 | 1 | ≤0.016 | 0.125 |
| 97 | 0.25 | 0.25 | 8 | 0.031 | 0.25 |
| 98 | 0.25 | 0.125 | 4 | 0.031 | 0.25 |
| 99 | 0.031 | 0.031 | 2 | ≤0.016 | 0.125 |
| 100 | ≤0.016 | ≤0.016 | 0.5 | ≤0.016 | 0.125 |
| 101 | ≤0.016 | ≤0.016 | 2 | ≤0.016 | 0.125 |
| 102 | 0.25 | 1 | 4 | 0.063 | 1 |
| 103 | 0.25 | 1 | 2 | 0.063 | 0.5 |
| 104 | 0.25 | 0.25 | 2 | 0.031 | 0.5 |
| 105 | 4 | 8 | >8 | 0.25 | 4 |
| 106 | 0.125 | 0.125 | 2 | ≤0.016 | 1 |
| 107 | 4 | 8 | 8 | 0.063 | 2 |
| 108 | 2 | 4 | >8 | 0.125 | 1 |
| 109 | 0.031 | 0.031 | 2 | ≤0.016 | 0.125 |
| 110 | 4 | 4 | >8 | 0.125 | 2 |
| 111 | 0.25 | 0.5 | 8 | 0.031 | 0.25 |
| Cipro | 0.5 | >32 | >8 | ≤0.016 | >32 |

The invention claimed is:
1. A compound of formula I

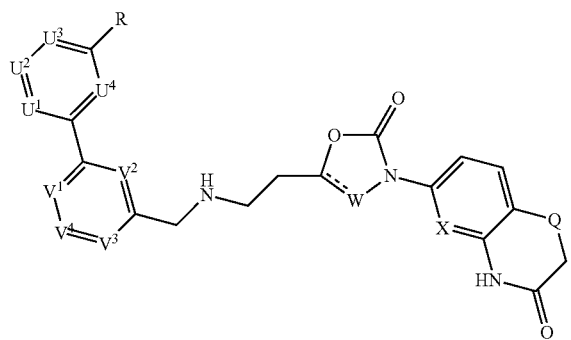

I wherein
R represents H, cyano, $(C_1$-$C_3)$alkoxy, cyanomethoxy, $(C_3$-$C_6)$cycloalkylmethoxy, hydroxy$(C_2$-$C^4)$alkoxy, $(C_1$-$C_3)$alkoxy-$(C_2$-$C_3)$alkoxy, $(C_1$-$C_4)$alkoxycarbonyl, 2-ethoxy-2-oxoethoxy, 2-(methylamino)-2-oxoethoxy, (1-cyanocyclobutyl)methoxy, 3-hydroxy-pyrrolidin-1-yl or (3,4-dihydroxycyclopentyl)methoxy;
$U^1$ represents N or $CR^1$, $U^2$ represents N or $CR^2$, $U^3$ represents N or $CR^3$ and $U^4$ represents N or $CR^4$, wherein at most three of $U^1$, $U^2$, $U^3$ and $U^4$ can represent N at the same time;
$V^1$ represents N or $CR^5$, $V^2$ represents N or $CR^6$, $V^3$ represents N or $CR^7$ and $V^4$ represents N or CH, wherein at most two of $V^1$, $V^2$, $V^3$ and $V^4$ can represent N at the same time;
$R^1$ represents H, cyano, hydroxy or $(C_1$-$C_3)$alkoxy;
$R^2$ represents H, hydroxy or $(C_1$-$C_3)$alkoxy;
$R^3$ represents H, cyano, hydroxy, $(C_1$-$C_3)$alkoxy or carboxamido;
$R^4$ represents H, cyano, hydroxy or $(C_1$-$C_3)$alkoxy;
$R^5$ represents H, hydroxy or halogen;
$R^6$ represents H, hydroxy or halogen;
$R^7$ represents H;
the dotted line "-----" represents a bond or is absent;
W represents CH or N when the dotted line "-----" is a bond, or W represents $CH_2$ when the dotted line "-----" is absent;
X represents CH or N; and
Q represents O or S;
or a salt of the compound.
2. The compound of formula I according to claim 1, wherein
R represents H, $(C_1$-$C_3)$alkoxy or cyano;
$V^1$ represents N or $CR^5$, $V^2$ represents N or $CR^6$ and $V^3$ represents N or $CR^7$, it being understood that at most one of $V^1$, $V^2$ and $V^3$ can represent N at the same time;
$V^4$ represents CH
$R^1$ represents H, hydroxy or cyano;
$R^3$ represents H, hydroxy, $(C_1$-$C_3)$alkoxy or carboxamido;

R⁴ represents H;
R⁵ represents H or halogen; and
R⁶ represents H or halogen;
or a salt of the compound.

3. The compound of formula I according to claim 1, wherein the dotted line "-----" is absent and W represents CH₂;
or a salt of the compound.

4. The compound of formula I according to claim 1, wherein the dotted line "-----" represents a bond;
or a salt of the compound.

5. The compound of formula I according to claim 1, wherein X represents CH and Q represents S or X represents N and Q represents O;
or a salt of the compound.

6. The compound of formula I according to claim 5, wherein X represents CH and Q represents S;
or a salt of the compound.

7. The compound of formula I according to claim 5, wherein X represents N and Q represents O;
or a salt of the compound.

8. The compound of formula I according to claim 1, wherein:
the dotted line "-----" is absent and W represents CH₂ or the dotted line "-----" is a bond and W represents CH;
R represents methoxy or cyano;
U², U³ or U⁴ each represent CH and U¹ represents CR¹ wherein R¹ represents H or hydroxy, or U¹ represents N, U² represents CR², U³ represents CR³ and U⁴ represents CR⁴, or U¹ represents CR¹, U² represents N, U³ represents CR³ and U⁴ represents CR⁴, or U¹ represents CR¹, U² represents CR², U³ represents N and U⁴ represents CR⁴, or U¹ represents CR¹, U² represents CR², U³ represents CR³ and U⁴ represents N, or U¹ and U² represent N and U³ and U⁴ represent CH; and
V¹ represents CH or N and V² and V³ each represent CH;
or a salt of the compound.

9. The compound of formula I according to claim 1, wherein:
R represents cyano or methoxy;
each of U¹, U², U³, U⁴, V¹, V², V³ and V⁴ represents CH, or U¹ represents N, V¹ represents CR⁵ wherein R⁵ is hydroxy, and each of U², U³, U⁴, V², V³ and V⁴ represents CH, or U⁴ represents N, V¹ represents CR⁵ wherein R⁵ is hydroxy, and each of U¹, U², U³, V², V³ and V⁴ represents CH, or U⁴ represents N, V² represents CR⁶ wherein R⁶ is hydroxy, and each of U¹, U², U³, V¹, V³ and V⁴ represents CH, or each of U¹ and U² represents N, V¹ represents CR⁵ wherein R⁵ is H or hydroxy, V¹ represents CR⁵ and each of U³, U⁴, V², V³ and V⁴ represents CH, or V¹ represents N, U¹ represents CR¹ wherein R¹ is hydroxy and each of U², U³, U⁴, V², V³ and V⁴ represents CH, or each of U¹, U² and V³ represents N and each of U³, U⁴, V¹, V² and V⁴ represents CH;
the dotted line "-----" represents a bond or is absent;
W represents CH when the dotted line "-----" is a bond, or W represents CH₂ when the dotted line "-----" is absent;
X represents CH or N; and
Q represents O or S;
or a salt of the compound.

10. The compound of formula I according to claim 1, wherein the compound is:
6-((R)-5-{2-[(3'-methoxy-biphenyl-3-ylmethyl)-amino]-ethyl}-2-oxo-oxazolidin-3-yl)-4H-benzo[1,4]thiazin-3-one;
2-methoxy-6-[3-({2-[(R)-2-oxo-3-(3-oxo-3,4-dihydro-2H-benzo[1,4]thiazin-6-yl)-oxazolidin-5-yl]-ethyl-amino}-methyl)-phenyl]-isonicotinonitrile;
3'-({2-[(S)-2-oxo-3-(3-oxo-3,4-dihydro-2H-benzo[1,4]thiazin-6-yl)-oxazolidin-5-yl]-ethylamino}-methyl)-biphenyl-3-carbonitrile;
6-((S)-5-{2-[(3'-methoxy-biphenyl-3-ylmethyl)-amino]-ethyl}-2-oxo-oxazolidin-3-yl)-4H-pyrido[3,2-b][1,4]oxazin-3-one;
3'-({2-[(R)-2-oxo-3-(3-oxo-3,4-dihydro-2H-benzo[1,4]thiazin-6-yl)-oxazolidin-5-yl]-ethylamino}-methyl)-biphenyl-3-carbonitrile;
6-((R)-5-{2-[(4'-methoxy-biphenyl-3-ylmethyl)-amino]-ethyl}-2-oxo-oxazolidin-3-yl)-4H-benzo[1,4]thiazin-3-one;
6-((R)-5-{2-[(4'-hydroxy-3'-methoxy-biphenyl-3-ylmethyl)-amino]-ethyl}-2-oxo-oxazolidin-3-yl)-4H-benzo[1,4]thiazin-3-one;
5-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-2-carbonitrile;
5-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-3-carbonitrile;
6-((R)-5-{2-[(3'-hydroxy-5'-methoxy-biphenyl-3-ylmethyl)-amino]-ethyl}-2-oxo-oxazolidin-3-yl)-4H-benzo[1,4]thiazin-3-one;
6-((R)-5-{2-[(6-fluoro-3'-methoxy-biphenyl-3-ylmethyl)-amino]-ethyl}-2-oxo-oxazolidin-3-yl)-4H-benzo[1,4]thiazin-3-one;
6-((R)-5-{2-[(2-fluoro-3'-methoxy-biphenyl-3-ylmethyl)-amino]-ethyl}-2-oxo-oxazolidin-3-yl)-4H-benzo[1,4]thiazin-3-one;
6-((R)-5-{2-[3-(5-methoxy-pyridin-3-yl)-benzylamino]-ethyl}-2-oxo-oxazolidin-3-yl)-4H-benzo[1,4]thiazin-3-one;
6-((R)-5-{2-[3-(4-methoxy-pyridin-2-yl)-benzylamino]-ethyl}-2-oxo-oxazolidin-3-yl)-4H-benzo[1,4]thiazin-3-one;
6-((R)-5-{2-[3-(6-methoxy-pyridin-2-yl)-benzylamino]-ethyl}-2-oxo-oxazolidin-3-yl)-4H-benzo[1,4]thiazin-3-one;
6-((R)-5-{2-[3-(6-methoxy-pyridin-3-yl)-benzylamino]-ethyl}-2-oxo-oxazolidin-3-yl)-4H-benzo[1,4]thiazin-3-one;
5-[3-({2-[(R)-2-oxo-3-(3-oxo-3,4-dihydro-2H-benzo[1,4]thiazin-6-yl)-oxazolidin-5-yl]-ethylamino}-methyl)-phenyl]-nicotinonitrile;
6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-pyridine-2-carbonitrile;
6-hydroxy-5-[3-({2-[(R)-2-oxo-3-(3-oxo-3,4-dihydro-2H-benzo[1,4]thiazin-6-yl)-oxazolidin-5-yl]-ethyl-amino}-methyl)-phenyl]-nicotinonitrile;
6-[(R)-5-(2-{[6-(3-methoxy-phenyl)-pyridin-2-ylmethyl]-amino}-ethyl)-2-oxo-oxazolidin-3-yl]-4H-benzo[1,4]thiazin-3-one;
6-[(R)-5-(2-{[4-(3-methoxy-phenyl)-pyridin-2-ylmethyl]-amino}-ethyl)-2-oxo-oxazolidin-3-yl]-4H-benzo[1,4]thiazin-3-one;
6-((R)-5-{2-[(6'-methoxy-[2,2]bipyridinyl-6-ylmethyl)-amino]-ethyl}-2-oxo-oxazolidin-3-yl)-4H-benzo[1,4]thiazin-3-one;
6-((R)-5-{2-[3-(4-methoxy-pyrimidin-2-yl)-benzylamino]-ethyl}-2-oxo-oxazolidin-3-yl)-4H-benzo[1,4]thiazin-3-one;

6-((R)-5-{2-[3-(6-methoxy-pyrimidin-4-yl)-benzylamino]-ethyl}-2-oxo-oxazolidin-3-yl)-4H-benzo[1,4]thiazin-3-one;

6-((R)-5-{2-[3-(6-methoxy-pyrazin-2-yl)-benzylamino]-ethyl}-2-oxo-oxazolidin-3-yl)-4H-benzo[1,4]thiazin-3-one;

6-((R)-5-{2-[3-(2,6-dimethoxy-pyrimidin-4-yl)-benzylamino]-ethyl}-2-oxo-oxazolidin-3-yl)-4H-benzo[1,4]thiazin-3-one;

6-((R)-5-{2-[3-(4,6-dimethoxy-pyrimidin-2-yl)-benzylamino]-ethyl}-2-oxo-oxazolidin-3-yl)-4H-benzo[1,4]thiazin-3-one;

6-((R)-5-{2-[3-(4,6-dimethoxy-[1,3,5]triazin-2-yl)-benzylamino]-ethyl}-2-oxo-oxazolidin-3-yl)-4H-benzo[1,4]thiazin-3-one;

3-methoxy-3'-({2-[(R)-2-oxo-3-(3-oxo-3,4-dihydro-2H-benzo[1,4]thiazin-6-yl)-oxazolidin-5-yl]-ethylamino}-methyl)-biphenyl-4-carboxylic acid amide;

6-((R)-5-{2-[3-(5-methoxy-pyridazin-3-yl)-benzylamino]-ethyl}-2-oxo-oxazolidin-3-yl)-4H-benzo[1,4]thiazin-3-one;

6-((R)-5-{2-[3-(6-methoxy-pyridin-2-yl)-benzylamino]-ethyl}-2-oxo-oxazolidin-3-yl)-4H-pyrido[3,2-b][1,4]oxazin-3-one;

5-methoxy-3'-({2-[(R)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile;

3'-({2-[(R)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

6-(5-{2-[(3'-methoxy-biphenyl-3-ylmethyl)-amino]-ethyl}-2-oxo-oxazol-3-yl)-4H-pyrido[3,2-b][1,4]oxazin-3-one;

6-(5-{2-[3-(6-methoxy-pyridin-2-yl)-benzylamino]-ethyl}-2-oxo-oxazol-3-yl)-4H-pyrido[3,2-b][1,4]oxazin-3-one;

3'-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-biphenyl-3-carbonitrile;

5-methoxy-3'-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-biphenyl-2-carbonitrile;

4-hydroxy-3-[4-({2-[(R)-2-oxo-3-(3-oxo-3,4-dihydro-2H-benzo[1,4]thiazin-6-yl)-oxazolidin-5-yl]-ethylamino}-methyl)-pyridin-2-yl]-benzonitrile;

6-[(R)-5-(2-{[2-(3-methoxy-phenyl)-pyridin-4-ylmethyl]-amino}-ethyl)-2-oxo-oxazolidin-3-yl]-4H-benzo[1,4]thiazin-3-one;

6-((S)-5-{2-[3-(6-methoxy-pyridin-2-yl)-benzylamino]-ethyl}-2-oxo-oxazolidin-3-yl)-4H-pyrido[3,2-b][1,4]oxazin-3-one;

5-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile; and 3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

6-((S)-5-{2-[3-(6-methoxy-pyridin-2-yl)-benzylamino]-ethyl}-2-oxo-oxazolidin-3-yl)-4H-benzo[1,4]thiazin-3-one;

6-((S)-5-{2-[3-(5-methoxy-pyridazin-3-yl)-benzylamino]-ethyl}-2-oxo-oxazolidin-3-yl)-4H-pyrido[3,2-b][1,4]oxazin-3-one;

6-hydroxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

3-[4-({2-[(S)-2-oxo-3-(3-oxo-3,4-dihydro-2H-pyrido[3,2-b][1,4]oxazin-6-yl)-oxazolidin-5-yl]-ethylamino}-methyl)-pyridin-2-yl]-benzonitrile;

2-hydroxy-6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-isonicotinonitrile;

6-((S)-5-{2-[(3',4'-dimethoxy-biphenyl-3-ylmethyl)-amino]-ethyl}-2-oxo-oxazolidin-3-yl)-4H-pyrido[3,2-b][1,4]oxazin-3-one;

3-[4-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-pyridin-2-yl]-benzonitrile;

6-((S)-5-{2-[(3'-cyclobutylmethoxy-biphenyl-3-ylmethyl)-amino]-ethyl}-2-oxo-oxazolidin-3-yl)-4H-pyrido[3,2-b][1,4]oxazin-3-one;

6-(5-{2-[3-(6-methoxy-pyridin-2-yl)-benzylamino]-ethyl}-2-oxo-[1,3,4]oxadiazol-3-yl)-4H-pyrido[3,2-b][1,4]oxazin-3-one;

5-methoxy-3'-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-biphenyl-2-carbonitrile;

6-[(S)-5-(2-{[3'-(3-hydroxy-propoxy)-biphenyl-3-ylmethyl]-amino}-ethyl)-2-oxo-oxazolidin-3-yl]-4H-pyrido[3,2-b][1,4]oxazin-3-one;

6-[(S)-5-(2-{[3'-(2-methoxy-ethoxy)-biphenyl-3-ylmethyl]-amino}-ethyl)-2-oxo-oxazolidin-3-yl]-4H-pyrido[3,2-b][1,4]oxazin-3-one;

6-((S)-5-{2-[3-(2-methoxy-pyridin-4-yl)-benzylamino]-ethyl}-2-oxo-oxazolidin-3-yl)-4H-pyrido[3,2-b][1,4]oxazin-3-one;

3'-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-biphenyl-3-carbonitrile;

6-[(S)-5-(2-{3-[6-((RS)-3-hydroxy-pyrrolidin-1-yl)-pyridin-2-yl]-benzylamino}-ethyl)-2-oxo-oxazolidin-3-yl]-4H-pyrido[3,2-b][1,4]oxazin-3-one;

6-((S)-5-{2-[(3'-cyclopropylmethoxy-biphenyl-3-ylmethyl)-amino]-ethyl}-2-oxo-oxazolidin-3-yl)-4H-pyrido[3,2-b][1,4]oxazin-3-one;

6-((S)-5-{2-[3-(6-methoxy-pyridazin-4-yl)-benzylamino]-ethyl}-2-oxo-oxazolidin-3-yl)-4H-pyrido[3,2-b][1,4]oxazin-3-one;

5-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridazine-3-carbonitrile;

6-[2-hydroxy-3-({2-[5-oxo-4-(3-oxo-3,4-dihydro-2H-pyrido[3,2-b][1,4]oxazin-6-yl)-4,5-dihydro-[1,3,4]oxadiazol-2-yl]-ethylamino}-methyl)-phenyl]-pyridine-2-carbonitrile;

2-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-nicotinonitrile;

6-((S)-5-{2-[(3'-hydroxy-biphenyl-3-ylmethyl)-amino]-ethyl}-2-oxo-oxazolidin-3-yl)-4H-pyrido[3,2-b][1,4]oxazin-3-one;

6-((S)-5-{2-[(2',5'-dimethoxy-biphenyl-3-ylmethyl)-amino]-ethyl}-2-oxo-oxazolidin-3-yl)-4H-pyrido[3,2-b][1,4]oxazin-3-one;

[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-acetonitrile;

3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-4-carbonitrile;

6-[(S)-5-(2-{[3'-(4-hydroxy-butoxy)-biphenyl-3-ylmethyl]-amino}-ethyl)-2-oxo-oxazolidin-3-yl]-4H-pyrido[3,2-b][1,4]oxazin-3-one;

[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-acetic acid ethyl ester;

6-[(S)-5-(2-{3-[6-((3R,4S)-3,4-dihydroxy-cyclopentylmethoxy)-pyridin-2-yl]-benzylamino}-ethyl)-2-oxo-oxazolidin-3-yl]-4H-pyrido[3,2-b][1,4]oxazin-3-one;

6-((S)-5-{2-[(3'-ethoxy-biphenyl-3-ylmethyl)-amino]-ethyl}-2-oxo-oxazolidin-3-yl)-4H-pyrido[3,2-b][1,4]oxazin-3-one;

1-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxymethyl]-cyclobutanecarbonitrile;

6-[(R)-5-(2-{[5-(3-methoxy-phenyl)-pyridin-3-ylmethyl]-amino}-ethyl)-2-oxo-oxazolidin-3-yl]-4H-benzo[1,4]thiazin-3-one;

3-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridine-2-carbonitrile;

6-(5-{2-[2-hydroxy-3-(6-methoxy-pyridin-2-yl)-benzylamino]-ethyl}-2-oxo-[1,3,4]oxadiazol-3-yl)-4H-pyrido[3,2-b][1,4]oxazin-3-one;

3-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-4-carbonitrile;

6-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carbonitrile;

3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-carboxylic acid methyl ester;

N-methyl-2-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-acetamide;

6-((S)-5-{2-[3-(6-methoxy-pyridazin-3-yl)-benzylamino]-ethyl}-2-oxo-oxazolidin-3-yl)-4H-pyrido[3,2-b][1,4]oxazin-3-one;

6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridazine-4-carbonitrile;

6-((S)-5-{2-[3-(5-methoxy-pyridazin-3-yl)-benzylamino]-ethyl}-2-oxo-oxazolidin-3-yl)-4H-benzo[1,4]oxazin-3-one;

3'-({2-[(S)-2-oxo-3-(3-oxo-3,4-dihydro-2H-benzo[1,4]oxazin-6-yl)-oxazolidin-5-yl]-ethylamino}-methyl)-biphenyl-3-carbonitrile;

6-(5-{2-[3-(5-methoxy-pyridazin-3-yl)-benzylamino]-ethyl}-2-oxo-oxazol-3-yl)-4H-pyrido[3,2-b][1,4]oxazin-3-one;

6-((S)-5-{2-[3-(5-ethoxy-pyridin-3-yl)-benzylamino]-ethyl}-2-oxo-oxazolidin-3-yl)-4H-pyrido[3,2-b][1,4]oxazin-3-one;

6-(5-{2-[2-hydroxy-3-(6-methoxy-pyridin-2-yl)-benzylamino]-ethyl}-2-oxo-oxazol-3-yl)-4H-pyrido[3,2-b][1,4]oxazin-3-one;

3-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-2-carbonitrile;

6-((S)-5-{2-[(6'-methoxy-[2,2]bipyridinyl-4-ylmethyl)-amino]-ethyl}-2-oxo-oxazolidin-3-yl)-4H-pyrido[3,2-b][1,4]oxazin-3-one;

6-[2-hydroxy-3-({2-[(S)-2-oxo-3-(3-oxo-3,4-dihydro-2H-benzo[1,4]oxazin-6-yl)-oxazolidin-5-yl]-ethylamino}-methyl)-phenyl]-pyridine-2-carbonitrile;

6-((S)-5-{2-[4-hydroxy-3-(5-methoxy-pyridazin-3-yl)-benzylamino]-ethyl}-2-oxo-oxazolidin-3-yl)-4H-pyrido[3,2-b][1,4]oxazin-3-one;

6-((S)-5-{2-[2-hydroxy-3-(6-methoxy-pyridin-2-yl)-benzylamino]-ethyl}-2-oxo-oxazolidin-3-yl)-4H-benzo[1,4]oxazin-3-one;

6-((S)-5-{2-[3-(6-methoxy-pyrazin-2-yl)-benzylamino]-ethyl}-2-oxo-oxazolidin-3-yl)-4H-pyrido[3,2-b][1,4]oxazin-3-one;

6-[2-hydroxy-3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridine-2-carbonitrile;

6-((S)-5-{2-[2-hydroxy-3-(6-methoxy-pyridin-2-yl)-benzylamino]-ethyl}-2-oxo-oxazolidin-3-yl)-4H-pyrido[3,2-b][1,4]oxazin-3-one;

6-[2-hydroxy-3-({2-[(S)-2-oxo-3-(3-oxo-3,4-dihydro-2H-pyrido[3,2-b][1,4]thiazin-6-yl)-oxazolidin-5-yl]-ethylamino}-methyl)-phenyl]-pyridine-2-carbonitrile;

6-((S)-5-{2-[2-hydroxy-3-(6-methoxy-pyridin-2-yl)-benzylamino]-ethyl}-2-oxo-oxazolidin-3-yl)-4H-pyrido[3,2-b][1,4]thiazin-3-one;

6-[2-hydroxy-3-({2-[2-oxo-3-(3-oxo-3,4-dihydro-2H-pyrido[3,2-b][1,4]oxazin-6-yl)-2,3-dihydro-oxazol-5-yl]-ethylamino}-methyl)-phenyl]-pyridine-2-carbonitrile;

6-((R)-5-{2-[3-(5-methoxy-pyridazin-3-yl)-benzylamino]-ethyl}-2-oxo-oxazolidin-3-yl)-4H-pyrido[3,2-b][1,4]oxazin-3-one;

6-((R)-5-{2-[3-(5-methoxy-pyridazin-3-yl)-benzylamino]-ethyl}-2-oxo-oxazolidin-3-yl)-4H-pyrido[3,2-b][1,4]thiazin-3-one;

6-((5)-5-{2-[3-(5-methoxy-pyridazin-3-yl)-benzylamino]-ethyl}-2-oxo-oxazolidin-3-yl)-4H-pyrido[3,2-b][1,4]thiazin-3-one;

3'-({2-[(S)-2-oxo-3-(3-oxo-3,4-dihydro-2H-pyrido[3,2-b][1,4]thiazin-6-yl)-oxazolidin-5-yl]-ethylamino}-methyl)-biphenyl-3-carbonitrile;

6-((S)-5-{2-[4-hydroxy-3-(4-methoxy-pyridin-2-yl)-benzylamino]-ethyl}-2-oxo-oxazolidin-3-yl)-4H-pyrido[3,2-b][1,4]oxazin-3-one;

6-[(S)-5-(2-{[2-(3-methoxy-phenyl)-pyrimidin-4-ylmethyl]-amino}-ethyl)-2-oxo-oxazolidin-3-yl]-4H-pyrido[3,2-b][1,4]oxazin-3-one;

6-[(S)-5-(2-{[5-(3-methoxy-phenyl)-pyridazin-3-ylmethyl]-amino}-ethyl)-2-oxo-oxazolidin-3-yl]-4H-pyrido[3,2-b][1,4]oxazin-3-one;

6-[(S)-5-(2-{[6-(3-methoxy-phenyl)-pyrazin-2-ylmethyl]-amino}-ethyl)-2-oxo-oxazolidin-3-yl]-4H-pyrido[3,2-b][1,4]oxazin-3-one;

6-[(S)-5-(2-{[6-(3-methoxy-phenyl)-pyridazin-4-ylmethyl]-amino}-ethyl)-2-oxo-oxazolidin-3-yl]-4H-pyrido[3,2-b][1,4]oxazin-3-one;

6-((S)-5-{2-[2-hydroxy-3-(4-methoxy-pyridin-2-yl)-benzylamino]-ethyl}-2-oxo-oxazolidin-3-yl)-4H-pyrido[3,2-b][1,4]oxazin-3-one;

6-(5-{2-[(3'-methoxy-biphenyl-3-ylmethyl)-amino]-ethyl}-2-oxo-[1,3,4]oxadiazol-3-yl)-4H-pyrido[3,2-b][1,4]oxazin-3-one;

6-(5-{2-[3-(5-methoxy-pyridazin-3-yl)-benzylamino]-ethyl}-2-oxo-[1,3,4]oxadiazol-3-yl)-4H-pyrido[3,2-b][1,4]oxazin-3-one;

(S)-6-(5-(2-((4-hydroxy-3-(6-methoxypyridin-2-yl)benzyl)amino)ethyl)-2-oxooxazolidin-3-yl)-2H-pyrido[3,2-b][1,4]oxazin-3(4H)-one;

(S)-6-(5-(2-(((5-(5-methoxypyridazin-3-yl)pyridin-3-yl)methyl)amino)ethyl)-2-oxooxazolidin-3-yl)-2H-pyrido[3,2-b][1,4]oxazin-3(4H)-one; or (S)-6-(5-(2-(((4-(5-methoxypyridazin-3-yl)pyridin-2-yl)methyl)amino)ethyl)-2-oxooxazolidin-3-yl)-2H-pyrido[3,2-b][1,4]oxazin-3(4H)-one;
or a salt of the compound.

11. The compound of formula I according to claim 1, or a pharmaceutically acceptable salt thereof, wherein the compound is formulated as a medicament.

12. A pharmaceutical composition comprising, as active principle, the compound of formula I according to claim 1, or a pharmaceutically acceptable salt thereof, and at least one therapeutically inert excipient.

13. A method of treating a bacterial infection comprising administering to a subject in need thereof the compound, or the salt of the compound according to claim 1.

14. The method according to claim 13, wherein the bacterial infection is a respiratory tract infection, otitis media, meningitis, skin and soft tissue infection, pneumonia, bacteremia, endocarditis, intraabdominal infection, gastrointestinal infection, *Clostridium difficile* infection, urinary tract infection, sexually transmitted infection, foreign body infection, osteomyelitis, Lyme disease, topical infection, opthalmological infection, tuberculosis and tropical diseases.

15. The method according to claim 13, wherein the compound prevents or treats bacterial infections mediated by *Staphylococcus aureus* bacteria or *Acinetobacter baumannii* bacteria.

16. A method of treating a bacterial infection comprising administering to a subject in need thereof the composition according to claim 12.

17. The method according to claim 16, wherein the bacterial infection is a respiratory tract infection, otitis media, meningitis, skin and soft tissue infection, pneumonia, bacteremia, endocarditis, intraabdominal infection, gastrointestinal infection, *Clostridium difficile* infection, urinary tract infection, sexually transmitted infection, foreign body infection, osteomyelitis, Lyme disease, topical infection, opthalmological infection, tuberculosis and tropical disease.

18. The method according to claim 16, wherein the composition treats bacterial infections mediated by *Staphylococcus aureus* bacteria or *Acinetobacter baumannii* bacteria.

* * * * *